United States Patent
Kajino et al.

(10) Patent No.: US 6,407,116 B1
(45) Date of Patent: Jun. 18, 2002

(54) NITROGENOUS FUSED-RING COMPOUNDS, PROCESS FOR THE PREPARATION OF THE SAME, AND DRUGS

(75) Inventors: Masahiro Kajino, Toyonaka; Shinji Morimoto, Osaka; Atsuhiro Inaba, Nagaokakyo; Hideaki Nagaya, Toyonaka, all of (JP)

(73) Assignee: Takeda Chemical Industries, Inc., Osaka (JP)

( * ) Notice: Subject to any disclaimer, the term of this patent is extended or adjusted under 35 U.S.C. 154(b) by 0 days.

(21) Appl. No.: 09/486,646

(22) PCT Filed: Sep. 11, 1998

(86) PCT No.: PCT/JP98/04103

§ 371 (c)(1),
(2), (4) Date: Feb. 28, 2000

(87) PCT Pub. No.: WO99/14203

PCT Pub. Date: Mar. 25, 1999

(30) Foreign Application Priority Data

Sep. 16, 1997 (JP) ............................................. 9-250960

(51) Int. Cl.$^7$ .................... C07D 239/96; C07D 401/06; A61K 31/505

(52) U.S. Cl. ................. 514/282.17; 544/285; 544/283; 514/258; 514/259

(58) Field of Search ................................ 544/285, 253; 514/258, 259, 252.17

(56) References Cited

U.S. PATENT DOCUMENTS

| | | | |
|---|---|---|---|
| 3,274,194 A | 9/1966 | Hayao | 260/256.4 |
| 4,426,383 A | 1/1984 | Sugimoto et al. | 514/253 |
| 4,543,254 A | 9/1985 | Kaneko et al. | 514/253 |
| 4,599,337 A | 7/1986 | Kaneko et al. | 514/265 |
| 4,608,375 A | 8/1986 | Ueda et al. | 514/218 |
| 4,632,925 A | 12/1986 | Mullin, Jr. | 514/256 |
| 4,705,787 A | 11/1987 | Ueda et al. | 514/259 |
| 5,215,987 A | 6/1993 | Hajos et al. | 514/230.5 |

FOREIGN PATENT DOCUMENTS

| | | | |
|---|---|---|---|
| EP | 0 040 793 | | 12/1981 |
| EP | 181793 | * | 5/1986 |
| JP | 57-206665 | | 12/1982 |
| JP | 60-152417 | | 8/1985 |
| JP | 62-87585 | | 4/1987 |
| JP | 1-213284 | | 8/1989 |
| JP | 5001067 | * | 1/1993 |
| WO | WO 98/49167 | | 11/1998 |

* cited by examiner

Primary Examiner—Mukund J. Shah
Assistant Examiner—Hong Liu
(74) Attorney, Agent, or Firm—Mark Chao; Elaine M. Ramesh

(57) ABSTRACT

A compound represented by the formula:

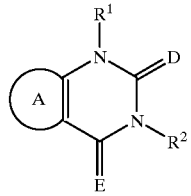

[wherein ring A represents a homocycle optionally having substituents or a nitrogen-containing heterocycle optionally having substituents; D and E are O or S; one of $R^1$ and $R^2$ represents a group represented by the formula:

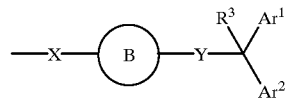

(wherein $Ar^1$ and $Ar^2$ represent an aromatic group optionally having substituents; $Ar^1$ and $Ar^2$ may form a condensed cyclic group optionally having substituents together with an adjacent carbon atom; ring B represents a nitrogen-containing heterocycle optionally having substituents; X and Y are a bond, O, S(O)p (p is an integer of 0 to 2), $NR^4$ ($R^4$ is H or a lower alkyl group) or a bivalent straight-chained lower hydrocarbon group, which may contain 1 to 3 hetero atoms, optionally having substituents; and $R^3$ represents H, a hydroxy group optionally having substituents or an optionally esterified carboxyl group); and the other is a hydrogen atom, a cyano group or a hydrocarbon group optionally having substituents], or a salt thereof, has an anti-histaminic action, an anti-inflammatory action, eosinophil chemotaxis-inhibiting action, and is useful for preventing or treating asthma, allergic conjunctivitis, allergic rhinitis, urticaria, atopic dermatitis and so on.

10 Claims, No Drawings

NITROGENOUS FUSED-RING COMPOUNDS, PROCESS FOR THE PREPARATION OF THE SAME, AND DRUGS

This Application is the National Stage of International Application Serial No. PCT/JP98/04103, filed Sep. 11, 1998.

TECHNICAL FIELD

The present invention relates to novel nitrogen-containing condensed cyclic compounds (preferably quinazoline derivatives) which have a superior anti-allergic action, anti-histaminic action, anti-inflammatory action, eosinophil chemotaxis-inhibiting action and so on, and are useful as agents for preventing or treating allergic diseases, atopic dermatitis, allergic rhinitis, asthma (e.g., bronchial asthma), allergic conjunctivitis, urticaria (e.g., chronic urticaria), etc., a method for producing them, a composition and so on.

BACKGROUND

In these days, compounds having a nitrogen-containing condensed ring (e.g., quinazoline) backbone as a drug against various diseases have been extensively synthesized, including:

(1) a compound disclosed in JP-A-57-206665 represented by the formula:

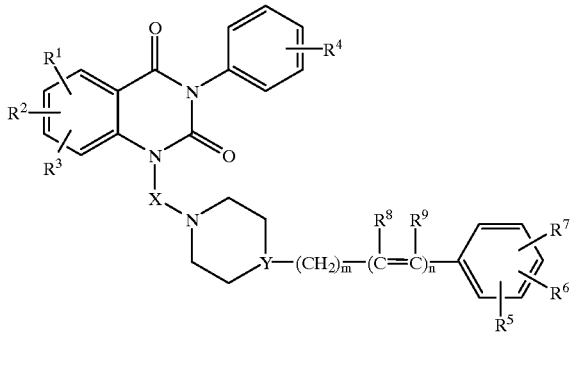

[wherein each of $R^1$ and $R^3$ is a lower alkyl group, $R^2$ is a straight or branched alkoxycarbonyl group, $R^1$, $R^2$ and $R^3$ are bound to 5-, 6- and 7-positions, or 6-, 7- and 8-position in a quinazoline ring, $R^4$ is a hydrogen atom, a halogen atom, an alkyl group, a trifluoromethyl group or a nitro group, X is an alkylene group optionally having an alkyl side chain, Y is a nitrogen atom or a CH moiety, each of $R^5$, $R^6$ and $R^7$ is a hydrogen atom, a halogen atom, an alkyl group or an alkoxy group, each of $R^8$ and $R^9$ is a hydrogen atom or a lower alkyl group, m is an integer of 0 to 3 and n is 0 or 1], or a salt thereof which is purported to be useful as a vasodilator, a blood flow-improving agent, a hypotensive agent or an anti-arteriosclerotic agent;

(2) a compound disclosed in JP-A-60-152417 represented by the formula:

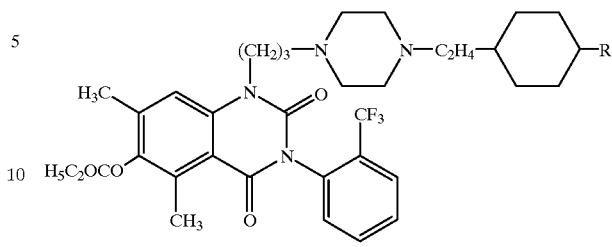

[wherein R is a hydrogen atom or a fluorine atom] or a salt thereof which is purported to be useful as an anti-cancer effect-promoting agent;

(3) a compound disclosed in EP-A-040793 represented by the formula:

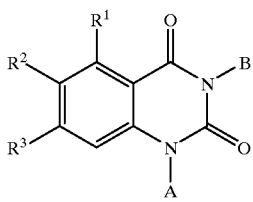

[wherein each of $R^1$ and $R^3$ is an alkyl group, $R^2$ is an alkoxycarbonyl group, B is an alkyl group or a phenyl group optionally substituted with at least one halogen, alkyl, alkoxy, dialkylamino, O—$CH_2$—O, $CF_3$ or $NO_2$, A is a hydrogen atom, an alkyl group, a carboxy-alkyl group, an alkoxycarbonyl-alkyl group, a hydroxyalkyl group, a benzyl group optionally substituted with $NO_2$ or a lower alkoxy, an aminoalkyl group substituted with pentamethylene, hexamethylene, heptamethylene, methylene optionally substituted with pyridylmethyl, alkyl, alkoxy, benzyl, tetramethylene, alkyl, a lower alkyl group substituted with piperidine or pyrrolidine, $R^4R^5N$—CO—X, $R^6R^7N$—$X^1$—O—CO—X, a group represented by the formula:

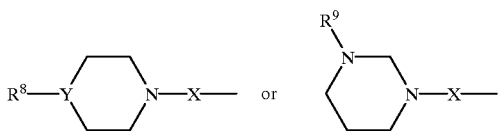

[wherein each of X and $X^1$ is a lower alkylene group, $R^4$ is a hydrogen atom or an alkyl group, $R^5$ is a hydrogen atom, an alkyl group, a dialkylamino-alkyl group, a benzyl group, piperidino-morpholino, 1-piperazinyl, a 4-(lower)acyl-1-piperazinyl, a 4-carbamoyl-1-piperazinyl-alkyl group whose carbamoyl group is optionally substituted with alkyl or phenyl, or $NR^4R^5$ is piperidino or 4-alkylpiperazino, $R^6$ is an alkyl group, $R^7$ is an alkyl group, a benzyl group, a piperidino group-alkyl, morpholino-alkyl], or a salt thereof which is purported to be useful as an anti-arteriosclerotic agent;

(4) a compound disclosed in U.S. Pat. No. 3,274,194. represented by the formula:

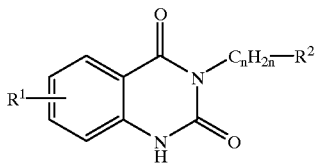

[wherein $R^1$ is a hydrogen atom, a halogen atom, a lower alkyl group, a lower alkoxy group, a nitro group or an amino group, n is an integer of 0 to 6, $R^2$ is a di-lower alkylamino or a heterocyclic group], or a salt thereof which is purported to be useful as an anti-inflammatory agent or a sedative; or, (5) a compound disclosed in JP-A-1-213284 represented by the formula:

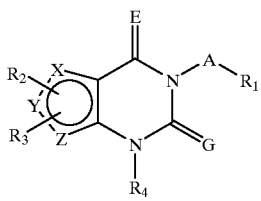

[wherein one of X, Y and Z is a sulfur atom, and the others are carbon atoms, E and G are same or different and each is an oxygen atom or a sulfur atom, $R^1$ is a substituted piperidino group or a substituted 1-piperazinyl group (substituent is an aralkyl group, an aralkyloxy group, an aralkylcarbonyl group, an aromatic acyl group or an aralkylidene group), $R^2$ and $R^3$ are same or different and each is a hydrogen atom, a lower alkyl group, an aryl group or a halogen atom, $R^4$ is a hydrogen atom, a lower alkyl group or an acyl group, A is an alkylene group having 1 to 4 carbon atoms], or a salt thereof which is purported to have an anti-histaminic action, an anti-serotonin action, an anti-allergic action and an anti-asthmatic action.

On the other hand, examples of a compound having an anti-allergic action or an anti-histaminic action are Terfenadine (The Merck Index, 12th ed., 9307) and Ebastine (The Merck Index, 12th ed., 3534), which are used clinically.

DISCLOSURE OF INVENTION

A novel compound which is more satisfactory in terms of efficacy, duration of action, safety and the like when compared with conventional anti-allergic agents, anti-histaminic agents, anti-inflammatory agents and the like is still desired.

The inventors of this invention made an effort and finally synthesized for the first time a novel nitrogen-containing condensed ring compound (preferably a quinazoline derivative) represented by the formula:

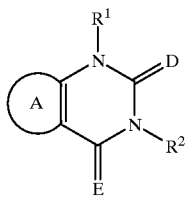

[wherein ring A represents a cyclic hydrocarbon optionally having substituents or a nitrogen-containing heterocycle optionally having substituents; D and E are the same or different and represent, independently, an oxygen atom or a sulfur atom; one of $R^1$ and $R^2$ represents a group represented by the formula:

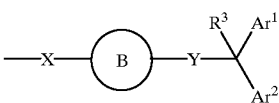

(wherein $Ar^1$ and $Ar^2$ represent, independently, an aromatic group optionally having substituents; $Ar^1$ and $Ar^2$ may form a condensed cyclic group optionally having substituents together with an adjacent carbon atom; ring B represents a nitrogen-containing heterocycle optionally having substituents; X and Y are the same or different and represent, independently, a bond, an oxygen atom, S(O)p (p represents an integer of 0 to 2), $NR^4$ ($R^4$ represents a hydrogen atom or a lower alkyl group) or a bivalent straight-chained lower hydrocarbon group, which may contain 1 to 3 hetero atoms, optionally having substituents; and $R^3$ represents ahydrogen atom, a hydroxy group optionally having substituents or an optionally esterified carboxyl group); and the other is a hydrogen atom, a cyano group or a hydrocarbon group optionally having substituents], or its salt whose chemical structure is characterized substantially in that two substituents bound to one of two nitrogen atoms of the nitrogen-containing condensed ring (preferably a quinazoline) backbone via a spacer having a nitrogen-containing heterocycle such as piperidine or piperazine, and discovered that this compound has unexpectedly excellent anti-allergic action, anti-histaminic action, anti-inflammatory action, eosinophil chemotaxis-inhibiting action (especially as a combination of an anti-histaminic action with an eosinophil chemotaxis-inhibiting action) and excellent duration of the action and safety and undergoes an extremely low migration into the brain, based on which it is considered to be useful as a prophylactic and therapeutic agent against atopic dermatitis, allergic rhinitis, bronchial asthma, allergic conjunctivitis, chronic urticaria and the like, thereby establishing the present invention.

That is, the present invention relates to:

[1] A compound represented by the formula:

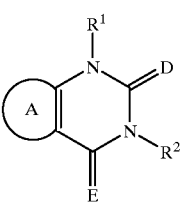

(I)

[wherein ring A represents a cyclic hydrocarbon optionally having substituents or a nitrogen-containing heterocycle optionally having substituents; D and E are the same or different and represent, independently, an oxygen atom or a sulfur atom; one of $R^1$ and $R^2$ represents a group represented by the formula:

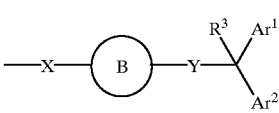

(II)

(wherein $Ar^1$ and $Ar^2$ represent, independently, an aromatic group optionally having substituents; $Ar^1$ and $Ar^2$ may form a condensed cyclic group optionally having substituents together with an adjacent carbon atom; ring B represents a nitrogen-containing heterocycle optionally having substituents; X and Y are the same or different and represent, independently, a bond, an oxygen atom, S(O)p (p represents an integer of 0 to 2), $NR^4$ ($R^4$ represents a hydrogen atom or a lower alkyl group) or a bivalent straight-chained lower hydrocarbon group, which may contain 1 to 3 hetero atoms, optionally having substituents; and $R^3$ represents a hydrogen atom, a hydroxy group optionally having substituents or an optionally esterified carboxyl group); and the other is a hydrogen atom, a cyano group or a hydrocarbon group optionally having substituents], or a salt thereof,

[2] A compound as defined in [1], wherein ring A represents
  (1) a 3- to 10-membered cyclic hydrocarbon or (2) a 3- to 13-membered nitrogen-containing heterocycle which contains one nitrogen atom and may further contain 1 to 3 hetero atoms selected from a nitrogen atom, an oxygen atom and a sulfur atom, which may have substituents selected from the group consisting of
  (i) a halogen atom,
  (ii) a $C_{1-3}$ alkylenedioxy group,
  (iii) a nitro group,
  (iv) a cyano group,
  (v) a $C_{1-6}$ alkyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (vi) $C_{2-6}$ alkenyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (vii) $C_{2-6}$ alkynyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino and, 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (viii) a $C_{3-6}$ cycloalkyl group which may be substituted by
    (a) a halogen atom,
    (b) $C_{1-3}$ alkylenedioxy,
    (c) nitro,
    (d) cyano,
    (e) optionally halogenated $C_{1-6}$ alkyl,
    (f) optionally halogenated $C_{2-6}$ alkenyl,
    (g) optionally halogenated $C_{2-6}$ alkynyl,
    (h) $C_{3-6}$ cycloalkyl,
    (i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
    (j) optionally halogenated $C_{1-6}$ alkylthio,
    (k) hydroxy,
    (l) amino,
    (m) mono-$C_{1-6}$ alkylamino,
    (n) di-$C_{1-6}$ alkylamino,
    (o) 5- to 6-membered cyclic amino,
    (p) $C_{1-6}$ alkyl-carbonyl,
    (q) carboxyl,
    (r) $C_{1-6}$ alkoxy-carbonyl,
    (s) carbamoyl,
    (t) mono-$C_{1-6}$ alkyl-carbamoyl,
    (u) a di-$C_{1-6}$ alkylcarbamoyl group,
    (V) $C_{6-10}$ aryl-carbamoyl,
    (w) sulfo,
    (x) $C_{1-6}$ alkylsulfonyl,
    (y) $C_{6-10}$ aryl,
    (z) $C_{6-10}$ aryloxy,
    (aa) $C_{7-6}$ aralkyloxy,
    (bb) oxo,
    (cc) thiocarbamoyl,
    (dd) mono-$C_{1-6}$ alkyl-thiocarbamoyl,
    (ee) di-$C_{1-6}$ alkyl-thiocarbamoyl,
    (ff) $C_{6-10}$ aryl-thiocarbamoyl,
    (gg) $C_{7-16}$ aralkyl,
    (hh) $C_{1-6}$ alkoxy-carbonyl-$C_{1-6}$ alkyl or
    (ii) a carboxyl-$C_{1-6}$ alkyl group,
  (ix) a $C_{1-6}$ alkoxy group optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (x) an optionally halogenated $C_{1-6}$ alkylthio group,
  (xi) a hydroxy group,
  (xii) an amino group,
  (xiii) a mono-$C_{1-6}$ alkylamino group,
  (xiv) a di-$C_{1-6}$ alkylamino group,
  (xv) a 5- to 6-membered cyclic amino group,
  (xvi) a $C_{1-6}$ alkyl-carbonyl group,
  (xvii) a carboxyl group,
  (xviii) a $C_{1-6}$ alkoxy-carbonyl group,
  (xix) a carbamoyl group,
  (xx) a mono-$C_{1-6}$ alkyl-carbamoyl group,
  (xxi) a di-$C_{1-6}$ alkylcarbamoyl group,
  (xxii) a $C_{6-10}$ aryl-carbamoyl group,
  (xxiii) a sulfo group,
  (xxiv) a $C_{1-6}$ alkylsulfonyl group,
  (xxv) a $C_{6-10}$ aryl group which may be substituted by (a) a halogen atom,
(b) $C_{1-3}$ alkylenedioxy,
(c) nitro,
(d) cyano,
(e) optionally halogenated $C_{1-6}$ alkyl,
(f) optionally halogenated $C_{2-6}$ alkenyl,
(g) optionally halogenated $C_{2-6}$ alkynyl,
(h) $C_{3-6}$ cycloalkyl,
(i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(j) optionally halogenated $C_{1-6}$ alkylthio,
(k) hydroxy,
(l) amino,
(m) mono-$C_{1-6}$ alkylamino,
(n) di-$C_{1-6}$ alkylamino,
(o) 5- to 6-membered cyclic amino,
(p) $C_{1-6}$ alkyl-carbonyl,
(q) carboxyl,
(r) $C_{1-6}$ alkoxy-carbonyl,
(s) carbamoyl,
(t) mono-$C_{1-6}$ alkyl-carbamoyl,
(u) di-$C_{1-6}$ alkylcarbamoyl,
(v) $C_{6-10}$ aryl-carbamoyl,
(w) sulfo,
(x) $C_{1-6}$ alkylsulfonyl,
(y) $C_{6-10}$ aryl,
(z) $C_{6-10}$ aryloxy,
(aa) $C_{7-16}$ aralkyloxy,
(bb) oxo,
(cc) thiocarbamoyl,
(dd) mono-$C_{1-6}$ alkyl-thiocarbamoyl,
(ee) di-$C_{1-6}$ alkyl-thiocarbamoyl,
(ff) $C_{6-10}$ aryl-thiocarbamoyl,
(gg) $C_{7-16}$ aralkyl,
(hh) $C_{1-6}$ alkoxy-carbonyl-$C_{1-6}$ alkyl or
(ii) a carboxyl-$C_{1-6}$ alkyl group,
(xxvi) a $C_{7-15}$ aralkyl group which may be substituted by
(a) a halogen atom,
(b) $C_{1-3}$ alkylenedioxy,
(c) nitro,
(d) cyano,
(e) optionally halogenated $C_{1-6}$ alkyl,
(f) optionally halogenated $C_{2-6}$ alkenyl,
(g) optionally halogenated $C_{2-6}$ alkynyl,
(h) $C_{3-6}$ cycloalkyl,
(i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(j) optionally halogenated $C_{1-6}$ alkylthio,
(k) hydroxy,
(l) amino,
(m) mono-$C_{1-6}$ alkylamino,
(n) di-$C_{1-6}$ alkylamino,
(o) 5- to 6-membered cyclic amino,
(p) $C_{1-6}$ alkyl-carbonyl,
(q) carboxyl,
(r) $C_{1-6}$ alkoxy-carbonyl,
(s) carbamoyl,
(t) mono-$C_{1-6}$ alkyl-carbamoyl,
(u) di-$C_{1-6}$ alkylcarbamoyl,
(v) $C_{6-10}$ aryl-carbamoyl,
(w) sulfo,
(X) $C_{1-6}$ alkylsulfonyl,
(y) $C_{6-10}$ aryl,
(z) $C_{6-10}$ aryloxy,
(aa) $C_{7-16}$ aralkyloxy,
(bb) oxo,
(cc) thiocarbamoyl,
(dd) mono-$C_{1-6}$ alkyl-thiocarbamoyl,
(ee) di-$C_{1-6}$ alkyl-thiocarbamoyl,
(ff) $C_{6-10}$ aryl-thiocarbamoyl,
(gg) $C_{7-16}$ aralkyl,
(hh) $C_{1-6}$ alkoxy-carbonyl-$C_{1-6}$ alkyl or
(ii) a carboxyl-$C_{1-6}$ alkyl group,
(xxvii) a $C_{6-10}$ aryloxy group which may be substituted by
(a) a halogen atom,
(b) $C_{1-3}$ alkylenedioxy,
(c) nitro,
(d) cyano,
(e) optionally halogenated $C_{1-6}$ alkyl,
(f) optionally halogenated $C_{2-6}$ alkenyl,
(g) optionally halogenated $C_{2-6}$ alkynyl,
(h) $C_{3-6}$ cycloalkyl,
(i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(j) optionally halogenated $C_{1-6}$ alkylthio,
(k) hydroxy,
(l) amino,
(m) mono-$C_{1-6}$ alkylamino,
(n) di-$C_{1-6}$ alkylamino,
(o) 5- to 6-membered cyclic amino,
(p) $C_{1-6}$ alkyl-carbonyl,
(q) carboxyl,
(r) $C_{1-6}$ alkoxy-carbonyl,
(s) carbamoyl,
(t) mono-$C_{1-6}$ alkyl-carbamoyl,
(u) di-$C_{1-6}$ alkylcarbamoyl,
(v) $C_{6-10}$ aryl-carbamoyl,
(w) sulfo,
(x) $C_{1-6}$ alkylsulfonyl,
(y) $C_{6-10}$ aryl,
(z) $C_{6-10}$ aryloxy,
(aa) $C_{7-16}$ aralkyloxy,
(bb) oxo,
(cc) thiocarbamoyl,
(dd) mono-$C_{1-6}$ alkyl-thiocarbamoyl,
(ee) di-$C_{1-6}$ alkyl-thiocarbamoyl,
(ff) $C_{6-10}$ aryl-thiocarbamoyl, (gg) $C_{7-16}$ aralkyl,
(hh) $C_{1-6}$ alkoxy-carbonyl-$C_{1-6}$ alkyl or
(ii) a carboxyl-$C_{1-6}$ alkyl group,
(xxviii) a $C_{7-16}$ aralkyloxy group which may be substituted by
(a) a halogen atom,
(b) $C_{1-3}$ alkylenedioxy,
(c) nitro,
(d) cyano,
(e) optionally halogenated $C_{1-6}$ alkyl,
(f) optionally halogenated $C_{2-6}$ alkenyl,
(g) optionally halogenated $C_{2-6}$ alkynyl,
(h) $C_{3-6}$ cycloalkyl,
(i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(j) optionally halogenated $C_{1-6}$ alkylthio,
(k) hydroxy,
(l) amino,
(m) mono-$C_{1-6}$ alkylamino,
(n) di-$C_{1-6}$ alkylamino,
(o) 5- to 6-membered cyclic amino,
(p) $C_{1-6}$ alkyl-carbonyl,
(q) carboxyl,
(r) $C_{1-6}$ alkoxy-carbonyl,
(s) carbamoyl,
(t) mono-$C_{1-6}$ alkyl-carbamoyl,
(u) di-$C_{1-6}$ alkylcarbamoyl,
(v) $C_{6-10}$ aryl-carbamoyl,
(w) sulfo,
(x) $C_{1-6}$ alkylsulfonyl,
(y) $C_{6-10}$ aryl,
(z) $C_{6-10}$ aryloxy,
(aa) $C_{7-16}$ aralkyloxy,
(bb) oxo,
(cc) thiocarbamoyl,
(dd) mono-$C_{1-6}$ alkyl-thiocarbamoyl,
(ee) di-$C_{1-6}$ alkyl-thiocarbamoyl,
(ff) $C_{6-10}$ aryl-thiocarbamoyl,
(gg) $C_{7-16}$ aralkyl,
(hh) $C_{1-6}$ alkoxy-carbonyl-$C_{1-6}$ alkyl or
(ii) a carboxyl-$C_{1-6}$ alkyl group,
(xxix) an oxo group,
(xxx) a thiocarbamoyl group,
(xxxi) a mono-$C_{1-6}$ alkyl-thiocarbamoyl group,
(xxxii) a di-$C_{1-6}$ alkyl-thiocarbamoyl group,
(xxxiii) a $C_{6-10}$ aryl-thiocarbamoyl group,
(xxxiv) $C_{6-10}$ aryl-carbonyloxy,
(xxxv) aminocarbonyl optionally having
(a) a halogen atom,
(b) optionally halogenated $C_{1-6}$ alkyl,
(c) optionally halogenated $C_{2-6}$ alkenyl,
(d) optionally halogenated $C_{2-6}$ alkynyl,
(e) $C_{3-6}$ cycloalkyl,
(f) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(g) optionally halogenated $C_{1-6}$ alkylthio,
(h) hydroxy,
(i) amino,
(j) mono-$C_{1-6}$ alkylamino,
(k) di-$C_{1-6}$ alkylamino,
(l) 5- to 6-membered cyclic amino,
(m) $C_{1-6}$ alkyl-carbonyl,
(n) carboxyl,
(o) $C_{1-6}$ alkoxy-carbonyl,
(p) carbamoyl,
(q) mono-$C_{1-6}$ alkyl-carbamoyl,
(r) di-$C_{1-6}$ alkylcarbamoyl,
(s) $C_{6-10}$ aryl-carbamoyl,
(t) sulfo,
(u) $C_{1-6}$ alkylsulfonyl,
(v) $C_{6-10}$ aryl,
(w) $C_{6-10}$ aryloxy,
(x) $C_{7-16}$ aralkyloxy,
(y) thiocarbamoyl,
(z) mono-$C_{1-6}$ alkyl-thiocarbamoyl,
(aa) di-$C_{1-6}$ alkyl-thiocarbamoyl,
(bb) $C_{6-10}$ aryl-thiocarbamoyl,
(cc) $C_{7-16}$ aralkyl,
(dd) $C_{1-6}$ alkoxy-carbonyl-$C_{1-6}$ alkyl or
(ee) a carboxyl-$C_{1-6}$ alkyl group,
(xxxvi) a 5- or 6-membered heterocyclic group which contains one or two kinds of and 1 to 4 hetero atoms selected from a nitrogen atom, an oxygen atom and a sulfur atom in addition to a carbon atom,
(xxxvii) a $C_{1-6}$ alkoxy-carbonyl-$C_{1-6}$ alkoxy-carbonyl group,
(xxxviii) a $C_{1-6}$ alkykoxy-carbonyl-$C_{1-6}$ alkyl-carbamoyl group,
(xxxix) a hydroxy-$C_{1-6}$ alkyl-carbamoyl group,
(xxxx) a $C_{1-6}$ alkoxy-carbonyl-carbamoyl group,
(xxxxi) $C_{6-14}$ arylsulfonamide,
(xxxxii) $C_{1-6}$ alkylsulfonamide,
(xxxxiii) a carboxy-$C_{1-6}$ alkyl-carbonyl-amino group,
(xxxxiv) a $C_{1-6}$ alkoxy-carbonyl-$C_{1-6}$ alkyl-carbonyl-amino group,
(xxxxv) a $C_{1-6}$ alkyl-carbonyloxy-$C_{1-6}$ alkyl-carbonyl-amino group,
(xxxxvi) a hydroxy-$C_{1-6}$ alkyl-carbonyl-amino group, and
(xxxxvii) a $C_{6-14}$ aryl-$C_{2-6}$ alkenyl-carbonylamido group which may be substituted by hydroxy or/and $C_{1-6}$ alkoxy;

D and E are the same or different and represent, independently, an oxygen atom or a sulfur atom;

one of $R^1$ and $R^2$ represents a group represented by the formula:

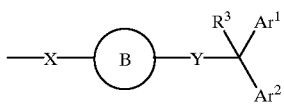

wherein R³ represents
(1) a hydrogen atom,
(2) a hydroxy group which may have a $C_{1-16}$ chained or cyclic hydrocarbon group optionally having substituents selected from the group consisting of
  (i) a halogen atom,
  (ii) a $C_{1-3}$ alkylenedioxy group,
  (iii) a nitro group,
  (iv) a cyano group,
  (v) a $C_{1-6}$ alkyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (vi) $C_{2-6}$ alkenyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (vii) $C_{2-6}$ alkynyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (viii) a $C_{3-6}$ cycloalkyl group,
  (ix) a $C_{1-6}$ alkoxy group optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (x) an optionally halogenated $C_{1-6}$ alkylthio group,
  (xi) a hydroxy group,
  (xii) an amino group,
  (xiii) a mono-$C_{1-6}$ alkylamino group,
  (xiv) a di-$C_{1-6}$ alkylamino group,
  (xv) a 5- to 6-membered cyclic amino group,
  (xvi) a $C_{1-6}$ alkyl-carbonyl group,
  (xvii) a carboxyl group,
  (xviii) a $C_{1-6}$ alkoxy-carbonyl group,
  (xix) a carbamoyl group,
  (xx) a mono-$C_{1-6}$ alkyl-carbamoyl group,
  (xxi) a di-$C_{1-6}$ alkylcarbamoyl group,
  (xxii) $C_{6-10}$ aryl-carbamoyl,
  (xxiii) a sulfo group,
  (xxiv) a $C_{1-6}$ alkylsulfonyl group,
  (xxv) a $C_{6-10}$ aryl group,
  (xxvi) a $C_{6-10}$ aryloxy group,
  (xxvii) a $C_{7-16}$ aralkyloxy group,
  (xxviii) an oxo group,
  (xxix) a thiocarbamoyl group,
  (xxx) a mono-$C_{1-6}$ alkyl-thiocarbamoyl group,
  (xxxi) a di-$C_{1-6}$ alkyl-thiocarbamoyl group and
  (xxxii) $C_{6-10}$ aryl-thiocarbamoyl and
  (xxxiii) a $C_{7-16}$ aralkyl group,
(3) a carboxyl group, or
(4) a carboxyl group which may have a $C_{1-16}$ chained or cyclic hydrocarbon group optionally having substituents selected from the group consisting of
  (i) a halogen atom,
  (ii) a $C_{1-3}$ alkylenedioxy group,
  (iii) a nitro group,
  (iv) a cyano group,
  (v) a $C_{1-6}$ alkyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (vi) $C_{2-6}$ alkenyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (vii) $C_{2-6}$ alkynyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (viii) a $C_{3-6}$ cycloalkyl group,
  (ix) a $C_{1-6}$ alkoxy group optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (x) an optionally halogenated $C_{1-6}$ alkylthio group, (xi) a hydroxy group, (xii) an amino group, (xiii) a mono-$C_{1-6}$ alkylamino group, (xiv) a di-$C_{1-6}$ alkylamino group, (xv) a 5- to 6-membered cyclic amino group, (xvi) a $C_{1-6}$ alkyl-carbonyl group, (xvii) a carboxyl group, (xviii) a $C_{1-6}$ alkoxy-carbonyl group, (xix) a carbamoyl group, (xx) a mono-$C_{1-6}$ alkyl-carbamoyl group, (xxi) a di-$C_{1-6}$ alkylcarbamoyl group, (xxii) $C_{6-10}$ aryl-carbamoyl, (xxiii) a sulfo group, (xxiv) a $C_{1-6}$ alkylsulfonyl group, (xxv) a $C_{6-10}$ aryl group, (xxvi) a $C_{6-10}$ aryloxy group, (xxvii) a $C_{7-16}$ aralkyloxy group, (xxviii) an oxo group, (xxix) a thiocarbamoyl group, (xxx) a mono-$C_{1-6}$ alkyl-thiocarbamoyl group, (xxxi) a di-$C_{1-6}$ alkyl-thiocarbamoyl group and (xxxii) $C_{6-10}$ aryl-thiocarbamoyl and (xxxiii) a $C_{7-16}$ aralkyl group, instead of a hydrogen atom of the carboxyl group;

$Ar^1$ and $Ar^2$ represent, independently, (1) a $C_{6-14}$ aryl group, (2) a 5- to 8-membered aromatic heterocyclic group which contains one or two kinds of and 1 to 4 hetero atoms selected from a nitrogen atom, a sulfur atom and an oxygen atom in addition to a carbon atom or (3) a condensed heterocyclic group of the 5- to 8-membered aromatic heterocyclic group and a $C_{6\ 14}$ aromatic cyclic hydrocarbon, which may have substituents selected from the group consisting of (i) a halogen atom, (ii) a $C_{1-3}$ alkylenedioxy group, (iii) a nitro group, (iv) a cyano group, (v) a $C_{1-6}$ alkyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (vi) $C_{2-6}$ alkenyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (vii) $C_{2-6}$ alkynyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (viii) a $C_{3-6}$ cycloalkyl group, (ix) a $C_{1-6}$ alkoxy group optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (x) an optionally halogenated $C_{1-6}$ alkylthio group, (xi) a hydroxy group, (xii) an amino group, (xiii) a mono-$C_{1-6}$ alkylamino group, (xiv) a di-$C_{1-6}$ alkylamino group, (xv) a 5- to 6-membered cyclic amino group, (xvi) a $C_{1-6}$ alkyl-carbonyl group, (xvii) a carboxyl group, (xviii) a $C_{1-6}$ alkoxy-carbonyl group, (xix) a carbamoyl group, (xx) a mono-$C_{1-6}$ alkyl-carbamoyl group, (xxi) a di-$C_{1-6}$ alkylcarbamoyl group, (xxii) $C_{6-10}$ aryl-carbamoyl, (xxiii) a sulfo group, (xxiv) a $C_{1-6}$ alkylsulfonyl group, (xxv) a $C_{6-10}$ aryl group, (xxvi) a $C_{6-10}$ aryloxy group, (xxvii) a $C_{7-6}$ aralkyloxy group, (xxviii) an oxo group, (xxix) a thiocarbamoyl group, (xxx) a mono-$C_{1-6}$ alkyl-thiocarbamoyl group, (xxxi) a di-$C_{1-6}$ alkyl-thiocarbamoyl group and (xxxii) $C_{6-10}$ aryl-thiocarbamoyl and (xxxiii) a $C_{7-16}$ aralkyl group;

$Ar^1$ and $Ar^2$ may form a condensed cyclic group represented by the formula:

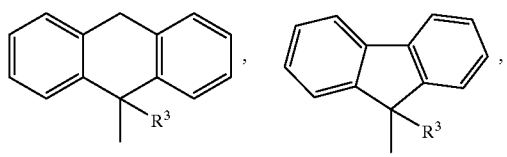

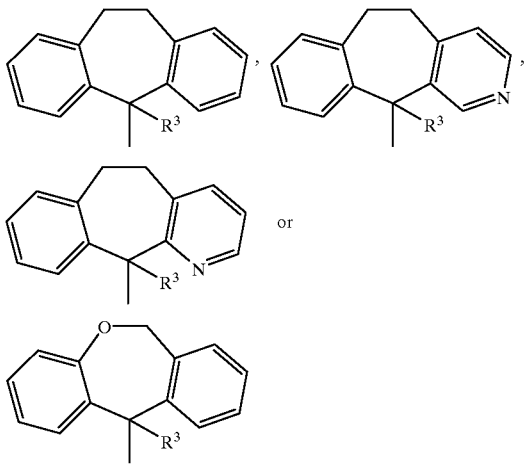

[wherein R³ represents the same meaning as defined above], optionally having the same substituents as the substituents for the aromatic group represented by the above-mentioned Ar¹ and Ar², together with an adjacent carbon atom; ring B represents a 3- to 13-membered nitrogen-containing heterocycle which contains one nitrogen atom and may further have 1 to 3 hetero atoms selected from a nitrogen atom, an oxygen atom and a sulfur atom, which may have substituents selected from the group consisting of (i) a halogen atom,
(ii) a $C_{1-3}$ alkylenedioxy group,
(iii) a nitro group,
(iv) a cyano group,
(v) a $C_{1-6}$ alkyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(vi) $C_{2-6}$ alkenyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(vii) $C_{2-6}$ alkynyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(viii) a $C_{3-6}$ cycloalkyl group,
(ix) a $C_{1-6}$ alkoxy group optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(x) an optionally halogenated $C_{1-6}$ alkylthio group,
(xi) a hydroxy group,
(xii) an amino group,
(xiii) a mono-$C_{1-6}$ alkylamino group,
(xiv) a di-$C_{1-6}$ alkylamino group,
(xv) a 5- to 6-membered cyclic amino group,
(xvi) a $C_{1-6}$ alkyl-carbonyl group,
(xvii) a carboxyl group,
(xviii) a $C_{1-6}$ alkoxy-carbonyl group,
(xix) a carbamoyl group,
(xx) a mono-$C_{1-6}$ alkyl-carbamoyl group,
(xxi) a di-$C_{1-6}$ alkylcarbamoyl group,
(xxii) $C_{6-10}$ aryl-carbamoyl,
(xxiii) a sulfo group,
(xxiv) a $C_{1-6}$ alkylsulfonyl group,
(xxv) a $C_{6-10}$ aryl group,
(xxvi) a $C_{6-10}$ aryloxy group,
(xxvii) a $C_{7-16}$ aralkyloxy group,
(xxviii) an oxo group,
(xxix) a thiocarbamoyl group,
(xxx) a mono-$C_{1-6}$ alkyl-thiocarbamoyl group,
(xxxi) a di-$C_{1-6}$ alkyl-thiocarbamoyl group and
(xxxii) $C_{6-10}$ aryl-thiocarbamoyl and
(xxxiii) a $C_{7-16}$ aralkyl group;

X and Y is the same or different and represent, (1) a bond, (2) an oxygen atom, (3) S(O)p (p represents an integer of 0 to 2), (4) NR⁴ (R⁴ represents a hydrogen atom or a $C_{1-6}$ alkyl group), or (5) a $C_{1-6}$ alkylene group, $C_{2-6}$ alkenylene group or $C_{2-6}$ alkynylene group which may contain 1 to 3 hetero atoms selected from an oxygen atom, a sulfur atom and a nitrogen atom in the hydrocarbon chain, which may have substituents selected from the group consisting of (i) a halogen atom,
(ii) a $C_{1-3}$ alkylenedioxy group,
(iii) a nitro group,
(iv) a cyano group,
(v) a $C_{1-6}$ alkyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(vi) $C_{2-6}$ alkenyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (vii) $C_{2-6}$ alkynyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (viii) a $C_{3-6}$ cycloalkyl group, (ix) a $C_{1-6}$ alkoxy group optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (x) an optionally halogenated $C_{1-6}$ alkylthio group, (xi) a hydroxy group, (xii) an amino group, (xiii) a mono-$C_{1-6}$ alkylamino group, (xiv) a di-$C_{1-6}$ alkylamino group, (xv) a 5- to 6-membered cyclic amino group, (xvi) a $C_{1-6}$ alkyl-carbonyl group, (xvii) a carboxyl group, (xviii) a $C_{1-6}$ alkoxy-carbonyl group, (xix) a carbamoyl group, (xx) a mono-$C_{1-6}$ alkyl-carbamoyl group, (xxi) a di-$C_{1-6}$ alkylcarbamoyl group, (xxii) $C_{6-10}$ aryl-carbamoyl, (xxiii) a sulfo group, (xxiv) a $C_{1-6}$ alkylsulfonyl group, (xxv) a $C_{6-10}$ aryl group, (xxvi) a $C_{6-10}$ aryloxy group, (xxvii) a $C_{7-16}$ aralkyloxy group, (xxviii) an oxo group, (xxix) a thiocarbamoyl group, (xxx) a mono-$C_{1-6}$ alkyl-thiocarbamoyl group, (xxxi) a di-$C_{1-6}$ alkyl-thiocarbamoyl group, and (xxxii) $C_{6-10}$ aryl-thiocarbamoyl and (xxxiii) a $C_{7-16}$ aralkyl group; and the other is (1) a hydrogen atom, (2) a cyano group, or (3) a $C_{-1-16}$ chained or cyclic hydrocarbon group which may have substituents selected from the group consisting of (i) a halogen atom, (ii) a $C_{1-3}$ alkylenedioxy group, (iii) a nitro group, (iv) a cyano group, (v) a $C_{1-6}$ alkyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5 to 10 membered heterocyclic group which contains 1 to 3 hetero atoms selected from a nitrogen atom, an oxygen atom and a sulfur atom in addition to a carbon atom or a benzo-condensed cyclic group thereof, (vi) $C_{2-6}$ alkenyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (vii) $C_{2-6}$ alkynyl group optionally having substituents selected from the group consisting of a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (viii) a $C_{3-6}$ cycloalkyl group which may be substituted by (a) a halogen atom, (b) $C_{1-3}$ alkylenedioxy, (c) nitro, (d) cyano, (e) optionally halogenated $C_{1-6}$ alkyl, (f) optionally halogenated $C_{2-6}$ alkenyl, (g) optionally halogenated $C_{2-6}$ alkynyl, (h) $C_{3-6}$ cycloalkyl, (i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof, (j) optionally halogenated $C_{1-6}$ alkylthio, (k) hydroxy, (l) amino, (m) mono-$C_{1-6}$ alkylamino, (n) di-$C_{1-6}$ alkylamino, (o) 5- to 6-membered cyclic amino, (p) $C_{1-6}$ alkyl-carbonyl, (q) carboxyl, (r) $C_{1-6}$ alkoxy-carbonyl, (s) carbamoyl, (t) mono-$C_{1-6}$ alkyl-carbamoyl, (u) a di-$C_{1-6}$ alkylcarbamoyl group, (v) $C_{6-10}$ aryl-carbamoyl, (w) sulfo,
(X) $C_{1-6}$ alkylsulfonyl,
(y) $C_{6-10}$ aryl,
(z) $C_{6-10}$ aryloxy,
(aa) $C_{7-16}$ aralkyloxy,
(bb) oxo,
(cc) thiocarbamoyl,
(dd) mono-$C_{1-6}$ alkyl-thiocarbamoyl,
(ee) di-$C_{1-6}$ alkyl-thiocarbamoyl,
(ff) $C_{6-10}$ aryl-thiocarbamoyl.
(gg) $C_{7-16}$ aralkyl,
(hh) $C_{1-6}$ alkoxy-carbonyl-$C_{1-6}$ alkyl or
(ii) a carboxyl-$C_{1-6}$ alkyl group,
(ix) a $C_{1-6}$ alkoxy group optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
(x) an optionally halogenated $C_{1-6}$ alkylthio group,
(xi) a hydroxy group,
(xii) an amino group,
(xiii) a mono-$C_{1-6}$ alkylamino group,
(xiv) a di-$C_{1-6}$ alkylamino group,
(xv) a 5- to 6-membered cyclic amino group,
(xvi) a $C_{1-6}$ alkyl-carbonyl group,
(xvii) a carboxyl group,
(xviii) a $C_{1-6}$ alkoxy-carbonyl group,
(xix) a carbamoyl group,
(xx) a mono-$C_{1-6}$ alkyl-carbamoyl group,
(xxi) a di-$C_{1-6}$ alkylcarbamoyl group,
(xxii) a $C_{6-10}$ aryl-carbamoyl group,
(xxiii) a sulfo group,
(xxiv) a $C_{1-6}$ alkylsulfonyl group,
(xxv) a $C_{6-10}$ aryl group which may be substituted by
   (a) a halogen atom,
   (b) $C_{1-3}$ alkylenedioxy,
   (c) nitro,
   (d) cyano,
   (e) optionally halogenated $C_{1-6}$ alkyl,
   (f) optionally halogenated $C_{2-6}$ alkenyl,
   (g) optionally halogenated $C_{2-6}$ alkynyl,
   (h) $C_{3-6}$ cycloalkyl,
   (i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
   (j) optionally halogenated $C_{1-6}$ alkylthio,
   (k) hydroxy,
   (l) amino,
   (m) mono-$C_{1-6}$ alkylamino,
   (n) di-$C_{1-6}$ alkylamino,
   (o) 5- to 6-membered cyclic amino,
   (p) $C_{1-6}$ alkyl-carbonyl,
   (q) carboxyl,
   (r) $C_{1-6}$ alkoxy-carbonyl,
   (s) carbamoyl,
   (t) mono-$C_{1-6}$ alkyl-carbamoyl,
   (u) di-$C_{1-6}$ alkylcarbamoyl,
   (v) $C_{6-10}$ aryl-carbamoyl,
   (w) sulfo,
   (x) $C_{1-6}$ alkylsulfonyl,
   (y) $C_{6-10}$ aryl,
   (z) $C_{6-10}$ aryloxy,
   (aa) $C_{7-16}$ aralkyloxy,
   (bb) oxo,
   (cc) thiocarbamoyl,
   (dd) mono-$C_{1-6}$ alkyl-thiocarbamoyl,
   (ee) di-$C_{1-6}$ alkyl-thiocarbamoyl,
   (ff) $C_{6-10}$ aryl-thiocarbamoyl,
   (gg) $C_{7-16}$ aralkyl,
   (hh) $C_{1-6}$ alkoxy-carbonyl-$C_{1-6}$ alkyl or
   (ii) carboxyl-$C_{1-6}$ alkyl,
(xxvi) a $C_{7-15}$ aralkyl group which may be substituted by
   (a) a halogen atom,
   (b) $C_{1-3}$ alkylenedioxy,
   (c) nitro,
   (d) cyano,
   (e) optionally halogenated $C_{1-6}$ alkyl,
   (f) optionally halogenated $C_{2-6}$ alkenyl,
   (g) optionally halogenated $C_{2-6}$ alkynyl,
   (h) $C_{3-6}$ cycloalkyl,
   (i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
   (j) optionally halogenated $C_{1-6}$ alkylthio,
   (k) hydroxy,
   (l) amino,
   (m) mono-$C_{1-6}$ alkylamino,
   (n) di-$C_{1-6}$ alkylamino,
   (o) 5- to 6-membered cyclic amino,
   (p) $C_{1-6}$ alkyl-carbonyl,
   (q) carboxyl,
   (r) $C_{1-6}$ alkoxy-carbonyl,
   (s) carbamoyl,
   (t) mono-$C_{1-6}$ alkyl-carbamoyl,
   (u) di-$C_{1-6}$ alkylcarbamoyl,
   (v) $C_{6-10}$ aryl-carbamoyl,
   (w) sulfo,
   (x) $C_{1-6}$ alkylsulfonyl,
   (y) $C_{6-10}$ aryl,
   (z) $C_{6-10}$ aryloxy,
   (aa) $C_{7-16}$ aralkyloxy,
   (bb) oxo,
   (cc) thiocarbamoyl,
   (dd) mono-$C_{1-6}$ alkyl-thiocarbamoyl,
   (ee) di-$C_{1-6}$ alkyl-thiocarbamoyl,
   (ff) $C_{6-10}$ aryl-thiocarbamoyl,
   (gg) $C_{7-16}$ aralkyl,
   (hh) $C_{1-6}$ alkoxy-carbonyl-$C_{1-6}$ alkyl or
   (ii) carboxyl-$C_{1-6}$ alkyl, (xxvii) a $C_{6-10}$ aryloxy group which may be substituted by
  (a) a halogen atom,
  (b) $C_{1-3}$ alkylenedioxy,
  (c) nitro,
  (d) cyano,
  (e) optionally halogenated $C_{1-6}$ alkyl,
  (f) optionally halogenated $C_{2-6}$ alkenyl,
  (g) optionally halogenated $C_{2-6}$ alkynyl,
  (h) $C_{3-6}$ cycloalkyl,
  (i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (j) optionally halogenated $C_{1-6}$ alkylthio,
  (k) hydroxy,
  (l) amino,
  (m) mono-$C_{1-6}$ alkylamino,
  (n) di-$C_{1-6}$ alkylamino,
  (o) 5- to 6-membered cyclic amino,
  (p) $C_{1-6}$ alkyl-carbonyl,
  (q) carboxyl,
  (r) $C_{1-6}$ alkoxy-carbonyl,
  (s) carbamoyl,
  (t) mono-$C_{1-6}$ alkyl-carbamoyl,
  (u) di-$C_{1-6}$ alkylcarbamoyl,
  (v) $C_{6-10}$ aryl-carbamoyl,
  (w) sulfo,
  (x) $C_{1-6}$ alkylsulfonyl,
  (y) $C_{6-10}$ aryl,
  (z) $C_{6-10}$ aryloxy,
  (aa) $C_{7-16}$ aralkyloxy,
  (bb) oxo,
  (cc) thiocarbamoyl,
  (dd) mono-$C_{1-6}$ alkyl-thiocarbamoyl,
  (ee) di-$C_{1-6}$ alkyl-thiocarbamoyl,
  (ff) $C_{6-10}$ aryl-thiocarbamoyl,
  (gg) $C_{7-16}$ aralkyl,
  (hh) $C_{1-6}$ alkoxy-carbonyl-$C_{1-6}$ alkyl, or
  (ii) carboxyl-$C_{1-6}$ alkyl,
(xxviii) a $C_{7-16}$ aralkyloxy group which may be substituted by
  (a) a halogen atom,
  (b) $C_{1-3}$ alkylenedioxy,
  (c) nitro,
  (d) cyano,
  (e) optionally halogenated $C_{1-6}$ alkyl,
  (f) optionally halogenated $C_{2-6}$ alkenyl,
  (g) optionally halogenated $C_{2-6}$ alkynyl,
  (h) $C_{3-6}$ cycloalkyl,
  (i) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono-or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (j) optionally halogenated $C_{1-6}$ alkylthio,
  (k) hydroxy,
  (l) amino,
  (m) mono-$C_{1-6}$ alkylamino,
  (n) di-$C_{1-6}$ alkylamino,
  (o) 5- to 6-membered cyclic amino,
  (p) $C_{1-6}$ alkyl-carbonyl,
  (q) carboxyl,
  (r) $C_{1-6}$ alkoxy-carbonyl,
  (s) carbamoyl,
  (t) mono-$C_{1-6}$ alkyl-carbamoyl,
  (u) di-$C_{1-6}$ alkylcarbamoyl,
  (v) $C_{6-10}$ aryl-carbamoyl,
  (w) sulfo,
  (x) $C_{1-6}$ alkylsulfonyl,
  (y) $C_{6-10}$ aryl,
  (z) $C_{6-10}$ aryloxy,
  (aa) $C_{7-16}$ aralkyloxy,
  (bb) oxo,
  (cc) thiocarbamoyl,
  (dd) mono-$C_{1-6}$ alkyl-thiocarbamoyl,
  (ee) di-$C_{1-6}$ alkyl-thiocarbamoyl,
  (ff) $C_{6-10}$ aryl-thiocarbamoyl,
  (gg) $C_{7-16}$ aralkyl,
  (hh) $C_{1-6}$ alkoxy-carbonyl-$C_{1-6}$ alkyl or
  (ii) carboxyl-$C_{1-6}$ alkyl,
(xxix) an oxo group,
(xxx) a thiocarbamoyl group,
(xxxi) a mono-$C_{1-6}$ alkyl-thiocarbamoyl group,
(xxxii) a di-$C_{1-6}$ alkyl-thiocarbamoyl group,
(xxxiii) a $C_{6-10}$ aryl-thiocarbamoyl group,
(xxxiv) $C_{6-10}$ aryl-carbonyloxy,
(xxxv) aminocarbonyl optionally having
  (a) a halogen atom,
  (b) optionally halogenated $C_{1-6}$ alkyl,
  (c) optionally halogenated $C_{2-6}$ alkenyl,
  (d) optionally halogenated $C_{2-6}$ alkynyl,
  (e) $C_{3-6}$ cycloalkyl,
  (f) $C_{1-6}$ alkoxy optionally having substituents selected from a halogen atom, hydroxy, carboxyl, $C_{1-6}$ alkoxy, $C_{1-6}$ alkoxy-carbonyl, $C_{1-6}$ alkyl-carbonyl, amino, mono- or di-$C_{1-6}$ alkylamino, mono- or di-$C_{1-6}$ alkyl-carbonylamino, sulfonamido, $C_{1-6}$ alkyl-sulfonamido optionally having mono- or di-$C_{1-6}$ alkylamino, and 5- to 10-membered heterocyclic group which contains 1 to 3 hetero atoms selected from a nitrogen atom, an oxygen atom and a sulfur atom in addition to a carbon atom or a benzo-condensed cyclic group thereof,
  (g) optionally halogenated $C_{1-6}$ alkylthio,
  (h) hydroxy,
  (i) amino,
  (j) mono-$C_{1-6}$ alkylamino,
  (k) di-$C_{1-6}$ alkylamino,
  (l) 5- to 6-membered cyclic amino,
  (m) $C_{1-6}$ alkyl-carbonyl,
  (n) carboxyl,
  (o) $C_{1-6}$ alkoxy-carbonyl,
  (p) carbamoyl,
  (q) mono-$C_{1-6}$ alkyl-carbamoyl,
  (r) a di-$C_{1-6}$ alkylcarbamoyl,
  (s) $C_{6-10}$ aryl-carbamoyl,
  (t) sulfo,
  (u) $C_{1-6}$ alkylsulfonyl,
  (v) $C_{6-10}$ aryl,
  (w) $C_{6-10}$ aryloxy, (x) C$_{7-16}$ aralkyloxy,
(y) thiocarbamoyl,
(z) mono-C$_{1-6}$ alkyl-thiocarbamoyl,
(aa) di-C$_{1-6}$ alkyl-thiocarbamoyl,
(bb) C$_{6-10}$ aryl-thiocarbamoyl,
(cc) C$_{7-16}$ aralkyl,
(dd) C$_{1-6}$ alkoxy-carbonyl-C$_{1-6}$ alkyl or
(ee) a carboxyl-C$_{1-6}$ alkyl group,
(xxxvi) a 5- or 6-membered heterocyclic group which contains one or two kinds of and 1 to 4 hetero atoms selected from a nitrogen atom, an oxygen atom and a sulfur atom in addition to a carbon atom,
(xxxvii) a C$_{1-6}$ alkoxy-carbonyl-C$_{1-6}$ alkoxy-carbonyl group,
(xxxviii) a C$_{1-6}$ alkoxy-carbonyl-C$_{1-6}$ alkyl-carbamoyl group,
(xxxix) a hydroxy-C$_{1-6}$ alkyl-carbamoyl group,
(xxxx) a C$_{1-6}$ alkoxy-carbonyl-carbamoyl group,
(xxxxi) C$_{6-14}$ arylsulfonamide,
(xxxxii) C$_{1-6}$ alkylsulfonamide,
(xxxxiii) carboxy-C$_{1-6}$ alkyl-carbonyl-amino group,
(xxxxiv) a C$_{1-6}$ alkoxy-carbonyl-C$_{1-6}$ alkyl-carbonyl-amino group,
(xxxxv) a C$_{1-6}$ alkyl-carbonyloxy-C$_{1-6}$ alkyl-carbonyl-amino group,
(xxxxvi) a hydroxy-C$_{1-6}$ alkyl-carbonyl-amino group, and
(xxxxvii) a C$_{6-14}$ aryl-C$_{2-6}$ alkenyl-carbonylamido group which may be substituted by hydroxy or/and C$_{1-6}$ alkoxy,

[3] A compound as defined in [1] wherein ring A is a benzene ring optionally having substituents, a pyridine ring optionally having substituents or a pyrazine ring optionally having substituents,

[4] A compound as defined in [1] wherein Ar$^1$ and Ar$^2$ are independently a phenyl group optionally having substituents,

[5] A compound as defined in [1] wherein X is a bond or C$_{1-6}$ alkylene group,

[6] A compound as defined in [1] wherein Y is a bond, an oxygen atom or a C$_{1-6}$ alkylene group, which may contain an oxygen atom in the alkylene chain, optionally substituted by a hydroxy group,

[7] A compound as defined in [1] wherein ring B is a ring represented by the formula:

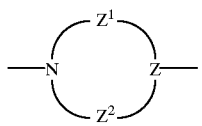

[wherein Z represents a nitrogen atom or a methyne group, Z$^1$ and Z$^2$ are the same or different and represent, independently, a straight chained C$_{1-6}$ alkylene group optionally substituted by a hydroxy group, an oxo group or a C$_{1-6}$ alkyl group],

[8] A compound as defined in [1] wherein ring B is

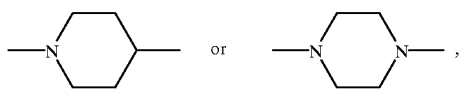

[9] A compound as defined in [1] wherein R$^3$ is a hydrogen atom or a hydroxy group,

[10] A compound as defined in [1] wherein one of R$^1$ and R$^2$ is a group represented by the formula:

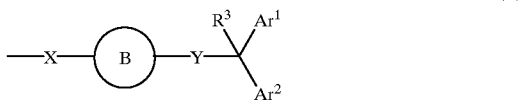

(wherein each symbol represents the same meaning as defined in [1], and the other is a hydrogen atom, a cyano group, an optionally substituted C$_{1-6}$ alkyl group or an optionally substituted C$_{3-6}$ cycloalkyl group,

[11] A compound as defined in [1] wherein both D and E are an oxygen atom,

[12] A compound as defined in [1] wherein ring A is a C$_{6-14}$ aryl ring optionally having substituents selected from the group consisting of (i) a halogen atom, (ii) a nitro group, (iii) a C$_{1-6}$ alkyl group optionally having carboxyl or C$_{1-6}$ alkoxy-carbonyl, (iv) a C$_{1-6}$ alkoxy group, (v) a hydroxy group, (vi) an amino group, (vii) a mono- or di-C$_{1-6}$ alkylamino group, (viii) a carboxyl group, (ix) a C$_{1-6}$ alkoxy-carbonyl group, (x) a 5- to 6-membered heterocyclic group which contains one or two kinds of and 1 to 4 hetero atoms selected from a nitrogen atom, an oxygen atom and a sulfur atom in addition to a carbon atom, (xi) C$_{1-6}$ alkylsulfonamide, (xii) a carboxy-C$_{1-6}$ alkyl-carbonyl-amino group, (xiii) a C$_{1-6}$ alkoxy-carbonyl-C$_{1-6}$ alkyl-carbonyl-amino group, (xiv) a C$_{1-6}$ alkyl-carbonyl-oxy-C$_{1-6}$ alkyl-carbonyl-amino group and (xv) a C$_{6-14}$ aryl-C$_{2-6}$ alkenyl-carbonylamido group which may be substituted by hydroxy or/and C$_{1-6}$ alkoxy; D and E are an oxygen atom; one of R$^1$ and R$^2$ is a group represented by the formula:

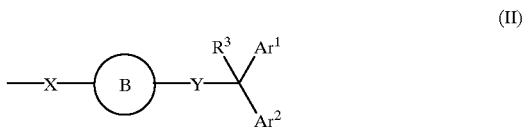

(wherein Ar$^1$ and Ar$^2$ are a phenyl group, ring B is

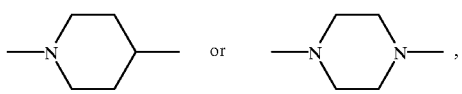

X is a C$_{1-6}$ alkylene group, Y is a bond or an oxygen atom, R$^3$ is a hydrogen atom or a hydroxy group); the other is (1) a hydrogen atom, (2) a cyano group, (3) a C$_{1-16}$ alkyl group optionally having substituents selected from the group consisting of (i) a halogen atom, (ii) a carboxyl group, (iii) a C$_{1-6}$ alkoxy-carbonyl group, (iv) a 5- to 6-membered nitrogen-containing heterocyclic group, (v) a carbamoyl group optionally having substituents selected from C$_{7-15}$ aralkyl, carboxyl-C$_{1-6}$ alkyl and C$_{1-6}$ alkoxycarbonyl-C$_{1-6}$ alkyl, (vi) C$_{6-14}$ aryl-carbonyloxy group, (vii) a sulfamoyl group, (viii) a mono- or di-C$_{1-6}$ alkyl-aminomethyleneaminosulfonyl group, (ix) a C$_{1-6}$ alkoxy group optionally having carboxyl or carbamoyl and (x) cyano, (4) a C$_{3-7}$ cycloalkyl group optionally having carboxyl or C$_{1-6}$ alkoxycarbonyl, (5) a C$_{6-14}$ aryl group, or (6) a C$_{7-15}$ aralkyl group optionally having substituents selected from C$_{1-6}$ alkoxy, carboxyl or C$_{1-6}$ alkoxy-carbonyl,

[13] A compound as defined in [1] wherein ring A is a benzene ring optionally having (i) a halogen atom or (ii) $C_{1-6}$ alkoxy-carbonyl;

D and E are an oxygen atom;

one of $R^1$ and $R^2$ is a group represented by the formula:

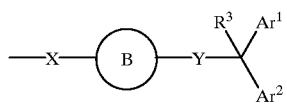

(II)

(wherein $Ar^1$ and $Ar^2$ are a phenyl group, ring B is

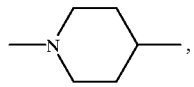

X is a $C_{1-6}$ alkylene group, Y is an oxygen atom, $R^3$ is a hydrogen atom or a hydroxy group); the other is (1) a hydrogen atom, (2) a cyano group, (3) a $C_{1-6}$ alkyl group optionally having substituents selected from the group consisting of (i) a halogen atom, (ii) a $C_{1-6}$ alkoxy-carbonyl group, (iii) a carbamoyl group, (iv) cyano, (4) a $C_{3-7}$ cycloalkyl group optionally having $C_{1-6}$ alkoxycarbonyl,

[14] A compound as defined in [1] wherein ring A is a benzene ring optionally having a halogen atom;

D and E are an oxygen atom;

one of $R^1$ and $R^2$ is a group represented by the formula:

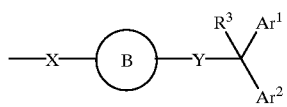

(II)

(wherein $Ar^1$ and $Ar^2$ are a phenyl group, ring B is

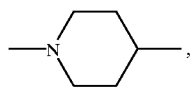

X is a $C_{1-6}$ alkylene group, Y is an oxygen atom, $R^3$ is a hydrogen atom); the other is a $C_{1-6}$ alkyl group optionally having carboxyl,

[15] 2,4-dioxo-1-[4-(4-diphenylmethoxypiperidino)butyl]-1,2,3,4-tetrahydroquinazoline-3-valeric acid or a salt thereof,

[16] 2-[2,4-dioxo-1-[4-(4-diphenylmethoxypiperidino) butyl]-1,2,3,4-tetrahydroquinazoline-3-yl]isobutyric acid or a salt thereof,

[17] 2-[2,4-dioxo-1-[4-(4-diphenylmethoxypiperidino) butyl]-6-fluoro-1,2,3,4-tetrahydroquinazoline-3-yl] isobutyric acid or a salt thereof,

[18] A method for producing a compound as defined in (1) which is characterized in reacting a compound represented by the formula:

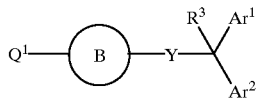

(IIa)

[wherein $Q^1$ represents a leaving group and other symbols represent the same meanings as defined in [1]], or a salt thereof with a compound represented by the formula:

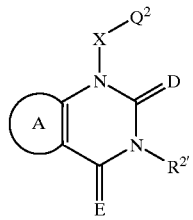

(III)

[wherein $Q^2$ represents a reactive group, $R^{2'}$ represents a hydrogen atom, a cyano group or a hydrocarbon group optionally having substituents and other symbols represent the same meanings as defined in [1]], or a salt thereof,

[19] A method for producing a compound as defined in [1] which is characterized in reacting a compound represented by the formula:

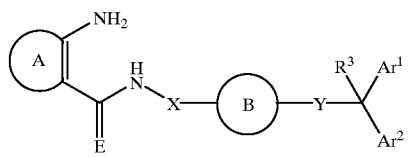

[IX]

[wherein each symbol represents the same meanings as defined in [1]], or a salt thereof with $Q^3$—CO—$Q^4$ ($Q^3$ and $Q^4$ represent independently a leaving group), and subjecting it to a ring-closure reaction,

[20] A pharmaceutical composition which comprises a compound as defined in [1] or a salt thereof,

[21] An anti-histaminic and/or eosinophil chemotaxis-inhibiting agent which comprises a compound as defined in [1] or a salt thereof,

[22] An anti-allergic agent which comprises a compound as defined in [1] or a salt thereof,

[23] An agent for preventing or treating asthma, allergic conjunctivitis, allergic rhinitis, urticaria or atopic dermatitis which comprises a compound as defined in [1] or a salt thereof,

[24] A method for treating asthma, allergic conjunctivitis, allergic rhinitis, urticaria or atopic dermatitis in mammals which comprises administrating to a subject in need an effective amount of a compound as defined in [1], and

[25] Use of a compound as defined in [1] for manufacturing an agent for preventing or treating asthma, allergic conjunctivitis, allergic rhinitis, urticaria or atopic dermatitis.

And, when the compound (I) or a salt thereof has asymmetric carbons in its structure, optically-active forms and racemates are included in a scope of the present invention, and the compound (I) or a salt thereof may be any one of hydrate and non-hydrate.

BEST MODE FOR CARRYING OUT THE INVENTION

In the formula (I), one of $R^1$ and $R^2$ represents a group represented by the formula:

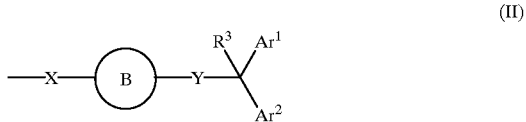

(II)

(wherein $Ar^1$ and $Ar^2$ represent, independently, an aromatic group optionally having substituents; $Ar^1$ and $Ar^2$ may form a condensed cyclic group optionally having substituents together with an adjacent carbon atom; ring B represents a nitrogen-containing heterocycle optionally having substituents; X and Y is the same or different and represent, independently, a bond, an oxygen atom, S(O)p (p represents an integer of 0 to 2), $NR^4$ ($R^4$ represents a hydrogen atom or a lower alkyl group) or a bivalent straight-chained lower hydrocarbon group, which may contain 1 to 3 hetero atoms, optionally having substituents; and $R^3$ represents ahydrogen atom, a hydroxy group optionally having substituents or an optionally esterified carboxyl group). The other is a hydrogen atom or a hydrocarbon group optionally having substituents.

In the above mentioned formula (II), $Ar^1$ and $Ar^2$ represent "an aromatic group optionally having substituents", and $Ar^1$ and $Ar^2$ may form a condensed cyclic group optionally having substituents together with an adjacent carbon atom.

As the "aromatic group" of the "aromatic group optionally having substituents" represented by $Ar^1$ and $Ar^2$, for example, ① monocyclic, condensed polycyclic or gathered cyclic aromatic hydrocarbon group, more specifically a 6- to 14-monocyclic, condensed polycyclic or gathered cyclic aromatic hydrocarbon group such as a $C_{6-14}$ aryl group such as phenyl, biphenyl, 1-naphthyl, 2-naphthyl, 2-indenyl, 2-anthryl, 1-anthryl, 2-anthryl, 3-anthryl, 1-phenanthryl, 2-phenanthryl, 3-phenanthryl, 4-phenanthryl or 9-phenanthryl (preferably, phenyl, biphenyl, 1-naphthyl or 2-naphthyl, particularly preferably phenyl, etc.), or ② monocycle (preferably 5- to 8-membered) or its condensed aromatic heterocyclic group which contains preferably one or two kinds of and not less than one (for example, 1 to 4, preferably 1 to 3) hetero atoms selected from a nitrogen atom, a sulfur atom and an oxygen atom in addition to a carbon atom, more specifically, aromatic heterocycles such as thiophene, benzo[b]thiophene, benzo[b]furan, benzimidazole, benzoxazole, benzothiazole, benzisothiazole, naphtho[2,3-b]thiophene, thianthrene, furan, isoindolylzine, xanthene, phenoxazine, pyrrole, imidazole, triazole, thiazole, oxazole, pyrazole, pyridine, pyrazine, pyrimidine, pyridazine, indole, isoindole, 1H-indazole, purine, 4H-quinolidine, isoquinoline, quinoline, phthalazine, naphthylidine, quinoxaline, quinazoline, cinnoline, carbazole, β-carboline, phenanthridine, acridine, phenazine, isothiazole, phenothiazine, isoxazole, furazan, phenoxazine or isochroman (preferably, pyridine, thiophene or furan, etc., more preferably pyridine, etc.), or a group formed by removing any one hydrogen atom from the condensed ring formed by these rings (preferably, above-mentioned monocyclic heterocycle) and one or a few (preferably 1 or 2, more preferably 1) aromatic rings (for example, the above-mentioned aromatic hydrocarbon group, etc., preferably benzene ring, etc.), etc. are exemplified.

As the "aromatic ring" of the "aromatic ring optionally having substituents" represented by $Ar^1$ and $Ar^2$, for example, phenyl, etc. are preferred.

As the "substituents" of the "aromatic ring optionally having substituents", for example, (i) a halogen atom (e.g., fluorine, chlorine, bromine, iodine, etc.), (ii) a lower alkylenedioxy group (e.g., $C_{1-3}$ alkylenedioxy such as methylenedioxy, ethylenedioxy, etc.), (iii) a nitro group, (iv) a cyano group, (v) an optionally substituted lower alkyl group (e.g., a $C_{1-6}$ alkyl group such as methyl, ethyl, propyl, isopropyl, butyl, isobutyl, sec-butyl, tert-butyl, pentyl, hexyl, etc.), (vi) an optionally substituted lower alkenyl group (e.g., a $C_{2-6}$ alkenyl group such as vinyl, propenyl, isopropenyl, 2-buten-1-yl, 4-penten-1-yl, 5-hexen-1-yl, etc.), (vii) an optionally substituted lower alkynyl group (e.g., a $C_{2-6}$ alkynyl group such as 2-butyn-1-yl, 4-pentyn-1-yl, 5-hexyn-1-yl, etc.), (viii) a lower cycloalkyl group (e.g., a $C_{3-6}$ cycloalkyl group such as cyclopropyl, cyclobutyl, cyclopentyl, cyclohexyl, etc.), (ix) an optionally substituted lower alkoxy (e.g., a $C_{1-6}$ alkoxy group such as methoxy, ethoxy, propoxy, isopropoxy, n-butoxy, isobutoxy, sec-butoxy, tert-butoxy, etc.), (x) an optionally halogenated lower alkylthio group, (xi) a hydroxy group, (xii) an amino group, (xiii) a mono-lower alkylamino group(e.g., a mono-$C_{1-6}$ alkylamino group such as methylamino, ethylamino, propylamino, isopropylamino, butylamino, etc.), (xiv) a di-lower alkylamino group (e.g., a di-$C_{1-6}$ alkylamino group such as dimethylamino, diethylamino, dipropylamino, dibutylamino, etc.), (xv) a 5- to 6-membered cyclic amino group (e.g., morpholino, thiomorpholino, piperazin-1-yl, piperidino, pyrrolodin-1-yl, etc.), (xvi) a lower alkylcarbonyl group (e.g., $C_{1-6}$ alkyl-carbonyl group such as acetyl, propionyl, etc.), (xvii) a carboxyl group, (xviii) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (xix) a carbamoyl group, (xx) a mono-lower alkyl-carbamoyl group (e.g., a mono-$C_{1-6}$ alkyl-carbamoyl group such as methylcarbamoyl, ethylcarbamoyl), (xxi) a di-lower alkyl-carbamoyl group (e.g., a di-$C_{1-6}$ alkyl-carbamoyl group such as dimethylcarbamoyl, diethylcarbamoyl, etc.), (xxii) an aryl-carbamoyl group (e.g., $C_{6-10}$ aryl-carbamoyl such as phenylcarbamoyl, naphthylcarbamoyl, etc.), (xxiii) a sulfo group, (xxiv) a lower alkyl sulfonyl group (e.g., a $C_{1-6}$ alkyl sulfonyl group such as methylsulfonyl, ethylsulfonyl, etc.), (xxv) an aryl group (e.g., a $C_{6-10}$ aryl group such as phenyl, naphthyl, etc.), (xxvi) an aryloxy group (e.g., a $C_{6-10}$ aryloxy group such as phenyloxy, naphthyloxy, etc.), (xxvii) an aralkyloxy group (e.g., a $C_{7-16}$ aralkyloxy group such as benzyloxy, etc.), (xxviii) an oxo group, (xxix) a thiocarbamoyl group, (xxx) a mono-lower alkyl-thiocarbamoyl group (e.g., a mono-$C_{1-6}$ alkyl-thiocarbamoyl group such as methylthiocarbamoyl, ethylthiocarbamoyl, etc.), (xxxi) a di-lower alkyl-thiocarbamoyl group (e.g., a di-$C_{1-6}$ alkyl-thiocarbamoyl group such as dimethylthiocarbamoyl, diethylthiocarbamoyl, etc.), (xxxii) an aryl-thiocarbamoyl group (e.g., a $C_{6-10}$ aryl-thiocarbamoyl group such as phenylthiocarbamoyl, naphthylthiocarbamoyl, etc.), (xxxiii) an aralkyl group (e.g., a $C_{7-16}$ aralkyl group such as benzyl, phenethyl, 2-phenylethyl, 1-phenylpropyl, 2-phenylpropyl, etc.), (xxxiv) a lower alkoxy-carbonyl-lower alkyl group (e.g., a $C_{1-6}$ alkoxy-carbonyl-$C_{1-6}$ alkyl group such as methylcarbonylmethyl, ethylcarbonylmethyl, etc.) or (xxxv) a carboxyl-lower alkyl group (e.g., a carboxyl-$C_{1-6}$ alkyl group such as carboxylmethyl, carboxylethyl, etc.), etc. are exemplified.

As the "substituents" of the "optionally substituted lower alkyl group", "optionally substituted lower alkenyl group", "optionally substituted lower alkynyl group" and "optionally substituted lower alkoxy group" represented as the "substituents" of the "aromatic group optionally having substituents" represented by the above $Ar^1$ and $Ar^2$, for example, 1 to 3 substituents selected from (i) a halogen atom (e.g., fluorine, chlorine, bromine, iodine, etc.), (ii) a mono- or di-lower alkylamino group (e.g., a mono- or di-$C_{1-6}$ alkylamino group such as methylamino, dimethylamino, ethylamino, dimethylamino, etc.), (iii) a lower alkoxy-carbonyl group (e.g., a $C_{1-6}$ alkoxy-carbonyl group such as methoxycarbonyl, ethoxycarbonyl, etc.), (iv) an aminocarbonyl group, (v) a carboxyl group and (vi) 5-to 10-membered heterocyclic group which contains 1 to 3 hetero atoms selected from a nitrogen atom, an oxygen atom and a sulfur atom in addition to a carbon atom or a benzo-condensed cyclic group thereof, are exemplified. Of the above-mentioned substituents, as the lower alkyl group optionally substituted by a halogen atom (optionally halogenated lower alkyl group), for example, a $C_{1-6}$ alkyl group optionally substituted by 1 to 3 halogen atoms (e.g., fluorine, chlorine, bromine, iodine, etc.) (e.g., methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.), etc. are used. As the lower alkenyl group optionally substituted by a halogen atom (optionally halogenated lower alkenyl) and the lower alkynyl group optionally substituted by a halogen atom (optionally halogenated lower alkynyl), a $C_{2-6}$ alkenyl group (e.g., vinyl, propenyl, isopropenyl, 2-buten-1-yl, 4-penten-1-yl, 5-hexen-1-yl, etc.) and a $C_{2-6}$ alkynyl group (e.g., 2-butyn-1-yl, 4-pentyn-1-yl, 5-hexyn-1-yl, etc.) which may be substituted by 1 to 3 halogen atoms (e.g., fluorine, chlorine, bromine, iodine, etc.) are used.

As the "optionally halogenated lower alkylthio group" represented as the "substituents" of the "aromatic group optionally having substituents" represented by the above $Ar^1$ and $Ar^2$, for example, a lower alkylthio group (e.g., a $C_{1-6}$ alkylthio group such as methylthio, ethylthio, n-propylthio, isopropylthio, n-butylthio, isobutylthio, sec-butylthio, tert-butylthio, etc.) optionally having 1 to 3 halogen atoms (e.g., fluorine, chlorine, bromine, iodine, etc.), etc. are exemplified, and as specific examples, methylthio, difluoromethylthio, trifluoromethylthio, ethylthio, propylthio, isopropylthio, butylthio, 4,4,4-trifluorobutylthio, pentylthio, hexylthio, etc. are exemplified.

1 to 5 (preferably 1 to 3, more preferably 1 or 2) substituents of the "aromatic group optionally having substituents" represented by the above $Ar^1$ and $Ar^2$ may substitute at the position on the aromatic group where substitution is possible.

And, when the "aromatic group" has not less than two substitutents, each substituent may be same or different.

As specific examples of the "condensed cyclic group" when $Ar^1$ and $Ar^2$ form a condensed cyclic group optionally having substituents together with an adjacent carbon atom for example, condensed cyclic groups represented by the formulae:

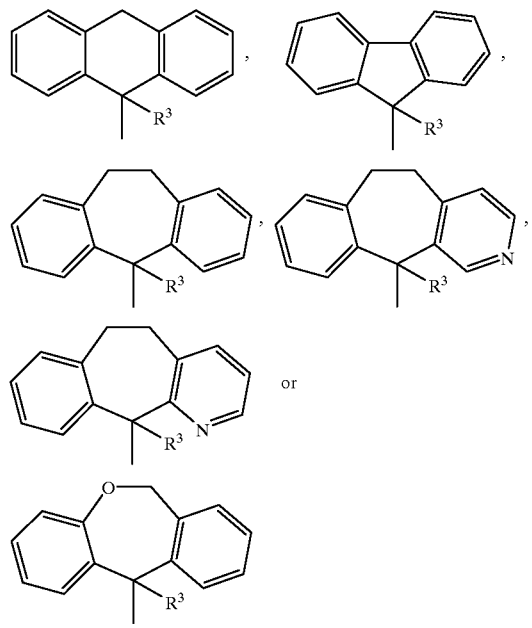

(wherein $R^3$ represents the same meaning as defined above), etc. are exemplified.

As the substituents for these condensed cyclic group, for example, the same those as the "substituents" of the "aromatic group optionally having substituents" represented by the above $Ar^1$ and $Ar^{2''}$, etc. are exemplified, and these condensed cyclic group may have same or different 1 to 5, preferably 1 to 3, more preferably 1 or 2 substituents at the position on the condensed ring where substitution is possible.

As $Ar^1$ and $Ar^2$, a monocyclic or condensed polycyclic aromatic hydrocarbon group is similarly or differently preferred, and a phenyl group optionally having substituents is more preferred, and an unsubstituted phenyl group is further more preferred.

In the above mentioned formula (II), ring B represents a "nitrogen-containing heterocycle optionally having substituents".

As the "nitrogen-containing heterocycle" of the "nitrogen-containing heterocycle optionally having substituents" represented by ring B, for example, a 3- to 13-membered nitrogen-containing heterocycle which contains one nitrogen atom and may contain further 1 to 3 (preferably 1 or 2, more preferably 1) hetero atoms selected from a nitrogen atom, an oxygen atom, a sulfur atom and so on, etc. are exemplified, and particularly those which bind to X of the above-mentioned formula (II) through the nitrogen atom of the nitrogen-containing heterocycle are preferred.

As preferable specific examples of ring B, for example, a ring represented by the formula:

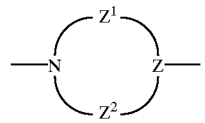

[wherein Z represents a nitrogen atom or a methyne group, $Z^1$ and $Z^2$ are the same or different and represent, independently, a straight chained $C_{1-6}$ alkylene group optionally substituted by a hydroxy, oxo or $C_{1-6}$ alkyl (preferably a sum of carbons of the straight chained $C_{1-6}$ alkylene group represented by Z1 and $Z^2$ is not less than 2 and not more than 11).], etc. are exemplified. (In specific examples for the ring B, they are described as a bivalent group in order to define a binding position of ring B and X and Y in the above-mentioned formula (II).)

As the "straight chained $C_{1-6}$ alkylene group" represented by $Z^1$ and $Z^2$ for example, a straight chained $C_{1-6}$ alkylene group such as methylene, ethylene, propylene, butylene, etc. is used.

As the "$C_{1-6}$ alkyl" represented as the substituent for the "straight chained $C_{1-6}$ alkylene group" represented by $Z^1$ and $Z^2$, for example, a straight chained or branched $C_{1-6}$ alkyl group such as methyl, ethyl, propyl, isopropyl, butyl, isobutyl, sec-butyl, tert-butyl, pentyl, hexyl, etc. are exemplified.

As preferable "straight chained $C_{1-6}$ alkylene group optionally substituted by a hydroxy group, an oxo group or a $C_{1-6}$ alkyl group", an unsubstituted straight chained $C_{1-6}$ alkylene group, etc. are exemplified.

As ring B, more preferably, piperidine, piperazine, etc. are exemplified. Specifically, for example, a 3- to 9-membered (more preferably 3- to 6-membered) nitrogen-containing heterocycle such as,

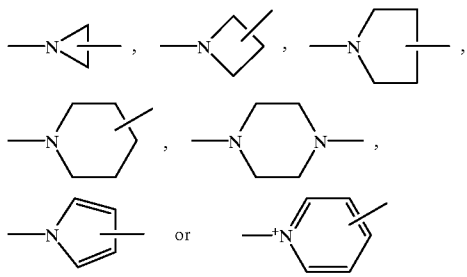

etc. are preferred (In specific examples for the ring B, they are described as a bivalent group in order to define a binding position of ring B and X and Y in the above-mentioned formula (II)). Particularly, those which bind to X of the above-mentioned formula (II) through the nitrogen atom of the nitrogen-containing heterocycle are preferred.

As the "substituents" of the "nitrogen-containing heterocycle optionally having substituents" represented by ring B, for example, the same those as the "substituents" of the "aromatic group optionally having substituents" represented by the above $Ar^1$ and $Ar^{2"}$ are used, and same or different 1 to 3, preferably 1 or 2, more preferably 1 substituent(s) may substitute at the position on the nitrogen-containing heterocycle where substitution is possible.

In the above-mentioned formula (II), X and Y are the same or different and represent, independently, ① a bond, ② an oxygen atom, ③ S(O)p (p represents an integer of 0 to 2), ④ $NR^4$ ($R^4$ represents a hydrogen atom or a lower alkyl group) or ⑤ a bivalent straight-chained lower hydrocarbon group, which may contain 1 to 3 hetero atoms, optionally having substituents.

As the lower alkyl group represented by $R^4$, a straight chained or branched $C_{1-6}$ alkyl group such as methyl, ethyl, propyl, isopropyl, butyl, isobutyl, sec-butyl, tert-butyl, pentyl, hexyl, etc. are exemplified.

The "bivalent straight-chained lower hydrocarbon group, which may contain 1 to 3 hetero atom" of the "bivalent straight-chained lower hydrocarbon group, which may contain 1 to 3 hetero atoms, optionally having substituents" represented by X and Y, represents, for example, a group which is formed by removing each one hydrogen atom (sum two), which binds to same or different carbon atom, from a lower ($C_{1-6}$) hydrocarbon, and which may contain hetero atoms selected from an oxygen atom, a sulfur atom, a nitrogen atom, etc. in the hydrocarbon chain.

As the "bivalent straight-chained lower hydrocarbon group", specifically,
(i) $C_{1-6}$ alkylene group (e.g., —$CH_2$—, —$(CH_2)_2$—, —$(CH_2)_3$—, —$(CH_2)_4$—, —$(CH_2)_5$— and —$(CH_2)_6$—, etc.),
(ii) $C_{2-6}$ alkenylene group (e.g., —CH=CH—, —CH=CH—$CH_2$—, —$CH_2$—CH=CH—$CH_2$—, —$(CH_2)_2$—CH=CH—$CH_2$—, —$(CH_2)_2$—CH=CH—$(CH_2)_2$—, —$(CH_2)_3$—CH=CH—$CH_2$—, etc.),
(iii) $C_{2-6}$ alkynylene (e.g., —C≡C—, —C≡C—$CH_2$—, —$CH_2$—C≡C—$CH_2$—, —$(CH_2)_2$—C≡C—$CH_2$—, —$(CH_2)_2$—C≡C—$(CH_2)_2$—, —$(CH_2)_3$—C≡C—$CH_2$—, etc.), etc. are exemplified.

As the "substituents" of the "bivalent straight-chained lower hydrocarbon group, which may contain 1 to 3 hetero atoms, optionally having substituents" represented by X and Y, for example, the same those as the "substituents" of the "aromatic group optionally having substituents" represented by the above $Ar^1$ and $Ar^2$ are used, and particularly a hydroxy group or an oxo group, etc. are preferred.

As specific examples in case that the "bivalent straight-chained lower hydrocarbon group" of the "bivalent straight-chained lower hydrocarbon group, which may contain 1 to 3 hetero atoms, optionally having substituents" represented by X and Y contains hetero atoms in the hydrocarbon chain, for example, —$(CH_2)_2$—O—, —$(CH_2)_3$—O—, —$(CH_2)_4$—O—, —$(CH_2)_6$—O—, —$(CH_2)_2$—NH—, —$(CH_2)_3$—NH—, —$(CH_2)_4$—NH—, —$(CH_2)_3$—S—, —$CH_2$—CO—$CH_2$—O—, —$(CH_2)_2$—CO—NH—, —$CH_2$—CO—NH—, —CO—O—$(CH_2)_2$—O—, —CO—O—$(CH_2)_3$—O—, —$(CH_2)_6$—NH—, —$(CH_2)_6$—S—, —$(CH_2)_2$—O —$(CH_2)_2$—O—, —$(CH_2)_2$—O—$(CH_2)_2$—S—, etc. are exemplified.

As X, a bond or a $C_{1-6}$ alkylene group, etc. are preferred, particularly a bond, etc. are preferred.

As Y, a bond, an oxygen atom or a $C_{1-6}$ alkylne group which may contain an oxygen atom in the alkylene chain and may be substituted by a hydroxy group, etc. are preferred, particularly a bond, an oxygen atom, —O—$CH_2$—, —$CH_2$—or —CH(OH)—, etc. are preferred.

In the above-mentioned formula (II), $R^3$ represents a hydrogen atom, a hydroxy group optionally having substituents or an optionally esterified carboxyl group.

The "hydroxy group optionally having substituents" represents, for example, (1) a hydroxy group or (2) a hydroxy group having one "a hydrocarbon group optionally having substituents", etc. instead of a hydrogen atom of the hydroxy group.

The "hydrocarbon group" of the "hydrocarbon group optionally having substituents" represented as the "hydroxy group having one hydrocarbon group optionally having substituents, etc." represent, for example, a group removed one hydrogen atom from a hydrocarbon compound, and as their examples, for example, a straight chained or cyclic hydrocarbon group such as an alkyl group, an alkenyl group, an alkynyl group, an cycloalkyl group, an aryl group, an aralkyl group, etc. are exemplified.

Among them, $C_{1-16}$ chained (straight chained or branched) or cyclic hydrocarbon group, etc. are preferred, and specifically,
(a) alkyl group [preferably, a lower alkyl group (e.g., a $C_{1-6}$ alkyl group such as methyl, ethyl, propyl, isopropyl, butyl, isobutyl, sec-butyl, tert-butyl, pentyl, hexyl, etc.)], (b) an alkenyl group [preferably, a lower alkenyl group (e.g., $C_{2-6}$ alkenyl such as vinyl, allyl, isopropenyl, butenyl, isobutenyl, sec-butenyl, etc.)], (c) an alkynyl group [preferably, a lower alkynyl group (e.g., $C_{2-6}$ alkynyl such as propargyl, ethynyl, butynyl, 1-hexynyl, etc.), (d) a cycloalkyl group [preferably, a lower cycloalkyl group (e.g., $C_{3-6}$ cycloalkyl such as cyclopropyl, cyclobutyl, cyclopentyl, cyclohexyl which may condense with a benzene ring optionally having 1 to 3 lower alkoxy groups (e.g., a $C_{1-6}$ alkoxy group such as methoxy))], (e) an aryl group (e.g., $C_{6-14}$ aryl group such as phenyl, biphenyl, 1-naphthyl, 2-naphthyl, 2-indenyl, 2-anthryl, 1-anthryl, 2-anthryl, 3-anthryl, 1-phenanthryl, 2-phenanthryl, 3-phenanthryl, 4-phenanthryl or 9-phenanthryl, etc., preferably a phenyl group), (f) an aralkyl group [preferably, a lower aralkyl group (e.g., $C_{7-16}$ aralkyl group such as benzyl, phenetyl, diphenylmethyl, 1-naphthylmethyl, 2-naphthylmethyl, 2-phenylethyl, 2-diphenylethyl, 1-phenylpropyl, 2-phenylpropyl, 3-phenylpropyl, 4-phenylbutyl, 5-phenylpentyl, etc, more preferably a benzyl group)], etc. are exemplified.

As the "substituents" of the "hydrocarbon group optionally having substituents" represented as the "hydroxy group having one hydrocarbon group optionally having substituents, etc.", for example, the same those as the "substituents" of the "aromatic group optionally having substituents" represented by the above $Ar^1$ and $Ar^2$, etc. are used.

The "optionally esterified carboxyl group" represented by $R^3$ represents, for example, (1) a carboxyl group or (2) a carboxyl group having, for example, one "a hydrocarbon group optionally having substituents", etc. instead of a hydrogen atom of the carboxyl group.

As the "hydrocarbon group optionally having substituents" represented as the "carboxyl group having one of hydrocarbon group optionally having substituents, etc.", for example, the same those as the "hydrocarbon group optionally having substituents" of the "hydroxy group having one hydrocarbon group optionally having substituents, etc.", etc. are exemplified.

As $R^3$, a hydrogen atom, a hydroxy group or a carboxyl group, etc. are preferred, and a hydrogen atom or a hydroxy group, etc. are more preferred, and particularly a hydrogen atom, etc. are preferred.

In the above-mentioned formula (I), one of $R^1$ and $R^2$ represents a hydrogen atom, a cyano group or a hydrocarbon group optionally having substituents.

As the "hydrocarbon group" of the "hydrocarbon group optionally having substituents" represented as the other of $R^1$ and $R^2$, for example, a group removed one hydrogen atom from a hydrocarbon compound and as their examples, for example, a straight chained or cyclic hydrocarbon group such as an alkyl group, an alkenyl group, an alkynyl group, an cycloalkyl group, an aryl group, an aralkyl group, etc. are exemplified.

Among them, $C_{1-16}$ chained (straight chained or branched) or cyclic hydrocarbon group, etc. are preferred, and specifically, (a) alkyl group [preferably, a lower alkyl group (e.g., a $C_{1-6}$ alkyl group such as methyl, ethyl, propyl, isopropyl, butyl, isobutyl, sec-butyl, tert-butyl, pentyl, hexyl, etc.)], (b) an alkenyl group [preferably, a lower alkenyl group (e.g., $C_{2-6}$ alkenyl such as vinyl, allyl, isopropenyl, butenyl, isobutenyl, sec-butenyl, etc.)], (c) an alkynyl group [preferably, a lower alkynyl group (e.g., $C_{2-6}$ alkynyl such as propargyl, ethynyl, butynyl, 1-hexynyl, etc.), (d) a cycloalkyl group [preferably, a lower cycloalkyl group (e.g., $C_{3-6}$ cycloalkyl such as cyclopropyl, cyclobutyl, cyclopentyl, cyclohexyl which may condense with a benzene ring optionally having 1 to 3 lower alkoxy groups (e.g., a $C_{1-6}$ alkoxy group such as methoxy))], (e) an aryl group (e.g., $C_{6-14}$ aryl group such as phenyl, biphenyl, 1-naphthyl, 2-naphthyl, 2-indenyl, 2-anthryl, 1-anthryl, 2-anthryl, 3-anthryl, 1-phenanthryl, 2-phenanthryl, 3-phenanthryl, 4-phenanthryl or 9-phenanthryl, etc., preferably a phenyl group), (f) an aralkyl group [preferably, a lower aralkyl group (e.g., $C_{7-16}$ aralkyl group such as benzyl, phenetyl, diphenylmethyl, 1-naphthylmethyl, 2-naphthylmethyl, 2-phenylethyl, 2-diphenylethyl, 1-phenylpropyl, 2-phenylpropyl, 3-phenylpropyl, 4-phenylbutyl, 5-phenylpentyl, etc, more preferably a benzyl group)], etc. are exemplified.

As the "substituents" of the "hydrocarbon group optionally having substituents" represented as the other of $R^1$ and $R^2$, for example, (i) a halogen atom (e. g., fluorine, chlorine, bromine, iodine, etc.), (ii) a lower alkylenedioxy group (e.g., $C_{1-3}$ alkylenedioxy such as methylenedioxy, ethylenedioxy, etc.), (iii) a nitro group, (iv) a cyano group, (v) an optionally substituted lower alkyl group, (vi) an optionally substituted lower alkenyl group, (vii) an optionally substituted lower alkynyl group, (viii) a lower cycloalkyl group (e.g. , a $C_{3-6}$ cycloalkyl group such as cyclopropyl, cyclobutyl, cyclopentyl, cyclohexyl, etc.), which may be substituted by (a) a halogen atom (e.g., fluorine, chlorine, bromine, iodine, etc.), (b) a lower alkylenedioxy group (e.g., $C_{1-3}$ alkylenedioxy such as methylenedioxy, ethylenedioxy, etc.), (c) a nitro group, (d) a cyano group, (e) an optionally substituted lower alkyl group, (f) an optionally substituted lower alkenyl group, (g) an optionally substituted lower alkynyl group, (h) a lower cycloalkyl group (e.g., a $C_{3-6}$ cycloalkyl group such as cyclopropyl, cyclobutyl, cyclopentyl, cyclohexyl, etc.), (i) an optionally substituted lower alkoxy, (j) an optionally halogenated lower alkylthio group, (k) a hydroxy group, (1) an amino group, (m) a mono-lower alkylamino group(e.g., amono-$C_{1-6}$ alkylamino group such as methylamino, ethylamino, propylamino, isopropylamino, butylamino, etc.), (n) a di-lower alkylamino group (e.g., a di-$C_{1-6}$ alkylamino group such as dimethylamino, diethylamino, dipropylamino, dibutylamino, etc.), (o) a 5- to 6-membered cyclic amino group (e.g., morpholino, thiomorpholino, piperazin-1-yl, piperidino, pyrrolidin-1-yl, etc.), (p) a lower alkylcarbonyl group (e.g., $C_{1-6}$ alkylcarbonyl group such as acetyl, propionyl, etc.), (q) a carboxyl group, (r) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (s) a carbamoyl group, (t) a mono-lower alkyl-carbamoyl group (e.g., a mono-$C_{1-6}$ alkyl-carbamoyl group such as methylcarbamoyl, ethylcarbamoyl), (u) a di-lower alkyl-carbamoyl group (e.g., a di-$C_{1-6}$ alkyl-carbamoyl group such as dimethylcarbamoyl, diethylcarbamoyl, etc.), (v) an aryl-carbamoyl group (e.g., $C_{6-10}$ aryl-carbamoyl such as phenylcarbamoyl, naphthylcarbamoyl, etc.), (w) a sulfo group, (x) a lower alkyl sulfonyl group (e.g., a $C_{1-6}$ alkyl sulfonyl group such as methylsulfonyl, ethylsulfonyl, etc.), (y) an aryl group (e.g., a $C_{6-10}$ aryl group such as phenyl, naphthyl, etc.), (z) an aryloxy group (e.g., a $C_{6-10}$ aryloxy group such as phenyloxy, naphthyloxy, etc.), (aa) an aralkyloxy group (e.g., a $C_{7-16}$ aralkyloxy group such as benzyloxy, etc.), (bb) an oxo group, (cc) a thiocarbamoyl group, (dd) a mono-lower alkyl-thiocarbamoyl group (e.g., a mono-$C_{1-6}$ alkyl-thiocarbamoyl group such as methylthiocarbamoyl, ethylthiocarbamoyl, etc.), (ee) a di-lower alkyl-thiocarbamoyl group (e.g., a di-$C_{1-6}$ alkyl-thiocarbamoyl group such as dimethylthiocarbamoyl, diethylthiocarbamoyl, etc.), (ff) an aryl-thiocarbamoyl group (e.g., a $C_{6-10}$ aryl-thiocarbamoyl group such as phenylthiocarbamoyl, naphthylthiocarbamoyl, etc.), (gg) an aralkyl group (e.g., a $C_{7-6}$ aralkyl group such as benzyl, phenethyl, 2-phenylethyl, 1-phenylpropyl, 2-phenylpropyl, etc.), (hh) a lower alkoxy-carbonyl-lower alkyl group (e.g., a $C_{1-6}$ alkoxy-carbonyl-$C_{1-6}$ alkyl group such as methylcarbonylmethyl, ethylcarbonylmethyl, etc.) or (ii) a carboxyl-lower alkyl group (e.g., a carboxyl-$C_{1-6}$ alkyl group such as carboxylmethyl, carboxylethyl, etc.), etc, (ix) an optionally substituted lower alkoxy, (x) an optionally halogenated lower alkylthio group, (xi) a hydroxy group, (xii) an amino group, (xiii) a mono-lower alkylamino group (e.g., a mono-$C_{1-6}$ alkylamino group such as methylamino, ethylamino, propylamino, isopropylamino, butylamino, etc.), (xiv) a di-lower alkylamino group (e.g., a di-$C_{1-6}$ alkylamino group such as dimethylamino, diethylamino, dipropylamino, dibutylamino, etc.), (xv) a 5- to 6-membered cyclic amino group (e.g., morpholino, thiomorpholino, piperazin-1-yl, piperidino, pyrrolidin-1-yl, etc.), (xvi) a lower alkylcarbonyl group (e.g., $C_{1-6}$ alkyl-carbonyl group such as acetyl, propionyl, etc.), (xvii) a carboxyl group, (xviii) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (xix) a carbamoyl group, (xx) a mono-lower alkyl-carbamoyl group (e.g., a mono-$C_{1-6}$ alkyl-carbamoyl group such as methylcarbamoyl, ethylcarbamoyl), (xxi) a di-lower alkyl-carbamoyl group (e.g., a di-$C_{1-6}$ alkyl-carbamoyl group such as dimethylcarbamoyl, diethylcarbamoyl, etc.), (xxii) an aryl-carbamoyl group (e.g., $C_{6-10}$ aryl-carbamoyl such as phenylcarbamoyl, naphthylcarbamoyl, etc.), (xxiii) a sulfo group, (xxiv) a lower alkyl sulfonyl group (e.g., a $C_{1-6}$ alkyl sulfonyl group such as methylsulfonyl, ethylsulfonyl, etc.), (xxv) an aryl group (e.g., a $C_{6-10}$ aryl group such as phenyl, naphthyl, etc.) which may be substituted by (a) a halogen atom (e.g., fluorine, chlorine, bromine, iodine, etc.), (b) a lower alkylenedioxy group (e.g., $C_{1-3}$ alkylenedioxy such as methylenedioxy, ethylenedioxy, etc.), (c) a nitro group, (d) a cyano group, (e) an optionally substituted lower alkyl group, (f) an optionally substituted lower alkenyl group, (g) an optionally substituted lower alkynyl group, (h) a lower cycloalkyl group (e.g., a $C_{3-6}$ cycloalkyl group such as cyclopropyl, cyclobutyl, cyclopentyl, cyclohexyl, etc.), (i) an optionally substituted lower alkoxy, (j) an optionally halogenated lower alkylthio group, (k) a hydroxy group, (l) an amino group, (m) a mono-lower alkylamino group(e. g., a mono-$C_{1-6}$ alkylamino group such as methylamino, ethylamino, propylamino, isopropylamino, butylamino, etc.) (n) a di-lower alkylamino group (e.g., a di-$C_{1-6}$ alkylamino group such as dimethylamino, diethylamino, dipropylamino, dibutylamino, etc.), (o) a 5- to 6-membered cyclic amino group (e.g., morpholino, thiomorpholino, piperazin-1-yl, piperidino, pyrrolodin-1-yl, etc.), (p) a lower alkylcarbonyl group (e.g., $C_{1-6}$ alkyl-carbonyl group such as acetyl, propionyl, etc.), (q) a carboxyl group, (r) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (s) a carbamoyl group, (t) a mono-lower alkyl-carbamoyl group (e.g., a mono-$C_{1-6}$ alkyl-carbamoyl group such as methylcarbamoyl, ethylcarbamoyl), (u) a di-lower alkyl-carbamoyl group (e.g., a di-$C_{1-6}$ alkyl-carbamoyl group such as dimethylcarbamoyl, diethylcarbamoyl, etc.), (v) an aryl-carbamoyl group (e.g., $C_{6-10}$ aryl-carbamoyl such as phenylcarbamoyl, naphthylcarbamoyl, etc.), (w) a sulfo group, (x) a lower alkyl sulfonyl group (e.g., a $C_{1-6}$ alkyl sulfonyl group such as methylsulfonyl, ethylsulfonyl, etc.), (y) an aryl group (e.g., a $C_{6-10}$ aryl group such as phenyl, naphthyl, etc.), (z) an aryloxy group (e.g., a $C_{6-10}$ aryloxy group such as phenyloxy, naphthyloxy, etc.), (aa) an aralkyloxy group (e.g., a $C_{7-16}$ aralkyloxy group such as benzyloxy, etc.), (bb) an oxo group, (cc) a thiocarbamoyl group, (dd) a mono-lower alkyl-thiocarbamoyl group (e.g., a mono-$C_{1-6}$ alkyl-thiocarbamoyl group such as methylthiocarbamoyl, ethylthiocarbamoyl, etc.), (ee) a di-lower alkyl-thiocarbamoyl group (e.g., a di-$C_{1-6}$ alkyl-thiocarbamoyl group such as dimethylthiocarbamoyl, diethylthiocarbamoyl, etc.), (ff) an aryl-thiocarbamoyl group (e.g., a $C_{6-10}$ aryl-thiocarbamoyl group such as phenylthiocarbamoyl, naphthylthiocarbamoyl, etc.), (gg) an aralkyl group (e.g., a $C_{7-16}$ aralkyl group such as benzyl, phenethyl, 2-phenylethyl, 1-phenylpropyl, 2-phenylpropyl, etc.), (hh) a lower alkoxy-carbonyl-lower alkyl group (e.g., a $C_{1-6}$ alkoxy-carbonyl-$C_{1-6}$ alkyl group such as methylcarbonylmethyl, ethylcarbonylmethyl, etc.) or (ii) a carboxyl-lower alkyl group (e.g., a carboxyl-$C_{1-6}$ alkyl group such as carboxylmethyl, carboxylethyl, etc.), etc, (xxvi) an aralkyl group (e.g., a $C_{7-15}$ ararlyl group such as benzyl, phenethyl, 2-phenylethyl, 1-phenylpropyl, 2-phenylpropyl, naphthylmethyl, etc.) which may be substituted by (a) a halogen atom (e.g., fluorine, chlorine, bromine, iodine, etc.), (b) a lower alkylenedioxy group (e.g., $C_{1-3}$ alkylenedioxy such as methylenedioxy, ethylenedioxy, etc.), (c) a nitro group, (d) a cyano group, (e) an optionally substituted lower alkyl group, (f) an optionally substituted lower alkenyl group, (g) an optionally substituted lower alkynyl group, (h) a lower cycloalkyl group (e.g., a $C_{3-6}$ cycloalkyl group such as cyclopropyl, cyclobutyl, cyclopentyl, cyclohexyl, etc.), (i) an optionally substituted lower alkoxy, (j) an optionally halogenated lower alkylthio group, (k) a hydroxy group, (l) an amino group, (m) a mono-lower alkylamino group(e. g., a mono-$C_{1-6}$ alkylamino group such as methylamino, ethylamino, propylamino, isopropylamino, butylamino, etc.) (n) a di-lower alkylamino group (e.g., a di-$C_{1-6}$ alkylamino group such as dimethylamino, diethylamino, dipropylamino, dibutylamino, etc.), (o) a 5- to 6-membered cyclic amino group (e.g., morpholino, thiomorpholino, piperazin-1-yl, piperidino, pyrrolodin-1-yl, etc.), (p) a lower alkylcarbonyl group (e.g., $C_{1-6}$ alkyl-carbonyl group such as acetyl, propionyl, etc.), (q) a carboxyl group, (r) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (s) a carbamoyl group, (t) a mono-lower alkyl-carbamoyl group (e.g., a mono-$C_{1-6}$ alkyl-carbamoyl group such as methylcarbamoyl, ethylcarbamoyl), (u) a di-lower alkyl-carbamoyl group (e.g., a di-$C_{1-6}$ alkyl-carbamoyl group such as dimethylcarbamoyl, diethylcarbamoyl, etc.), (v) an aryl-carbamoyl group (e.g., $C_{6-10}$ aryl-carbamoyl such as phenylcarbamoyl, naphthylcarbamoyl, etc.), (w) a sulfo group, (x) a lower alkyl sulfonyl group (e.g., a $C_{1-6}$ alkyl sulfonyl group such as methylsulfonyl, ethylsulfonyl, etc.), (y) an aryl group (e.g., a $C_{6-10}$ aryl group such as phenyl, naphthyl, etc.), (z) an aryloxy group (e.g., a $C_{6-10}$ aryloxy group such as phenyloxy, naphthyloxy, etc.), (aa) an aralkyloxy group (e.g., a $C_{7-16}$ aralkyloxy group such as benzyloxy, etc.), (bb) an oxo group, (cc) a thiocarbamoyl group, (dd) a mono-lower alkyl-thiocarbamoyl group (e.g., a mono-$C_{1-6}$ alkyl-thiocarbamoyl group such as methylthiocarbamoyl, ethylthiocarbamoyl, etc.), (ee) a di-lower alkyl-thiocarbamoyl group (e.g., a di-$C_{1-6}$ alkyl-thiocarbamoyl group such as dimethylthiocarbamoyl, diethylthiocarbamoyl, etc.), (ff) an aryl-thiocarbamoyl group (e.g., a $C_{6-10}$ aryl-thiocarbamoyl group such as phenylthiocarbamoyl, naphthylthiocarbamoyl, etc.), (gg) an aralkyl group (e.g., a $C_{7-16}$ aralkyl group such as benzyl, phenethyl, 2-phenylethyl, 1-phenylpropyl, 2-phenylpropyl, etc.), (hh) a lower alkoxy-carbonyl-lower alkyl group (e.g., a $C_{1-6}$ alkoxy-carbonyl-$C_{1-6}$ alkyl group such as methylcarbonylmethyl, ethylcarbonylmethyl, etc.) or (ii) a carboxyl-lower alkyl group (e.g., a carboxyl-$C_{1-6}$ alkyl group such as carboxylmethyl, carboxylethyl, etc.), etc, (xxvii) an aryloxy group (e.g., a $C_{6-10}$ aryloxy group such as phenyloxy, naphthyloxy, etc.) which may be substituted by (a) a halogen atom (e.g., fluorine, chlorine, bromine, iodine, etc.), (b) a lower alkylenedioxy group (e.g., $C_{1-3}$ alkylenedioxy such as methylenedioxy, ethylenedioxy, etc.), (c) a nitro group, (d) a cyano group, (e) an optionally substituted lower alkyl group, (f) an optionally substituted lower alkenyl group, (g) an optionally substituted lower alkynyl group, (h) a lower cycloalkyl group (e.g., a $C_{3-6}$ cycloalkyl group such as cyclopropyl, cyclobutyl, cyclopentyl, cyclohexyl, etc.), (i) an optionally substituted lower alkoxy, (j) an optionally halogenated lower alkylthio group, (k) a hydroxy group, (1) an amino group, (m) a mono-lower alkylamino group(e.g., a mono-$C_{1-6}$ alkylamino group such as methylamino, ethylamino, propylamino, isopropylamino, butylamino, etc.), (n) a di-lower alkylamino group (e.g., a di-$C_{1-6}$ alkylamino group such as dimethylamino, diethylamino, dipropylamino, dibutylamino, etc.), (o) a 5- to 6-membered cyclic amino group (e.g., morpholino, thiomorpholino, piperazin-1-yl, piperidino, pyrrolodin-1-yl, etc.), (p) a lower alkylcarbonyl group (e.g., $C_{1-6}$ alkyl-carbonyl group such as acetyl, propionyl, etc.), (q) a carboxyl group, (r) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (s) a carbamoyl group, (t) a mono-lower alkyl-carbamoyl group (e.g., a mono-$C_{1-6}$ alkyl-carbamoyl group such as methylcarbamoyl, ethylcarbamoyl), (u) a di-lower alkyl-carbamoyl group (e.g., a di-$C_{1-6}$ alkyl-carbamoyl group such as dimethylcarbamoyl, diethylcarbamoyl, etc.), (v) an aryl-carbamoyl group (e.g., $C_{6-10}$ aryl-carbamoyl such as phenylcarbamoyl, naphthylcarbamoyl, etc.), (w) a sulfo group, (x) a lower alkyl sulfonyl group (e.g., a $C_{1-6}$ alkyl sulfonyl group such as methylsulfonyl, ethylsulfonyl, etc.), (y) an aryl group (e.g., a $C_{6-10}$ aryl group such as phenyl, naphthyl, etc.), (z) an aryloxy group (e.g., a $C_{6-10}$ aryloxy group such as phenyloxy, naphthyloxy, etc.), (aa) an aralkyloxy group (e.g., a $C_{7-16}$ aralkyloxy group such as benzyloxy, etc.), (bb) an oxo group, (cc) a thiocarbamoyl group, (dd) a mono-lower alkyl-thiocarbamoyl group (e.g., a mono-$C_{1-6}$ alkyl-thiocarbamoyl group such as methylthiocarbamoyl, ethylthiocarbamoyl, etc.), (ee) a di-lower alkyl-thiocarbamoyl group (e.g., a di-$C_{1-6}$ alkyl-thiocarbamoyl group such as dimethylthiocarbamoyl, diethylthiocarbamoyl, etc.), (ff) an aryl-thiocarbamoyl group (e.g., a $C_{6-10}$ aryl-thiocarbamoyl group such as phenylthiocarbamoyl, naphthylthiocarbamoyl, etc.), (gg) an aralkyl group (e.g., a $C_{7-16}$ aralkyl group such as benzyl, phenethyl, 2-phenylethyl, 1-phenylpropyl, 2-phenylpropyl, etc.), (hh) a lower alkoxy-carbonyl-lower alkyl group (e.g., a $C_{1-6}$ alkoxy-carbonyl-$C_{1-16}$ alkyl group such as methylcarbonylmethyl, ethylcarbonylmethyl, etc.) or (ii) a carboxyl-lower alkyl group (e.g., a carboxyl-$C_{1-6}$ alkyl group such as carboxylmethyl, carboxylethyl, etc.), etc, (xxviii) an aralkyloxy group (e.g., a $C_{7-16}$ aralkyloxy group such as benzyloxy, etc.) which may be substituted by (a) a halogen atom (e.g., fluorine, chlorine, bromine, iodine, etc.), (b) a lower alkylenedioxy group (e.g., $C_{1-3}$ alkylenedioxy such as methylenedioxy, ethylenedioxy, etc.), (c) a nitro group, (d) a cyano group, (e) an optionally substituted lower alkyl group, (f) an optionally substituted lower alkenyl group, (g) an optionally substituted lower alkynyl group, (h) a lower cycloalkyl group (e.g., a $C_{3-6}$ cycloalkyl group such as cyclopropyl, cyclobutyl, cyclopentyl, cyclohexyl, etc.), (i) an optionally substituted lower alkoxy, (j) an optionally halogenated lower alkylthio group, (k) a hydroxy group, (1) an amino group, (m) a mono-lower alkylamino group(e.g., a mono-$C_{1-6}$ alkylamino group such as methylamino, ethylamino, propylamino, isopropylamino, butylamino, etc.), (n) a di-lower alkylamino group (e.g., a di-$C_{1-6}$ alkylamino group such as dimethylamino, diethylamino, dipropylamino, dibutylamino, etc.), (o) a 5- to 6-membered cyclic amino group (e.g., morpholino, thiomorpholino, piperazin-1-yl, piperidino, pyrrolodin-1-yl, etc.), (p) a lower alkylcarbonyl group (e.g., $C_{1-6}$ alkyl-carbonyl group such as acetyl, propionyl, etc.), (q) a carboxyl group, (r) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (s) a carbamoyl group, (t) a mono-lower alkyl-carbamoyl group (e.g., a mono-$C_{1-6}$ alkyl-carbamoyl group such as methylcarbamoyl, ethylcarbamoyl), (u) a di-lower alkyl-carbamoyl group (e.g., a di-$C_{1-6}$ alkyl-carbamoyl group such as dimethylcarbamoyl, diethylcarbamoyl, etc.), (v) an aryl-carbamoyl group (e.g., $C_{6-10}$ aryl-carbamoyl such as phenylcarbamoyl, naphthylcarbamoyl, etc.), (w) a sulfo group, (x) a lower alkyl sulfonyl group (e.g., a $C_{1-6}$ alkyl sulfonyl group such as methylsulfonyl, ethylsulfonyl, etc.), (y) an aryl group (e.g., a $C_{6-10}$ aryl group such as phenyl, naphthyl, etc.), (z) an aryloxy group (e.g., a $C_{6-10}$ aryloxy group such as phenyloxy, naphthyloxy, etc.), (aa) an aralkyloxy group (e.g., a $C_{7-16}$ aralkyloxy group such as benzyloxy, etc.), (bb) an oxo group, (cc) a thiocarbamoyl group, (dd) a mono-lower alkyl-thiocarbamoyl group (e.g., a mono-$C_{1-6}$ alkyl-thiocarbamoyl group such as methylthiocarbamoyl, ethylthiocarbamoyl, etc.), (ee) a di-lower alkyl-thiocarbamoyl group (e.g., a di-$C_{1-6}$ alkyl-thiocarbamoyl group such as dimethylthiocarbamoyl, diethylthiocarbamoyl, etc.), (ff) an aryl-thiocarbamoyl group (e.g., a $C_{6-10}$ aryl-thiocarbamoyl group such as phenylthiocarbamoyl, naphthylthiocarbamoyl, etc.), (gg) an aralkyl group (e.g., a $C_{7-16}$ aralkyl group such as benzyl, phenethyl, 2-phenylethyl, 1-phenylpropyl, 2-phenylpropyl, etc.), (hh) a lower alkoxy-carbonyl-lower alkyl group (e.g., a $C_{1-6}$ alkoxy-carbonyl-$C_{1-6}$ alkyl group such as methylcarbonylmethyl, ethylcarbonylmethyl, etc.) or (ii) a carboxyl-lower alkyl group (e.g., a carboxyl-$C_{1-6}$ alkyl group such as carboxylmethyl, carboxylethyl, etc.), etc, (xxix) an oxo group, (xxx) a thiocarbamoyl group, (xxxi) a mono-lower alkyl-thiocarbamoyl group (e.g., a mono-$C_{1-6}$ alkyl-thiocarbamoyl group such as methylthiocarbamoyl, ethylthiocarbamoyl, etc.), (xxxii) a di-lower alkyl-thiocarbamoyl group (e.g., a di-$C_{1-6}$ alkyl-thiocarbamoyl group such as dimethylthiocarbamoyl, diethylthiocarbamoyl, etc.), (xxxiii) an aryl-thiocarbamoyl group (e.g., a $C_{6-10}$ aryl-thiocarbamoyl group such as phenylthiocarbamoyl, naphthylthiocarbamoyl, etc.), (xxxiv) aryl-carbonyloxy (e.g., a $C_{6-10}$ aryl-carbonyloxy group such as phenylcarbonyloxy, etc.), (xxxv) optionally substituted aminocarbonyl, (xxxvi) 5- or 6-membered heterocyclic group, (xxxvii) lower alkoxy-carbonyl-lower alkoxycarbonyl (e.g., $C_{1-6}$ alkoxy-carbonyl-$C_{1-6}$ alkoxy-carbonyl such as methoxycarbonylmethoxycarbonyl, ethoxycarbonylethoxycarbonyl, etc.), (xxxviii) lower alkoxy-carbonyl-lower alkyl-carbamoyl (e.g., $C_{1-6}$ alkoxy-carbonyl-$C_{1-6}$ alkyl-carbamoyl such as methoxycarbonylmethylcarbamoyl, ethoxycarbonylethylcarbamoyl, etc.), (xxxix) hydroxy-lower alkyl-carbamoyl (e.g., hydroxy-$C_{1-6}$ alkyl-carbamoyl such as hydroxymethylcarbamoyl, hydroxyethylcarbamoyl, etc.), (xxxx) a lower alkoxy-carbonyl-carbamoyl group (e.g., a $C_{1-6}$ alkoxy-carbonyl-carbamoyl group such as methoxycarbonylcarbamoyl, ethoxycarbonylcarbamoyl, etc.), (xxxxi) an arylsulfonamide group (e.g., a $C_{6-14}$ aryl-sulfonamide group such as phenylsulfonamide, etc.), (xxxxii) an alkylsulfonamide group (e.g., a $C_{1-6}$ alkylsul-fonamide group such as methylsulfonamide, ethylsulfonamide, etc.), (xxxxiii) a carboxy-$C_{1-6}$ alkyl-carbonyl-amino group (e.g., carbonylmethylcarbonylamino, carbonylmethylcarbonylamino, etc.), (xxxxiv) a $C_{1-6}$ alkoxy-carbonyl-$C_{1-6}$ alkyl-carbonyl-amino group (e.g., methoxycarbonylmethylcarbonylamino, etc), (xxxxv) a $C_{1-6}$ alkyl-carbonyloxy-$C_{1-6}$ alkyl-carbonyl-amino group (e.g., methylcarbonyloxymethylcarbonylamino, etc.), (xxxxvi) a hydroxy-$C_{1-6}$ alkyl-carbonyl-amino group (e.g., hydroxymethylcarbonylamino, etc.), (xxxxvii) a $C_{6-14}$ aryl-$C_{2-6}$ alkenyl-carbonylamido group (e.g., (4-hydroxy-3,5-methoxy)phenyl-ethylcarbonylamido) which may be substituted by hydroxy or/and $C_{1-6}$ alkoxy (e.g., methoxy, ethoxy, etc.), etc. are used.

As the "optionally substituted aminocarbonyl" represented as the "substituents" of the "hydrocarbon group optionally having substituents" represented as the other of the above $R^1$ and $R^2$, for example, aminocarbonyl optionally having one or two (a) a halogen atom.(e.g., fluorine, chlorine, bromine, iodine, etc.), (b) an optionally substituted lower alkyl group, (c) an optionally substituted lower alkenyl group, (d) an optionally substituted lower alkynyl group, (e) a lower cycloalkyl group (e.g., a $C_{3-6}$ cycloalkyl group such as cyclopropyl, cyclobutyl, cyclopentyl, cyclohexyl, etc.), (f) an optionally substituted lower alkoxy, (g) an optionally halogenated lower alkylthio group, (h) a hydroxy group, (i) an amino group, (j) a mono-lower alkylamino group(e.g., a mono-$C_{1-6}$ alkylamino group such as methylamino, ethylamino, propylamino, isopropylamino, butylamino, etc.), (k) a di-lower alkylamino group (e.g., a di-$C_{1-6}$ alkylamino group such as dimethylamino, diethylamino, dipropylamino, dibutylamino, etc.), (l) a 5- to 6-membered cyclic amino group (e.g., morpholino, thiomorpholino, piperazin-1-yl, piperidino, pyrrolodin-1-yl, etc.), (m) a lower alkylcarbonyl group (e.g., $C_{1-6}$ alkyl-carbonyl group such as acetyl, propionyl, etc.), (n) a carboxyl group, (o) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (p) a carbamoyl group, (q) a mono-lower alkyl-carbamoyl group (e.g., a mono-$C_{1-6}$ alkyl-carbamoyl group such as methylcarbamoyl, ethylcarbamoyl), (r) a di-lower alkyl-carbamoyl group (e.g., a di-$C_{1-6}$ alkyl-carbamoyl group such as dimethylcarbamoyl, diethylcarbamoyl, etc.), (s) an aryl-carbamoyl group (e.g., $C_{6-10}$ aryl-carbamoyl such as phenylcarbamoyl, naphthylcarbamoyl, etc.), (t) a sulfo group, (u) a lower alkyl sulfonyl group (e.g., a $C_{1-6}$ alkyl sulfonyl group such as methylsulfonyl, ethylsulfonyl, etc.), (v) an aryl group (e.g., a $C_{6-10}$ aryl group such as phenyl, naphthyl, etc.), (w) an aryloxy group (e.g., a $C_{6-10}$ aryloxy group such as phenyloxy, naphthyloxy, etc.), (x) an aralkyloxy group (e.g., a $C_{7-16}$ aralkyloxy group such as benzyloxy, etc.), (y) a thiocarbamoyl group, (z) a mono-lower alkyl-thiocarbamoyl group (e.g., a mono-$C_{1-6}$ alkyl-thiocarbamoyl group such as methylthiocarbamoyl, ethylthiocarbamoyl, etc.), (aa) a di-lower alkyl-thiocarbamoyl group (e.g., a di-$C_{1-6}$ alkyl-thiocarbamoyl group such as dimethylthiocarbamoyl, diethylthiocarbamoyl, etc.), (bb) an aryl-thiocarbamoyl group (e.g., a $C_{6-10}$ aryl-thiocarbamoyl group such as phenylthiocarbamoyl, naphthylthiocarbamoyl, etc.), (cc) an aralkyl group (e.g., a $C_{7-16}$ aralkyl group such as benzyl, phenethyl, 2-phenylethyl, 1-phenylpropyl, 2-phenylpropyl, etc.), (dd) a lower alkoxy-carbonyl-lower alkyl group (e.g., a $C_{1-6}$ alkoxy-carbonyl-$C_{1-6}$ alkyl group such as methylcarbonylmethyl, ethylcarbonylmethyl, etc.) or (ee) a carboxyl-lower alkyl group (e.g., a carboxyl-$C_{1-6}$ alkyl group such as carboxylmethyl, carboxylethyl, etc.), etc. are exemplified.

As the "5- to 6-membered heterocyclic group" represented as the "substituents" of the "hydrocarbon group optionally having substituents" represented as the other of the above $R^1$ and $R^2$, for example, a 5- to 6-membered aromatic monocyclic heterocyclic group such as furyl, thienyl, pyrolyl, oxazolyl, isooxazolyl, thiazolyl, isothiazolyl, imidazolyl, pyrazolyl, 1,2,3-oxadiazolyl, 1,2,4-oxadiazolyl, $_{1,3}$, 4-oxadiazolyl, furazanyl, 1,2,3-thiadiazolyl, 1,2,4-thiadiazolyl, $_{1,3}$, 4-thiadiazolyl, 1,2,3-triazolyl, 1,2,4-triazolyl, tetrazolyl, pyridyl, pyridazinyl, pyrimidinyl, pyrazinyl, triazinyl, etc. are exemplified, of them pyridyl, etc. are preferred.

As the "lower alkyl group optionally having substituents", "lower alkenyl group optionally having substituents", "lower alkynyl group optionally having substituents", lower alkoxy group optionally having substituents" and "optionally halogenated lower alkylthio group" represented as the "substituents" of the "hydrocarbon group optionally having substituents" represented as the other of the above $R^1$ and $R^2$, for example, the same those exemplified as the "substituents" of the "aromatic group optionally having substituents" represented by the above $Ar^1$ and $Ar^2$ are used. Furthermore, as the "substituents" of the "optionally substituted lower alkyl group", a mono- or di-$C_{1-6}$ alkyl-amino-methyleneaminosulfonyl group (e.g., dimethylaminomethyleneaminosulfonyl, etc.), etc. are also used.

As the "optionally halogenated lower alkyl group", "optionally halogenated lower alkenyl group", "optionally halogenated lower alkynyl group" and "optionally halogenated lower alkylthio group" represented as the "optionally substituted lower cycloalkyl group", "optionally substituted aryl group", "optionally substituted aryloxy group" and "optionally substituted aralkyloxy group" represented as the "substituents" of the "hydrocarbon group optionally having substituents" represented as the other of the above $R^1$ and $R^2$, for example, the same those exemplified as the "substituents" of the "aromatic group optionally having substituents" represented by the above $Ar^1$ and $Ar^2$ are used.

As preferable "hydrocarbon group" of the "hydrocarbon group optionally having substituents" represented as the other of the above $R^1$ and $R^2$, for example, a lower alkyl group (e.g., a $C_{1-6}$ alkyl group such as methyl, ethyl, propyl, isopropyl, butyl, isobutyl, sec-butyl, tert-butyl, pentyl, hexyl, etc.), etc. are exemplified.

As preferable "substituents" of the "hydrocarbon group optionally having substituents" represented as the other of the above $R^1$ and $R^2$, for example, (i) a lower cycloalkyl group (e.g., a $C_{3-6}$ cycloalkyl group such as cyclopropyl, cyclobutyl, cyclopentyl, cyclohexyl, etc.) which may be substituted by (a) a lower aklyl-carbonyl group (e.g., $C_{1-6}$ alkyl-carbonyl group such as acetyl, propionyl, etc.), (b) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), etc. (ii) a carboxyl group, (iii) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (iv) an aryl group (e.g., a $C_{6-10}$ aryl group such as phenyl, naphthyl, etc.) which may be substituted by (a) a lower alkoxy group (e.g., a $C_{1-6}$ alkoxy group such as methoxy, ethoxy, propoxy, isopropoxy, n-butoxy, isobutoxy, sec-butoxy, tert-butoxy, etc.), (b) a lower alkoxy-carbonyl group (e.g., $C_{1-6}$ alkoxy-carbonyl group such as methoxycarbonyl, ethoxycarbonyl, propoxycarbonyl, butoxycarbonyl, etc.) or (c) a carboxyl group, etc. (v) aryl-carbonyloxy (e.g., a $C_{6-10}$ aryl-carbonyloxy such as phenylcarbonyloxy, etc.), (vi) optionally substituted aminocarbonyl, (vii) 5- or 6-membered heterocyclic group, (viii) sulfonamido which may be substituted by lower alkyl optionally substituted by di-lower alkylamino(e.g., sulfonamide, sulfonamido-$C_{1-6}$ alkyl which may be substituted by $C_{1-6}$ alkyl optionally substituted by di-$C_{1-6}$ alkylamino of dimethylaminomethylsulfonamido, etc.), (ix) lower alkoxy-carbonyl-lower alkoxy-carbonyl (e.g., $C_{1-6}$ alkoxy-carbonyl-$C_{1-6}$ alkoxy-carbonyl such as methoxycarbonylmethoxycarbonyl, ethoxycarbonylethoxycarbonyl, etc.), (x) a lower alkoxy group optionally substituted by (a) aminocarbonyl or (b) carboxyl (e.g., a $C_{1-6}$ alkoxy group optionally substituted by aminocarbonyl such as methoxy, ethoxy, aminocarbonylmethoxy, carboxylmethoxy, etc.), (xi) a lower alkoxy-carbonyl-lower alkyl-carbamoyl (e.g., $C_{1-6}$ alkoxy-carbonyl-$C_{1-6}$ alkyl-carbamoyl such as methoxycarbonylmethylcarbamoyl, etc.), (xii) a hydroxy-lower alkyl-carbamoyl group (e.g., hydroxy-$C_{1-6}$ alkyl-carbamoyl such as hydroxymethylcarbamoyl, hydroxyethylcarbamoyl, etc.), (xiii) a lower alkoxy-carbonyl-carbamoyl group (e.g., a $C_{1-6}$ alkoxy-carbonyl-carbamoyl group such as methoxycarbonylcarbamoyl, ethoxycarbonylcarbamoyl, etc.) or (xiv) a cyano group, etc. are exemplified.

As the other of $R^1$ and $R^2$, preferably, a hydrogen atom, a cyano group, a $C_{1-6}$ alkyl group optionally having substituents, or a $C_{3-6}$ cycloalkyl group, etc. are exemplified, particularly, a hydrogen atom, a cyano group, methyl, tert-butyl, cyclohexyl, —$CH_2CO_2Me$, —$(CH_2)_2CO_2Et$, —$(CH_2)_3CO_2Et$, —$C(Me)_2CO_2Et$, —$C(Me)_2CO_2Me$, —$C(Me)_2CO_2H$, —$(CH_2)_4CO_2Et$, —$CH_2CO_2H$, —$(CH_2)_2OCH_2CONH_2$, —$(CH_2)_2OCH_2CO_2H$, —$(CH_2)_2CO_2H$, —$(CH_2)_4CO_2H$, —$(CH_2)_2OCOPh$, —$CH_2CONMeCH_2CH_2Ph$, —$CH_2Ph$, —$(CH_2)_2Ph$, —$(CH_2)_3Ph$, —$(CH_2)_2C(Me)_2CO_2Et$, —$CH_2C_6H_4(2-CO_2Me)$, —$CH_2C_6H_4(3-CO_2Me)$, —$CH_2C_6H_4(4-CO_2Me)$, —$CH_2C_6H_4(2-CO_2H)$, —$CH_2C_6H_4(3-CO_2H)$, —$(CH_2)_2C(Me)_2SO_2NHCHNMe_2$, —$(CH_2)_2C(Me)_2SO_2NH_2$, —$CH_2CO_2CH_2CO_2Me$, —$CH_2CON(Me)CH_2CO_2Et$, —$CH_2CON(Me)CH_2CO_2H$, —$CH_2CONHC(Me)_2CO_2Et$, —$CH_2CONHCH_2CO_2Me$, —$CH_2CONHCH_2CO_2H$, —$CH_2CONH(CH_2)_2CO_2Et$, —$CH_2CONH(CH_2)_2CO_2H$, —$(CH_2)_2CONHCO_2Me$, —$(CH_2)_2CONHCO_2H$, —$(CH_2)_4CN$,

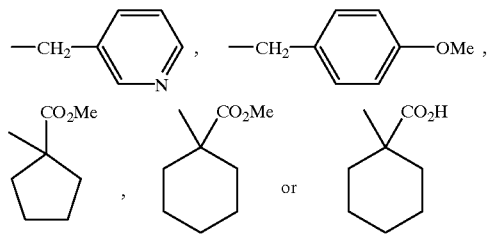

etc. are exemplified (Me represents methyl, Et represents ethyl, Ph represents phenyl).

As the "substituents" of the "$C_{1-6}$ alkyl group optionally having substituents" and "$C_{3-6}$ cyclo alkyl group optionally having substituents" represented as preferable examples of the other of the $R^1$ and $R^2$, the same those as the "substituents" of the "hydrocarbon group optionally having substituents" represented by the other of the above $R^1$ and $R^2$ are exemplified, and as the "substituents" of the "a $C_{3-6}$ cycloalkyl group optionally having substituents", the same those represented as the "substituents" of the "aromatic group optionally having substituents" represented by the above $Ar^1$ and $Ar^2$, etc. are preferred.

Of the above-mentioned, as $R^1$ and $R^2$, it is preferred that any one of them represents a group represented by the formula:

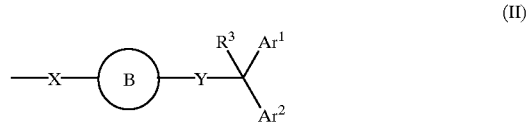

(II)

(wherein $Ar^1$ and $Ar^2$ represent a phenyl; ring B represents

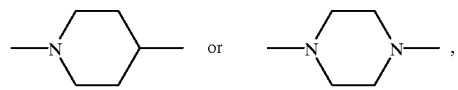

X represents a $C_{1-6}$ alkylene group; Y represents a bond or an oxygen atom; $R^3$ represents a hydrogen atom or a hydroxy group), and the other represents (1) a hydrogen atom, (2) a cyano group, (3) a $C_{1-16}$ alkyl group optionally having substituents selected from the group consisting of (i) a halogen atom, (ii) a carboxyl group, (iii) a $C_{1-6}$ alkoxy-carbonyl group, (iv) a 5- to 6-membered nitrogen-containing heterocyclic group, (v) a carbamoyl group optionally having substituents selected from $C_{7-15}$ aralkyl, carboxyl-$C_{1-6}$ alkyl and $C_{1-6}$ alkoxycarbonyl-$C_{1-6}$ alkyl, (vi) $C_{6-14}$ aryl-carbonyloxy group, (vii) a sulfamoyl, (viii) a mono- or di-$C_{1-6}$ alkyl-amino-methyleneaminosulfonyl group, (ix) a $C_{1-6}$ alkoxy group optionally having carboxyl or carbamoyl and (x) cyano, (4) a $C_{3-7}$ cycloalkyl group optionally having carboxyl or $C_{1-6}$ alkoxycarbonyl, (5) a $C_{6-14}$ aryl group or (6) a $C_{7-}$ aralkyl group optionally having substituents selected from $C_{1-6}$ alkoxy, carboxyl or $C_{1-6}$ alkoxy-carbonyl.

Furthermore, as $R^1$ and $R^2$, it is preferred that any one of them represents a group represented by the formula:

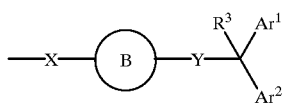

(II)

(wherein Ar$^1$ and Ar$^2$ represent a phenyl; ring B represents

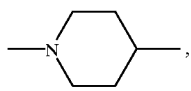

X represents a C$_{1-6}$ alkylene group; Y represents an oxygen atom; R$^3$ represents a hydrogen atom or a hydroxy group), and the other represents (1) a hydrogen atom, (2) a cyano group, (3) a C$_{1-6}$ alkyl group optionally having substituents selected from the group consisting of (i) a halogen atom, (ii) a C$_{1-6}$ alkoxy-carbonyl group, (iii) a carbamoyl group, (iv) cyano or (4) a C$_{3-7}$ cycloalkyl group optionally having C$_{1-6}$ alkoxycarbonyl.

Particularly, as R$^1$ and R$^2$, it is preferred that any one of them represents a group represented by the formula:

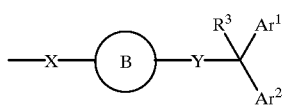

(II)

(wherein Ar$^1$ and Ar$^2$ represent a phenyl; ring B represents

X represents a C$_{1-6}$ alkylene group; Y represents an oxygen atom; R$^3$ represents a hydrogen atom) and the other represents a C$_{1-6}$ alkyl group optionally having carboxyl.

In the above-mentioned formula (I), ring A represents a homocycle optionally having substituents or a nitrogen-containing heterocycle optionally having substituents.

The "homo or (nitrogen-containing)heterocycle" represented as the ring A have any number (preferably 1 to 5, more preferably 1 to 3) of substituents at the position where substitution is possible, and when the number of substituents is not less than 2, each substituent is same or different, and adjacent two substituents may form a ring by binding to each other.

As examples in the case that adjacent two substituents form a ring by binding to each other, for example,
(1) a 3- to 10-membered cyclic hydrocarbon (preferably 5-to 6-membered cyclic hydrocarbon),
(2) a 3- to 9-membered aromatic nitrogen-containing heterocycle (preferably 5- to 6-membered aromatic nitrogen-containing heterocycle) which contains one or two kinds of and not less than one (for example, 1 to 4, preferbaly 1 to 3) hetero atoms selected from a nitrogen atom, an oxygen atom and a sulfur atom in addition to a carbon atom and nitrogen, or
(3) a 3- to 9-membered non-aromatic nitrogen-containing heterocycle (preferably 5- to 6-membered non-aromatic nitrogen-containing heterocycle) which contains one or two kinds of and not less than one (for example, 1 to 4, preferably 1 to 3) hetero atoms selected from a nitrogen atom, an oxygen atom and a sulfur atom in addition to a carbon atom and nitrogen, etc. are exemplified.

More specifically, as the "cyclic hydrocarbon" of the above-mentioned (1), for example, C$_{6-10}$ aryl (e.g., benzene, etc.), C$_{3-10}$ cycloalkene (e.g., cyclobutene, cyclopentene, cyclohexene, cycloheptene, cyclooctene, etc.), C$_{3-10}$ cycloalkane (e.g., cyclobutane, cyclopentane, cyclohexane, cycloheptane, cyclooctane, etc.), etc. are exemplified. Among them, for example, a 5- to 6-membered homocycle such as benzene, cyclopentane, cyclohexane rings, etc. are preferred, and particularly a benzene ring is preferred.

As the "aromatic nitrogen-containing heterocycle" of the above-mentioned (2), for example, a 5- to 9-membered (preferably 5- to 6-membered) aromatic nitrogen-containing heterocycle which contains 1 to 3 hetero atoms selected from a nitrogen atom, an oxygen atom and a sulfur atom in addition to a carbon and nitrogen atom such as pyridine, pyrazine, pyrimidine, pyridazine, pyrrole, imidazole, pyrazole, triazole, thiazole, isothiazole, oxazole and isoxazole, etc. are exemplified.

As the "non-aromatic nitrogen-containing heterocycle" of the above-mentioned (3), for example, a 5- to 9-membered (preferably 5- to 6-membered) non-aromatic nitrogen-containing heterocycle which contains 1 to 3 hetero atoms selected from a nitrogen atom, an oxygen atom and a sulfur atom in addition to a carbon and nitrogen atom such as tetrahydropyridine, dihydropyridine, tetrahydropyrazine, tetrahydropyrimidine, tetrahydropyridazine, dihydropyran, dihydropyrrole, dihydroimidazole, dihydropyrazole, dihydrothiazole, dihydroisothiazole, dihydrooxazole, dihydroisoxazole, piperidine, piperazine, hexahydropyrimidine, hexahydropyridazine, tetrahydropyran, morpholine, thimorpholine, pyrrolidine, imidazolidine, pyrazolidine, tetrahydrothiophene, tetrahydrofuran, tetrahydrothiazole, tetrahydroisothiazole, tetrahydrooxazole, tetrahydroisoxazole rings, etc. are exemplified.

The "homocycle" of the "homocycle optionally having substituents" represented by ring A means a 3- to 10-membered cyclic hydrocarbon, and preferably a 5- or 6-membered cyclic hydrocarbon, etc. are included. Specifically, benzene, C$_{3-10}$ cycloalkene (e.g., cyclobutene, cyclopentene, cyclohexene, cycloheptene, cyclooctene, etc.), C$_{3-10}$ cycloalkane (e.g., cyclobutane, cyclopentane, cyclohexane, cycloheptane, cyclooctane, etc.), etc. are exemplified. Among them, for example, a 5- to 6-membered homocycle such as benzene, cyclopentane, cyclohexane rings, etc. are preferred, and particularly a benzene ring is preferred.

As the "substituents" of the "homocycle optionally having substituents" represented by ring A, the same those as the "substituents" of the "hydrocarbon group optionally having substituents" represented by the other of the above-mentioned R$^1$ and R$^2$, etc. are exemplified. Among them, (i) a halogen atom (e.g., fluorine, chlorine, bromine, iodine, etc.), (ii) a nitro group, (iii) an optionally halogenated lower alkyl group, (iv) an amino group, (v) a mono-lower alkylamino group (e.g., a mono-C$_{1-6}$ alkylamino group such as methylamino, ethylamino, propylamino, isopropylamino, butylamino, etc.), (vi) a di-lower alkylamino group (e.g., a di-C$_{1-6}$ alkylamino group such as dimethylamino, diethylamino, dipropylamino, dibutylamino, etc.), (vii) a carboxyl group, (viii) a lower alkoxy-carbonyl group (e.g., C$_{1-6}$ alkoxy-carbonyl group such as methoxycarbonyl, ethoxycarbonyl, propoxycarbonyl, butoxycarbonyl, etc.), (ix) sulfonamido which may be substituted by lower alkyl optionally having di-lower alkylamino (e.g., sulfonamido, sulfonamido-$C_{1-6}$ alkyl which may be substituted by $C_{1-6}$ alkyl optionally substituted by di-lower alkylamino of dimethylaminomethylsulfonamido, etc.), (x) lower alkoxy-carbonyl-lower alkyl (e.g., $C_{1-6}$ alkoxy-carbonyl-$C_{1-6}$ alkyl such as methoxycarbonylmethyl, ethoxycarbonylmethyl, methoxycarbonylethyl, ethoxycarbonylethyl, etc.), (xi) hydroxy-lower alkyl-carbamoyl (e.g., hydroxy-$C_{1-6}$ alkyl-carbamoyl such as hydroxymethylcarbamoyl hydroxyethylcarbamoyl, etc.), (xii) phenylsulfonamido, (xiii) a hydroxy group and (xiv) a lower alkoxy group optionally having substituents, etc. are exemplified.

As the "optionally halogenated lower alkyl group" represented as the "substituents" of the "homocycle optionally having substituents" represented by ring A, the same those as the "optionally halogenated lower alkyl group" exemplified as the "substituents" of the "aromatic group optionally having substituents" represented by the above-mentioned $Ar^1$ and $Ar^2$ are used.

As the "lower alkoxy group optionally having substituents" represented as the "substituents" of the "homocycle optionally having substituents" represented by ring A, the same those as the "lower alkoxy group optionally having substituents" exemplified as the "substituents" of the "aromatic group optionally having substituents" represented by the above-mentioned $Ar^1$ and $Ar^2$, and as the "substituents" of the "lower alkoxy group optionally having substituents", for example, a lower alkoxy group (e.g., a $C_{1-6}$ alkoxy group such as methoxy, ethoxy, propoxy, isopropoxy, n-butoxy, isobutoxy, sec-butoxy, tert-butoxy, etc.) optionally having 1 or 2 substituents selected from (i) a lower alkoxy-carbonyl group (e.g. $C_{1-6}$ alkoxy-carbonyl group such as methoxycarbonyl, ethoxycarbonyl, etc.) and (ii) an aromatic group (for example, the "aromatic group" of the "aromatic group optionally having substituents" represented by the above-mentioned $Ar^1$ and $Ar^2$, etc.), etc. are exemplified.

As the "nitrogen-containing heterocycle" of the "nitrogen-containing heterocycle optionally having substituents" represented by ring A, for example, a 3- to 13-membered nitrogen-containing heterocycle which contains one nitrogen atom and may further contain, for example, 1 to 3 hetero atoms selected from a nitrogen atom, an oxygen atom, a sulfur atom, etc. are exemplified.

Specifically, for example, a 3- to 9-membered (more preferably 3- to 6-membered) nitrogen-containing heterocyclic group such as

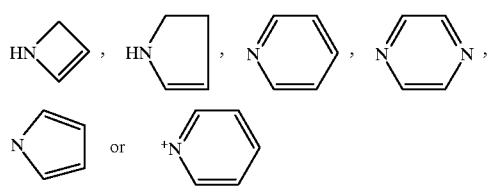

etc. are preferred. Among them,

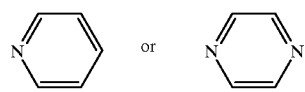

etc. are particularly preferred.

As the "substituents" of the "nitrogen-containing heterocycle optionally having substituents" represented by ring A, for example, the same those exemplified as the "substituents" of the "homocycle optionally having substituents" represented by the above-mentioned ring A, etc. are used.

As ring A, a benzene ring optionally having substituents, a pyridine ring optionally having substituents and a pyrazine ring optionally having substituents, etc. are preferred.

As the "substituents" of the "benzene ring optionally having substituents", "pyridine ring optionally having substituents" and "pyrazine ring optionally having substituents" represented as preferable ring A, for example, the same those exemplified as the "substituents" of the "homocycle optionally having substituents" represented by the above-mentioned ring A or the "nitrogen-containing heterocycle optionally having substituents", etc. are used.

As ring A, (1) an unsubstituted benzene ring or (2) a benzene ring having 1 to 3 substituents selected from (i) a halogen atom (e.g., fluorine, chlorine, bromine, iodine, etc.), (ii) a nitro group, (iii) an optionally halogenated lower alkyl group, (iv) an amino group, (v) a mono-lower alkylamino group (e.g., a mono-$C_{1-6}$ alkylamino group such as methylamino, ethylamino, propylamino, isopropylamino, butylamino, etc.), (vi) a di-lower alkylamino group (e.g., a di-$C_{1-6}$ alkylamino group such as dimethylamino, diethylamino, dipropylamino, dibutylamino, etc.), (vii) a carboxyl group, (viii) a lower alkoxy-carbonyl group (e.g., $C_{1-6}$ alkoxy-carbonyl group such as methoxycarbonyl, ethoxycarbonyl, propoxycarbonyl, butoxycarbonyl, etc.), (ix) sulfonamido which may by substituted by lower alkyl optionally having di-lower alkylamino (e.g., sulfonamido, sulfonamido-$C_{1-6}$ alkyl which may be substituted by $C_{1-6}$ alkyl optionally substituted by di-lower alkylamino of dimethylaminomethylsulfonamido, etc.), (x) lower alkoxy-carbonyl-lower alkyl (e.g., $C_{1-6}$ alkoxy-carbonyl-$C_{1-6}$ alkyl such as methoxycarbonylmethyl, ethoxycarbonylmethyl, methoxycarbonylethyl, ethoxycarbonylethyl, etc.), (xi) hydroxy-lower alkyl-carbamoyl (e.g., hydroxy-$C_{1-6}$ alkyl-carbamoyl such as hydroxymethylcarbamoyl, hydroxyethylcarbamoyl, etc.), (xii) phenylsulfonamido, (xiii) a hydroxy group and (xix) a lower alkoxy group optionally having substituents, etc. are exemplified.

As the "optionally halogenated lower alkyl group" and "optionally halogenated lower alkoxy group" represented as the "substituents" of the ring A, the same those as the "optionally halogenated lower alkyl group" and "optionally halogenated lower alkoxy group" exemplified as the "substituents" of the "aromatic group optionally having substituents" represented by the above-mentioned $Ar^1$ and $Ar^2$, etc. are exemplified.

In the above-mentioned formula (I), D and E are the same or different and represent, independently, an oxygen atom or a sulfur atom. As D and E, the case where both represent an oxygen atom is preferred.

As preferable examples of the compound (I) of the present invention, the following compounds are exemplified.

(I) Compound (Ia)

A compound wherein ring A is a $C_{6-14}$ aryl ring optionally having substituents selected from the group consisting of (i) a halogen atom, (ii) a nitro group, (iii) a $C_{1-6}$ alkyl group optionally having carboxyl or $C_{1-6}$ alkoxy-carbonyl, (iv) $C_{1-6}$ alkoxy group, (v) a hydroxy group, (vi) an amino group, (vii) a mono- or di-$C_{1-6}$ alkylamino group, (viii) a carboxyl group, (ix) a $C_{1-6}$ alkoxy-carbonyl group, (x) a 5-to 6-membered heterocyclic group which contains one or two kinds of and 1 to 4 hetero atoms selected from a nitrogen atom, an oxygen atom and a sulfur atom in addition to a carbon atom, (xi) $C_{1-6}$ alkylsulfonamido, (xii) a carboxy-$C_{1-6}$ alkyl-carbonyl-amino group, (xiii) a $C_{1-6}$ alkoxy-carbonyl-$C_{1-6}$ alkyl-carbonyl-amino group, (xiv)a $C_{1-6}$ alkyl-carbonyl-oxy-$C_{1-6}$ alkyl-carbonyl-amino group and (xv) $C_{6-14}$ aryl-$C_{2-6}$ alkenyl-carbonylamido group optionally substituted by hydroxy or/and $C_{1-6}$ alkoxy; D and E are an oxygen atom; one of $R^1$ and $R^2$ is a group represented by the formula:

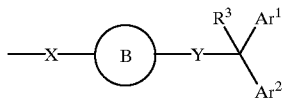
(II)

(wherein $Ar^1$ and $Ar^2$ are a phenyl group, ring B is

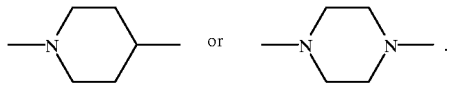

X represents a $C_{1-6}$ alkylene group; Y represents a bond or an oxygen atom; $R^3$ represents a hydrogen atom or a hydroxy group); and the other is (1) a hydrogen atom, (2) a cyano group, (3) a $C_{1-6}$ alkyl group optionally having substituents selected from the group consisting of (i) a halogen atom, (ii) a carboxyl group, (iii) a $C_{1-6}$ alkoxy-carbonyl group, (iv) a 5- to 6-membered nitrogen-containing heterocyclic group, (v) a carbamoyl group optionally having substituents selected from $C_{7-15}$ aralkyl, carboxyl-$C_{1-6}$ alkyl and $C_{1-6}$ alkoxycarbonyl-$C_{1-6}$ alkyl, (vi) $C_{6-14}$ arylcarbonyloxy group, (vii) a sulfamoyl, (viii) a mono- or di-$C_{1-6}$ alkyl-amino-methyleneaminosulfonyl group, (ix) a $C_{1-6}$ alkoxy group optionally having carboxyl or carbamoyl and (x) cyano, (4) a $C_{3-7}$ cycloalkyl group optionally having carboxyl or $C_{1-6}$ alkoxycarbonyl, (5) a $C_{6-14}$ aryl group or (6) a $C_{7-15}$ aralkyl group optionally having substituents selected from $C_{1-6}$ alkoxy, carboxyl or $C_{1-6}$ alkoxycarbonyl.

(II) Compound (Ib)

A compound wherein ring A is a benzene ring optionally having (i) a halogen atom or (ii) $C_{1-6}$ alkoxy-carbonyl; D and E are an oxygen atom; one of $R^1$ and $R^2$ is a group represented by the formula:

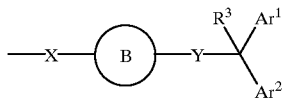
(II)

(wherein $Ar^1$ and $Ar^2$ are a phenyl group, ring B is

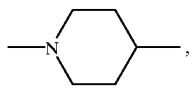

X is a $C_{1-6}$ alkylene group, Y is an oxygen atom, $R^3$ is a hydrogen atom or a hydroxy group); and the other is (1) a hydrogen atom, (2) a cyano group, (3) a $C_{1-6}$ alkyl group optionally having substituents selected from the group consisting of (i) a halogen atom, (ii) a $C_{1-6}$ alkoxy-carbonyl group, (iii) a carbamoyl group, (iv) cyano or (4) a $C_{3-7}$ cycloalkyl group optionally having $C_{1-6}$ alkoxycarbonyl.

(III) Compound (Ic)

A compound wherein ring A is a benzene ring optionally having a halogen atom; D and E are an oxygen atom; one of $R^1$ and $R^2$ is a group represented by the formula:

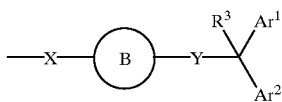
(II)

(wherein $Ar^1$ and $Ar^2$ are a phenyl group, ring B is

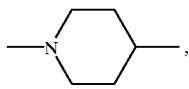

X is a $C_{1-6}$ alkylene group, Y is an oxygen atom, $R^3$ is a hydrogen atom); and the other is a $C_{1-6}$ alkyl group optionally having carboxyl.

(IV) Compound (Id)

1. 2,4-dioxo-1-[4-(4-diphenylmethoxypiperidino)butyl]-1,2,3,4-tetrahydroquinazoline-3-valeric acid or a salt thereof,
2. 2-[2,4-dioxo-1-[4-(4-diphenylmethoxypiperidino)butyl]-1,2,3,4-tetrahydroquinazoline-3-yl]isobutyric acid or a salt thereof (particularly, a salt of hydrochloride), and
3. 2-[2,4-dioxo-1-[4-(4-diphenylmethoxypiperidino)butyl]-6-fluoro-1,2,3,4-tetrahydroquinazoline-3-yl]isobutyric acid or a salt thereof (particularly, a salt of hydrochloride).

A method for producing the compound (I) of the present invention or its salt is described below.

The compound (I) of the present invention or its salt wherein $R^1$ is a group represented by the formula:

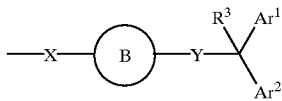

may for example be produced by Method A described below or an equivalent.

(Method A)

A method which reacts a compound represented by the formula:

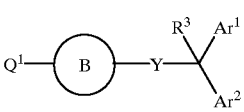
(IIa)

[wherein $Q^1$ represents a leaving group and other symbols represent the same meanings as defined above], or a salt thereof with a compound represented by the formula:

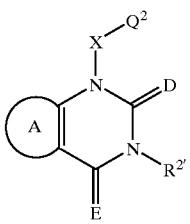
(III)

[wherein $Q^2$ represents a reactive group, $R^{2'}$ represents a hydrogen atom, a cyano group or a hydrocarbon group optionally having substituents and other symbols represent the same meanings as defined above], or a salt thereof.

As the leaving group represented by $Q^1$, for example, alkali metals such as sodium, potassium, etc. are used. And, $Q^1$ may be a hydrogen atom.

As the reacting group represented by $Q^2$, for example, a halogen atom (e.g., chlorine, bromine, iodine, etc.), $C_{6-10}$ arylsulfonyloxy (e.g., benzenesulfonyloxy, p-tolylsulfonyloxy, etc.), $C_{1-4}$ alkyl-sulfonyloxy (e.g., methanesulfonyloxy, etc.), etc. are used.

As the "hydrocarbon group optionally having substituents" represented by the above mentioned $R^{2'}$, for example, the same those as the "hydrocarbon group optionally having substituents" represented by one of the above mentioned $R^1$ and $R^2$, etc. are used.

In the Method A shown above, about 1.1 to about 2.0 moles, preferably about 1.2 to about 1.5 moles of the compound (IIa) or its salt is usually used per 1 mole of the compound (III) or its salt.

The reaction described in Method A shown above is conducted preferably in the presence of a base, and as the base, (1) for example, an alkyllithium reagent such as methyllithium, n-butyllithium, s-butyllithium, t-butyllithium and the like, (2) for example, an inorganic base such as sodium hydroxide, potassium hydroxide, sodium carbonate, potassium carbonate, sodium hydrogen carbonate, potassium hydrogen carbonate, cesium carbonate, sodium hydride, potassium hydride and the like, (3) for example, an organic base such as triethylamine, pyridine, diethylisopropylamine and the like, (4) a metal alcholate such as sodium methoxide, sodium ethoxide, potassium t-butoxide and the like are used, and an alkaline metal such as metal lithium, metal potassium, metal sodium and the like are used instead of the base described in (1) to (4). Among them, potassium carbonate or triethylamine is preferred.

The amount of the base employed is usually about 1.1 moles to about 2.0 moles per 1 mole of the compound (III) or its salt, preferably about 1.2 moles to about 1.5 moles per 1 mole of the compound (III) or its salt.

The reaction described in Method A shown above is conducted also in an inert solvent such as (1) alcohols such as methanol, ethanol, propanol and the like, (2) ethers such as diethyl ether, dioxane, tetrahydrofuran and the like, (3) hydrocarbons such as pentane, hexane, benzene, toluene, xylene and the like, (4) nitrites such as acetonitrile and the like, (5) amides such as N,N-dimethylformamide, N,N-dimethylacetoamide, hexamethylphosphoric triamide and the like, (6) sulfoxides such as dimethyl sulfoxide and the like, (7) aromatic amines such as pyridine, etc.

Among them, those preferred are acetonitrile and N,N-dimethylformamide, etc.

Each of these solvents can be used alone, or in combination with one or more of other solvents in suitable ratios, or with water.

The amount of a solvent employed is about 5 ml to about 50 ml, preferably about 20 ml to about 30 ml per 1 g of the compound (IIa).

And, when a reactive group represented by $Q^2$ is chlorine, etc., it is preferred to add sodium iodide, etc. to the solvent.

Preferred examples of the base and the solvent employed in the reaction described in Method A shown above, for example, (1) triethylamine as a base and acetonitrile as a solvent, (2) triethylamine as a base and N,N-dimethylformamide as a solvent; or, (3) potassium carbonate as a base and N,N-dimethylformamide as a solvent.

The reaction temperature usually ranges from about 10° C. to about 150° C., preferably from room temperature (about 10° C. to about 30° C.) to about 100° C.

The reaction time usually ranges from about 12 hours to about 36 hours, preferably about 15 hours to about 28 hours.

Methods for producing the compounds (IIa), (III) and their salts in Method A shown above are described below.

The compound (IIa) or its salt described above can be produced by a method described, for example, in ①EP-A-0399414, ② J.Org.Chem.,26,4084 (1961), ③ Eur.J.Med.Chem., 26, 69 (1991) or ④ J.Med.Chem., 38, 2472 (1995) or equivalent methods.

The compound (III) or. its salt is for example produced by a method described in Scheme A shown below or equivalent.

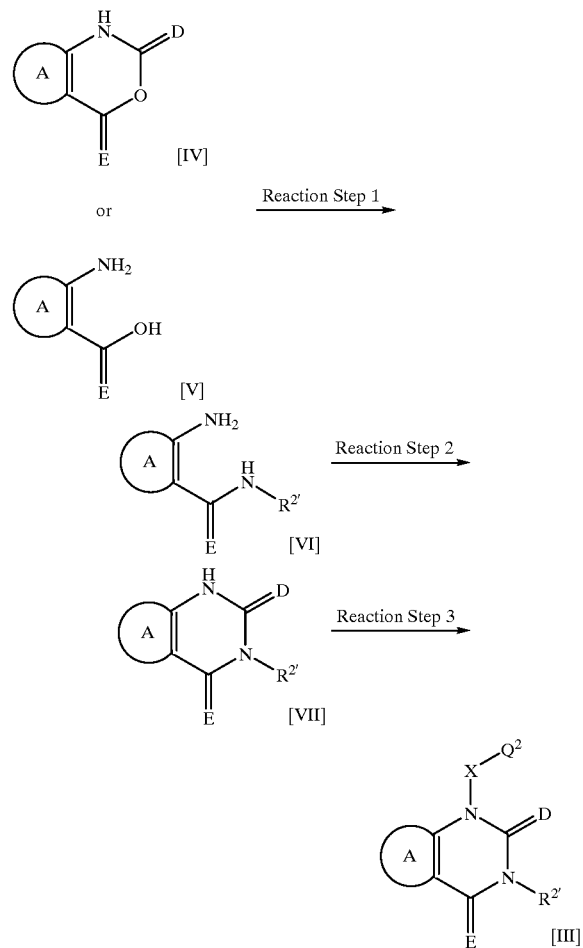

[In the compound [III] to [VII] of the above mentioned scheme A, each symbol represents the same meanings as mentioned above.]

Reaction Step 1 is a process for producing the compound [VI] or its salt by reacting the compound [IV] or the compound [V] or their salts with $R^{2'}$—$NH_2$ (compound [VIII]) ($R^{2'}$ is defined as above) or its salt.

When $R^{2'}$ is a hydrogen atom, etc., however, it is preferable that the group represented by —$NHR^{2'}$ in the compound [VI] shown above is protected with a protective group such as 4-methoxybenzylamine, 4-methoxyphenylamine, 4-(4-methoxy)phenylamine or 2,4-dimethoxybenzylamine (4-methoxybenzylamine being particularly preferred), and a method for protection or deprotection may be one known per se [T. W. Green and P. G. M. Wuts, "Protective Groups in Organic Chemistry", 2nd. ed., John Willey & Sons, Inc., (1991)] or equivalent. When producing the compound [I] of the present invention or its salt, it is preferable that the above mentioned protective group is deprotected in the process in Reaction Step 3 described above.

As specific methods for deprotection, a method which admixes the compound [III] or its salt which has been protected with a protective group listed above, in a solvent mixture of acetonitrile and water (usually about 20 ml to about 40 ml, preferably about 30 ml to about 35 ml (usually acetonitrile:water=5:1) per 1 g of the protected compound), with ammonium cerium (IV) nitrate (usually about 1.2 moles to about 2.0 moles, preferably about 1.5 moles), etc. are exemplified. In Reaction Step 1 described above, about 1.1 moles to about 1.5 moles, preferably about 1.2 moles of the compound [VIII] or its salt is usually used per 1 mole of the compound [IV] or its salt or the compound [V] or their salts.

The compound [IV] and the compound [V] or their salts may be commercially available or may be synthesized by a method described in 1̂ Synthesis, 505 (1980) or 2̂ Adv. Heterocycl. Chem. 28, 127 (1981) or equivalent.

A reaction in Reaction Step 1 described above is, for example, conducted also in an inert solvent such as (1) alcohols such as methanol, ethanol, propanol and the like,
(2) ethers such as diethyl ether, dioxane, tetrahydrofuran and the like,
(3) hydrocarbons such as pentane, hexane, benzene, toluene, xylene and the like,
(4) nitrites such as acetonitrile and the like,
(5) amides such as N,N-dimethylformamide, N,N-dimethylacetoamide, hexamethylphosphoric triamide and the like,
(6) sulfoxides such as dimethyl sulfoxide and the like,
(7) aromatic amines such as pyridine, etc. and among them, tetrahydrofuran, N,N-dimethylformamide, etc. are exemplified as a preferable solvent.

When using the compound [IV] or its salt as a starting material, it is preferable to use tetrahydrofuran and the like as a solvent, while when using the compound [V] or its salt as a starting material, it is preferable to use N,N-dimethylformamide and the like as a solvent. Each of these solvents can be used alone, or in combination with one or more of other solvents in suitable ratios, or with water. The amount of the solvent employed per 1 g of the compound (IV) is about 10 ml to about 50 ml, preferably about 10 ml to about 15 ml.

The reaction described in Reaction Step 1 described above may be conducted in the presence of a base, and especially when using the compound [V] or its salt as a starting material, it is usually preferred to conduct the reaction in the presence of a base. As the base, (1) for example, an alkyllithium reagent such as methyllithium, n-butyllithium, s-butyllithium, t-butyllithium and the like,
(2) for example, an inorganic base such as sodium hydroxide, potassium hydroxide, sodium carbonate, potassium carbonate, sodium hydrogen carbonate, potassium hydrogen carbonate, cesium carbonate, sodium hydride, potassium hydride and the like,
(3) for example, an organic base such as triethylamine, pyridine, diethylisopropylamine and the like,
(4) a metal alcholate such as sodium methoxide, sodium ethoxide, potassium t-butoxide and the like are used, and an alkaline metal such as metal lithium, metal potassium, metal sodium and the like are used instead of the base described in (1) to (4). Among them, triethylamine is exemplified as a preferable base.

The amount of the base employed is usually about 1.2 moles to about 3.0 moles, preferably about 2.0 moles to about 2.5 moles per 1 mole of the compound (V) or its salt.

When the compound [V] or its salt is employed as a starting material in Reaction Step 1 shown above, it is preferable to use about 1.2 equivalents of a condensing agent relative to the compound [V] or its salt, and as the condensing agent, for example, diethyl cyanophosphonate (DEPC), diphenylphosphoric azide (DPPA), N,N-carbonyldiimidazole, 1,3-dicyclohexylcarbodiimide, 2-bromo-1-methylpyridinium iodide, 2-chloro-1-methylpyridinium iodide or 2,2-dithiopyridine and the like are used, and DEPC is preferably used.

The reaction time of the reaction step described above ranges usually from about 15 hours to about 36 hours, preferably about 15 hours to about 24 hours, while the reaction temperature ranges usually from room temperature (about 10° C. to 30° C.) to about 100° C., preferably from room temperature to about 60° C.

The Reaction Step 2 is a process for producing the compound [VII] or its salt by subjecting the compound [VI] or its salt to a ring-closure reaction by means of subjecting a reaction with N,N-carbonyldiimidazole (CDI) or ethyl chloroformate and the like.

In Reaction Step 2 shown above, about 1.0 mole to about 1.5 moles, preferably about 1.2 moles of $Q^3$—CO—$Q^4$ (wherein each of $Q^3$ and $Q^4$ is a leaving group) is usually used per 1 mole of the compound [VI] or its salt.

As the leaving group represented by $Q^3$ or $Q^4$, same or different from each other, (1) a hydrogen atom, (2) a halogen atom (fluorine, chlorine, bromine, iodine and the like), (3) a lower alkyl group (e.g., $C_{1-6}$ alkyl group such as methyl, ethyl, propyl and the like) optionally substituted with a halogen atom (fluorine, chlorine, bromine, iodine and the like), (4) a lower alkoxy group (e.g., $C_{1-6}$ alkoxy group such as methoxy, ethoxy, propoxy and the like) optionally substituted with a halogen atom (fluorine, chlorine, bromine, iodine and the like), or (5) a 5- to 6-membered heterocyclic group (e.g., imidazolyl and the like), etc. are exemplified, and as the $Q^3$—CO—$Q^4$ (wherein $Q^3$ and $Q^4$ are defined as above), specifically N,N-carbonyldiimidazole (CDI), ethyl chlorformate or triphosgene and the like (preferably CDI and ethyl chloroformate and the like), etc. are exemplified.

The reaction in Reaction Step 2 shown above can be conducted in an inert solvent such as (1) alcohols such as methanol, ethanol, propanol and the like,
(2) ethers such as diethyl ether, dioxane, tetrahydrofuran and the like,
(3) hydrocarbons such as pentane, hexane, benzene, toluene, xylene and the like,
(4) nitrites such as acetonitrile and the like,
(5) amides such as N,N-dimethylformamide, N,N-dimethylacetoamide, hexamethylphosphoric triamide and the like,
(6) sulfoxides such as dimethyl sulfoxide and the like,
(7) aromatic amines such as pyridine, and, among them, those preferred are ethanol, N,N-dimethylformamide, pyridine and the like.

N,N-dimethylformamide is a preferred solvent when the compound [VI] or its salt is reacted with CDI, while pyridine is a preferred solvent when the compound [VI] or its salt is reacted with ethyl chloroformate. Each of these solvents can be used alone, or in combination with one or more of other solvents in suitable ratios, or with water. The amount of the solvent employed is about 3 ml to about 10 ml, preferably about 3 ml to about 7 ml per 1 g of the compound (VI).

When the compound [VI] or its salt has a bulky substituent such as isobutyrate group (—C(Me)$_2$CO$_2$Et) as a group $R^{2'}$ in the reaction described in Reaction Step 2 shown above, the compound [VII] is obtained through a conversion into a carbamate form by a reaction with ethyl chloroformate and the like, followed by a ring-closure reaction of the carbamate form in the presence of a base, and when describing more accurately, further followed by a neutralization with an acid.

As the base,
(1) for example, an alkyllithium reagent such as methyllithium, n-butyllithium, s-butyllithium, t-butyllithium and the like,
(2) for example, an inorganic base such as sodium hydroxide, potassium hydroxide, sodium carbonate, potassium carbonate, sodium hydrogen carbonate, potassium hydrogen carbonate, cesium carbonate, sodium hydride, potassium hydride and the like,
(3) for example, an organic base such as triethylamine, pyridine, diethylisopropylamine and the like,
(4) a metal alcholate such as sodium methoxide, sodium ethoxide, potassium t-butoxide and the like are used, and an alkaline metal such as metal lithium, metal potassium, metal sodium and the like are used instead of the base described in (1) to (4). Among them, sodium ethoxide, etc. are exemplified as a preferable base.

The amount of the base employed is usually about 1.0 moles to about 2.0 moles, preferably about 1.0 moles to about 1.2 moles per 1 mole of the compound [VI] or its salt.

The reaction temperature of Reaction Step 2 shown above ranges usually from room temperature (about 10° C. to about 30° C.) to about 180° C., preferably from 120° C. to 150° C., while the reaction time ranges usually from 8 hours to 24 hours, preferably 15 hours to 24 hours.

The ring-closure reaction of a carbamate form when the compound [VI] or its salt, in the reaction described in Reaction Step 2 shown above, has a bulky substituent such as isobutyrate group (—C(Me)$_2$CO$_2$Et) as a group $R^{2'}$ is performed usually under reflux at a reaction temperature ranging from about 100° C. to about 120° C. The reaction time usually ranges from about 8 hours to about 24 hours, preferably about 12 hours to about 18 hours. And, as the solvent, for example, an inert solvent such as
(1) alcohols such as methanol, ethanol, propanol and the like,
(2) ethers such as diethyl ether, dioxane, tetrahydrofuran and the like,
(3) hydrocarbons such as pentane, hexane, benzene, toluene, xylene and the like,
(4) nitriles such as acetonitrile and the like,
(5) amides. such as N,N-dimethylformamide, N,N-dimethylacetoamide, hexamethylphosphoric triamide and the like,
(6) sulfoxides such as dimethyl sulfoxide and the like,
(7) aromatic amines such as pyridine, etc. are exemplified, and the amount of the solvent employed is usually about 10 ml to about 30 ml, preferably about 15 ml to about 20 ml per 1 g of the compound [VI].

The Reaction Step 3 is a process for producing the compound [III] or its salt by reacting compound [VII] or its salt with $Q^{2'}$—X—$Q^{2'}$(wherein $Q^2$ and X are defined as above, and $Q^{2'}$ is same to $Q^2$) or its salt.

The reaction in Reaction Step 3 shown above can be conducted in an inert solvent such as
(1) alcohols such as methanol, ethanol, propanol and the like,
(2) ethers such as diethyl ether, dioxane, tetrahydrofuran and the like,
(3) hydrocarbons such as pentane, hexane, benzene, toluene, xylene and the like,
(4) nitrites such as acetonitrile and the like,
(5) amides such as N,N-dimethylformamide, N,N-dimethylacetoamide, hexamethylphosphoric triamide and the like,
(6) sulfoxides such as dimethyl sulfoxide and the like,
(7) aromatic amines such as pyridine, and, among them, N,N-dimethylformamide and the like are exemplified as a preferable solvent.

Each of these solvents can be used alone, or in combination with one or more of other solvents in suitable ratios, or with water. The amount of the solvent employed is about 5 ml to about 20 ml, preferably about 5 ml to about 15 ml per 1 g of the compound (VII).

The reaction described in Reaction Step 3 shown above may also be conducted in the presence of a base. As the base,
(1) for example, an alkyllithium reagent such as methyllithium, n-butyllithium, s-butyllithium, t-butyllithium and the like,
(2) for example, an inorganic base such as sodium hydroxide, potassium hydroxide, sodium carbonate, potassium carbonate, sodium hydrogen carbonate, potassium hydrogen carbonate, cesium carbonate, sodium hydride, potassium hydride and the like,
(3) for example, an organic base such as triethylamine, pyridine, diethylisopropylamine and the like,
(4) a metal alcholate such as sodium methoxide, sodium ethoxide, potassium t-butoxide and the like, etc. are used, and an alkaline metal such as metal lithium, metal potassium, metal sodium and the like are used instead of the base described in (1) to (4). Among them, sodium hydride is exemplified as a preferable base.

The amount of the base employed is usually about 1.1 moles to about 2.0 moles, preferably about 1.2 moles to about 1.5 moles per 1 mole of the compound [VII] or its salt.

The reaction temperature of Reaction Step 3 shown above ranges usually from 10° C. to 30° C., preferably from 15° C. to 25° C., while the reaction time ranges usually from 8 hours to 24 hours, preferably 15 hours to 24 hours.

When $R^{2'}$ is a hydrogen atom (such as a compound in Reaction Step 3 in which 4-methoxybenzyl group is deprotected) in the compound [III] described above, the compound [I] of the present invention or its salt can be produced by a reaction (Reaction Step 4) of the compound [III] with a compound represented by the formula: $R^{2'}$-$L^1$ [XI] (wherein $R^{2'}$ is defined as above (but other than hydrogen atom), $L^1$ is a halogen atom (e.g., chlorine, bromine, iodine and the like)) in the presence of a suitable base (preferably potassium carbonate and the like) in a suitable solvent (preferably N,N-dimethylformamide) with using NaI and the like if necessary.

As the solvent employed in Reaction Step 4 shown above, for example, an inert solvent such as (1) alcohols such as methanol, ethanol, propanol and the like,
(2) ethers such as diethyl ether, dioxane, tetrahydrofuran and the like,
(3) hydrocarbons such as pentane, hexane, benzene, toluene, xylene and the like,
(4) nitrites such as acetonitrile and the like,
(5) amides such as N,N-dimethylformamide, N,N-dimethylacetoamide, hexamethylphosphoric triamide and the like, etc. are exemplified, and, among them, N,N-dimethylformamide and the like are preferably used.

Each of these solvents can be used alone, or in combination with one or more of other solvents in suitable ratios, or with water. The amount of the solvent employed is about 10 ml to about 30 ml, preferably about 15 ml to about 20 ml per 1 g of the compound (I).

As the base employed in Reaction Step 4 shown above,
(1) an alkyllithium reagent such as methyllithium, n-butyllithium, s-butyllithium, t-butyllithium and the like,
(2) an inorganic base such as sodium hydroxide, potassium hydroxide, sodium carbonate, potassium carbonate, sodium hydrogen carbonate, potassium hydrogen carbonate, cesium carbonate, sodium hydride, potassium hydride and the like,
(3) an organic base such as triethylamine, pyridine, diethylisopropylamine and the like,
(4) a metal alcholate such as sodium methoxide, sodium ethoxide, potassium t-butoxide and the like are used, and an alkaline metal such as metal lithium, metal potassium, metal sodium and the like are used instead of the base described in (1) to (4).

The amount of the base employed is usually about 1.1 moles to about 2.0 moles, preferably about 1.1 moles to about 1.5 moles per 1 mole of the compound [I] or its salt.

The reaction temperature of Reaction Step 4 shown above ranges usually from 10° C. to 100° C., preferably from 20° C. to 60° C., while the reaction time ranges usually from 12 hours to 36 hours, preferably 16 hours to 30 hours.

When $R^2$ is a group represented by the formula:

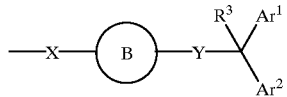

in compound (I) of the present invention or its salt, the production may follow Method B shown below or equivalent.

(Method B)

A production method in which a compound represented by the formula:

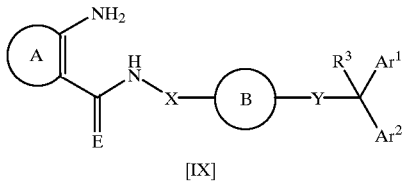

[wherein each symbol is defined as above] or its salt is reacted with $Q^3$—CO—$Q^4$ (each of $Q^3$ and $Q^4$ is a leaving group) whereby subjecting to a ring-closure reaction.

As the leaving group represented by each of $Q^3$ and $Q^4$, the same those as described above are used.

A ring-closure reaction in Method B may be conducted similarly to the ring-closure reaction in Reaction Step 2 in Method A described above, and preferably the compound [IX] and CDI (usually in an amount of about 1.1 moles to about 1.5 moles, preferably about 1.2 moles per 1 mole of the compound [IX]) are reacted in N,N-dimethylformamide (usually in a volume of about 10 ml to 20 ml, preferably about 15 ml per 1 g of the compound [IX]).

The compound [IX] described above is produced by reacting the compound [IV] or its salt described in Scheme A shown above with a compound represented by the formula:

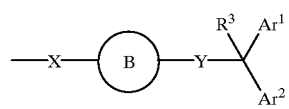

[wherein each symbol is defined as above] or its salt (Method C).

The compound [X] described above or its salt may be synthesized by a method described, for example, in 1̂ J.Heterocycl. Chem. 22, 1035(1985) or 2̂ Chem. Pham. Bull., 37 (1), 100(1989) or equivalent.

In Method C shown above, about 1.1 moles to about 1.5 moles, preferably about 1.2 moles of the compound (X) or its salt is usually used per 1 mole of the compound (IV) or its salt.

The reaction described in Method C shown above may be conducted also in the presence of a base, and as the base
(1) for example, an alkyllithium reagent such as methyllithium, n-butyllithium, s-butyllithium, t-butyllithium and the like,
(2) for example, an inorganic base such as sodium hydroxide, potassium hydroxide, sodium carbonate, potassium carbonate, sodium hydrogen carbonate, potassium hydrogen carbonate, cesium carbonate, sodium hydride, potassium hydride and the like,
(3) for example, an organic base such as triethylamine, pyridine, diethylisopropylamine and the like,
(4) a metal alcholate such as sodium methoxide, sodium ethoxide, potassium t-butoxide and the like are used, and an alkaline metal such as metal lithium, metal potassium, metal sodium and the like are used instead of the base described in (1) to (4). Among them, potassium carbonate or triethylamine and the like are exemplified as a preferable base.

The amount of the base employed is usually about 1.1 moles to about 1.5 moles, preferably about 1.2 moles per 1 mole of the compound [IV] or its salt.

A reaction described in Method C shown above is conducted also in an inert solvent such as
(1) alcohols such as methanol, ethanol, propanol and the like,
(2) ethers such as diethyl ether, dioxane, tetrahydrofuran and the like,
(3) hydrocarbons such as pentane, hexane, benzene, toluene, xylene and the like,
(4) nitrites such as acetonitrile and the like,
(5) amides such as N,N-dimethylformamide, N,N-dimethylacetoamide, hexamethylphosphoric triamide and the like, (6) sulfoxides such as dimethyl sulfoxide and the like,
(7) aromatic amines such as pyridine.

Among them, tetrahydrofuran, N,N-dimethylformamide and the like are exemplified as a preferable solvent.

Each of these solvents can be used alone, or in combination with one or more of other solvents in suitable ratios, or with water. The amount of the solvent employed is about 20 ml to about 40 ml, preferably about 25 ml to about 30 ml per 1 g of the compound (IV).

The reaction temperature usually ranges from about 10° C. to about 100° C., preferably from about 20° C. to about 25° C.

The reaction time usually ranges from about 12 hours to about 36 hours, preferably about 16 hours to about 24 hours.

The compound (I) or its salt thus obtained, when it is in a free form, can be converted by a standard method to a salt, or when in the form of a salt can be converted by a standard method into a free form or other salts. The compound (I) or its salt thus obtained can be isolated and purified by a known method such as solvent extraction, liquid phase conversion, partition, salting-out, crystallization, recrystallization, chromatography and the like. When the compound (I) or its salt includes any optical isomer, a standard optical resolution method is employed to resolve it into R and S forms.

In each reaction of the present invention and in each reaction for synthesizing each starting material, an amino group, a carboxyl group and a hydroxyl group, each as a substituent, if any, in a starting material may be protected by a protective group employed customarily in peptide chemistry, which may be deprotected after reaction if necessary in order to yield an intended compound.

As a protective group for an amino group, formyl, an optionally substituted $C_{1-6}$ alkylcarbonyl (e.g., acetyl, ethylcarbonyl and the like), phenylcarbonyl, an optionally substituted $C_{1-6}$ alkyloxycarbonyl (e.g., methoxycarbonyl, ethoxycarbonyl and the like), optionally substituted phenyloxycarbonyl, an optionally substituted $C_{7-10}$ aralkylcarbonyl (e.g., benzylcarbonyl and the like), optionally substituted trityl, optionally substituted phthaloyl or optionally substituted N,N-dimethylaminomethylene, optionally substituted 4-methoxybenzylamine, optionally substituted 4-methoxyphenylamine, optionally substituted 4-(4-methoxy)phenylamine or optionally substituted 2,4-dimethoxybenzylamine and the like are used. As the substituents for them, a halogen atom (e.g., fluorine, chlorine, bromine, iodine and the like), a $C_{1-6}$ alkylcarbonyl (e.g., methylcarbonyl, ethylcarbonyl, butylcarbonyl and the like), nitro group and the like are used, and the number of the substituents is one to about three.

As a protective group for a carboxyl group, an optionally substituted $C_{1-6}$ alkyl (e.g., methyl, ethyl, n-propyl, i-propyl, n-butyl, tert-butyl and the like), optionally substituted phenyl, optionally substituted trityl or optionally substituted silyl and the like are used. As substituents for them, a halogen atom (e.g., fluorine, chlorine, bromine, iodine and the like), formyl, a $C_{1-6}$ alkylcarbonyl (e.g., acetyl, ethylcarbonyl, butylcarbonyl and the like), nitro group and the like are used, and the number of the substituents is one to about three.

As a protective group for a hydroxyl group, an optionally substituted $C_{1-6}$ alkyl (e.g., methyl, ethyl, n-propyl, i-propyl, n-butyl, tert-butyl and the like), optionally substituted phenyl, an optionally substituted $C_{7-10}$ aralkyl (e.g., benzyl and the like), formyl, an optionally substituted $C_{1-6}$ alkylcarbonyl (e.g., acetyl, ethylcarbonyl and the like), optionally substituted phenyloxycarbonyl, optionally substituted benzoyl, an optionally substituted $C_{7-10}$ aralkylcarbonyl (e.g., benzylcarbonyl and the like), optionally substituted pyranyl, optionally substituted furanyl or optionally substituted silyl and the like are used. As substituents for them, a halogen atom (e.g., fluorine, chlorine, bromine, iodine and the like), a $C_{1-6}$ alkyl (e.g., methyl, ethyl, n-propyl and the like), phenyl, a $C_{7-10}$ aralkyl (e.g., benzyl), nitro group and the like are used, and the number of the substituents is one to about four.

A method for deprotecting a protective group is, or may be in accordance with one known per se, and may employ a treatment with an acid, a base, a reducing agent, UV, hydrazine, phenylhydrazine, sodium N-methylthiocarbamate, tetrabutylammonium fluoride, palladium acetate and the like.

And, a salt of the compound (I) is preferably one which is pharmaceutically acceptable, for example, a salt with an inorganic base, a salt with an organic base, a salt with an inorganic acid, a salt with an organic acid, a salt with a basic or acidic amino acid.

Preferred examples of a salt with an inorganic base are an alkali metal salt (e.g., sodium salt, potassium salt and the like), an alkaline earth metal salt (e.g., calcium salt, magnesium salt and the like), an aluminum salt, an ammonium salt and the like.

Preferred examples of a salt with an organic base are a salt with trimethylamine, triethylamine, pyridine, picoline, ethanolamine, diethanolamine, triethanolamine, dicyclohexylamine, N,N'-dibenzylethylenediamine and the like.

Preferred examples of a salt with an inorganic acid are a salt with hydrochloric acid, hydrobromic acid, nitric acid, sulfuric acid, phosphoric acid and the like.

Preferred examples of a salt with an organic acid are a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluene sulfonic acid and the like.

Preferred examples of a salt with a basic amino acid are a salt with arginine, lysine, ornitine and the like.

Preferred examples of a salt with a acidic amino acid are a salt with aspartic acid, glutamic acid and the like. When an intended compound is obtained as a free form, it may be converted into a salt by a standard method, and when an intended compound is obtained as a salt, it may be converted into a free form by a standard method.

The compound (I) of the present invention or its salt may be a hydrate or an anhydride.

Since the compound (I) of the present invention or its salt has excellent anti-allergic action, anti-histaminic action, anti-inflammatory action, anti-PAF (platelet activating factor) action, eosinophil chemotaxis-inhibiting action and the like and has a lower toxicity (acute toxicity: LD50>2 g/kg), it can safely be used as an anti-allergic agent in mammals (e.g., human, mouse, dog, rat, cattle and the like). Moreover, the compound (I) or its salt also has an eosinophil chemotaxis-inhibiting effect in combination with an anti-histaminic action, and can be used for preventing or treating an allergic disease such as urticaria (e.g., chronic urticaria), atopic dermatitis, allergic rhinitis, allergic conjunctivitis, hypersensitive pneumonitis and the like, a dermal disease such as eczema, herpetic dermatitis, psoriasis and the like, a respiratory disease such as eosinophilic pneumonia (PIE syndrome), asthma (e.g., bronchial asthma) and the like in mammals as discussed above. Among them, it is used as an agent for preventing or treating an allergic disease, asthma (e.g., bronchial asthma), allergic conjunctivitis, allergic rhinitis, urticaria (e.g., chronic urticaria) and atopic dermatitis. The way of administration may be oral or parenteral.

A formulation employed in this invention may contain a pharmaceutical component as an active ingredient in addition to the compound (I) or its salt. As such pharmaceutically active component, for example, an anti-asthmatic agent (e.g., theophylline, procaterol, ketotifen, azelastine, seratrodast and the like), an anti-allergic agent (e.g., ketotifen, terfenadine, azelastine, epinastine and the like), an anti-inflammatory agent (e.g., dichlofenac sodium, ibuprofen, indomethacin and the like), an anti-bacterial agent (e.g., cefixime, cefdinir, ofloxacin, tosufloxacin and the like), an anti-fungal agent (e.g., fluconazole, itraconazole and the like), etc. are exemplified. These components are not to particularly be limited as long as an objective of the invention can be achieved, and may be added in a suitable amount. When the compound or its salt and a pharmaceutically active component described above are administered as active ingredients, two or more pharmaceutically active components may be formulated into a single formulation, or formulated independently and then administered simultaneously or at a certain interval. As specific examples of a dosage form, for example, tablet (including sugar-coated and film-coated tablets), pill, capsule (including microcapsule), granule, powder, dust, syrup, emulsion, suspension, formulation for injection, formulation for inhalation, ointment and the like are used. These formulations may be prepared by a standard method (e.g., one described in Japanese Pharmacopoeia).

While the amount of the compound (I) or its salt contained in an inventive formulation may vary depending on dosage forms, it ranges from about 0.01 to about 100% by weight based on the total weight of the formulation, preferably about 0.1 to about 50% by weight, more preferably about 0.5 to about 20% by weight.

Specifically a tablet is produced by mixing a pharmaceutical as it is with an excipient, a binder, a disintegrant or other suitable additives to form a uniform mixture which is then granulated by a suitable method and admixed with a glidant and the like and then compressed into a tablet, or by mixing a pharmaceutical as it is with an excipient, a binder, a disintegrant or other suitable additives to form a uniform mixture which is then directly compressed into a tablet, or by compressing a previously formulated granule directly, or after mixing uniformly with suitable additives, into a tablet. The formulation may contain a colorant and a flavor if necessary. The formulation may also be coated with a suitable coating.

A formulation for injection may be produced by dissolving, suspending or emulsifying a certain amount of a pharmaceutical in water for injection, physiological saline or Linger's solution when preparing an aqueous formulation, or in an ordinary vegetable oil when preparing a non-aqueous formulation, whereby obtaining a certain volume, or by enclosing a certain amount of a pharmaceutical in a vial for injection.

As a carrier for an oral formulation, for example, a material used customarily in the art of drug formulation such as starch, mannitol, crystalline cellulose, sodium carboxymethylcellulose and the like are used. As a carrier for injection, for example, distilled water, physiological saline, glucose solution, infusion fluid and the like are used. Otherwise, additives employed customarily in the art of drug formulation may also be added appropriately.

The dose of the formulation may vary depending on age, body weight, condition, administration route, administration frequency and the like, and a daily dose as an active ingredient (the compound (I) or its salt) in an adult having asthma is usually about 0.1 to 100 mg/kg, preferably about 1 to 50 mg/kg, more preferably about 1 to 10 mg/kg, which is given orally once a day or twice as divided doses.

The present invention will be described in more detail hereinunder, with reference to Examples and Reference Examples. However, the present invention is not restricted by these examples, and changes and modifications can be made within the range which does not deviate the scope of the present invention.

Elution in the column chromatography in the following Reference Examples and Examples was conducted under observation by TLC (thin layer chromatography), unless otherwise specifically indicated. In the TLC observation, 60F$_{254}$ produced by Merck Co. was used as the TLC plate, and the solvent employed in the column chromatography was used as the developing eluent. For the detection, a UV detector was used. As silica gel for the column chromatography, Silica Gel 60 (70–230 mesh) produced by Merck Co. was used. Room temperature as referred to hereinunder generally means temperatures falling between about 10° C. and about 35° C. For drying the extract solutions, sodium sulfate or magnesium sulfate was used.

The meanings of the abbreviations as used in the following Examples and Reference Examples are as follows:
NMR: Nuclear magnetic resonance spectrum
Hz: Herz
J: coupling constant
m: multiplet
q: quartet
t: triplet
d: doublet
s: singlet
b: broad
like: approximate

REFERENCE EXAMPLE 1

2-Amino-N-(4-methoxybenzyl)benzamide

Isatoic anhydride (10.0 g) was suspended in tetrahydrofuran (150 ml) and treated dropwise with 4-methoxybenzylamine (9.61 ml). The reaction mixture was stirred at room temperature for 20 hours and then the solvent was distilled off under reduced pressure to give a crude crystal (17.8 g, about 100%) of the title compound. Recrystallization from ethyl acetate-isopropyl ether yielded a colorless crystal, melting point 104 to 105° C.

IR (Nujor): 3450, 3350, 3300, 1625, 1600, 1580, 1530, 1510 cm$^{-1}$.

$^1$H-NMR (CDCl$_3$) δ:3.81 (3H, s), 4.54 (2H, d, J=5.4 Hz), 5.56 (2H, bs), 6.25 (1H, bs), 6.58–6.73 (2H, m), 6.89 (2H, d, J=8.2 Hz), 7.15–7.34 (4H, m).

Elemental Analysis for C$_{15}$H$_{16}$N$_2$O$_2$: Calcd. (%): C, 70.29; H, 6.29; N, 10.93. Found (%): C, 70.19; H, 6.32; N, 11.08.

REFERENCE EXAMPLE 2

2-Amino-N-(4-methoxybenzyl)nicotinamide

2-Aminonicotinic acid (7.15 g) was suspended in N,N-dimethylformamide (100 ml) and 4-methoxybenzylamine (8.12 ml), diethyl cyanophosphonate (9.92 ml) and triethylamine (8.66 ml) were added sequentially with stirring and cooling on ice. The reaction mixture was stirred at room temperature for 15.5 hours, concentrated under reduced pressure, and extracted with ethyl acetate. The extract was washed with water, dried (Na$_2$SO$_4$) and then the solvent was distilled off under reduced pressure to give the title compound (15.9 g, about 100%). Recrystallization from ethyl acetate-ethyl ether yielded a colorless crystal, melting point 165 to 166° C.

IR (Nujor): 3420, 3280, 3110, 1620, 1570, 1520, 1510 cm$^{-1}$.

$^1$H-NMR (CDCl$_3$) δ: 3.81 (3H, s), 4.54 (2H, d, J=5.2 Hz), 6.21 (1H, bs), 6.37 (2H, bs), 6.58 (1H, dd, J=7.6, 5.0 Hz), 6.90 (2H, d, J=8.6 Hz), 7.28 (2H, d, J=8.2 Hz), 7.58 (1H, dd, J=7.8, 1.8 Hz), 8.16 (1H, dd, J=4.8, 1.6 Hz).

Elemental Analysis for $C_{14}H_{15}N_3O_2$: Calcd. (%): C, 65.36; H, 5.88; N, 16.33. Found (%): C, 65.52; H, 5.93; N, 16.41.

REFERENCE EXAMPLE 3

3-Amino-N-(4-methoxybenzyl)pyrazine-2-carboxamide

Using the method similar to that in Reference Example 2 and starting from 3-aminopyrazine-2-carboxylic acid (4.90 g), the title compound (5.57 g, 61%) was synthesized. Recrystallization from ethyl acetate-ethyl ether yielded a colorless crystal, melting point 93 to 95° C.

IR (KBr): 3320, 1659, 1595, 1510 cm$^{-1}$.

$^1$H-NMR (CDCl$_3$) δ: 3.80 (3H, s), 4.54 (2H, d, J=5.8 Hz), 6.88 (2H, d, J=8.4 Hz), 7.28 (2H, d, J=8.0 Hz), 7.76 (1H, d, J=2.2 Hz), 8.13 (1H, d, J=2.2 Hz), 8.15 (1H, bs).

Elemental Analysis for $C_{13}H_{14}N_4O_2 \cdot 0.5H_2O$: Calcd. (%): C, 58.42; H, 5.66; N, 20.96. Found (%): C, 58.31; H, 5.48; N, 21.26.

REFERENCE EXAMPLE 4

2-Amino-4-chloro-N-(4-methoxybenzyl)benzamide

Using the method similar to that in Reference Example 2 and starting from 2-amino-4-chlorobenzoic acid (5.00 g), the title compound (8.86 g, 47%) was synthesized. Recrystallization from ethyl acetate-isopropyl ether yielded a colorless crystal, melting point 113 to 115° C.

IR (KBr): 3452, 3340, 2933, 1633, 1612, 1575, 1513, 1488 cm$^{-1}$.

$^1$H-NMR (CDCl$_3$) δ: 3.81 (3H, s), 4.52 (2H, d, J=5.4 Hz), 6.19 (1H, bs), 6.58 (1H, dd, J=8.4, 2.0 Hz), 6.68 (1H, d, J=2.2 Hz), 6.89 (1H, d, J=8.8 Hz), 7.21 (1H, d, J=8.4 Hz), 7.27 (2H, d, J=8.4 Hz).

Elemental Analysis for $C_{15}H_{15}N_2O_2Cl \cdot 0.7H_2O$: Calcd. (%): C, 59.39; H, 5.45; N, 9.23. Found (%): C, 59.42; H, 5.53; N, 8.67.

REFERENCE EXAMPLE 5

2-Amino-5-chloro-N-(4-methoxybenzyl)benzamide

Using the method similar to that in Reference Example 1 and starting from 5-chloroisatoic anhydride (5.00 g), the title compound (4.40 g, 60%) was synthesized. Recrystallization from ethyl acetate-ethyl ether yielded a colorless crystal, melting point 137 to 139° C.

IR (KBr): 3458, 3357, 3289, 1612, 1579, 1536, 1515, 1484 cm$^{-1}$.

$^1$H-NMR (CDCl$_3$) δ: 3.82 (3H, s), 4.52 (2H, d, J=5.4 Hz), 6.20 (1H, bs), 6.63 (1H, d, J=8.8 Hz), 6.85–6.96 (4H, m), 7.15 (1H, dd, J=8.6, 2.4 Hz), 7.24–7.34 (1H, m).

Elemental Analysis for $C_{15}H_{15}N_2O_2Cl$: Calcd. (%): C, 61.97; H, 5.20; N, 9.63. Found (%): C, 61.82; H, 5.07; N, 9.72.

REFERENCE EXAMPLE 6

2-Amino-N-(4-methoxybenzyl)-4-nitrobenzamide

Using the method similar to that in Reference Example 2 and starting from 2-amino-4-nitrobenzoic acid (5.00 g), the title compound (8.03 g, 97%) was synthesized. Recrystallization from ethyl acetate-isopropyl ether yielded a yellow crystal, melting point 129 to 131° C.

IR (KBr): 3469, 3344, 2935, 1644, 1571, 1513, 1492 cm$^{-1}$.

$^1$H-NMR (CDCl$_3$) δ: 3.81 (3H, s), 4.55 (2H, d, J=5.6 Hz), 5.85 (2H, bs), 6.29 (1H, bs), 6.90 (2H, d, J=8.4 Hz), 7.28 (2H, d, J=8.4 Hz), 7.38–7.43 (2H, m), 7.51 (1H, s).

Elemental Analysis for $C_{15}H_{15}N_3O_4$: Calcd. (%): C, 59.80; H, 5.02; N, 13.95. Found (%): C, 59.70; H, 4.83; N, 13.59.

REFERENCE EXAMPLE 7

2-Amino-N-(4-methoxybenzyl)-5-nitrobenzamide

Using the method similar to that in Reference Example 2 and starting from 2-amino-5-nitrobenzoic acid (10.0 g), the title compound (13.8 g, 84%) was synthesized. Recrystallization from ethyl acetate-isopropyl ether yielded a yellow crystal, melting point 189 to 191° C.

IR (KBr): 3476, 3360, 3289, 2921, 1622, 1593, 1537, 1514, 1501 cm$^{-1}$.

$^1$H-NMR (CDCl$_3$) δ:3.82 (3H, s), 4.55 (2H, d, J=5.4 Hz), 6.42 (1H, bs), 6.55 (2H, bs), 6.66 (1H, d, J=9.0 Hz), 6.91 (2H, d, J=8.4 Hz), 7.29 (2H, d, J=8.4 Hz), 8.09 (1H, dd, J=9.0, 2.2 Hz), 8.30 (1H, d, J=2.2 Hz).

Elemental Analysis for $C_{15}H_{15}N_3O_4$: Calcd. (%): C, 59.80; H, 5.02; N,13.95. Found (%): C, 59.67; H, 5.01; N, 13.91.

REFERENCE EXAMPLE 8

2-Amino-N-(4-methoxybenzyl)-5-methylbenzamide

Using the method similar to that in Reference Example 2 and starting from 2-amino-5-methylbenzoic acid (5.00 g), the title compound (7.11 g, 80%) was synthesized. Recrystallization from ethyl acetate-isopropyl ether yielded a colorless crystal, melting point 144 to 145° C.

IR (KBr): 3415, 3294, 2914, 1631, 1587, 1513, 1498 cm$^{-1}$.

$^1$H-NMR (CDCl$_3$) δ: 2.21 (3H, s), 3.81 (3H, s), 4.53 (2H, d, J=5.4 Hz), 6.24 (1H, bs), 6.62 (1H, d, J=8.4 Hz), 6.90 (2H, d, J=8.8 Hz), 7.03 (1H, d, J=8.8 Hz), 7.09 (1H, s), 7.28 (2H, d, J=9.4 Hz).

Elemental Analysis for $C_{16}H_{18}N_2O_2$: Calcd. (%): C, 71.09; H, 6.71; N, 10.36. Found (%): C, 70.75; H, 6.78; N, 10.30.

REFERENCE EXAMPLE 9

Methyl 2-(2-aminobenzamide)acetate

Synthesis was made in accordance with the synthetic method described in JP-A-3-181469. Glycine methyl ester hydrochloride (10.0 g) was suspended in a mixture of tetrahydrofuran (450 ml) and water (10.0 ml), which was treated with triethylamine (13.1 ml) followed by isatoic anhydride (11.8 g) with stirring. The reaction mixture was stirred at room temperature for 16 hours and then combined with water and extracted with ethyl acetate. The extract was washed with water, dried (Na₂SO₄) and the solvent was distilled off under reduced pressure to give a crude crystal of the title compound (14.0 g, 93%). Recrystallization from ethyl acetate-isopropyl ether yielded a colorless crystal, melting point 84.0 to 85.0° C.

IR (Nujor): 3450, 3360, 3340, 1740, 1630, 1600, 1570, 1530 cm$^{-1}$.

$^1$H-NMR (CDCl$_3$) δ: 3.81 (3H, s), 4.21 (2H, d, J=5.0 Hz), 5.57 (2H, bs), 6.58 (1H, bs), 6.63–6.72 (2H, m), 7.24 (1H, ddd, J=9.0, 7.6, 1.4 Hz), 7.42 (1H, dd, J=8.0, 1.4 Hz).

Elemental Analysis for C$_{10}$H$_{12}$N$_2$O$_3$: Calcd. (%): C, 57.69; H, 6.81; N, 13.45. Found (%): C, 57.97; H, 5.64; N, 13.57.

REFERENCE EXAMPLE 10

Ethyl 3-(2-aminobenzamide)propionate

Using the method similar to that in Reference Example 9 and starting from β-alanine ethyl ether hydrochloride (10.0 g), the title compound (14.5 g, about 100%) was obtained as an oil.

$^1$H-NMR (CDCl$_3$) δ: 1.27 (3H, t, J=7.0 Hz), 2.63 (2H, t, J=6.2 Hz), 3.68 (2H, q, J=5.8 Hz), 4.17 (2H, q, J=7.0 Hz), 5.53 (2H, bs), 6.60–6.70 (2H, m), 6.74 (1H, bs), 7.20 (1H, t, J=7.0 Hz), 7.30 (1H, d, J=8.6 Hz).

REFERENCE EXAMPLE 11

4-(2-aminobenzamide)butyric acid ethyl ester

Using the method similar to that in Reference Example 9 and starting from 4-aminobutyric acid ethyl ester hydrochloride (10.0 g), the title compound (13.3 g, 98%) was obtained as an oil.

$^1$H-NMR (CDCl$_3$) δ: 1.25 (3H, t, J=7.4 Hz), 1.84–2.02 (2H, m), 2.44 (2H, t, J=7.0 Hz), 3.47 (2H, q, J=6.0 Hz), 4.14 (2H, q, J=7.2 Hz), 5.53 (2H, bs), 6.39 (1H, bs), 6.60–6.72 (2H, m), 7.35 (2H, m).

REFERENCE EXAMPLE 12

2-Amino-N-methylbenzamide

Isatoic anhydride (10.0 g) was suspended in tetrahydrofuran (200 ml) and treated dropwise with 40% solution of methylamine in methanol (10.0 ml) with stirring. After stirring at room temperature for 16 hours, the solvent was distilled off under reduced pressure to give the title compound (10.3 g, about 100%). Melting point: 78.0 to 79.0° C. (recrystallized from ethyl acetate-n-hexane).

IR (KBr): 3450, 3333, 1615, 1580, 1539 cm$^{-1}$.

$^1$H-NMR (CDCl$_3$) δ: 2.97 (3H, d, J=5.0 Hz), 6.05 (1H, bs), 6.60–6.72 (2H, m), 7.14–7.32 (2H, m).

Elemental Analysis for C$_8$H$_{10}$N$_2$O: Calcd. (%): C, 63.98; H, 6.71; N, 18.65. Found (%): C, 63.44; H, 6.60; N, 18.58.

REFERENCE EXAMPLE 13

2-Amino-N-(1,1-dimethylethyl)benzamide

Using the method similar to that in Reference Example 12 and starting from tert-butylamine (5.38 g), the title compound (13.2 g, about 100%) was synthesized. This product was used in the next reaction without further purification.

$^1$H-NMR (CDCl$_3$) δ: 1.46 (9H, s), 4.49 (1H, bs), 5.86 (2H, bs), 6.60–6.70 (2H, m), 7.13–7.30 (2H, m).

REFERENCE EXAMPLE 14

2-Amino-N-(3-pyridylmethyl)benzamide

Using the method similar to that in Reference Example 12 and starting from 3-aminomethylpyridine (5.99 ml), the title compound (12.0 g, about 100%) was synthesized. Recrystallization from ethyl acetate-isopropyl ether yielded a colorless crystal, melting point 117 to 118° C.

IR (KBr): 3337, 1638, 1583, 1528, 1491 cm$^{-1}$.

$^1$H-NMR (CDCl$_3$) δ: 4.62 (2H, d, J=5.8 Hz), 5.54 (2H, bs), 6.50 (1H, bs), 6.58–6.74 (2H, m), 7.15–7.38 (3H, m), 7.71 (1H, d, J=7.6 Hz), 8.54 (1H, d, J=5.2 Hz) 8.60 (1H, s).

Elemental Analysis for C$_{13}$H$_{13}$N$_3$O: Calcd. (%): C, 68.71; H, 5.76; N, 18.49. Found (%): C, 68.45; H, 5.59; N, 18.45.

REFERENCE EXAMPLE 15

2-Amino-N-phenylbenzamide

Using the method similar to that in Reference Example 12 and starting from aniline (5.36 ml), the title compound (12.6 g, about 100%) was obtained as a crystal. This product was used in the next reaction without further purification.

$^1$H-NMR (CDCl$_3$) δ: 5.49 (2H, bs), 6.67–6.77 (2H, m), 7.15 (1H, ddd, J=8.2, 7.4, 0.8 Hz), 7.20–7.31 (1H, m), 7.32–7.42 (2H, m), 7.47 (1H, d, J=7.6 Hz), 7.52–7.60 (2H, m), 7.75 (1H, bs).

REFERENCE EXAMPLE 16

2-Amino-N-cyclohexylbenzamide

Using the method similar to that in Reference Example 12 and starting from cyclohexylamine (6.73 ml), the title compound (11.7 g, about 100%) was synthesized. Recrystallization from ethyl acetate-isopropyl ether yielded a colorless crystal, melting point 152 to 154° C.

IR (KBr): 3478, 3418, 3370, 2934, 2853, 1620, 1588, 1568, 1537, 1489 cm$^{-1}$.

$^1$H-NMR (CDCl$_3$) δ: 1.10–1.56 (5H, m), 1.56–1.82 (3H, m), 1.94–2.10 (2H, m), 3.82–4.02 (1H, m), 5.89 (1H, bs), 6.60–6.71 (2H, m), 7.20 (1H, ddd, J=8.6, 7.0, 1.6 Hz), 7.26–7.60 (1H, m).

Elemental Analysis for C$_{13}$H$_{18}$N$_2$O.0.1H$_2$O: Calcd. (%): C, 70.94; H, 8.33; N, 12.73. Found (%): C, 70.98; H, 8.37; N, 12.70.

REFERENCE EXAMPLE 17

2-Amino-N-[3-(4-diphenylmethoxypiperidino) propyl]benzamide

Using the method similar to that in Reference Example 1 and using 1-(3-aminopropyl)-4-diphenylmethoxypiperidine instead of 4-methoxybenzylamine and starting from isatoic anhydride (2.87 g), the title compound (6.19 g, 66%) was synthesized. This product was used in the next reaction without further purification.

$^1$H-NMR (CDCl$_3$) δ: 1.54–1.98(6H, m), 2.10–2.32(2H, m), 2.52 (2H, t, J=5.6 Hz), 2.74–2.88 (2H, m), 3.40–3.56 (3H, m), 5.50 (1H, s), 5.61 (2H, bs), 6.59–6.70 (2H, m), 7.12–7.42 (13H, m), 8.38 (1H, bs).

REFERENCE EXAMPLE 18

2-Amino-N-[4-(4-diphenylmethoxypiperidino)butyl]benzamide

Using the method similar to that in Reference Example 1 and using 1-(4-aminobutyl)-4-diphenylmethoxypiperidine instead of 4-methoxybenzylamine and starting from isatoic anhydride (3.18 g), the title compound (9.14 g, about 100%) was synthesized. Recrystallization from ethyl acetate-isopropyl ether yielded a colorless crystal, melting point 74.0 to 75.0° C.

IR (KBr): 3446, 3338, 2941, 1637, 1585, 1533, 1494 cm$^{-1}$.

$^1$H-NMR (CDCl$_3$) δ: 1.50–1.96 (8H, m), 2.04–2.10 (2H, m), 2.30–2.40 (2H,m), 2.68–2.80 (2H, m), 3.32–3.50(3H, m), 5.46 (2H, bs), 5.50 (1H, s), 6.59–6.70 (3H, m), 7.16–7.40 (11H, m).

Elemental Analysis for $C_{29}H_{35}N_3O_2 \cdot 0.3H_2O$: Calcd. (%): C, 75.23; H, 7.75; N, 9.08. Found (%): C, 75.12; H, 7.65; N, 9.13.

REFERENCE EXAMPLE 19

Ethyl 2-(2-aminobenzamide)isobutyrate

Ethyl 2-aminoisobutyrate hydrochloride (9.22 g, 55.0 mmol) was suspended in tetrahydrofuran (250 ml) and water (25 ml) and treated sequentially with triethylamine (9.06 ml, 65.0 mmol) followed by isatoic anhydride (8.16 g, 50.0 mmol) with stirring. The reaction mixture was stirred at room temperature for 15 hours and then at 60° C. for 24 hours. The solvent was distilled off under reduced pressure and the residue was taken up with water and extracted with ethyl acetate. The extract was washed with water, dried (MgSO$_4$) and then solvent was distilled off under reduced pressure. The residue was subjected to a column chromatography on a silica gel eluting with n-hexane-ethyl acetate (2:1, v/v) to give the title compound (5.26 g, 42%) as a crystal having melting point of 106° C.

IR (KBr): 3471, 3356, 1726, 1644, 1617, 1585 cm$^{-1}$.

$^1$H-NMR (CDCl$_3$) δ: 1.28 (3H, t, J=7.2 Hz), 1.65 (6H, s), 4.23 (2H, q, J=7.2 Hz), 5.47 (2H, bs), 6.61 (1H, bs), 6.62–6.69 (2H, m), 7.16–7.25 (1H, m), 7.36 (1H, dd, J=1.4 Hz, 8.0 Hz).

Elemental Analysis for $C_{13}H_{18}N_2O_3$: Calcd. (%): C, 62.38; H, 7.25; N, 11.19. Found (%): C, 62.23; H, 7.34; N, 11.38.

REFERENCE EXAMPLE 20

Methyl 2-(2-aminobenzamide)isobutyrate

Using the method similar to that in Reference Example 19 and using methyl 2-aminoisobutyrate hydrochloride (11.8 g, 77.0 mmol) instead of ethyl 2-aminoisobutyrate hydrochloride and starting from isatoic anhydride (11.4 g, 70 mmol), the title compound (7.53 g, 46%) was obtained as an oil.

IR (KBr): 3471, 3356, 1733, 1641, 1616, 1583, 1521 cm$^{-1}$.

$^1$H-NMR (CDCl$_3$) δ: 1.65 (6H, s), 3.77 (3H, s), 5.55 (2H, bs), 6.56 (1H, bs), 6.62–6.69 (2H, m), 7.17–7.25 (1H, m), 7.36 (1H, dd, J=8.3 Hz, 1.5 Hz).

REFERENCE EXAMPLE 21

Ethyl 2-(2-amino-5-methylbenzamide)isobutyrate

Ethyl 2-aminoisobutyrate hydrochloride (6.04 g, 36.0 mmol) was dissolved in N,N-dimethylformamide (60 ml) and treated dropwise with triethylamine (10.04 ml, 72.0 mmol). After stirring at room temperature for 15 minutes followed by adding 2-amino-5-methylbenzoic acid (5.15 g, 30.0 mmol), ethyl cyanophosphonate (6.07 ml, 36.0 mmol) was added dropwise with cooling on ice. Stirring was continued at the same temperature for 1 hours and then at room temperature for 15 hours. The reaction mixture was combined with water and extracted with ethyl ether. The extract was washed with water, dried (MgSO$_4$), and the solvent was distilled off under reduced pressure, and the residue was subjected to a column chromatography on a silica gel eluting with n-hexane-ethyl acetate (3:1, v/v) to give the title compound (7.48 g, 88%) as an oil.

IR (KBr): 3465, 3358, 2984, 2838, 1725, 1642, 1613, 1580, 1522 cm$^{-1}$.

$^1$H-NMR (CDCl$_3$) δ: 1.28 (3H, t, J=7.2 Hz), 1.64 (6H, s), 4.23 (2H, q, J=7.2 Hz), 5.60 (2H, bs), 6.56 (1H, bs), 6.61 (1H, dd, J=8.2 Hz, 2.0 Hz), 6.66 (1H, d, J=1.8 Hz), 7.28 (1H, d, J=8.4 Hz).

By the method similar to that described above, compounds of Reference Examples 22 to 24 were synthesized.

REFERENCE EXAMPLE 22

Ethyl 2-(2-amino-5-nitrobenzamide)isobutyrate

Starting from 2-amino-5-nitrobenzoic acid (5.75 g, 30.0 mmol), the title compound (7.05 g, 80%) was obtained as an oil.

IR (KBr): 3453, 3343, 2986, 2940, 1725, 1651, 1645, 1617, 1593, 1526, 1505 cm$^{-1}$.

$^1$H-NMR (CDCl$_3$) δ: 1.28 (3H, t, J=7.2 Hz), 1.67 (6H, s), 4.24 (2H, q, J=7.2 Hz), 6.46 (2H, bs), 6.70 (1H, bs), 6.65 (1H, d, J=9.2 Hz), 8.09 (1H, dd, J=9.1 Hz, 2.5 Hz), 8.37 (1H, d, J=2.6 Hz).

REFERENCE EXAMPLE 23

Ethyl 2-(2-amino-5-fluorobenzamide)isobutyrate

Starting from 2-amino-5-fluorobenzoic acid (1.60 g, 10.0 mmol), the title compound (2.32 g, 87%) was obtained as an oil.

IR (KBr): 3461, 3362, 2986, 2940, 1725, 1651, 1593, 1564, 1526 cm$^{-1}$.

$^1$H-NMR (CDCl$_3$) δ: 1.28 (3H, t, J=7.2 Hz), 1.65 (6H, s), 4.24 (2H, q, J=7.2 Hz), 5.24 (2H, bs), 6.59 (1H, bs), 6.62 (1H, dd, J=8.9 Hz, 4.7 Hz), 6.96 (1H, ddd, J=9.0 Hz, 7.9 Hz, 2.9 Hz), 7.08 (1H, dd, J=9.2 Hz, 2.8 Hz).

REFERENCE EXAMPLE 24

Ethyl 2-(2-amino-4-chlorobenzamide)isobutyrate

Starting from 2-amino-4-chlorobenzoic acid (5.15 g, 30.0 mmol), the title compound (7.48 g, 88%) was obtained as an oil.

IR (KBr): 3465, 3358, 2984, 2938, 1725, 1642, 1613, 1580, 1522 cm$^{-1}$.

$^1$H-NMR (CDCl$_3$) δ: 1.28 (3H, t, J=7.2 Hz), 1.64 (6H, s), 4.23 (2H, q, J=7.2 Hz), 5.60 (2H, bs), 6.56 (1H, bs), 6.61 (1H, dd, J=8.2 Hz, 2.0 Hz), 6.66 (1H, d, J=1.8 Hz), 7.28 (1H, d, J=8.4 Hz).

REFERENCE EXAMPLE 25

Ethyl 2-(2-amino-5-chlorobenzamide)isobutyrate

Using the method similar to that in Reference Example 19 and using 5-chloroisatoic anhydride (8.15 g, 40.0 mmol) and ethyl 2-aminoisobutyrate (7.38 g, 44.0 mmol), the title compound (4.65 g, 41%) was obtained as an oil.

IR (KBr): 3469, 3356, 2987, 2939, 1724, 1649, 1617, 1581, 1523, 1508 cm$^{-1}$.

$^1$H-NMR (CDCl$_3$) δ: 1.28 (3H, t, J=7.1 Hz), 1.65 (6H, s), 4.23 (2H, q, J=7.1 Hz), 5.60 (2H, bs), 6.54 (1H, bs), 6.61 (1H, d, J=8.8 Hz), 7.15 (1H, dd, J=8.7 Hz, 2.5 Hz), 7.32 (1H, d, J=2.4 Hz).

REFERENCE EXAMPLE 26

2,4-Dioxo-3-(4-methoxybenzyl)-1,2,3,4-tetrahydroquinazoline (Method 1) 2-Amino-N-(methoxybenzyl)benzamide (17.8 g) obtained in Reference Example 1 and N,N-carbonyldiimidazole (14.9 g) were stirred in N,N-dimethylformamide (100 ml) at 150° C. for 15 hours. After cooling, the reaction mixture was poured into an iced water, and the precipitated crystal was isolated by filtration, and washed sequentially with water, methanol and ethyl ether, dried to give the title compound (17.0 g, 98%) as a colorless crystal.

(Method 2) 2-Amino-N-(methoxybenzyl)benzamide (23.6 g) was dissolved in pyridine (150 ml) and treated dropwise with ethyl chloroformate (10.6 ml) with stirring and cooling on ice. The reaction mixture was stirred at room temperature for 8 hours, and then heated under reflux for 18.5 hours. After cooling followed by pouring into an iced water followed by the treatment similar to that in Method 1, the title compound (25.5 g, 98%) was obtained as a colorless crystal.

Melting point 229 to 230° C.

IR (Nujor): 1710, 1655, 1600, 1500, 1480 cm$^{-1}$.

$^1$H-NMR (CDCl$_3$) δ: 3.76 (3H, s), 5.21 (2H, s), 6.84 (2H, d, J=8.8 Hz), 7.06 (1H, d, J=8.0 Hz), 7.23 (1H, t, J=7.6 Hz), 7.51 (2H, d, J=8.8 Hz), 7.61 (1H, ddd, J=8.2, 6.6, 1.6 Hz), 8.14 (1H, dd, J=7.0, 1.2 Hz), 9.77 (1H, bs).

Elemental Analysis for $C_{16}H_{14}N_2O_3$: Calcd. (%): C, 68.08; H, 5.00; N, 9.92. Found (%): C, 67.93; H, 4.83; N, 10.06.

REFERENCE EXAMPLE 27

2,4-Dioxo-3-(4-methoxybenzyl)-1,2,3,4-tetrahydropyrido[2,3-d]pyrimidine

Using the method similar to that in Reference Example 26 (Method 1) and starting from 2-amino-N-(4-methoxybenzyl)nicotinamide (3.00 g), the title compound (2.93 g, 88%) was synthesized. Recrystallization from ethyl acetate yielded a colorless crystal having a melting point of 272 to 273° C.

IR (Nujor): 1720, 1660, 1600, 1510 cm$^{-1}$.

$^1$H-NMR (CDCl$_3$) δ: 3.76 (3H, s), 5.14 (2H, s), 6.81 (2H, d, J=8.6 Hz), 7.10–7.20 (1H, m), 7.46 (2H, d, J=7.4 Hz), 8.36 (1H, d, J=7.6 Hz), 8.54–8.63 (1H, m), 11.49 (1H, bs).

Elemental Analysis for $C_{15}H_{13}N_3O_3$: Calcd. (%): C, 63.60; H, 4.63; N, 14.83. Found (%): C, 63.17; H, 4.43; N, 14.89.

REFERENCE EXAMPLE 28

2,4-Dioxo-3-(4-methoxybenzyl)-1,2,3,4-tetrahydropteridine

Using the method similar to that in Reference Example 26 (Method 1) and starting from 2-amino-N-(4-methoxybenzyl)pyrazine-2-carboxamide (11.0 g), the title compound (5.98 g, 49%) was synthesized. Recrystallization from ethyl acetate yielded a colorless crystal having a melting point of 233 to 234° C.

IR (KBr): 2971, 1732, 1682, 1611, 1582, 1510 cm$^{-1}$.

$^1$H-NMR (CDCl$_3$) δ: 3.78 (3H, s), 5.22 (2H, s), 6.84 (2H, d, J=8.8 Hz), 7.54 (2H, d, J=8.8 Hz), 8.58 (1H, d, J=2.2 Hz), 8.63 (1H, d, J=2.2 Hz), 8.95 (1H, bs).

Elemental Analysis for $C_{14}H_{12}N_4O_3$: Calcd. (%): C, 59.15; H, 4.25; N, 19.71. Found (%): C, 59.07; H, 4.31; N, 19.51.

REFERENCE EXAMPLE 29

7-Chloro-2,4-dioxo-3-(4-methoxybenzyl)-1,2,3,4-tetrahydroquinazoline

Using the method similar to that in Reference Example 26 (Method 1) and starting from 2-amino-4-chloro-N-(4-methoxybenzyl)benzamide (8.00 g), the title compound (7.13 g, 82%) was synthesized. Recrystallization from ethyl acetate yielded a colorless crystal having a melting point of 254 to 256° C.

IR (KBr): 2987, 1714, 1668, 1616, 1600, 1515 cm$^{-1}$.

$^1$H-NMR (CDCl$_3$) δ: 3.77 (3H, s), 5.19 (2H, s), 6.85 (2H, d, J=8.8 Hz), 7.08 (1H, s), 7.20 (1H, d, J=7.4 Hz), 7.50 (2H, d, J=8.8 Hz), 8.07 (1H, d, J=8.8 Hz), 9.88 (1H, bs).

Elemental Analysis for $C_{16}H_{13}N_2O_3Cl$: Calcd. (%): C, 60.67; H, 4.14; N, 8.84. Found (%): C, 60.70; H, 4.05; N, 9.07.

REFERENCE EXAMPLE 30

6-Chloro-2,4-dioxo-3-(4-methoxybenzyl)-1,2,3,4-tetrahydroquinazoline

Using the method similar to that in Reference Example 26 (Method 1) and starting from 2-amino-5-chloro-N-(4-methoxybenzyl)benzamide (Reference Example 5) (9.22 g), the title compound (7.14 g, 71%) was synthesized. Recrystallization from ethyl acetate yielded a colorless crystal having a melting point of 252 to 253° C.

IR (KBr): 1718, 1662, 1610, 1513,,1479 cm$^{-1}$.

$^1$H-NMR (CDCl$_3$) δ: 3.77 (3H, s), 5.18 (2H, s), 6.83 (2H, d, J=8.4 Hz), 6.98 (1H, d, J=8.6 Hz), 7.48 (2H, d, J=8.8 Hz), 7.54 (1H, dd, J=8.8, 2.2 Hz), 8.11 (1H, d, J=2.6 Hz), 9.23 (1H, bs).

Elemental Analysis for $C_{16}H_{13}N_2O_3Cl$: Calcd. (%): C, 60.67; H, 4.14; N, 8.84. Found (%): C, 60.65; H, 4.36; N, 9.07.

REFERENCE EXAMPLE 31

2,4-Dioxo-3-(4-methoxybenzyl)-7-nitro-1,2,3,4-tetrahydroquinazoline

Using the method similar to that in Reference Example 26 (Method 2) and starting from 2-amino-N-(4-methoxybenzyl)-4-nitrobenzamide (Reference Example 6) (5.00 g), the title compound (5.17 g, 95%) was synthesized. Recrystallization from ethyl acetate yielded a colorless crystal having a melting point of 244 to 246° C.

IR (KBr): 1722, 1704, 1662, 1633, 1612, 1538, 1513 cm$^{-1}$.

$^1$H-NMR (CDCl$_3$) δ: 3.77 (3H, s), 5.22 (2H, s), 6.86 (2H, d, J=8.8 Hz), 7.52 (2H, d, J=8.8 Hz), 7.95 (1H, d, J=2.0 Hz), 8.03 (1H, dd, J=8.4, 2.2 Hz), 8.34 (1H, d, J=8.4 Hz), 10.01 (1H, bs).

Elemental Analysis for $C_{16}H_{13}N_3O_5 \cdot 0.2H_2O$: Calcd. (%): C, 58.08; H, 4.08; N, 12.70. Found (%): C, 57.90; H, 4.02; N, 12.60.

REFERENCE EXAMPLE 32

2,4-Dioxo-3-(4-methoxybenzyl)-6-nitro-1,2,3,4-tetrahydroquinazoline

Using the method similar to that in Reference Example 26 (Method 1) and starting from 2-amino-N-(4- methoxybenzyl)-5-nitrobenzamide (10.0 g) obtained in Reference Example 7, the title compound (9.65 g, 89%) was synthesized. Recrystallization from ethyl acetate-ethyl ether yielded a colorless crystal having a melting point of 254 to 256° C.

IR (KBr): 2880, 1721, 1651, 1609, 1541, 1514, 1487 cm$^{-1}$.

$^1$H-NMR (CDCl$_3$) δ: 3.77 (3H, s), 5.15 (2H, s), 6.83 (2H, d, J=8.8 Hz), 7.32 (1H, d, J=9.2 Hz), 7.47 (2H, d, J=8.8 Hz), 8.34 (1H, dd, J=8.8, 2.6 Hz), 8.94 (1H, d, J=2.6 Hz), 11.82 (1H, bs).

Elemental Analysis for C$_{16}$H$_{13}$N$_3$O$_5$: Calcd. (%): C, 58.72; H, 4.00; N, 12.84. Found (%): C, 58.67; H, 3.96; N, 12.82.

REFERENCE EXAMPLE 33

2,4-Dioxo-3-(4-methoxybenzyl)-6-methyl-1,2,3,4-tetrahydroquinazoline

Using the method similar to that in Reference Example 26 (Method 2) and starting from 2-amino-N-(4-methoxybenzyl)-5-methylbenzamide (7.00 g) obtained in Reference Example 8, the title compound (7.97 g, about 100%) was synthesized. Recrystallization from ethyl acetate-ethyl ether yielded a colorless crystal having a melting point of 263 to 265° C.

IR (KBr): 2901, 1705, 1661, 1609, 1581, 1512 cm$^{-1}$.

$^1$H-NMR (CDCl$_3$) δ: 2.39 (3H, s), 3.76 (3H, s), 5.20 (2H, s), 6.83 (2H, d, J=8.8 Hz), 6.95 (1H, d, J=8.2 Hz), 7.41 (1H, dd, J=8.0, 1.8 Hz), 7.50 (2H, d, J=8.8 Hz), 7.93 (1H, s), 9.65 (1H, bs).

Elemental Analysis for C$_{17}$H$_{16}$N$_2$O$_3$: Calcd. (%): C, 68.91; H, 5.44; N, 9.45. Found (%): C, 68.73; H, 5.31; N, 9.74.

REFERENCE EXAMPLE 34

Methyl 2,4-dioxo-1,2,3,4-tetrahydroquinazoline-3-acetate

Using the method similar to that in Reference Example 26 (Method 1) and starting from methyl 2-(2-aminobenzamide)acetate (14.0 g) obtained in Reference Example 9, the title compound (13.0 g, 83%) was synthesized. Recrystallization from ethyl acetate-ethyl ether yielded a colorless crystal having a melting point of 205 to 206° C.

IR (Nujor): 1750, 1710, 1650, 1620, 1590, 1510, 1480 cm$^{-1}$.

$^1$H-NMR (CDCl$_3$) δ: 3.80 (3H, s), 4.86 (2H, s), 7.64 (1H, ddd, J=8.8, 7.4, 1.4 Hz), 8.13 (1H, d, J=7.8 Hz), 9.75 (1H, bs).

Elemental Analysis for C$_{11}$H$_{10}$N$_2$O$_4$: Calcd. (%): C, 56.41; H, 4.30; N, 11.96. Found (%): C, 56.38; H, 4.42; N, 11.99.

REFERENCE EXAMPLE 35

Ethyl 2,4-dioxo-1,2,3,4-tetrahydroquinazoline-3-propionate

Using the method similar to that in Reference Example 26 (Method 1) and starting from ethyl 3-(2-aminobenzamide)propionate (14.5 g) obtained in Reference Example 10, the title compound (14.0 g, 87%) was synthesized. Recrystallization from ethyl acetate-ethyl ether yielded a colorless crystal having a melting point of 192 to 194° C.

IR (Nujor): 1725, 1715, 1655, 1620, 1600, 1490 cm$^{-1}$.

$^1$H-NMR (CDCl$_3$) δ: 1.25 (3H, t, J=7.0 Hz), 2.75 (2H, t, J=7.8 Hz), 4.16 (2H, q, J=7.4 Hz), 4.41 (2H, t, J=7.8 Hz), 7.10 (1H, d, J=8.8 Hz), 7.63 (1H, ddd, J=8.8, 7.2, 1.6 Hz), 8.14 (1H, dd, J=7.8, 1.4 Hz), 9.69 (1H, bs).

Elemental Analysis for C$_{13}$H$_{14}$N$_2$O$_4$: Calcd. (%): C, 59.54; H, 5.38; N, 10.68. Found (%): C, 59.42; H, 5.23; N, 10.81.

REFERENCE EXAMPLE 36

Ethyl 2,4-dioxo-1,2,3,4-tetrahydroquinazoline-3-butyrate

Using the method similar to that in Reference Example 26 (Method 1) and starting from ethyl 4-(2-aminobenzamide)butyrate (13.3 g) obtained in Reference Example 11, the title compound (13.8 g, 94%) was synthesized. Recrystallization from ethyl acetate-ethyl ether yielded a colorless crystal having a melting point of 133 to 135° C.

IR (KBr): 3195, 3136, 2977, 1727, 1633, 1492 cm$^{-1}$.

$^1$H-NMR (CDCl$_3$) δ: 1.23 (3H, t, J=7.0 Hz), 2.00–2.18 (2H, m), 2.44 (2H, t, J=7.2 Hz), 4.04–4.22 (4H, m), 7.11 (2H, d, J=8.4 Hz), 7.24 (1H, t, J=7.6 Hz), 7.62 (1H, ddd, J=8.2, 7.0, 1.2 Hz), 8.13 (1H, dd, J=7.8, 0.8 Hz), 9.89 (1H, bs).

Elemental Analysis for C$_{14}$H$_{16}$N$_2$O$_4$: Calcd. (%): C, 60.86; H, 5.84; N, 10.14. Found (%): C, 60.86; H, 5.62; N, 10.21.

REFERENCE EXAMPLE 37

2,4-Dioxo-3-methyl-1,2,3,4-tetrahydroquinazoline

Using the method similar to that in Reference Example 26 (Method 1) and starting from 2-amino-N-methylbenzamide (10.3 g) obtained in Reference Example 12, the title compound (5.34 g, 44%) was synthesized. Recrystallization from ethyl acetate yielded a colorless crystal having a melting point of 233 to 235° C.

IR (KBr): 1717, 1669, 1645, 1624, 1599, 1493 cm$^{-1}$.

$^1$H-NMR (CDCl$_3$) δ: 3.50 (3H, s), 7.11 (1H, d, J=8.0 Hz), 7.25 (1H, ddd, J=8.2, 7.2, 1.0 Hz), 7.63 (1H, ddd, J=8.6, 7.2, 1.4 Hz), 8.15 (1H, d, J=8.0 Hz), 9.66 (1H, bs).

Elemental Analysis for C$_9$H$_8$N$_2$O$_2$: Calcd. (%): C, 61.36; H, 4.58; N, 15.90. Found (%): C, 61.31; H, 4.49; N, 16.01.

REFERENCE EXAMPLE 38

3-(1,1-dimethylethyl)-2,4-dioxo-1,2,3,4-tetrahydroquinazoline

Using the method similar to that in Reference Example 26 (Method 1) and starting from 2-amino-N-(1,1-dimethylethyl)benzamide (10.0 g) obtained in Reference Example 13, the title compound (8.73 g, 77%) was synthesized. Recrystallization from ethyl acetate-isopropyl ether yielded a colorless crystal having a melting point of 218 to 220° C.

IR (KBr): 1715, 1651, 1609, 1489 cm$^{-1}$.

$^1$H-NMR (CDCl$_3$) δ: 1.79 (9H, s), 6.97 (1H, d, J=7.8 Hz), 7.17 (1H, t, J=7.0 Hz), 7.55 (1H, ddd, J=8.8, 7.2, 1.6 Hz), 8.02 (1H, dd, J=7.0, 1.0 Hz), 9.28 (1H, bs).

Elemental Analysis for C$_{12}$H$_{14}$N$_2$O$_2$: Calcd. (%): C, 66.04; H, 6.47; N, 12.84. Found (%): C, 66.02; H, 6.44; N, 12.96.

REFERENCE EXAMPLE 39

2,4-Dioxo-3-(3-pyridinylmethyl)-1,2,3,4-tetrahydroquinazoline

Using the method similar to that in Reference Example 26 (Method 1) and starting from 2-amino-N-(3-pyridylmethyl)

benzamide (11.7 g) obtained in Reference Example 14, the title compound (9.50 g, 78%) was synthesized. Recrystallization from ethyl acetate-isopropyl ether yielded a colorless crystal having a melting point of 241 to 243° C.

IR (KBr): 3059, 1715, 1669, 1618, 1516, 1508, 1491 cm$^{-1}$.

$^1$H-NMR (CDCl$_3$) δ: 5.27 (2H, s), 7.07 (1H, d, J=7.6 Hz), 7.20–7.32 (2H, m), 7.63 (1H, t, J=7.6 Hz), 7.88 (1H, d, J=8.4 Hz), 8.15 (1H, d, J=8.0 Hz), 8.53 (1H, d, J=4.4 Hz), 8.84 (1H, s), 9.60 (1H, bs s).

Elemental Analysis for C$_{14}$H$_{11}$N$_3$O$_2$: Calcd. (%): C, 66.40; H, 4.38; N, 16.59. Found (%): C, 66.10; H, 4.32; N, 16.64.

REFERENCE EXAMPLE 40

2,4-Dioxo-3-phenyl-1,2,3,4-tetrahydroquinazoline

Using the method similar to that in Reference Example 26 (Method 2) and starting from 2-amino-N-phenylbenzamide (12.5 g) obtained in Reference Example 15, the title compound (6.96 g, 50%) was synthesized. Recrystallization from ethyl acetate-ethyl ether yielded a colorless crystal having a melting point of 287 to 289° C.

IR (KBr): 3200, 1732, 1649, 1607, 1493 cm$^{-1}$.

$^1$H-NMR (CDCl$_3$) δ: 6.95 (1H, d, J=8.0 Hz), 7.18–7.36 (2H, m), 7.46–7.64 (5H, m), 8.16 (1H, d, J=7.4 Hz), 9.46 (1H, bs).

Elemental Analysis for C$_{14}$H$_{10}$N$_2$O$_2$.0.1H$_2$O: Calcd. (%): C, 70.05; H, 4.28; N, 11.67. Found (%): C, 69.84; H, 4.25; N, 11.43.

REFERENCE EXAMPLE 41

3-Cyclohexyl-2,4-dioxo-1,2,3,4-tetrahydroquinazoline

Using the method similar to that in Reference Example 26 (Method 2) and starting from 2-amino-N-cyclohexylbenzamide (11.7 g) obtained in Reference Example 16, the title compound (10.8 g, 84%) was synthesized. Recrystallization from ethyl acetate-ethyl ether yielded a colorless crystal having a melting point of 236 to 238° C.

IR (KBr): 3285, 2930, 2857, 1732, 1717, 1626, 1597, 1526 cm$^{-1}$.

$^1$H-NMR (CDCl$_3$) δ: 1.18–2.10 (8H, m), 2.40–2.62 (2H, m), 4.80–5.00 (1H, m), 7.03 (1H, d, J=8.2 Hz), 7.20–7.30 (2H, m), 7.60 (1H, t, J=8.0 Hz), 8.12 (1H, d, J=8.2 Hz), 9.39 (1H, bs).

Elemental Analysis for C$_{14}$H$_{16}$N$_2$O$_2$.0.2H$_2$O: Calcd. (%): C, 67.83; H, 6.67; N, 11.30. Found (%): C, 67.81; H, 6.69; N, 11.26.

REFERENCE EXAMPLE 42

Ethyl 2-(2,4-dioxo-1,2,3,4-tetrahydroquinazolin-3-yl)isobutyrate

Using the method similar to that in Reference Example 26 (Method 1) and starting from ethyl 2-(2-aminobenzamide) isobutyrate (5.01 g, 20 mmol) obtained in Reference Example 19, the title compound (2.52 g, 46%) was synthesized.

Melting point 133 to 134° C.

IR (KBr): 3265, 3213, 3141, 1720, 1668, 1621, 1610 cm$^{-1}$.

$^1$H-NMR (CDCl$_3$) δ: 1.23 (3H, t, J=7.2 Hz), 1.89 (6H, s), 4.20 (2H, q, J=7.2 Hz), 7.04 (1H, d, J=8.0 Hz), 7.18–7.26 (1H, m), 7.57–7.66 (1H,m), 8.04–8.09 (1H, m), 10.06 (1H, bs).

Elemental Analysis for C$_{14}$H$_{16}$N$_2$O$_4$: Calcd. (%): C, 60.86; H, 5.84; N, 10.14. Found (%): C, 60.86; H, 5.64; N, 10.24.

(Method 2) Ethyl 2-(2-aminobenzamide)isobutyrate (6.98 g, 27.9 mmol) obtained in Reference Example 19 was dissolved in pyridine (30 ml) and treated dropwise with ethyl chloroformate (2.94 ml, 30.7 mmol) with cooling on ice and stirring. The reaction mixture was stirred at room temperature for 2 hours, combined with water and then extracted with ethyl acetate. The extract was washed with an aqueous solution of potassium hydrogen sulfate followed by saturated brine, and dried (MgSO$_4$), and then the solvent was distilled off under reduced pressure. The residue was taken up with ethanol (150 ml) and combined with sodium ethylate (2.09 g, 30.7 mmol) and heated under reflux for 15 hours. The solvent was distilled off under reduced pressure and the residue was diluted with water and neutralized with 1N hydrochloric acid. The crystal precipitated was recovered by filtration to give the title compound (6.57 g, 85%) as a colorless crystal.

REFERENCE EXAMPLE 43

Methyl 2-(2,4-dioxo-1,2,3,4-tetrahydroquinazolin-3-yl)isobutyrate

Using the method similar to that in Reference Example 26 (Method 2) and starting from methyl 2-(2-aminobenzamide) isobutyrate (7.52 g, 31.8 mmol) obtained in Reference Example 20, the title compound (1.65 g, 20%) was synthesized.

Melting point 158 to 159° C.

IR (KBr): 3280, 3210, 3138, 3072, 2997, 2949, 1745, 1718, 1668, 1621, 1610 cm$^{-1}$.

$^1$H-NMR (CDCl$_3$) δ: 1.89 (6H, s), 3.73 (3H, s), 7.04 (1H, d, J=8.0 Hz), 7.18–7.26 (1H, m), 7.57–7.66 (1H, m), 8.04–8.08 (1H, m), 10.01 (1H, bs).

Elemental Analysis for C$_{13}$H$_{14}$N$_2$O$_4$: Calcd. (%): C, 59.54; H, 5.38; N, 10.68. Found (%): C, 59.46; H, 5.30; N, 10.56.

REFERENCE EXAMPLE 44

Ethyl 2-(2,4-dioxo-6-methyl-1,2,3,4-tetrahydroquinazolin-3-yl)isobutyrate

Using the method similar to that in Reference Example 42 (Method 3) and starting from ethyl 2-(2-amino-5-methylbenzamide)isobutyrate (6.33 g, 23.9 mmol) obtained in Reference Example 21, the title compound (5.51 g, 79%) was synthesized.

Melting point 156 to 157° C. (recrystallized from ethanol).

IR (KBr): 3196, 3169, 3071, 2986, 2938, 1742, 1711, 1661, 1626, 1514 cm$^{-1}$.

$^1$H-NMR (CDCl$_3$) δ: 1.23 (3H, t, J=7.2 Hz), 1.87 (6H, s), 2.38 (3H, s), 4.19 (2H, q, J=7.0 Hz), 6.93 (1H, d, J=8.2 Hz), 7.40 (1H, dd, J=1.9 Hz, 8.1 Hz), 7.84 (1H, s), 9.92 (1H, bs).

Elemental Analysis for C$_{15}$H$_{18}$N$_2$O$_4$: Calcd. (%): C, 62.06; H, 6.25; N, 9.65. Found (%): C, 61.92; H, 6.29; N, 9.73.

REFERENCE EXAMPLE 45

Ethyl 2-(2,4-dioxo-6-nitro-1,2,3,4-tetrahydroquinazolin-3-yl)isobutyrate

Using the method similar to that in Reference Example 42 (Method 3) and starting from ethyl 2-(2-amino-5- nitrobenzamide)isobutyrate (7.04 g, 23.8 mmol) obtained in Reference Example 22, the title compound (5.02 g, 66%) was synthesized.

Melting point 184 to 185° C. (recrystallized from ethanol).

IR (KBr): 3210, 3094, 2988, 2942, 1732, 1682, 1628, 1609, 1537, 1510 cm$^{-1}$.

$^{1}$H-NMR (CDCl$_{3}$) δ: 1.26 (3H, t, J=7.2 Hz), 1.89 (6H, s), 4.22 (2H, q, J=7.2 Hz), 7.17 (1H, d, J=9.0 Hz), 8.47 (1H, dd, J=8.9 Hz, 2.5 Hz), 8.96 (1H, d, J=2.4 Hz), 10.32 (1H, bs).

Elemental Analysis for C$_{14}$H$_{15}$N$_{3}$O$_{6}$: Calcd. (%): C, 52.34; H, 4.71; N, 13.08. Found (%): C, 52.34; H, 4.60; N, 13.16.

REFERENCE EXAMPLE 46

Ethyl 2-(2,4-dioxo-6-fluoro-1,2,3,4-tetrahydroquinazolin-3-yl)isobutyrate

Using the method similar to that in Reference Example 42 (Method 3) and starting from ethyl 2-(2-amino-5-fluorobenzamide)isobutyrate (2.31 g, 8.6 mmol) obtained in Reference Example 23, the title compound (1.19 g, 47%) was synthesized.

Melting point 167 to 169° C. (recrystallized from ethanol).

IR (KBr): 3280, 3240, 3204, 3129, 3083, 2990, 2940, 1721, 1669, 1510 cm$^{-1}$.

$^{1}$H-NMR (CDCl$_{3}$) δ: 1.24 (3H, t, J=7.1 Hz), 1.88 (6H, s), 4.19 (2H, q, J=7.1 Hz), 7.03 (1H, dd, J=8.8 Hz, 4.2 Hz), 7.35 (1H, ddd, J=8.8 Hz, 7.9 Hz, 2.9 Hz), 7.73 (1H, dd, J=8.3 Hz, 2.9 Hz), 10.14 (1H, bs).

Elemental Analysis for C$_{14}$H$_{15}$N$_{2}$O$_{4}$F: Calcd. (%): C, 57.14; H, 5.14; N, 9.52. Found (%): C, 57.01; H, 5.01; N, 9.58.

REFERENCE EXAMPLE 47

Ethyl 2-(7-chloro-2,4-dioxo-1,2,3,4-tetrahydroquinazolin-3-yl)isobutyrate

Using the method similar to that in Reference Example 42 (Method 3) and starting from ethyl 2-(2-amino-4-chlorobenzamide)isobutyrate (7.47 g, 26.2 mmol) obtained in Reference Example 24, the title compound (7.28 g, 89%) was synthesized.

Melting point 201 to 202° C. (recrystallized from ethanol).

IR (KBr): 3194, 3110, 3071, 2990, 2934, 2876, 1734, 1715, 1663, 1620, 1601 cm$^{-1}$.

$^{1}$H-NMR (CDCl$_{3}$) δ: 1.25 (3H, t, J=7.2 Hz), 1.87 (6H, s), 4.21 (2H, q, J=7.2 Hz), 7.03 (1H, d, J=1.8 Hz), 7.17 (1H, dd, J=8.4 Hz, 1.8 Hz), 7.99 (1H, d, J=8.6 Hz), 9.77 (1H, bs).

Elemental Analysis for C$_{14}$H$_{15}$N$_{2}$O$_{4}$Cl: Calcd. (%): C, 54.11; H, 4.87; N, 9.02. Found (%): C, 54.06; H, 4.62; N, 9.13.

REFERENCE EXAMPLE 48

Ethyl 2-(6-chloro-2,4-dioxo-1,2,3,4-tetrahydroquinazolin-3-yl)isobutyrate

Using the method similar to that in Reference Example 42 (Method 3) and starting from ethyl 2-(2-amino-5-chlorobenzamide)isobutyrate (3.12 g, 11.0 mmol) obtained in Reference Example 25, the title compound (1.88 g, 55%) was synthesized.

Melting point 179 to 180° C. (recrystallized from ethanol).

IR (KBr): 3195, 3043, 2987, 2939, 1720, 1670, 1617, 1500 cm$^{-1}$.

$^{1}$H-NMR (CDCl$_{3}$) δ: 1.24 (3H, t, J=7.1 Hz), 1.87 (6H, s), 4.19 (2H, q, J=7.1 Hz), 6.99 (1H, d, J=8.6 Hz), 7.55 (1H, dd, J=8.7 Hz, 2.5 Hz), 8.03 (1H, d, J=2.2 Hz), 10.08 (1H, bs).

Elemental Analysis for C$_{14}$H$_{15}$N$_{2}$O$_{4}$Cl: Calcd. (%): C, 54.11; H, 4.87; N, 9.02. Found (%): C, 53.99; H, 4.80; N, 9.06.

REFERENCE EXAMPLE 49

1-(3-Chloropropyl)-2,4-dioxo-3-(4-methoxybenzyl)-1,2,3,4-tetrahydroquinazoline

To a suspension of sodium hydride (60% in oil, 0.34 g) in N,N-dimethylformamide (30 ml), 2,4-dioxo-3-(4-methoxybenzyl)-1,2,3,4-tetrahydroquinazoline (2.0 g) obtained in Reference Example 26 was added, and the mixture was stirred at room temperature for 30 minutes. To this mixture, 1-bromo-3-chloropropane (1.05 ml) was added and the mixture was stirred for further 13.5 hours. The solvent was distilled off under reduced pressure, and the residue was combined with iN hydrochloric acid and extracted with ethyl acetate. The extract was washed with water, dried (Na$_{2}$SO$_{4}$), and the solvent was distilled off under reduced pressure. The residue was subjected to a column chromatography on a silica gel eluting with n-hexane-ethyl acetate (5:1, v/v) to give the title compound (1.58 g, 62%). Recrystallization from ethyl acetate-isopropyl ether yielded a colorless crystal having a melting point of 124 to 125° C.

IR (Nujor): 1700, 1645, 1600, 1500 cm$^{-1}$.

$^{1}$H-NMR (CDCl$_{3}$) δ: 2.14–2.30 (2H, m), 3.68 (2H, t, J=6.2 Hz), 3.77 (3H, s), 4.29 (2H, t, J=7.6 Hz), 5.21 (2H, s), 6.84 (2H, d, J=8.8 Hz), 7.20–7.31 (2H, m), 7.50 (2H, d, J=8.8 Hz), 7.68 (1H, ddd, J=8.8, 7.0, 1.8 Hz), 8.26 (1H, dd, J=8.4, 1.6 Hz).

Elemental Analysis for C$_{19}$H$_{19}$N$_{2}$O$_{3}$Cl: Calcd. (%): C, 63.60; H, 5.34; N, 7.81. Found (%): C, 63.52; H, 5.07; N, 7.90.

REFERENCE EXAMPLE 50

1-(4-Chlorobutyl)-2,4-dioxo-3-(4-methoxybenzyl)-1,2,3,4-tetrahydroquinazoline 2,4-dioxo-3-(4-methoxybenzyl)-1,2,3,4-tetrahydroquinazoline (4.84 g) obtained in Reference Example 26 was reacted with 4-bromo-1-chlorobutane by the method similar to that in Reference Example 49 to synthesize the title compound (4.54 g, 71%). Recrystallization from ethyl acetate yielded a colorless crystal having a melting point of 123 to 124° C.

IR (Nujor): 1690, 1645, 1600, 1510, 1480 cm$^{-1}$.

$^{1}$H-NMR (CDCl$_{3}$) δ: 1.84–2.00 (4H, m), 3.61 (2H, t, J=5.8 Hz), 3.77 (3H, s), 4.16 (2H, t, J=7.0 Hz), 5.21 (2H, s), 6.83 (2H, d, J=8.8 Hz), 7.14–7.30 (2H, m), 7.49 (2H, d, J=8.8 Hz), 7.66 (1H, ddd, J=8.6, 7.0, 1.6 Hz), 8.25 (1H, dd, J=7.8, 1.4 Hz).

Elemental Analysis for C$_{20}$H$_{21}$N$_{2}$O$_{3}$Cl: Calcd. (%): C, 64.43; H, 5.68; N, 7.51. Found (%): C, 64.73; H, 5.80; N, 7.48.

REFERENCE EXAMPLE 51

1-(5-Chloropentyl)-2,4-dioxo-3-(4-methoxybenzyl)-1,2,3,4-tetrahydroquinazoline 2,4-dioxo-3-(4-methoxybenzyl)-1,2,3,4-tetrahydroquinazoline (5.00 g) obtained in Reference Example 26 was reacted with 5-bromo-1-chloropentane by the method similar to that in Reference Example 49 to synthesize the title compound (7.54 g, about 100%). Recrystallization from ethyl acetate-ethyl ether yielded a colorless crystal having a melting point of 110 to 111° C.

IR (KBr): 1781, 1702, 1658, 1610, 1513, 1484 cm$^{-1}$.

$^1$H-NMR (CDCl$_3$) δ: 1.50–1.68 (2H, m), 1.68–1.94 (4H, m), 3.55 (2H, t, J=6.4 Hz), 3.77 (3H, s), 4.13 (2H, t, J=7.8 Hz), 5.22 (2H, s), 6.84 (2H, d, J=8.6 Hz), 7.11 (1H, d, J=8.4 Hz), 7.24 (1H, t, J=8.0 Hz), 7.50 (2H, d, J=8.8 Hz), 7.66 (1H, ddd, J=8.6, 7.0, 1.6 Hz), 8.25 (1H, dd, J=7.8, 1.4 Hz)

Elemental Analysis for C$_{21}$H$_{23}$N$_2$O$_3$Cl: Calcd. (%): C, 65.20; H, 5.99; N, 7.24. Found (%): C, 64.86; H, 5.93; N, 7.26.

REFERENCE EXAMPLE 52

1-(4-Bromobutyl)-2,4-dioxo-3-(4-methoxybenzyl)-1,2,3,4-tetrahydroquinazoline

To a suspension of sodium hydride (60% in oil, 4.34 g) in N,N-dimethylformamide (100 ml), 2,4-dioxo-3-(4-methoxybenzyl)-1,2,3,4-tetrahydroquinazoline (25.5 g) obtained in Reference Example 26 was added, and the mixture was stirred at room temperature for 2 hours. This mixture was treated dropwise with a solution of 1,4-dibromobutane (21.6 ml) in N,N-dimethylformamide (50 ml), and stirred at room temperature for 19 hours. The reaction mixture was admixed with 1N hydrochloric acid, and extracted with ethyl acetate. The extract was washed with water, dried (MgSO$_4$), and the solvent was distilled off under reduced pressure to give the title compound (30.8 g, 82%). Recrystallization from ethyl acetate-ethyl ether yielded a colorless crystal having a melting point of 124 to 125° C.

IR (KBr): 2958, 1700, 1656, 1610, 1511, 1482 cm$^{-1}$.

$^1$H-NMR (CDCl$_3$) δ: 1.82–2.08 (4H, m), 3.48 (2H, t, J=6.2 Hz), 3.77 (3H, s), 4.16 (2H, t, J=7.0 Hz), 5.21 (2H, s), 6.84 (2H, d, J=8.8 Hz), 7.16–7.30 (2H, m), 7.50 (2H, d, J=8.8 Hz), 7.67 (1H, ddd, J=8.8, 7.2, 1.6 Hz), 8.26 (1H, dd, J=7.8, 1.4 Hz).

Elemental Analysis for C$_{20}$H$_{21}$N$_2$O$_3$Br: Calcd. (%): C, 57.56; H, 5.07; N, 6.71. Found (%): C, 57.52; H, 4.88; N, 6.76.

REFERENCE EXAMPLE 53

1-(3-Chloropropyl)-2,4-dioxo-3-(4-methoxybenzyl)-1,2,3,4-tetrahydropyrido[2,3-d]pyrimidine Using the method similar to that in Reference Example 49 and starting from 2,4-dioxo-3-(4-methoxybenzyl)-1,2,3,4-tetrahydropyrido[2,3-d]pyrimidine (500 mg) obtained in Reference Example 27, the title compound (525 mg, 83%) was synthesized. Recrystallization from n-hexane-isoprpyl ether yielded a colorless crystal having a melting point of 114 to 115° C.

IR (Nujor): 1700, 1660, 1590, 1510, 1480 cm$^{-1}$.

$^1$H-NMR (CDCl$_3$) δ: 2.16–2.32 (2H, m), 3.63 (2H, t, J=6.6 Hz), 3.77 (3H, s), 4.50 (2H, t, J=7.4 Hz), 5.20 (2H, s), 6.84 (2H, d, J=8.8 Hz), 7.20 (1H, dd, J=7.8, 4.8 Hz), 7.50 (2H, d, J=8.8 Hz), 8.46 (1H, dd, J=7.6, 1.8 Hz), 8.64 (1H, dd, J=4.8, 1.8 Hz).

Elemental Analysis for C$_{18}$H$_{18}$N$_3$O$_3$Cl: Calcd. (%): C, 60.09; H, 5.04; N, 11.68. Found (%): C, 59.81; H, 4.95; N, 11.47.

REFERENCE EXAMPLE 54

1-(4-Bromobutyl)-2,4-dioxo-3-(4-methoxybenzyl)-1,2,3,4-tetrahydropyrido[2,3-d]pyrimidine Using the method similar to that in Reference Example 52 and starting from 2,4-dioxo-3-(4-methoxybenzyl)-1,2,3,4-tetrahydropyrido[2,3-d]pyrimidine (8.00 g) obtained in Reference Example 27, the title compound (12.8 g, about 100%) was synthesized. Recrystallization from ethyl acetate-ethyl ether yielded a colorless crystal having a melting point of 80 to 82° C.

IR (KBr): 2962, 1714, 1668, 1600, 1515, 1486 cm$^{-1}$.

$^1$H-NMR (CDCl$_3$) δ: 1.80–2.02 (4H, m), 3.47 (2H, t, J=6.2 Hz), 3.77 (3H, s), 4.38 (2H, t, J=6.8 Hz), 5.20 (2H, s), 6.84 (2H, d, J=8.8 Hz), 7.19 (1H, dd, J=7.8, 4.4 Hz), 7.49 (2H, d, J=8.8 Hz), 8.46 (1H, dd, J=8.0, 1.8 Hz), 8.63 (1H, dd, J=4.8, 1.8 Hz).

Elemental Analysis for C$_{19}$H$_{20}$N$_3$O$_3$Br: Calcd. (%).: C, 54.56; H, 4.82; N, 10.05. Found (%): C, 54.49; H, 4.70; N, 10.08.

REFERENCE EXAMPLE 55

1-(4-Bromobutyl)-2,4-dioxo-3-(4-methoxybenzyl)-1,2,3,4-tetrahydropteridine

Using the method similar to that in Reference Example 52 and starting from 2,4-dioxo-3-(4-methoxybenzyl)-1,2,3,4-tetrahydropteridine (5.77 g) obtained in Reference Example 28, the title compound (3.92 g, 46%) was synthesized. Recrystallization from ethyl acetate-ethyl ether yielded a colorless crystal having a melting point of 117 to 119° C.

IR (KBr): 2961, 1721, 1672, 1611, 1582, 1547, 1510, 1489 cm$^{-1}$.

$^1$H-NMR (CDCl$_3$) δ: 1.80–2.04 (4H, m), 3.46 (2H, t, J=6.2 Hz), 3.77 (3H, s), 4.33 (2H, t, J=7.0 Hz), 5.25 (2H, s), 6.84 (2H, d, J=8.8 Hz), 7.53 (2H, d, J=8.8 Hz), 8.58 (1H, d, J=2.2 Hz), 8.61 (1H, d, J=2.2 Hz).

Elemental Analysis for C$_{18}$H$_{19}$N$_4$O$_3$Br: Calcd. (%): C, 51.56; H, 4.57; N, 13.36. Found (%): C, 51.80; H, 4.44; N, 13.50.

REFERENCE EXAMPLE 56

1-(4-Bromobutyl)-7-chloro-2,4-dioxo-3-(4-methoxybenzyl)-1,2,3,4-tetrahydroquinazoline Using the method similar to that in Reference Example 52 and starting from 7-chloro-2,4-dioxo-3-(4-methoxybenzyl)-1,2,3,4-tetrahydroquinazoline (5.00 g) obtained in Reference Example 29, the title compound (8.32 g, about 100%) was synthesized. Recrystallization from ethyl acetate-n-hexane yielded a colorless crystal having a melting point of 107 to 109° C.

IR (KBr): 2958, 1708, 1662, 1606, 1583, 1513, 1494 cm$^{-1}$.

$^1$H-NMR (CDCl$_3$) δ: 1.85–2.08 (4H, m), 3.49 (2H, t, J=6.4 Hz), 3.77 (3H, s), 4.11 (2H, t, J=5.2 Hz), 5.19 (2H, s), 6.84 (2H, d, J=8.8 Hz), 7.17–7.24 (2H, m), 7.48 (2H, d, J=8.8 Hz), 8.18 (1H, d, J=8.8 Hz).

Elemental Analysis for C$_{20}$H$_{20}$N$_2$O$_3$BrCl: Calcd. (%): C, 53.18; H, 4.46; N, 6.20. Found (%): C, 53.76; H, 4.45; N, 6.34.

REFERENCE EXAMPLE 57

1-(4-Bromobutyl)-6-chloro-2,4-dioxo-3-(4-methoxybenzyl)-1,2,3,4-tetrahydroquinazoline Using the method similar to that in Reference Example 52 and starting from 6-chloro-2,4-dioxo-3-(4-methoxybenzyl)-1,2,3,4-tetrahydroquinazoline (5.00 g) obtained in Reference Example 30, the title compound (5.35 g, 75%) was synthesized. Recrystallization from ethyl acetate-n-hexane yielded a colorless crystal having a melting point of 146 to 147° C.

IR (KBr): 2958, 1704, 1662, 1610, 1587. 1511, 1490, 1463 cm$^{-1}$.

$^1$H-NMR (CDCl$_3$) δ:1.78–2.06 (4H, m), 3.47 (2H, t, J=6.2 Hz), 3.77 (3H, s), 4.13 (2H, t, J=7.2 Hz), 5.19 (2H, s), 6.83 (2H, d, J=8.8 Hz), 7.13 (1H, d, J=8.8Hz), 7.47 (2H, d, J=8.4 Hz), 7.60 (1H, dd, J=9.2, 2.6 Hz), 8.21 (1H, d, J=2.6 Hz).

Elemental Analysis for C$_{20}$H$_{20}$N$_2$O$_3$BrCl.0.5H$_2$O: Calcd. (%): C, 52.14; H, 4.59; N, 6.08. Found (%): C, 52.11; H, 4.24; N, 6.18.

REFERENCE EXAMPLE 58

1-(4-Bromobutyl)-2,4-dioxo-3-(4-methoxybenzyl)-7-nitro-1,2,3,4-tetrahydroquinazoline Using the method similar to that in Reference Example 52 and starting from 2,4-dioxo-3-(4-methoxybenzyl)-7-nitro-1,2,3,4-tetrahydroquinazoline (6.84 g) obtained in Reference Example 31, the title compound (11.1 g, about 100%) was synthesized. Recrystallization from ethyl acetate-ethyl ether yielded a colorless crystal having a melting point of 122 to 123° C.

IR (KBr): 2962, 1710, 1666, 1625, 1598, 1538, 1513, 1469 cm$^{-1}$.

$^1$H-NMR (CDCl$_3$) δ: 1.84–2.12 (4H, m), 3.49 (2H, t, J=6.2 Hz), 3.78 (3H, s), 4.22 (2H, t, J=7.0 Hz), 5.21 (2H, s), 6.84 (2H, d, J=8.8 Hz), 7.49 (2H, d, J=8.4 Hz), 8.00–8.09 (2H, m), 8.43 (1H, d, J=9.2 Hz).

Elemental Analysis for C$_{20}$H$_{20}$N$_3$O$_5$Br: Calcd. (%): C, 51.96; H, 4.36; N, 9.09. Found (%): C, 51.72; H, 4.27; N, 8.96.

REFERENCE EXAMPLE 59

1-(4-Bromobutyl)-2,4-dioxo-3-(4-methoxybenzyl)-6-nitro-1,2,3,4-tetrahydroquinazoline Using the method similar to that in Reference Example 52 and starting from 2,4-dioxo-3-(4-methoxybenzyl)-6-nitro-1,2,3,4-tetrahydroquinazoline (4.68 g) obtained in Reference Example 32, the title compound (6.05 g, 92%) was synthesized. Recrystallization from ethyl acetate-ethyl ether yielded a yellow crystal having a melting point of 143 to 144° C.

IR (KBr): 2961, 1715, 1667, 1615, 1514, 1497 cm$^{-1}$.

$^1$H-NMR (CDCl$_3$) δ: 1.82–2.10 (4H, m), 3.49 (2H, t, J=5.8 Hz), 3.78 (3H, s), 4.20 (2H, t, J=7.0 Hz), 5.21 (2H, s), 6.85 (2H, d, J=8.8 Hz), 7.32 (1H, d, J=9.6 Hz), 7.49 (2H, d, J=8.8 Hz), 8.50 (1H, dd, J=9.0, 3.0 Hz), 9.12 (1H, d, J=3.8 Hz).

Elemental Analysis for C$_{20}$H$_{20}$N$_3$O$_5$Br: Calcd. (%): C, 51.96; H, 4.36; N, 9.09. Found (%): C, 51.85; H, 4.11; N, 9.06.

REFERENCE EXAMPLE 60

1-(4-Bromobutyl)-2 4-dioxo-3-(4-methoxybenzyl)-6-methyl-1,2,3,4-tetrahydroquinazoline Using the method similar to that in Reference Example 52 and starting from 2,4-dioxo-3-(4-methoxybenzyl)-6-methyl-1,2,3,4-tetrahydroquinazoline (5.00 g) obtained in Reference Example 33, the title compound (6.21 g, 85%) was synthesized. Recrystallization from ethyl acetate yielded a colorless crystal having a melting point of 164 to 165° C.

IR (KBr): 2959, 1698, 1659, 1590, 1510 cm$^{-1}$.

$^1$H-NMR (CDCl$_3$) δ: 1.80–2.04 (4H, m), 2.40 (3H, s), 3.47 (2H, t, J=6.2 Hz), 3.77 (3H, s), 4.13 (2H, t, J=7.4 Hz), 5.21 (2H, s), 6.83 (2H, d, J=8.4 Hz), 7.08 (1H, d, J=8.6 Hz), 7.44–7.53 (3H, m), 8.04 (1H, s).

Elemental Analysis for C$_{21}$H$_{23}$N$_2$O$_3$Br: Calcd. (%): C, 58.48; H, 5.37; N, 6.49. Found (%): C, 58.56; H, 5.30; N. 6.52.

REFERENCE EXAMPLE 61

Methyl 1-(3-chloropropyl)-2,4-dioxo-1,2,3,4-tetrahydroquinazoline-3-acetate

Using the method similar to that in Reference Example 49 and starting from methyl 2,4-dioxo-1,2,3,4-tetrahydroquinazoline-3-acetate (4.08 g) obtained in Reference Example 34, the title compound (1.81 g, 34%) was synthesized. Recrystallization from ethyl acetate-ethyl ether yielded a colorless crystal having a melting point of 144 to 146° C.

IR (Nujor): 1750, 1700, 1660, 1610 cm$^{-1}$.

$^1$H-NMR (CDCl$_3$) δ: 2.16–2.32 (2H, m), 3.69 (2H, t, J=6.0 Hz), 3.78 (3H, s), 4.32 (2H, t, J=7.6Hz), 4.86 (2H, s), 7.24–7.38 (2H, m), 7.73 (1H, ddd, J=8.6, 7.2, 1.4 Hz), 8.26 (1H, dd, J=7.6, 1.2 Hz).

Elemental Analysis for C$_{14}$H$_{15}$N$_2$O$_4$Cl: Calcd. (%): C, 54.11; H, 4.87; N, 9.02. Found (%): C, 53.80; H, 4.75; N, 9.31.

REFERENCE EXAMPLE 62

Methyl 1-(4-chlorobutyl)-2,4-dioxo-1,2,3,4-tetrahydroquinazoline-3-acetate

Using the method similar to that in Reference Example 49 and starting from methyl 2,4-dioxo-1,2,3,4-tetrahydroquinazoline-3-acetate (3.00 g) obtained in Reference Example 34, the title compound (2.21 g, 53%) was synthesized. Recrystallization from ethyl acetate-isopropyl ether yielded a colorless crystal having a melting point of 119 to 120° C.

IR (KBr): 1756, 1704, 1668, 1610, 1486 cm$^{-1}$.

$^1$H-NMR (CDCl$_3$) δ: 1.88–2.00 (4H, m), 3.62 (2H, t, J=5.8 Hz), 3.78 (3H, s), 4.19 (2H, t, J=7.0 Hz), 4.86 (2H, s), 7.22–7.34 (2H, m), 7.72 (1H, ddd, J=8.6, 7.0, 1.6 Hz), 8.26 (1H, dd, J=7.8, 1.6 Hz).

Elemental Analysis for C$_{15}$H$_{17}$N$_2$O$_4$Cl: Calcd. (%): C, 55.48; H, 5.28; N, 8.63. Found (%): C, 55.01; H, 5.01; N, 8.34.

REFERENCE EXAMPLE 63

Ethyl 1-(3-chloropropyl)-2,4-dioxo-1,2,3,4-tetrahydroquinazoline-3-propionate

Using the method similar to that in Reference Example 49 and starting from ethyl 2,4-dioxo-1,2,3,4-tetrahydroquinazoline-3-propionate (3.00 g) obtained in Reference Example 35, the title compound (1.85 g, 48%) was synthesized. Recrystallization from ethyl acetate-ethyl ether yielded a colorless crystal having a melting point of 80 to 81° C.

IR (Nujor): 1720, 1690, 1660, 1600 cm$^{-1}$.

$^1$H-NMR (CDCl$_3$) δ: 1.24 (3H, t, J=7.2 Hz), 2.13–2.35 (2H, m), 2.72 (2H, t, J=7.6 Hz), 3.70 (2H, t, J=6.0 Hz), 4.14 (2H, q, J=7.2 Hz), 4.31 (2H, t, J=7.6 Hz), 4.41 (2H, t, J=7.2

Hz), 7.22–7.36 (2H, m), 7.70 (1H, ddd, J=8.8, 7.2, 1.6 Hz), 8.25 (1H, dd, J=8.0, 1.4 Hz).

Elemental Analysis for $C_{16}H_{19}N_2O_4Cl\cdot 0.2H_2O$: Calcd. (%): C, 56.13; H, 5.71; N, 8.18. Found (%): C, 55.91; H, 5.40; N, 8.17.

REFERENCE EXAMPLE 64

Ethyl 1-(4-chlorobutyl)-2,4-dioxo-1,2,3,4-tetrahydroquinazoline-3-propionate

Using the method similar to that in Reference Example 49 and starting from ethyl 2,4-dioxo-1,2,3,4-tetrahydroquinazoline-3-propionate (5.00 g) obtained in Reference Example 35, the title compound (5.40 g, 80%) was synthesized. Recrystallization from ethyl acetate-isopropyl ether yielded a colorless crystal having a melting point of 71 to 72° C.

IR (KBr): 1733, 1699, 1662, 1608, 1484 cm$^{-1}$.

$^1$H-NMR (CDCl$_3$) δ: 1.24 (3H, t, J=7.4 Hz), 1.86–1.98 (4H, m), 2.71 (2H, t, J=7.6 Hz), 3.60–3.66 (2H, m), 4.14 (2H, q, J=7.0 Hz), 4.10–4.23 (2H, m), 4.40 (2H, t, J=7.4 Hz), 7.16–7.30 (2H, m), 7.69 (1H, t, J=7.0 Hz), 8.24 (1H, dd, J=7.8, 1.4 Hz).

Elemental Analysis for $C_{17}H_{21}N_2O_4Cl$: Calcd. (%): C, 56.43; H, 6.13; N, 7.74. Found (%): C, 56.39; H, 5.87; N, 7.70.

REFERENCE EXAMPLE 65

Ethyl 1-(4-chlorobutyl)-2,4-dioxo-1,2,3,4-tetrahydroquinazoline-3-butyrate

Using the method similar to that in Reference Example 49 and starting from ethyl 2,4-dioxo-1,2,3,4-tetrahydroquinazoline-3-butyrate (8.00 g) obtained in Reference Example 36, the title compound (13.8 g, about 100%) was obtained as an oil.

$^1$H-NMR (CDCl$_3$) d: 1.23 (3H, t, J=7.2 Hz), 1.88–2.14 (6H, m), 2.40 (2H, t, J=7.6 Hz), 3.40–3.56 (2H, m), 4.02–4.22 (6H, m), 7.18–7.30 (2H, m), 7.69 (1H, ddd, J=8.6, 6.8, 1.8 Hz), 8.24 (1H, dd, J=8.0, 1.6 Hz).

REFERENCE EXAMPLE 66

1-(3-Chloropropyl)-2,4-dioxo-3-methyl-1,2,3,4-tetrahydroquinazoline

Using the method similar to that in Reference Example 49 and starting from 2,4-dioxo-3-methyl-1,2,3,4-tetrahydroquinazoline (3.34 g) obtained in Reference Example 37, the title compound (1.34 g, 28%) was synthesized.

$^1$H-NMR (CDCl$_3$) δ: 2.16–2.32 (2H, m), 3.49 (3H, s), 3.70 (2H, t, J=6.2 Hz), 4.32 (2H, t, J=1.8 Hz), 7.24–7.36 (2H, m), 7.70 (1H, ddd, J=8.6, 7.0, 1.6 Hz), 8.26 (1H, dd, J=7.8, 1.4 Hz).

REFERENCE EXAMPLE 67

1-(4-Chlorobutyl)-2,4-dioxo-3-methyl-1,2,3,4-tetrahydroquinazoline

Using the method similar to that in Reference Example 49 and starting from 2,4-dioxo-3-methyl-1,2,3,4-tetrahydroquinazoline (3.00 g) obtained in Reference Example 37, the title compound (1.93 g, 43%) was synthesized. Recrystallization from ethyl acetate-ethyl ether yielded a colorless crystal having a melting point of 99 to 100° C.

IR (KBr): 1699, 1652, 1608, 1486 cm$^{-1}$.

$^1$H-NMR (CDCl$_3$) δ: 1.88–2.00 (4H, m), 3.49 (3H, s), 3.58–3.64 (2H, m), 4.14–4.26 (2H, m), 7.18–7.32 (2H, m), 7.69 (1H, ddd, J=8.6, 7.0, 1.6 Hz), 8.25 (1H, d, J=7.6 Hz).

Elemental Analysis for $C_{13}H_{15}N_2O_2Cl$: Calcd. (%): C, 58.54; H, 5.67; N, 10.50. Found (%): C, 58.07; H, 5.56; N, 10.39.

REFERENCE EXAMPLE 68

1-(3-Chloropropyl)-3-(1,1-dimethylethyl)-2,4-dioxo-1,2,3,4-tetrahydroquinazoline Using the method similar to that in Reference Example 49 and starting from 3-(1,1-dimethylethyl)-2,4-dioxo-1,2,3,4-tetrahydroquinazoline (4.00 g) obtained in Reference Example 38, the title compound (3.20 g, 59%) was obtained as an oil.

$^1$H-NMR (CDCl$_3$) d: 1.74 (9H, s), 2.12–2.28 (2H, m), 3.68 (2H, t, J=6.2 Hz), 4.21 (2H, t, J=7.4 Hz), 7.14–7.24 (2H, m), 7.62 (1H, ddd, J=9.2, 7.4, 1.8 Hz), 8.09 (1H, dd, J=8.2, 1.6 Hz).

REFERENCE EXAMPLE 69

1-(4-Chlorobutyl)-3-(1,1-dimethylethyl)-2,4-dioxo-1,2,3,4-tetrahydroquinazoline

Using the method similar to that in Reference Example 49 and starting from 3-(1,1-dimethylethyl)-2,4-dioxo-1,2,3,4-tetrahydroquinazoline (4.00 g) obtained in Reference Example 38, the title compound (7.05 g, about 100%) was obtained as an oil.

$^1$H-NMR (CDCl$_3$) δ: 1.74 (9H, s), 1.82–2.04 (4H, m), 3.55–3.68 (2H, m), 4.03–4.12 (2H, m), 7.10 (1H, d, J=8.4 Hz), 7.18 (1H, t, J=7.6 Hz), 7.60 (1H, ddd, J=8.4, 7.4, 1.0 Hz), 8.08 (1H, dd, J=8.2, 1.4 Hz).

REFERENCE EXAMPLE 70

1-(4-Bromobutyl)-2,4-dioxo-3-(3-pyridinylmethyl)-1,2,3,4-tetrahydroquinazoline

Using the method similar to that employed for synthesizing Reference Example 52 and starting from 2,4-dioxo-3-(3-pyridinylmethyl)-1,2,3,4-tetrahydroquinazoline (4.00 g) obtained in Reference Example 39, the title compound (1.57 g, 26%) was obtained as an oil.

$^1$H-NMR (CDCl$_3$) δ: 1.84–2.08 (4H, m), 3.48 (2H, t, J=6.4 Hz), 4.16 (2H, t, J=7.0 Hz), 5.28 (2H, s), 7.18–7.32 (3H, m), 7.69 (1H, ddd, J=8.4, 7.0, 1.4 Hz), 7.86 (1H, d, J=8.0 Hz), 8.25 (1H, dd, J=8.0, 1.2 Hz), 8.51 (1H, d, J=3.4 Hz), 8.78 (1H, s).

REFERENCE EXAMPLE 71

1-(4-Bromobutyl)-2,4-dioxo-3-phenyl-1,2,3,4-tetrahydroquinazoline

Using the method similar to that in Reference Example 52 and starting from 2,4-dioxo-3-phenyl-1,2,3,4-tetrahydroquinazoline (4.00 g) obtained in Reference Example 40, the title compound (8.20 g, about 100%) was obtained as an oil.

$^1$H-NMR (CDCl$_3$) δ: 1.84–2.16 (4H, m), 3.38–3.54 (2H, m), 4.21 (2H, t, J=7.0 Hz), 7.24–7.35 (4H, m), 7.44–7.59 (3H, m), 7.75 (1H, t, J=8.0 Hz), 8.29 (1H, d, J=7.4 Hz).

REFERENCE EXAMPLE 72

1-(4-Bromobutyl)-3-cyclohexyl-2,4-dioxo-1,2,3,4-tetrahydroquinazoline

Using the method similar to that in Reference Example 52 and starting from 3-cyclohexyl-2,4-dioxo-1,2,3,4- tetrahydroquinazoline (4.00 g) obtained in Reference Example 41, the title compound (6.84 g, about 100%) was obtained as an oil.

$^1$H-NMR (CDCl$_3$) δ: 1.20–2.12 (12H, m), 2.46–2.60 (2H, m), 3.40–3.54 (2H, m), 4.13 (2H, t, J=7.4 Hz), 4.82–5.02 (1H, m), 7.12–7.28 (2H, m), 7.65 (1H, ddd, J=8.8, 7.0, 1.8 Hz), 8.22 (1H, dd, J=8.0, 1.4 Hz).

REFERENCE EXAMPLE 73

Ethyl 2-[1-(4-bromobutyl)-2,4-dioxo-1,2,3,4-tetrahydroquinazolin-3-yl]isobutyrate Using the method similar to that in Reference Example 52 and starting from ethyl 2-(2,4-dioxo-1,2,3,4-tetrahydroquinazolin-3-yl)isobutyrate (2.21 g) obtained in Reference Example 42, the title compound (2.86 g, 87%) was synthesized. Recrystallization from ethyl acetate-n-hexane yielded a colorless crystal having a melting point of 113 to 114° C.

IR (KBr): 1741, 1708, 1664, 1608 cm$^{-1}$.

$^1$H-NMR (CDCl$_3$) δ: 1.24 (3H, t, J=7.1 Hz), 1.85 (6H, s), 1.87–2.04 (4H, m), 3.48 (2H, t, J=6.2 Hz), 4.11 (2H, t, J=7.2 Hz), 4.20 (2H, q, J=7.1 Hz), 7.16–7.28 (2H, m), 7.63–7.71 (1H, m), 8.16 (1H, dd, J=7.8 Hz, 1.6 Hz).

Elemental Analysis for C$_{18}$H$_{23}$N$_2$O$_4$Br: Calcd. (%): C, 52.57; H, 5.64; N, 6.81. Found (%): C, 52.76; H, 5.52; N, 6.90.

REFERENCE EXAMPLE 74

Methyl 2-[1-(4-bromobutyl)-2,4-dioxo-1,2,3,4-tetrahydroquinazolin-3-yl]isobutyrate Using the method similar to that in Reference Example 52 and starting from methyl 2-(2,4-dioxo-1,2,3,4-tetrahydroquinazolin-3-yl)isobutyrate (1.31 g) obtained in Reference Example 43, the title compound (1.37 g, 69%) was obtained as an oil.

IR (KBr): 1747, 1708, 1662, 1608 cm$^{-1}$.

$^1$H-NMR (CDCl$_3$) δ: 1.85 (6H, s), 1.89–2.02 (4H, m), 3.48 (2H, t, J=6.3 Hz), 3.72 (3H, s), 4.08–4.18 (2H, m), 7.16–7.29 (2H, m), 7.63–7.72 (1H, m), 8.16 (1H, dd, J=7.9 Hz, 1.7 Hz).

REFERENCE EXAMPLE 75

Ethyl 2-[1-(4-bromobutyl)-2,4-dioxo-6-methyl-1,2,3,4-tetrahydroquinazolin-3-yl]isobutyrate Using the method similar to that in Reference Example 52 and starting from ethyl 2-(2,4-dioxo-6-methyl-1,2,3,4-tetrahydroquinazolin-3-yl)isobutyrate (0.58 g) obtained in Reference Example 44, the title compound (0.57 g, 67%) was obtained as an oil.

IR (KBr): 2990, 2940, 1744, 1705, 1665, 1624, 1595, 1508 cm$^{-1}$.

$^1$H-NMR (CDCl$_3$) δ: 1.24 (3H, t, J=7.2 Hz), 1.84 (6H, s), 1.85–2.05 (4H, m), 3.40 (3H, s), 3.47 (2H, t, J=6.2 Hz), 4.04–4.11 (2H, m), 4.19 (2H, q, J=7.2 Hz), 7.07 (1H, d, J=8.6 Hz), 7.47 (1H, dd, J=8.4 Hz, 1.8 Hz), 7.95 (1H, d, J=1.4 Hz).

REFERENCE EXAMPLE 76

Ethyl 2-[1-(4-bromobutyl)-2,4-dioxo-6-nitro-1,2,3,4-tetrahydroquinazolin-3-yl]isobutyrate Using the method similar to that in Reference Example 52 and starting from ethyl 2-(2,4-dioxo-6-nitro-1,2,3,4-tetrahydroquinazolin-3-yl)isobutyrate (0.64 g) obtained in Reference Example 45, the title compound (0.30 g, 33%) was obtained as an oil.

IR (KBr): 2984, 2942, 1742, 1717, 1674, 1615, 1530 cm$^{-1}$.

$^1$H-NMR (CDCl$_3$) δ: 1.26 (3H, t, J=7.2 Hz), 1.85 (6H, s), 1.86–2.05 (4H, m), 3.50 (2H, t, J=6.0 Hz), 4.12–4.19 (2H, m), 4.21 (2H, q, J=7.2 Hz), 7.31 (1H, d, J=9.2 Hz), 8.51 (1H, dd, J=9.2 Hz, 2.6 Hz), 9.02 (1H, d, J=2.6 Hz).

REFERENCE EXAMPLE 77

Ethyl 2-[1-(4-bromobutyl)-2,4-dioxo-6-fluoro-1,2,3,4-tetrahydroquinazolin-3-yl]isobutyrate Using the method similar to that in Reference Example 52 and starting from ethyl 2-(2,4-dioxo-6-fluoro-1,2,3,4-tetrahydroquinazolin-3-yl)isobutyrate (0.59 g) obtained in Reference Example 46, the title compound (0.58 g, 68%) was obtained.

IR (KBr): 2986, 2940, 1742, 1709, 1667, 1624, 1505 cm$^{-1}$.

$^1$H-NMR (CDCl$_3$) δ: 1.24 (3H, t, J=7.2 Hz), 1.84 (6H, s), 1.85–2.07 (4H, m), 3.48 (2H, t, J=6.2 Hz), 4.05–4.12 (2H, m), 4.20 (2H, q, J=7.2 Hz), 7.16 (1H, dd, J=4.0 Hz, 9.2 Hz), 7.40 (1H, ddd, J=9.2 Hz, 7.6 Hz, 3.0 Hz), 7.83 (1H, dd, J=8.2 Hz, 3.0 Hz).

REFERENCE EXAMPLE 78

Ethyl 2-[1-(4-bromobutyl)-7-chloro-2,4-dioxo-1,2,3,4-tetrahydroquinazolin-3-yl]isobutyrate Using the method similar to that in Reference Example 52 and starting from ethyl 2-(7-chloro-2,4-dioxo-1,2,3,4-tetrahydroquinazolin-3-yl)isobutyrate (0.62 g) obtained in Reference Example 47, the title compound (0.50 g, 56%) was obtained.

IR (KBr): 2984, 2940, 1744, 1713, 1667, 1605 cm$^{-1}$.

$^1$H-NMR (CDCl$_3$) δ: 1.24 (3H, t, J=7.1 Hz), 1.83 (6H, s), 1.85–2.06 (4H, m), 3.49 (2H, t, J=6.2 Hz), 4.03–4.10 (2H, m), 4.19 (2H, q, J=7.2 Hz), 7.17–7.23 (2H, m, ArH), 8.08 (2H, d, J=8.2 Hz).

REFERENCE EXAMPLE 79

Ethyl 2-[1-(4-bromobutyl)-6-chloro-2,4-dioxo-1,2,3,4-tetrahydroquinazolin-3-yl]isobutyrate Using the method similar to that in Reference Example 52 and starting from ethyl 2-(6-chloro-2,4-dioxo-1,2,3,4-tetrahydroquinazolin-3-yl)isobutyrate (0.62 g) obtained in Reference Example 48, the title compound (0.62 g, 70%) was obtained as an oil.

IR (KBr): 2984, 2940, 1742, 1711, 1667, 1609, 1591 cm$^{-1}$.

$^1$H-NMR (CDCl$_3$) δ: 1.24 (3H, t, J=7.2 Hz), 1.83 (6H, s), 1.85–2.05 (4H, m), 3.48 (2H, t, J=6.2 Hz), 4.08 (2H, t, J=7.2 Hz), 4.19 (2H, q, J=7.2 Hz), 7.13 (1H, d, J=8.8 Hz), 7.61 (1H, dd, J=8.8 Hz, 2.6 Hz), 8.12 (1H, d, J=2.6 Hz).

REFERENCE EXAMPLE 80

Ethyl 2-[1-(3-bromopropyl)-2,4-dioxo-1,2,3,4-tetrahydroquinazolin-3-yl]isobutyrate Using the method similar to that in Reference Example 52 and starting from ethyl 2,4-dioxo-1,2,3,4- tetrahydroquinazolin-3-yl]isobutyrate (0.55 g, 2.0 mmol) obtained in Reference Example 42, the title compound (0.53 g, 67%) was obtained as an oil.

IR (KBr): 2982, 2940, 1742, 1709, 1663, 1609 cm$^{-1}$.

$^1$H-NMR (CDCl$_3$) δ: 1.24 (3H, t, J=7.1 Hz), 1.85 (6H, s), 2.22–2.37 (2H, m), 3.52 (2H, t, J=6.3 Hz), 4.16–4.27 (4H, m), 7.26–7.29 (2H, m, ArH), 7.64–7.73 (1H, m, ArH), 8.16 (1H, dd, J=8.2 Hz, 1.6 Hz).

REFERENCE EXAMPLE 81

Ethyl 2-[1-(5-bromopentyl)-2,4-dioxo-1,2,3,4-tetrahydroquinazolin-3-yl]isobutyrate Using the method similar to that employed for synthesizing Reference Example 52 and starting from ethyl 2,4-dioxo-1,2,3,4-tetrahydroquinazolin-3-yl]isobutyrate (0.55 g, 2.0 mmol) obtained in Reference Example 42, the title compound (0.63 g, 74%) was obtained as an oil.

IR (KBr): 2990, 2938, 2867, 1742, 1707, 1665, 1609 cm$^{-1}$.

$^1$H-NMR (CDCl$_3$) δ: 1.24 (3H, t, J=7.1 Hz), 1.53–2.01 (6H, m), 1.85 (6H, s), 3.43 (2H, t, J=6.7 Hz), 4.07 (2H, t, J=8.6 Hz), 4.19 (2H, q, J=7.2 Hz), 7.12–7.27 (2H, m, ArH), 7.62–7.70 (1H, m, ArH), 8.16 (1H, dd, J=7.9 Hz, 1.7 Hz).

REFERENCE EXAMPLE 82

Ethyl 2-[1-(6-bromohexyl)-2,4-dioxo-1,2,3,4-tetrahydroquinazolin-3-yl]isobutyrate Using the method similar to that in Reference Example 52 and starting from ethyl 2,4-dioxo-1,2,3,4-tetrahydroquinazolin-3-yl]isobutyrate (0.55 g, 2.0 mmol) obtained in Reference Example 42, the title compound (0.66 g, 75%) was obtained as an oil.

IR (KBr): 2984, 2936, 2863, 1744, 1709, .1663, 1609 cm$^{-1}$.

$^1$H-NMR (CDCl$_3$) δ: 1.24 (3H, t, J=7.1 Hz), 1.40–1.93 (8H, m), 1.84 (6H, s), 3.42 (2H, t, J=6.6 Hz), 4.01–4.09 (2H, m), 4.19 (2H, q, J=7.1 Hz), 7.12–7.27 (2H, m, ArH), 7.61–7.70 (1H, m, ArH), 8.15 (1H, dd, J=7.8 Hz, 1.6 Hz).

REFERENCE EXAMPLE 83

1-(3-Chloropropyl)-2,4-dioxo-1,2,3,4-tetrahydroquinazoline 1-(3-Chloropropyl)-2,4-dioxo-3-(4-methoxybenzyl)-1,2,3,4-tetrahydroquinazoline (3.02 g) obtained in Reference Example 49 was dissolved in a solvent mixture of acetonitrile (80 ml) and water (16 ml), and, to this, ammonium cerium (IV) nitrate (9.23 g) was then added in portions. The reaction mixture was stirred at room temperature for 21 hours and the solvent was distilled off under reduced pressure. The residue was extracted with ethyl acetate, and the extract was washed with water, dried (Na$_2$SO$_4$), and the solvent was distilled off under reduced pressure to give the title compound (1.42 g, 71%). Recrystallization from ethyl acetate-ethyl ether yielded a colorless crystal having a melting point of 183 to 184° C.

IR (Nujor): 1690, 1600 cm$^{-1}$.

$^1$H-NMR (CDCl$_3$) d: 2.15–2.30 (2H, m), 3.70 (2H, t, J=6.2 Hz), 4.29 (2H, t, J=7.6 Hz), 7.29–7.38 (2H, m), 7.74 (1H, ddd, J=9.0, 7.6, 1.4 Hz), 8.23 (1H, dd, J=7.8, 1.6 Hz).

Elemental Analysis for C$_{11}$H$_{11}$N$_2$O$_2$Cl: Calcd. (%): C, 55.36; H, 4.65; N, 11.74. Found (%): C, 55.18; H, 4.47; N, 11.70.

REFERENCE EXAMPLE 84

1-(4-Chlorobutyl)-2,4-dioxo-1,2,3,4-tetrahydroquinazoline

Using the method similar to that in Reference Example 83 and starting from 1-(4-chlorobutyl)-2,4-dioxo-3-(4-methoxybenzyl)-1,2,3,4-tetrahydroquinazoline (4.54 g) obtained in Reference Example 50, the title compound (2.28 g, 74%) was synthesized. Recrystallization from ethyl acetate-ethyl ether yielded a colorless crystal having a melting point of 127 to 128° C.

IR (Nujor): 1710, 1660, 1600 cm$^{-1}$.

$^1$H-NMR (CDCl$_3$) δ: 1.90–2.00(4H, m), 3.63(2H, t, J=6.0 Hz), 4.16 (2H, t, J=7.0 Hz), 7.20–7.34 (2H, m), 7.73 (1H, ddd, J=8.6, 7.0, 1.6 Hz), 8.24 (1H, dd, J=7.8, 1.6 Hz).

Elemental Analysis for C$_{12}$H$_{13}$N$_2$O$_2$Cl: Calcd. (%): C, 57.04; H, 5.19; N, 11.09. Found (%): C, 56.97; H, 5.03; N, 11.26.

REFERENCE EXAMPLE 85

1-(5-Chloropentyl)-2,4-dioxo-1,2,3,4-tetrahydroquinazoline

Using the method similar to that in Reference Example 83 and starting from 1-(5-chloropentyl)-2,4-dioxo-3-(4-methoxybenzyl)-1,2,3,4-tetrahydroquinazoline (6.00 g) obtained in Reference Example 51, the title compound (2.37 g, 57%) was synthesized. Recrystallization from ethyl acetate yielded a colorless crystal having a melting point of 162 to 163° C.

IR (KBr): 3170, 3039, 2954, 2864, 1704, 1695, 1610, 1500, 1484 cm$^{-1}$.

$^1$H-NMR (CDCl$_3$) δ: 1.50–1.68 (2H, m), 1.68–1.92 (4H, m), 3.57 (2H, t, J=6.6 Hz), 4.12 (2H, t, J=7.6 Hz), 7.21 (1H, d, J=8.4 Hz), 7.28 (1H, t, J=7.8 Hz), 7.71 (1H, ddd, J=8.4, 6.6, 1.8 Hz), 8.23 (1H, dd, J=7.8, 1.8 Hz).

Elemental Analysis for C$_{13}$H$_{15}$N$_2$O$_2$Cl. 0.1H$_2$O: Calcd. (%): C, 58.15; H, 5.71; N, 10.43. Found (%): C, 57.93; H, 5.73; N, 10.39.

REFERENCE EXAMPLE 86

1-(4-Bromobutyl)-2,4-dioxo-1,2,3,4-tetrahydroquinazoline

Using the method similar to that in Reference Example 83 and starting from 1-(4-bromobutyl)-2,4-dioxo-3-(4-methoxybenzyl)-1,2,3,4-tetrahydroquinazoline (8.83 g) obtained in Reference Example 52, the title compound (5.11 g, 81%) was synthesized. Recrystallization from ethyl acetate yielded a colorless crystal having a melting point of 152 to 153° C.

IR (KBr): 3176, 3043, 2842, 1704, 1683, 1608, 1482 cm$^{-1}$.

$^1$H-NMR (CDCl$_3$) δ: 1.84–2.10 (4H, m), 3.50 (2H, t, J=6.2 Hz), 4.16 (2H, t, J=7.4 Hz), 7.25 (1H, d, J=7.8 Hz), 7.29 (1H, t, J=7.6 Hz), 7.72 (1H, ddd, J=8.4, 7.2, 1.2 Hz), 8.24 (1H, dd, J=8.2, 1.6 Hz).

Elemental Analysis for C$_{12}$H$_{13}$N$_2$O$_2$Br.0.2H$_2$O: Calcd. (%): C, 47.92; H, 4.49; N, 9.31. Found (%): C, 47.94; H, 4.43; N, 9.37.

REFERENCE EXAMPLE 87

1-(3-Chloropropyl)-2,4-dioxo-1,2,3,4-tetrahydropyrido[2,3-d]pyrimidine

Using the method similar to that in Reference Example 83 and starting from 1-(3-chloropropyl)-2,4-dioxo-3-(4- methoxybenzyl)-1,2,3,4-tetrahydropyrido[2,3-d]pyrimidine (1.72 g) obtained in Reference Example 53, the title compound (918 mg, 80%) was synthesized. Recrystallization from ethyl acetate-isopropyl ether yielded a colorless crystal having a melting point higher than 300° C.

IR (Nujor): 3150, 1710, 1695, 1670, 1590, 1485 cm$^{-1}$.

$^1$H-NMR (CDCl$_3$) δ: 2.28–2.34 (2H, m), 3.65 (2H, t, J=6.6 Hz), 4.49 (2H, t, J=7.6 Hz), 7.20–7.30 (1H, m), 8.46 (1H, dd, J=8.0, 2.0 Hz), 8.70 (1H, dd, J=4.8, 2.2 Hz).

Elemental Analysis for C$_{10}$H$_{10}$N$_3$O$_2$Cl: Calcd. (%): C, 50.12; H, 4.21; N, 17.53. Found (%): C, 50.62; H, 3.99; N, 17.38.

REFERENCE EXAMPLE 88

1-(4-Bromobutyl)-2,4-dioxo-1,2,3,4-tetrahydropyrido[2,3-d]pyrimidine

Using the method similar to that in Reference Example 83 and starting from 1-(4-bromobutyl)-2,4-dioxo-3-(4-methoxybenzyl)-1,2,3,4-tetrahydropyrido[2,3-d]pyrimidine (15.0 g) obtained in Reference Example 54, the title compound (6.10 g, 57%) was synthesized. Recrystallization from ethyl acetate-ethyl ether yielded a colorless crystal having a melting point of 139 to 141° C.

IR (KBr): 3043, 1704, 1699, 1600, 1587, 1488 cm$^{-1}$.

$^1$H-NMR (CDCl$_3$) δ: 1.80–2.08 (4H, m), 3.48 (2H, t, J=6.6 Hz), 4.35(2H, t, J=7.0 Hz), 7.19–7.26(1H, m), 8.45 (1H, dd, J=7.8, 1.8 Hz), 8.69 (1H, dd, J=4.68, 1.8 Hz).

Elemental Analysis for C$_{11}$H$_{12}$N$_3$O$_2$Br: Calcd. (%): C, 44.32; H, 4.06; N, 14.09. Found (%): C, 44.44; H, 4.11; N, 14.03.

REFERENCE EXAMPLE 89

1-(4-Bromobutyl)-2,4-dioxo-1,2,3,4-tetrahydropteridine

Using the method similar to that in Reference Example 83 and starting from 1-(4-bromobutyl)-2,4-dioxo-3-(4-methoxybenzyl)-1,2,3,4-tetrahydropteridine (3.82 g) obtained in Reference Example 55, the title compound (1.70 g, 62%) was synthesized. Recrystallization from ethyl acetate-ethyl ether yielded a colorless crystal having a melting point of 154 to 155° C.

IR (KBr): 3196, 3075, 2965, 1715, 1578, 1547, 1489 cm$^{-1}$.

$^1$H-NMR (CDCl$_3$) δ: 1.84–2.04 (4H, m), 3.48 (2H, t, J=6.2 Hz), 4.34 (2H, t, J=7.0 Hz), 8.63 (1H, d, J=2.2 Hz), 8.68 (1H, d, J=2.2 Hz), 9.06 (1H, bs).

Elemental Analysis for C$_{10}$H$_{11}$N$_4$O$_2$Br: Calcd. (%): C, 40.15; H, 3.71; N, 18.73. Found (%): C, 40.33; H, 3.73; N, 18.55.

REFERENCE EXAMPLE 90

1-(4-Bromobutyl)-7-chloro-2,4-dioxo-1,2,3,4-tetrahydroquinazoline

Using the method similar to that in Reference Example 83 and starting from 1-(4-bromobutyl)-7-chloro-2,4-dioxo-3-(4-methoxybenzyl)-1,2,3,4-tetrahydroquinazoline (6.32 g) obtained in Reference Example 56, the title compound (1.94 g, 42%) was synthesized. Recrystallization from ethyl acetate yielded a colorless crystal having a melting point of 180 to 182° C.

IR (KBr): 3163, 3041, 2842, 1699, 1579, 1498 cm$^{-1}$.

$^1$H-NMR (CDCl$_3$) δ: 1.87–2.10 (4H, m), 3.51 (2H, t, J=6.2 Hz), 4.12 (2H, t, J=7.4 Hz), 7.22–7.30 (2H, m), 8.16 (1H, d, J=9.0 Hz), 8.71 (1H, bs).

Elemental Analysis for C$_{12}$H$_{12}$N$_2$O$_2$BrCl: Calcd. (%): C, 43.47; H, 3.65; N, 8.45. Found (%): C, 43.67; H, 3.67; N, 8.48.

REFERENCE EXAMPLE 91

1-(4-Bromobutyl)-6-chloro-2,4-dioxo-1,2,3,4-tetrahydroquinazoline

Using the method similar to that in Reference Example 83 and starting from 1-(4-bromobutyl)-6-chloro-2,4-dioxo-3-(4-methoxybenzyl)-1,2,3,4-tetrahydroquinazoline (8.00 g) obtained in Reference Example 57, the title compound (3.39 g, 58%) was synthesized. Recrystallization from ethyl acetate-ethyl ether yielded a colorless crystal having a melting point of 154 to 156° C.

IR (KBr): 3055, 1699, 1683, 1610, 1583, 1488, 1471 cm$^{-1}$.

$^1$H-NMR (CDCl$_3$) δ: 1.82–2.10 (4H, m), 3.49 (2H, t, J=6.2 Hz), 4.14 (2H, t, J=7.4 Hz), 7.20 (1H, d, J=9.0 Hz), 7.67 (1H, dd, J=9.0, 2.6 Hz), 8.20 (1H, d, J=2.4 Hz), 9.19 (1H, bs).

Elemental Analysis for C$_{12}$H$_{12}$N$_2$O$_2$BrCl: Calcd. (%): C, 43.47; H, 3.65; N, 8.45. Found (%): C, 43.17; H, 3.52; N, 8.27.

REFERENCE EXAMPLE 92

1-(4-Bromobutyl)-2,4-dioxo-7-nitro-1,2,3,4-tetrahydroquinazoline

Using the method similar to that in Reference Example 83 and starting from 1-(4-bromobutyl)-2,4-dioxo-3-(4-methoxybenzyl)-7-nitro-1,2,3,4-tetrahydroquinazoline (11.1 g) obtained in Reference Example 58, the title compound (4.14 g, 50%) was synthesized. Recrystallization from ethyl acetate-ethyl ether yielded a colorless crystal having a melting point of 202 to 203° C.

IR (KBr): 3047, 1720, 1699, 1623, 1594, 1538, 1478 cm$^{-1}$.

$^1$H-NMR (CDCl$_3$) δ: 1.88–2.16 (4H, m), 3.51 (2H, t, J=6.0 Hz), 4.23 (2H, t, J=7.0 Hz), 8.06–8.14 (2H, m), 8.42 (1H, d, J=8.4 Hz), 8.81 (1H, bs).

Elemental Analysis for C$_{12}$H$_{12}$N$_3$O$_4$Br: Calcd. (%): C, 42.13; H, 3.54; N, 12.28. Found (%): C, 42.35; H, 3.67; N, 12.23.

REFERENCE EXAMPLE 93

1-(4-Bromobutyl)-2,4-dioxo-6-nitro-1,2,3,4-tetrahydroquinazoline

Using the method similar to that in Reference Example 83 and starting from 1-(4-bromobutyl)-2,4-dioxo-3-(4-methoxybenzyl)-6-nitro-1,2,3,4-tetrahydroquinazoline (16.0 g) obtained in Reference Example 59, the title compound (5.19 g, 44%) was obtained as a crystal. This product was used in the next reaction without further purification.

$^1$H-NMR (CDCl$_3$) δ: 1.86–2.14 (4H, m), 3.51 (2H, t, J=5.8 Hz), 4.21 (2H, t, J=7.4 Hz), 7.40 (1H, d, J=9.2 Hz), 8.56 (1H, dd, J=9.6, 2.6 Hz), 8.97 (1H, bs), 9.09 (1H, d, J=2.4 Hz).

REFERENCE EXAMPLE 94

1-(4-Bromobutyl)-2,4-dioxo-6-methyl-1,2,3,4-tetrahydroquinazoline

Using the method similar to that in Reference Example 83 and starting from 1-(4-bromobutyl)-2,4-dioxo-3-(4- methoxybenzyl)-6-methyl-1,2,3,4-tetrahydroquinazoline (2.53 g) obtained in Reference Example 60, the title compound (940 mg, 52%) was obtained as a crystal. This product was used in the next reaction without further purification.

$^1$H-NMR (CDCl$_3$) δ: 1.82–2.12 (4H, m), 2.42 (3H, s), 3.49 (2H, t, J=6.2 Hz), 4.14 (2H, t, J=7.4 Hz), 7.14 (1H, d, J=8.6 Hz), 7.53 (1H, dd, J=8.4, 2.2 Hz), 8.04 (1H, d, J=1.4 Hz), 8.86 (1H, bs).

REFERENCE EXAMPLE 95

2,4-Dioxo-3-(2-hydroxyethyl)-1,2,3,4-tetrahydroquinazoline

Lithium borohydride (1.12 g) was dissolved in tetrahydrofuran (100 ml) and methyl 2,4-dioxo-1,2,3,4-tetrahydroquinazoline-3-acetate (6.00 g) obtained in Reference Example 34 was added in portions with stirring and cooling on ice. The reaction mixture was stirred at room temperature for 21 hours and then made acidic with 1N hydrochloric acid. The crystal precipitated was collected by filtration, washed with water, methanol and then ethyl ether to give the title compound (4.41 g, 84%). Recrystallization from ethyl acetate-ethyl ether yielded a colorless crystal having a melting point of 240 to 242° C.

IR (Nujor): 3370, 1710, 1660, 1610, 1600, 1510, 1485 cm$^{-1}$.

$^1$H-NMR (CDCl$_3$) δ: 3.87 (2H, t, J=5.8 Hz), 4.29 (2H, t, J=5.4 Hz), 7.10–7.24 (2H, m), 7.55 (1H, t, J=8.0 Hz), 8.07 (1H, d, J=8.4 Hz), 11.05 (1H, bs).

Elemental Analysis for C$_{10}$H$_{10}$N$_2$O$_3$·0.1H$_2$O: Calcd. (%): C, 57.74; H, 4.94; N, 13.47. Found (%): C, 57.53; H, 5.20; N, 13.52.

REFERENCE EXAMPLE 96

Ethyl 2-(2,4-Dioxo-1,2,3,4-tetrahydroquinazolin-3-yl)benzoate 2,4-Dioxo-3-(2-hydroxyethyl)-1,2,3,4-tetrahydroquinazoline (2.50 g) obtained in Reference Example 95 was suspended in pyridine (50.0 ml) and treated dropwise with benzoyl chloride (1.55 ml). After stirring the reaction mixture at room temperature for 16 hours, the solvent was distilled off under reduced pressure and the mixture was neutralized with iN hydrochloric acid and then extracted with ethyl acetate. The extract was washed with water, dried (Na$_2$SO$_4$), and the solvent was distilled off under reduced pressure to give the title compound (3.27 g, 87%). Recrystallization from ethyl acetate-ethyl ether yielded a colorless crystal having a melting point of 196 to 197° C.

IR (KBr): 3072, 1720, 1664, 1621, 1608, 1492 cm$^{-1}$.

$^1$H-NMR (CDCl$_3$) δ: 4.52–4.59 (2H, m), 4.61–4.69 (2H, m), 7.00 (1H, d, J=8.4 Hz), 7.18–7.34 (3H, m), 7.41 (1H, d, J=7.0 Hz), 7.59 (1H, t, J=8.4 Hz), 7.97 (2H, d, J=7.2 Hz), 8.13 (1H, d, J=8.0 Hz).

Elemental Analysis for C$_{17}$H$_{14}$N$_2$O$_4$: Calcd. (%): C, 65.80; H, 4.55; N, 9.03. Found (%): C, 65.26; H, 4.59; N, 9.43.

REFERENCE EXAMPLE 97

Ethyl 2-[1-(4-bromobutyl)-2,4-dioxo-1,2,3,4-tetrahydroquinazolin-3-yl]benzoate

Using the method similar to that in Reference Example 52 and starting from ethyl 2-(2,4-dioxo-1,2,3,4-tetrahydroquinazolin-3-yl)benzoate (3.27 g) obtained in Reference Example 96, the title compound (3.02 g, 65%) was synthesized. Recrystallization from ethyl acetate-isopropyl ether yielded a colorless crystal having a melting point of 101 to 102° C.

IR (KBr): 2961, 1705, 1661, 1609, 1485 cm$^{-1}$.

$^1$H-NMR (CDCl$_3$) δ: 1.92–2.00(4H, m), 3.40 (2H, t, J=6.2 Hz) 4.14 (2H, t, J=6.8 Hz), 4.51–4.66 (4H, m), 7.14–7.30 (2H, m), 7.34–7.45 (2H, m), 7.52 (1H, d, J=7.4 Hz), 7.69 (1H, t, J=7.4 Hz), 7.99 (2H, d, J=8.4 Hz), 8.25 (1H, d, J=8.0 Hz).

Elemental Analysis for C$_{21}$H$_{21}$N$_2$O$_4$Br: Calcd. (%): C, 56.64; H, 4.75; N, 6.29. Found (%): C, 57.13; H, 4.68; N, 6.38.

REFERENCE EXAMPLE 98

2,4-Dioxo-1,2,3,4-tetrahydroquinazolin-3-acetic acid

Using the method similar to that in Reference Example 47 and starting from methyl 2,4-dioxo-1,2,3,4-tetrahydroquinazoline-3-acetate (3.50 g) obtained in Reference Example 34, the title compound (3.04 g, 93%) was synthesized. Recrystallization from ethyl acetate-ethyl ether yielded a colorless crystal having a melting point of 282 to 284° C.

IR (KBr): 3500–2200, 1717, 1659, 1626, 1510, 1495 cm$^{-1}$.

$^1$H-NMR (CDCl$_3$) δ: 4.76 (2H, s), 7.11–7.24 (2H, m), 7.56 (1H, t, J=7.2 Hz), 8.07 (1H, d, J=7.8 Hz), 11.13 (1H, bs).

Elemental Analysis for C$_{10}$H$_8$N$_2$O$_4$: Calcd. (%): C, 54.55; H, 3.66; N, 12.72. Found (%): C, 54.31; H, 3.60; N, 12.80.

REFERENCE EXAMPLE 99

2,4-Dioxo-N-methyl-N-(2-phenethyl)-1,2,3,4-tetrahydroquinazolin-3-acetamide 2,4-Dioxo-1,2,3,4-tetrahydroquinazolin-3-acetic acid (3.04 g) obtained in Reference Example 98 and N-methylphenethylamine (2.41 ml) were dissolved in N,N-dimethylformamide (60.0 ml) and diethyl cyanophosphonate (DEPC) (2.65 ml) and then triethylamine (2.31 ml) were added dropwise. The reaction mixture was stirred at room temperature for 26 hours, poured onto an iced water, and then extracted with ethyl acetate. The extract was washed with water, dried (Na$_2$SO$_4$), and the solvent was distilled off under reduced pressure to give the title compound (2.06 g, 45%). Recrystallization from ethyl acetate-ethyl ether yielded a colorless crystal having a melting point of 210 to 212° C.

IR (KBr): 3198, 2932, 1723, 1667, 1493 cm$^{-1}$.

$^1$H-NMR (CDCl$_3$) δ: 2.90 (2H, t, J=7.0 Hz, major), 3.00, (3H, s, minor), 3.02 (3H, s, major), 3.05 (2H, t, J=7.6 Hz, minor), 3.64 (2H, t, J=7.4 Hz), 4.82 (2H, s, minor), 4.87 (2H, s, major), 7.01 (1H, d, J=8.4 Hz), 7.06–7.54 (8H, m), 7.90–8.02 (1H, m), 9.37 (1H, bs).

Elemental Analysis for C$_{19}$H$_{19}$N$_3$O$_3$: Calcd. (%): C, 67.64; H, 5.68; N, 12.45. Found (%): C, 67.34; H. 5.74; N, 12.47.

REFERENCE EXAMPLE 100

1-(4-Bromobutyl)-2,4-dioxo-N-methyl-N-(2-phenethyl)-1,2,3,4-tetrahydroquinazolin-3-acetamide Using the method similar to that in Reference Example 52 and starting from 2,4-dioxo-N-methyl-N-(2-phenethyl)-1,2, 3,4-tetrahydroquinazolin-3-acetamide (1.50 g) obtained in Reference Example 99, the title compound (1.55 g, 74%) was obtained as an oil.

$^1$H-NMR (CDCl$_3$) δ: 1.76–2.00 (4H, m), 2.76 (2H, t, J=8.0 Hz, major), 2.86, (3H, s, minor), 2.90 (3H, s, major), 2.93 (2H, t, J=7.6 Hz, minor), 3.39 (2H, t, J=6.2 Hz), 3.44–3.58 (2H, m), 4.04–4.15 (2H, m), 4.75 (2H, s, minor), 4.79 (2H, s, major), 7.04–7.30 (7H, m), 7.60 (1H, t, J=8.0 Hz), 8.10–8.20 (1H, m).

REFERENCE EXAMPLE 101

Dimethyl 3-nitrophthalate

To a suspension of 3-nitrophthalic acid (25.5 g, 0.120 mol) and potassium carbonate (40.1 g, 0.289 mol) in acetone (500 ml), dimethyl sulfate (27.4 ml, 0.289 mmol) was added dropwise, and the reaction mixture was heated under reflux for 21 hours. The solvent was distilled off under reduced pressure, and the residue was combined with water and extracted with ethyl acetate. After the extract was washed with water and dried (MgSO$_4$), the solvent was distilled off under reduced pressure. The residue was subjected to a column chromatography on a silica gel eluting with n-hexane-ethyl acetate (5:1, v/v) to give the title compound (18.0 g, 63%). Recrystallization from ethyl acetate yielded a colorless crystal having a melting point of 66.0 to 67.0° C.

IR (KBr): 2955, 1738, 1630, 1613, 1574, 1541 cm$^{-1}$.

$^1$H-NMR (CDCl$_3$) δ: 3.96 (3H, s), 4.03 (3H, s), 7.69 (1H, t, J=8.2 Hz), 8.32–8.42 (2H, m).

Elemental Analysis for C$_{10}$H$_9$NO$_6$: Calcd. (%) C, 50.22; H, 3.79; N, 5.86. Found (%) : C, 50.25; H, 3.71; N, 5.94.

REFERENCE EXAMPLE 102

Dimethyl 3-aminophthalate

Dimethyl 3-nitrophthalate (18.0 g, 75.2 mmol) obtained in Reference Example 101 was dissolved in a mixture of concentrated hydrochloric acid (50.0 ml) water (250 ml) and methanol (25.0 ml), and an excess of zinc powder was added in portions. After completion of the reaction, the reaction mixture was filtered, and the filtrate was made basic with 25% aqueous ammonium hydroxide, and extracted with ethyl acetate. After the extract was washed with water and dried (MgSO$_4$), the solvent was distilled off under reduced pressure. The residue was subjected to a column chromatography on a silica gel eluting with n-hexane-ethyl acetate (10:1, v/v) to give the title compound (13.1 g, 83%) as an oil.

$^1$H-NMR (CDCl$_3$) δ: 3.85 (3H, s), 3.86 (3H, s), 5.20 (2H, bs), 6.78 (1H, dd, J=8.4, 1.2 Hz), 6.90 (1H, dd, J=7.4, 0.8 Hz), 7.24 (1H, d, J=8.0 Hz).

REFERENCE EXAMPLE 103

4-Nitroisophthalic acid 1,3-Dimethyl-4-nitrobenzene (10.0 g, 66.2 mmol) was dissolved in a mixture of pyridine (65.0 ml) and water (130 ml) and potassium permanganate (62.7 g, 0.397 mol) was added in portions, and the mixture was stirred at room temperature for 30 minutes. After completion of the reaction, the reaction mixture was filtered, and the filtrate was distilled off under reduced pressure. The residue was made acidic with 1N hydrochloric acid and extracted with ethyl acetate. After the extract was washed with water and dried (MgSO$_4$), the solvent was distilled off under reduced pressure to give the title compound (12.4 g, 89%) as a yellow crystal. This product was used in the next reaction without further purification.

REFERENCE EXAMPLE 104

Dimethyl 4-nitroisophthate

Using the method similar to that employed in Reference Example 101 and starting from 4-nitroisophthalic acid (19.8 g, 93.9 mmol) obtained in Reference Example 103, the title compound (17.0 g, 76%) was synthesized. Recrystallization from ethyl acetate-ethyl ether yielded a colorless crystal having a melting point of 84.0 to 86.0° C.

IR (KBr): 3443, 3118, 2957, 1732, 1539 cm$^{-1}$.

$^1$H-NMR (CDCl$_3$) δ: 3.96 (3H, s), 4.00 (3H, s), 7.93 (1H, d, J=8.4 Hz), 8.30 (1H, dd, J=8.4, 1.8 Hz), 8.45 (1H, d, J=1.8 Hz).

Elemental Analysis for C$_{10}$H$_9$NO$_6$: Calcd. (%) : C, 50.22; H, 3.79; N, 5.86. Found (%): C, 50.32; H, 3.71; N, 5.95.

REFERENCE EXAMPLE 105

Dimethyl 4-aminoisophthate

A mixture of dimethyl 4-nitroisophthate (17.0 g, 71.2 mmol) obtained in Reference Example 104, 10% Pd/C (50.3% hydrated) (7.12 g), methanol (100 ml) and THF (100 ml) was stirred in a hydrogen atmosphere at room temperature for 20 hours. The reaction mixture was filtered, and the solvent in the filtrate was distilled off under reduced pressure to give the title compound (12.4 g, 83%). Recrystallization from ethyl acetate-isopropyl ether yielded a colorless crystal having a melting point of 125 to 126° C.

IR (KBr): 3461, 3355, 2953, 1694, 1620, 1590, 1563, 1501 cm$^{-1}$.

$^1$H-NMR (CDCl$_3$) δ: 3.88 (3H, s), 3.90 (3H, s), 6.40 (2H, bs), 6.65 (1H, d, J=8.8 Hz), 7.91 (1H, dd, J=8.8, 2.2 Hz), 8.59 (1H, d, J=1.8 Hz).

Elemental Analysis for C$_{10}$H$_{11}$NO$_4$·1.2H$_2$O: Calcd. (%) : C, 52.04; H, 5.85; N, 6.07. Found (%) : C, 51.75; H, 5.47; N, 6.09.

REFERENCE EXAMPLE 106

5-Fluoro-2-nitrobenzoic acid

Using the method similar to that employed in Reference Example 103 and starting from 4-fluoro-2-methylnitrobenzene (14.0 g, 90.2 mmol), the title compound (5.12 g, 31%) was obtained as a yellow crystal. This product was used in the next reaction without further purification.

$^1$H-NMR (CDCl$_3$) δ: 7.36 (1H, ddd, J=9.0, 6.2, 2.8 Hz), 7.53 (1H, dd, J=7.6, 2.8 Hz), 8.01 (1H, dd, J=8.8, 4.4 Hz).

REFERENCE EXAMPLE 107

Methyl 5-fluoro-2-nitrobenzoate

Thionyl chloride (2.41 ml) was added dropwise to methanol (30.0 ml) with cooling on ice, and the mixture was stirred for 30 minutes at the same temperature. 5-Fluoro-2-nitrobenzoic acid (5.12 g, 27.5 mmol) obtained in Reference Example 106 was added to the reaction mixture with cooling on ice and the mixture was heated under reflux for 15.5 hours. The solvent was distilled off under reduced pressure, and the residue was combined with water and extracted with ethyl acetate. After the extract was washed with water and dried (MgSO$_4$), the solvent was distilled off under reduced pressure. The residue was subjected to a column chromatography on a silica gel eluting with n-hexane-ethyl acetate (10:1, v/v) to give the title compound (4.69 g, 96%) as an oil.

$^1$H-NMR (CDCl$_3$) δ: 3.95 (3H, s), 7.31 (1H, ddd, J=8.8, 7.4, 1.4 Hz), 7.39 (1H, dd, J=7.6, 3.0 Hz), 8.03 (1H, dd, J=8.8, 4.4 Hz).

REFERENCE EXAMPLE 108

Diethyl 3-methoxycarbonyl-4-nitrophenylmalonate

To a solution of diethyl malonate (8.04 ml, 52.9 mmol) in N,N-dimethylformamide (30.0 ml), potassium tert-butoxide (5.94 g, 52.9 mmol) was added, and, after complete dissolution, methyl 5-fluoro-2-nitrobenzoate (4.69 g, 26.5 mmol) obtained in Reference Example 107 was added. The reaction mixture was stirred at 60° C. for 25 hours and poured onto an iced water, made acidic with iN hydrochloric acid, and then extracted with ethyl acetate. After the extract was washed with water and dried (MgSO$_4$), the solvent was distilled off under reduced pressure to give the title compound as an oil. This product was used in the next reaction without further purification.

REFERENCE EXAMPLE 109

3-Carboxy-4-nitrophenylacetic acid

A mixture of diethyl 3-methoxycarbonyl-4-nitrophenylmalonate obtained in Reference Example 108, concentrated hydrochloric acid (10.0 ml) and acetic acid (40.0 ml) was heated under reflux for 17.5 hours. The solvent was distilled off under reduced pressure, and the residue was combined with water and extracted with ethyl acetate. After the extract was washed with water and dried (MgSO$_4$), the solvent was distilled off under reduced pressure to give the title compound as a white crystal. This product was used in the next reaction without further purification.

REFERENCE EXAMPLE 110

Methyl 3-methoxycarbonyl-4-nitrophenylacetic acid

Using the method similar to that employed in Reference Example 101 and starting from 3-carboxy-4-nitrophenylacetic acid obtained in Reference Example 109, the title compound (4.49 g, 67%) was obtained as an oil.

$^1$H-NMR (CDCl$_3$) δ: 3.93 (3H, s), 3.97 (3H, s), 3.97 (2H, s), 7.57 (1H, dd, J=8.6, 2.2 Hz), 7.65 (1H, d, J=1.8 Hz), 7.91 (1H, d, J=8.6 Hz).

REFERENCE EXAMPLE 111

Methyl 4-amino-3-methoxycarbonylphenylacetate

Using the method similar to that employed in Reference Example 102 and starting from 3-methoxycarbonyl-4-nitrophenylacetic acid (9.11 g, 36.0 mmol) obtained in Reference Example 110, the title compound (5.53 g, 69%) was obtained as an oil.

$^1$H-NMR (CDCl$_3$) δ: 3.65 (3H, s), 3.87 (3H, s), 3.87 (2H, s), 6.64 (1H, d, J=8.4 Hz), 7.23 (1H, dd, J=8.4, 2.2 Hz), 7.77 (1H, d, J=2.2 Hz).

REFERENCE EXAMPLE 112

Methyl 2-methyl-2-(3-methoxycarbonyl-4-nitrophenyl)propionate

To a suspension of sodium hydride (60% in oil) in N,N-dimethylformamide, methyl 4-amino-3-methoxycarbonylphenylacetate (4.49 g, 17.7 mmol) obtained in Reference Example 101 was added and the mixture was stirred at room temperature for 2 hours. To this mixture, iodomethane was added and the mixture was stirred further for 18.5 hours. The solvent was distilled off under reduced pressure and the residue was combined with 1N hydrochloric acid and extracted with ethyl acetate. After the extract was washed with water and dried (MgSO$_4$), the solvent was distilled off under reduced pressure. The residue was subjected to a column chromatography on a silica gel eluted with n-hexane-ethyl acetate (10:1, v/v) to give the title compound (4.25 g, 96%) as an oil.

$^1$H-NMR (CDCl$_3$) δ: 1.63 (6H, s), 3.68 (3H, s), 3.94 (3H, s), 7.58 (1H, dd, J=8.4, 1.8 Hz), 7.67 (1H, d, J=2.2 Hz), 7.91 (1H, d, J=8.4 Hz).

REFERENCE EXAMPLE 113

Methyl 2-methyl-2-(4-amino-3-methoxycarbonylphenyl)propionate

Using the method similar to that in Reference Example 105 and starting from methyl 2-methyl-2-(3-methoxycarbonyl-4-nitrophenyl)propionate (6.39 g, 25.6 mmol) obtained in Reference Example 112, the title compound (4.82 g, 75%) was synthesized. Recrystallization from n-hexane yielded a colorless crystal having a melting point of 58.0 to 60.0° C.

IR (KBr): 3482, 3372, 2951, 1730, 1694, 1626, 1590, 1563, 1501 cm$^{-1}$.

$^1$H-NMR (CDCl$_3$) δ: 1.55 (6H, s), 3.64 (3H, s), 3.87 (3H, s), 5.69 (2H, bs), 6.64 (1H, d, J=8.8 Hz), 7.27 (1H, dd, J=8.8, 2.6 Hz), 7.84 (1H, d, J=2.4 Hz).

Elemental Analysis for C$_{13}$H$_{17}$NO$_4$: Calcd. (%): C, 62.14; H, 6.82; N, 5.57. Found (%): C, 62.08; H, 6.92; N, 5.60.

REFERENCE EXAMPLE 114

Methyl 2,4-dioxo-3-(4-methoxybenzyl)-1,2,3,4-tetrahydroquinazoline-5-carboxylate 4-Methoxyphenylacetic acid (11.5 g, 69.4 mmol) was suspended in toluene (200 ml) and then admixed sequentially with triethylamine (11.6 ml, 85.2 mmol) and diphenylphosphoric azide (17.9 ml, 85.2 mmol). The reaction mixture was stirred at room temperature for 1 hour, and then heated under reflux for 3 hours. The mixture was combined with dimethyl 3-aminophthalate (13.1 g, 62.4 mmol) obtained in Reference Example 102 and then heated under reflux further for 20 hours. The solvent was distilled off under reduced pressure, and the residue was combined with water and extracted with ethyl acetate. After the extract was washed with water and dried (MgSO$_4$), the solvent was distilled off under reduced pressure. The residue was subjected to a column chromatography on a silica gel eluted with n-hexane-ethyl acetate (10:1, v/v) to give the title compound (8.49 g, 40%) as a white crystal. This product was used in the next reaction without further purification.

$^1$H-NMR (CDCl$_3$) δ: 3.77 (3H, s), 4.01 (3H, s), 5.14 (2H, s), 6.78–6.90 (3H, m), 7.09 (1H, d, J=8.4 Hz), 7.46 (2H, d, J=8.4 Hz), 7.60 (1H, d, J=8.2 Hz), 9.52 (1H, bs).

REFERENCE EXAMPLE 115

Methyl 2,4-dioxo-3-(4-methoxybenzyl)-1,2,3,4-tetrahydroquinazoline-6-carboxylate Using the method similar to that in Reference Example 114 and starting from dimethyl 4-aminoisophthate (12.0 g, 57.4 mmol) obtained in Reference Example 105, the title compound (11.2 g, 57%) was synthesized. Recrystallization from ethyl acetate yielded a colorless crystal having a melting point of 235 to 237° C.

IR (KBr): 3663, 2928, 1734, 1715, 1671, 1624, 1607, 1512, 1489 cm$^{-1}$.

$^1$H-NMR (CDCl$_3$) δ: 3.77 (3H, s), 3.95 (3H, s), 5.21 (2H, s), 6.84 (2H, d, J=8.8 Hz), 7.09 (1H, d, J=8.6 Hz), 7.50 (2H, d, J=8.8 Hz), 8.26 (1H, dd, J=8.6, 2.0 Hz), 8.84 (1H, d, J=1.4 Hz), 9.77 (1H, bs).

Elemental Analysis for C$_{18}$H$_{16}$N$_2$O$_5$: Calcd. (%): C, 63.52; H, 4.74; N, 8.23. Found (%): C, 63.29; H, 4.61; N, 8.19.

REFERENCE EXAMPLE 116

Methyl 2,4-dioxo-3-(4-methoxybenzyl)-1,2,3,4-tetrahydroquinazoline-7-carboxylate Using the method similar to that in Reference Example 114 and starting from dimethyl aminoterephthalate (6.29 g, 30.1 mmol), the title compound (4.96 g, 48%) was synthesized. Recrystallization from ethyl acetate yielded a colorless crystal having a melting point of 254 to 256° C.

IR (KBr): 3279, 3007, 2965, 1732, 1709, 1651, 1615, 1601, 1586, 1510 cm$^{-1}$.

$^1$H-NMR (CDCl$_3$) δ: 3.76 (3H, s), 3.98 (3H, s), 5.20 (2H, s), 6.84 (2H, d, J=8.8 Hz), 7.53 (2H, d, J=8.8 Hz), 7.76 (1H, s), 7.84 (1H, d, J=8.4 Hz), 8.21 (1H, d, J=8.4 Hz), 9.39 (1H, bs).

Elemental Analysis for C$_{18}$H$_{16}$N$_2$O$_5$: Calcd. (%): C, 63.52; H, 4.74; N, 8.23. Found (%): C, 63.05; H, 4.65; N, 8.17.

REFERENCE EXAMPLE 117

Methyl 2,4-dioxo-3-(4-methoxybenzyl)-1,2,3,4-tetrahydroquinazoline-6-acetate

Using the method similar to that in Reference Example 114 and starting from methyl 4-amino-3-methoxycarbonylphenylacetate (5.56 g, 24.9 mmol) obtained in Reference Example 111, the title compound (5.96 g, 68%) was obtained as a white crystal. This product was used in the next reaction without further purification.

$^1$H-NMR (CDCl$_3$) δ: 3.66 (3H, s), 3.76 (3H, s), 3.79 (2H, s), 5.19 (2H, s), 6.88–6.90 (1H, m), 6.83 (2H, d, J=8.8 Hz), 7.56 (1H, dd, J=8.4, 2.2 Hz), 8.05 (1H, d, J=2.2 Hz), 6.35 (1H, bs).

REFERENCE EXAMPLE 118

Methyl 2-[2,4-dioxo-3-(4-methoxybenzyl)-1,2,3,4-tetrahydroquinazolin-6-yl]-2-methylpropionate Using the method similar to that in Reference Example 114 and starting from methyl 2-methyl-2-(4-amino-3-methoxycarbonylphenyl)propionate (4.70 g, 18.7 mmol) obtained in Reference Example 113, the title compound (4.85 g, 61%) was obtained as an oil.

$^1$H-NMR (CDCl$_3$) δ: 1.61 (6H, s), 3.65 (3H, s), 3.77 (3H, s), 5.19 (2H, s), 7.00 (1H, d, J=8.4 Hz), 7.20 (2H, d, J=8.8 Hz), 7.49 (2H, d, J=8.6 Hz), 7.57 (1H, dd, J=8.6, 2.4 Hz), 8.13 (1H, d, J=2.4 Hz), 9.28 (1H, bs).

REFERENCE EXAMPLE 119

Methyl 1-(4-bromobutyl)-2,4-dioxo-3-(4-methoxybenzyl)-1,2,3,4-tetrahydroquinazoline-5-carboxylate Using the method similar to that in Reference Example 52 and starting from methyl 2,4-dioxo-3-(4-methoxybenzyl)-1,2,3,4-tetrahydroquinazoline-5-carboxylate (4.73 g, 13.9 mol) obtained in Reference Example 114, the title compound (4.51 g, 68%) was obtained as an oil.

$^1$H-NMR (CDCl$_3$) δ: 1.80–2.08 (4H, m), 3.47 (2H, t, J=6.0 Hz), 3.77 (3H, s), 4.01 (3H, s), 4.16 (2H, t, J=7.2 Hz), 5.16 (2H, s), 6.76–6.90 (3H, m), 7.20 (1H, t, J=7.4 Hz), 7.45 (2H, d, J=8.8 Hz), 7.68 (1H, t, J=7.4 Hz).

REFERENCE EXAMPLE 120

Methyl 1-(4-bromobutyl)-2,4-dioxo-3-(4-methoxybenzyl)-1,2,3,4-tetrahydroquinazoline-6-carboxylate Using the method similar to that in Reference Example 52 and starting from methyl 2,4-dioxo-3-(4-methoxybenzyl)-1,2,3,4-tetrahydroquinazoline-6-carboxylate (10.9 g, 32.0 mmol) obtained in Reference Example 115, the title compound (12.4 g, 81%) was obtained as an oil.

$^1$H-NMR (CDCl$_3$) δ: 1.86–2.08 (4H, m), 3.48 (2H, t, J=5.8 Hz), 3.80 (3H, s), 3.94 (3H, s), 4.18 (2H, t, J=7.2 Hz), 5.21 (2H, s), 6.84 (2H, d, J=8.8 Hz), 7.16–7.30 (1H, m), 7.50 (2H, d, J=8.8 Hz) 8.31 (1H, d, J=9.2 Hz), 8.91 (1H, d, J=2.2 Hz).

REFERENCE EXAMPLE 121

Methyl 1-(4-bromobutyl)-2,4-dioxo-3-(4-methoxybenzyl)-1,2,3,4-tetrahydroquinazoline-7-carboxylate Using the method similar to that in Reference Example 52 and starting from methyl 2,4-dioxo-3-(4-methoxybenzyl)-1,2,3,4-tetrahydroquinazoline-7-carboxylate (4.96 g, 14.6 mmol) obtained in Reference Example 116, the title compound (3.92 g, 56%) was obtained as an oil.

$^1$H-NMR (CDCl$_3$) δ: 1.87–2.08 (4H, m), 3.48 (2H, t, J=6.0 Hz), 3.77 (3H, s), 3.98 (3H, s), 4.21 (2H, t, J=6.2 Hz), 5.21 (2H, s), 6.84 (2H, d, J=8.8 Hz), 7.50 (2H, d, J=8.2 Hz), 7.82–7.90 (2H, m), 8.31 (1H, d, J=8.6 Hz).

REFERENCE EXAMPLE 122

Methyl 1-(4-bromobutyl)-2,4-dioxo-3-(4-methoxybenzyl)-1,2,3,4-tetrahydroquinazoline-6-acetate Using the method similar to that in Reference Example 52 and starting from methyl 2,4-dioxo-3-(4-methoxybenzyl)-1,2,3,4-tetrahydroquinazoline-6-acetate (5.86 g, 16.5 mmol) obtained in Reference Example 117, the title compound (6.61 g, 82%) was obtained as an oil. This product was used in the next reaction without further purification.

REFERENCE EXAMPLE 123

Methyl 2-[1-(4-bromobutyl)-2,4-dioxo-3-(4-methoxybenzyl)-1,2,3,4-tetrahydroquinazolin-6-yl]-2-methylpropionate Using the method similar to that in Reference Example 52 and starting from methyl 2-[2,4-dioxo-3-(4-methoxybenzyl)-1,2,3,4-tetrahydroquinazolin-6-yl]-2-methylpropionate (4.50 g, 11.8 mmol) obtained in Reference Example 118, the title compound (4.77 g, 78%) was obtained as an oil.

$^1$H-NMR (CDCl$_3$) δ: 1.62 (6H, s), 1.84–2.08 (4H, m), 3.41–3.52 (2H, m), 3.65 (3H, s), 3.77 (3H, s), 4.14 (2H, t, J=7.0 Hz), 5.21 (2H, s), 6.83 (2H, d, J=8.4 Hz), 7.15 (1H, d,

REFERENCE EXAMPLE 124

Methyl 1-(4-bromobutyl)-2,4-dioxo-1,2,3,4-tetrahydroquinazoline-5-carboxylate

Using the method similar to that in Reference Example 83 and starting from methyl 1-(4-bromobutyl)-2,4-dioxo-3-(4-methoxybenzyl)-1,2,3,4-tetrahydroquinazoline-5-carboxylate (4.51 g, 9.47 mmol) obtained in Reference Example 119, the title compound (1.83 g, 54%) was obtained as a white crystal. This product was used in the next reaction without further purification.

$^1$H-NMR (CDCl$_3$) δ: 1.82–2.12 (4H, m), 3.49 (2H, t, J=6.2 Hz), 3.98 (3H, s), 4.16 (2H, t, J=7.8 Hz), 7.21 (1H, d, J=7.2 Hz), 7.32 (1H, d, J=8.4 Hz), 7.74 (1H, t, J=7.2 Hz), 8.72 (1H, bs).

REFERENCE EXAMPLE 125

Methyl 1-(4-bromobutyl)-2,4-dioxo-1,2,3,4-tetrahydroquinazoline-6-carboxylate

Using the method similar to that in Reference Example 83 and starting from methyl 1-(4-bromobutyl)-2,4-dioxo-3-(4-methoxybenzyl)-1,2,3,4-tetrahydroquinazoline-6-carboxylate (12.4 g, 26.0 mmol) obtained in Reference Example 120, the title compound (2.71 g, 29%) was obtained as a white crystal. This product was used in the next reaction without further purification.

$^1$H-NMR (CDCl$_3$) δ: 1.85–2.12 (4H, m), 3.49 (2H, t, J=6.2 Hz), 3.96 (3H, s), 4.18 (2H, t, J=7.0 Hz), 7.24–7.32 (1H, m), 8.37 (1H, d, J=8.6 Hz), 8.57 (1H, bs), 8.88 (1H, s).

REFERENCE EXAMPLE 126

Methyl 1-(4-bromobutyl)-2,4-dioxo-1,2,3,4-tetrahydroquinazoline-7-carboxylate

Using the method similar to that in Reference Example 83 and starting from methyl 1-(4-bromobutyl)-2,4-dioxo-3-(4-methoxybenzyl)-1,2,3,4-tetrahydroquinazoline-7-carboxylate (3.92 g, 8.23 mmol) obtained in Reference Example 121, the title compound (1.78 g, 61%) was synthesized. Recrystallization from ethyl acetate yielded a colorless crystal having a melting point of 184 to 185° C.

IR (KBr): 3166, 3044, 1726, 1715, 1682, 1622, 1510 cm$^{-1}$.

$^1$H-NMR (CDCl$_3$) δ: 1.88–2.16 (4H, m), 3.50 (2H, t, J=6.2 Hz), 4.00 (3H, s), 4.21 (2H, t, J=6.6 Hz), 7.86–7.95 (2H, m), 8.30 (1H, d, J=8.0 Hz), 8.45 (1H, bs).

Elemental Analysis for C$_{14}$H$_{15}$N$_2$O$_4$Br.0.6H$_2$O: Calcd. (%): C, 45.94; H, 4.46; N, 7.65. Found (%): C, 45.89; H, 4.18; N, 7.71.

REFERENCE EXAMPLE 127

Methyl 1-(4-bromobutyl)-2,4-dioxo-1,2,3,4-tetrahydroquinazoline-6-acetate

Using the method similar to that in Reference Example 83 and starting from methyl 1-(4-bromobutyl)-2,4-dioxo-3-(4-methoxybenzyl)-1,2,3,4-tetrahydroquinazoline-6-acetate (6.61 g, 13.6 mmol) obtained in Reference Example 122, the title compound (3.16 g, 63%) was obtained as an oil. This product was used in the next reaction without further purification.

REFERENCE EXAMPLE 128

Methyl 2-[1-(4-bromobutyl)-2,4-dioxo-1,2,3,4-tetrahydroquinazolin-6-yl]-2-methylpropionate Using the method similar to that in Reference Example 52 and starting from methyl 2-[1-(4-bromobutyl)-2,4-dioxo-3-(4-methoxybenzyl)-1,2,3,4-tetrahydroquinazolin-6-yl]-2-methylpropionate (4.77 g, 9.22 mmol) obtained in Reference Example 123, the title compound (2.12 g, 58%) was synthesized. Recrystallization from ethyl acetate-ethyl ether yielded a colorless crystal having a melting point of 164 to 165° C.

IR (KBr): 3165, 3044, 2841, 1726, 1686, 1620, 1584, 1507, 1474 cm$^{-1}$.

$^1$H-NMR (CDCl$_3$) δ: 1.64 (6H, s), 1.84–2.08 (4H, m), 3.49 (2H, t, J=6.2 Hz), 3.67 (3H, s), 4.13 (2H, t, J=7.4 Hz), 7.21 (1H, d, J=9.2 Hz), 7.70 (1H, dd, J=8.6, 2.6 Hz), 8.21 (1H, d, J=2.6 Hz), 8.32 (1H, bs).

Elemental Analysis for C$_{17}$H$_{21}$N$_2$O$_4$Br: Calcd. (%): C, 51.40; H, 5.33; N, 7.05. Found (%): C, 51.16; H, 5.38; N, 6.85.

REFERENCE EXAMPLE 129

Ethyl 6-aminovalerate hydrochloride

Using the method similar to that in Reference Example 107 and starting from 5-aminovaleric acid (25.0 g, 0.216 mol), the title compound (51.5 g, 86%) was synthesized. Recrystallization from ethyl ether yielded a colorless crystal having a melting point of 103 to 105° C.

IR (KBr): 3412, 2980, 1732, 1603, 1495, 1472 cm$^{-1}$.

$^1$H-NMR (CDCl$_3$) δ: 1.26 (3H, t, J=7.2 Hz), 1.64–1.92 (4H, m), 2.37 (2H, t, J=6.2 Hz), 2.94–3.16 (2H,m), 4.13 (2H, q, J=7.0 Hz), 8.30 (2H, bs).

Elemental Analysis for C$_7$H$_{16}$NO$_2$Cl.0.1H$_2$O: Calcd. (%): C, 45.82; H, 8.90; N, 7.67. Found (%): C, 45.50; H, 8.52; N, 7.56.

REFERENCE EXAMPLE 130

Ethyl 6-aminohexanoate hydrochloride

Using the method similar to that in Reference Example 107 and starting from 6-aminohexanoic acid (10.0 g, 76.2 mmol), the title compound (15.1 g, about 100%) was obtained as a white crystal. This product was used in the next reaction without further purification.

$^1$H-NMR (CDCl$_3$) δ: 1.25 (3H, t, J=7.0 Hz), 1.38–1.58 (2H, m), 1.58–1.90 (4H, m), 2.32 (2H, t, J=7.4 Hz), 2.90–3.12 (2H,m), 4.12 (2H, q, J=7.4 Hz), 8.27 (2H, bs).

REFERENCE EXAMPLE 131

Ethyl 8-aminooctanoate hydrochloride

Using the method similar to that in Reference Example 107 and starting from 8-aminooctanoic acid (5.0 g, 31.4 mmol), the title compound (7.21 g, about 100%) was obtained as a white crystal. This product was used in the next reaction without further purification.

IR (KBr): 3374, 3300–2400, 2932, 1736, 1607 cm$^{-1}$.

$^1$H-NMR (CDCl$_3$) δ: 1.26 (3H, t, J=7.2 Hz), 1.26–1.52 (6H, m), 1.61 (2H, t, J=7.0 Hz), 1.72–1.84 (2H, m), 2.29 (2H, t, J=7.4 Hz), 2.90–3.08 (2H,m), 4.12 (2H, q, J=7.4 Hz), 8.29 (2H, bs).

REFERENCE EXAMPLE 132

Methyl 1-amino-1-cyclopentylcarboxylate hydrochloride

Using the method similar to that in Reference Example 107 and starting from 1-amino-1-cyclopentylcarboxylic acid (25.0 g, 0.216 mmol), the title compound (7.21 g, about 100%) was synthesized. Recrystallization from ethyl ether yielded a colorless crystal having a melting point of 200 to 202° C.

IR (KBr): 3428, 2961, 1746, 1576, 1514 cm$^{-1}$.

$^1$H-NMR (CDCl$_3$) δ: 1.70–2.16 (8H, m), 3.83 (3H, s), 8.96 (2H, bs).

Elemental Analysis for C$_7$H$_{13}$NO$_2$.HCl: Calcd. (%): C, 46.80; H, 7.85; N, 7.80. Found (%): C, 46.74; H, 7.76; N, 8.05.

REFERENCE EXAMPLE 133

Methyl 1-amino-1-cyclohexylcarboxylate hydrochloride

Using the method similar to that in Reference Example 107 and starting from 1-amino-1-cyclohexylcarboxylic acid (15.1 g, 0.106 mmol), the title compound (21.8 g, about 100%) was synthesized. Recrystallization from ethyl ether yielded a colorless crystal having a melting point of 199 to 201° C.

IR (KBr): 3466, 3320–2350, 1744, 1590, 1522 cm$^{-1}$.

$^1$H-NMR (CDCl$_3$) δ: 1.30–1.50 (2H, m), 1.58–2.22 (8H, m), 3.82 (3H, s), 8.98 (2H, bs).

Elemental Analysis for C$_8$H$_{15}$NO$_2$.HCl0.2H$_2$O: Calcd. (%): C, 48.71; H, 8.38; N, 7.10. Found (%): C, 48.50; H, 8.10; N, 7.39.

REFERENCE EXAMPLE 134

Ethyl 6-(2-aminobenzamide)hexanoate

Using the method similar to that in Reference Example 9 and using ethyl 6-aminohexanoate hydrochloride (15.1 g, 77.2 mmol) instead of glycine methyl ester hydrochloride, the title compound (18.9 g, 97%) was obtained as an oil.

$^1$H-NMR (CDCl$_3$) δ: 1.25 (3H, t, J=7.0 Hz), 1.34–1.54 (2H, m), 1.55–1.74 (4H, m), 2.32 (2H, t, J=7.2 Hz), 3.42 (2H, q, J=6.2 Hz), 4.13 (2H, q, J=7.0 Hz), 5.49 (2H, bs), 6.12 (1H, bs), 6.60–6.71 (2H, m), 7.20 (1H, ddd, J=8.4, 7.0, 1.4 Hz), 7.31 (1H, dd, J=8.0, 1.2 Hz).

REFERENCE EXAMPLE 135

Ethyl 8-(2-aminobenzamide)octanoate

Using the method similar to that in Reference Example 9 and using ethyl 8-aminooctanoate hydrochloride (7.00 g, 31.1 mmol) instead of glycine methyl ester hydrochloride, the title compound (9.82 g, about 100%) was obtained as an oil.

$^1$H-NMR (CDCl$_3$) δ: 1.26 (3H, t, J=7.0 Hz), 1.32–1.44 (6H, m), 1.55–1.68 (4H, m), 2.29 (2H, t, J=7.2 Hz), 3.40 (2H, q, J=6.2 Hz), 4.12 (2H, q, J=7.0 Hz), 5.49 (2H, bs), 6.06 (1H, bs), 6.58–6.70 (2H, m), 7.20 (1H, ddd, J=8.4, 7.0, 1.4 Hz), 7.30 (1H, dd, J=8.2, 1.6 Hz).

REFERENCE EXAMPLE 136

Methyl 1-(2-aminobenzamide)-1-cyclopentylcarboxylate

Using the method similar to that in Reference Example 9 and using methyl 1-amino-1-cyclopentylcarboxylate hydrochloride (7.10 g, 39.5 mmol) instead of glycine methyl ester hydrochloride, the title compound (3.05 g, 32%) was synthesized. Recrystallization from isopropyl ether yielded a colorless crystal having a melting point of 108 to 109° C.

IR (KBr): 3465, 3362, 2953, 1728, 1645, 1614, 1583, 1520 cm$^{-1}$.

$^1$H-NMR (CDCl$_3$) δ: 1.74–1.94 (4H, m), 1.94–2.12 (2H, m), 2.28–2.46 (2H, m), 3.74 (3H, s), 5.47 (2H, bs), 6.40 (1H, bs), 6.60–6.70 (2H, m), 7.21 (1H, t, J=7.6 Hz), 7.35 (1H, d, J=7.4 Hz).

Elemental Analysis for C$_{14}$H$_{18}$N$_2$O$_3$: Calcd. (%): C, 64.11; H, 6.92; N, 10.68. Found (%): C, 64.19; H, 6.77; N, 10.70.

REFERENCE EXAMPLE 137

Methyl 1-(2-aminobenzamide)-1-cyclohexylcarboxylate

Using the method similar to that in Reference Example 9 and using methyl 1-amino-1-cyclohexylcarboxylate hydrochloride (10.0 g, 51.6 mmol) instead of glycine methyl ester hydrochloride, the title compound (5.88 g, 45%) was synthesized. Recrystallization from isopropyl ether yielded a colorless crystal having a melting point of 123 to 124° C.

IR (KBr): 3465, 3360, 2942, 2859, 1728, 1644, 1613, 1586 cm$^{-1}$.

$^1$H-NMR (CDCl$_3$) δ: 1.28–2.20 (10H, m), 3.73 (3H, s), 5.42 (2H, bs), 6.19 (1H, bs), 6.62–6.72 (2H, m), 7.22 (1H, ddd, J=8.8, 7.2, 1.6 Hz), 7.38 (1H, dd, J=8.2, 1.4 Hz).

Elemental Analysis for C$_{15}$H$_{20}$N$_2$O$_3$: Calcd. (%): C, 65.20; H, 7.30; N, 10.14. Found (%): C, 65.06; H, 7.19; N, 10.11.

REFERENCE EXAMPLE 138

Ethyl 5-(2-amino-5-fluorobenzamide)valerate

Using the method similar to that in Reference Example 2 and ethyl 5-aminovalerate hydrochloride (6.54 g, 25.2 mmol) instead of 4-methoxybenzylamine and starting from 2-amino-5-fluorobenzoic acid (3.00 g, 19.3 mmol), the title compound (4.91 g, 90%) was obtained as an oil.

$^1$H-NMR (CDCl$_3$) δ: 1.26 (3H, t, J=7.0 Hz), 1.56–1.80 (4H, m), 2.37 (2H, t, J=7.0 Hz), 3.12 (2H, q, J=5.6 Hz), 4.28 (2H, q, J=7.2 Hz), 5.29 (2H, bs), 6.26 (1H, bs), 6.64 (1H, dd, J=9.2, 4.8 Hz), 6.81 (1H, dt, J=8.0, 2.6 Hz), 7.06 (1H, dd, J=9.0, 3.0 Hz).

REFERENCE EXAMPLE 139

Ethyl 5-(2-amino-5-methoxybenzamide)valerate

Using the method similar to that in Reference Example 2 and ethyl 5-aminovalerate hydrochloride instead of 4-methoxybenzylamine and starting from 2-amino-5-methoxybenzoic acid (2.50 g, 15.0 mmol), the title compound (3.76 g, 85%) was obtained as an oil.

$^1$H-NMR (CDCl$_3$) δ: 1.26 (3H, t, J=7.0 Hz), 1.58–1.80 (4H, m), 2.37 (2H, t, J=6.2 Hz), 3.42 (2H, dt, J=6.2 5.8 Hz), 3.77 (3H, s), 4.14 (2H, q, J=7.4 Hz), 6.35 (2H, bs), 6.66 (1H, d, J=8.4 Hz), 6.72–6.84 (2H, m).

REFERENCE EXAMPLE 140

Ethyl 5-(2-amino-5-nitrobenzamide)valerate

Using the method similar to that in Reference Example 2 and ethyl 5-aminovalerate hydrochloride instead of 4-methoxybenzylamine and starting from 2-amino-5-nitrobenzoic acid (4.66 g, 25:6 mmol), the title compound (5.39 g, 68%) was synthesized. Recrystallization from ethyl acetate-isopropyl ether yielded a colorless crystal having a melting point of 86.0 to 88.0° C.

IR (KBr): 3328, 2936, 1717, 1615, 1591, 1539, 1505 cm$^{-1}$.

$^1$H-NMR (CDCl$_3$) δ: 1.27 (3H, t, J=7.0 Hz), 1.58–1.84 (4H, m), 2.39 (2H, t, J=6.2 Hz), 3.45 (2H, dt, J=6.2 5.8 Hz), 4.17 (2H, q, J=7.4 Hz), 6.55 (2H, bs), 6.58–6.70 (1H, m), 6.65 (1H, d, J=9.2 Hz), 8.09 (1H, dd, J=9.2, 1.8 Hz), 8.40 (1H, d, J=2.6 Hz).

Elemental Analysis for C$_{14}$H$_{19}$N$_3$O$_5$: Calcd. (%): C, 54.36; H, 6.19; N, 13.58. Found (%): C, 54.25; H, 6.32; N, 13.62.

REFERENCE EXAMPLE 141

Ethyl 5-(2-amino-5-hydroxybenzamide)valerate

Using the method similar to that in Reference Example 2 and ethyl 5-aminovalerate hydrochloride instead of 4-methoxybenzylamine and starting from 2-amino-5-hydroxybenzoic acid (7.38 g, 48.2 mmol), the title compound (12.9 g, 96%) was obtained as an oil. This product was used in the next reaction without further purification.

REFERENCE EXAMPLE 142

Ethyl 2,4-dioxo-1,2,3,4-tetrahydroquinazoline-3-hexanoate

Using the method similar to that in Reference Example 26 (Method 1) and starting from ethyl 6-(2-aminobenzamide) hexanoate (18.9 g, 67.8 mmol) obtained in Reference Example 134, the title compound (19.3 g, 93%) was synthesized. Recrystallization from ethyl acetate-isopropyl ether yielded a colorless crystal having a melting point of 103 to 104° C.

IR (KBr): 3196, 3132, 2965, 2940, 1730, 1703, 1630, 1601, 1493 cm$^{-1}$.

$^1$H-NMR (CDCl$_3$) δ: 1.24 (3H, t, J=6.8 Hz), 1.38–1.54 (2H, m), 1.60–1.84 (4H, m), 2.32 (2H, t, J=7.6 Hz), 4.04–4.20 (4H, m), 7.09 (1H, d, J=8.4 Hz), 7.24 (1H, t, J=7.2 Hz), 7.63 (1H, t, J=8.8 Hz), 8.14 (1H, d, J=8.0 Hz).

Elemental Analysis for C$_{16}$H$_{20}$N$_2$O$_4$: Calcd. (%): C, 63.14; H, 6.62; N, 9.20. Found (%): C, 63.15; H, 6.54; N, 9.28.

REFERENCE EXAMPLE 143

Ethyl 2,4-dioxo-1,2,3,4-tetrahydroquinazoline-3-octanoate

Using the method similar to that in Reference Example 26 (Method 1) and starting from ethyl 8-(2-aminobenzamide) octanoate (9.82 g, 32.0 mmol) obtained in Reference Example 135, the title compound (8.14 g, 77%) was synthesized. Recrystallization from ethyl acetate-isopropyl ether yielded a colorless crystal having a melting point of 88 to 89° C.

IR (KBr): 3196, 2930, 1728, 1634, 1601, 1497 cm$^{-1}$.

$^1$H-NMR (CDCl$_3$) δ: 1.25 (3H, t, J=6.8 Hz), 1.30–1.50 (6H, m), 1.58–1.80 (4H, m), 2.28 (2H, t, J=7.6 Hz), 4.06 (2H, t, J=5.4 Hz), 4.12 (2H, q, J=7.4 Hz), 7.09 (1H, d, J=8.4 Hz), 7.23 (1H, t, J=7.4 Hz), 7.62 (1H, t, J=8.4 Hz), 8.14 (1H, d, J=7.8 Hz).

Elemental Analysis for C$_{18}$H$_{24}$N$_2$O$_4$: Calcd. (%): C, 65.04; H, 7.28; N, 8.43. Found (%): C, 65.00; H, 7.14; N, 8.55.

REFERENCE EXAMPLE 144

Methyl 1-(2,4-dioxo-1,2,3,4-tetrahydroquinazolin-3-yl)-1-cyclopentylcarboxylate

Using the method similar to that in Reference Example 26 (Method 2) and starting from methyl 1-(2-aminobenzamide)-1-cyclopentylcarboxylate (3.05 g, 11.6 mmol) obtained in Reference Example 136, the title compound (1.94 g, 58%) was synthesized. Recrystallization from ethyl acetate-isopropyl ether yielded a colorless crystal having a melting point of 164 to 165° C.

IR (KBr): 2949, 1719, 1671, 1618, 1609, 1493 cm$^{-1}$.

$^1$H-NMR (CDCl$_3$) δ: 1.68–2.06 (4H, m), 2.46–2.57 (4H, m), 3.71 (3H, s), 7.03 (1H, d, J=8.4 Hz), 7.21 (1H, d, J=8.2 Hz), 7.60 (1H, t, J=7.2 Hz), 8.06 (1H, d, J=7.0 Hz).

Elemental Analysis for C$_{15}$H$_{16}$N$_2$O$_4$: Calcd. (%): C, 62.49; H, 5.59; N, 9.72. Found (%): C, 63.09; H, 5.55; N, 10.13.

REFERENCE EXAMPLE 145

Methyl 1-(2,4-dioxo-1,2,3,4-tetrahydroquinazolin-3-yl)-1-cyclohexylcarboxylate

Using the method similar to that in Reference Example 26 (Method 2) and starting from methyl 1-(2-aminobenzamide)-1-cyclohexylcarboxylate (10.3 g, 37.1 mmol) obtained in Reference Example 137, the title compound (5.72 g, 51%) was synthesized. Recrystallization from ethyl acetate-isopropyl ether yielded a colorless crystal having a melting point of 145 to 147° C.

IR (KBr): 2938, 1746, 1717, 1667, 1620, 1609, 1510, 1493 cm$^{-1}$.

$^1$H-NMR (CDCl$_3$) δ: 1.50–1.88 (6H, m), 2.16–2.30 (2H, m), 2.80–3.00 (2H, m), 3.72 (3H, s), 7.02 (1H, d, J=8.0 Hz), 7.21 (1H, t, J=7.6 Hz), 7.60 (1H, ddd, J=8.4, 7.0, 1.4 Hz), 8.05 (1H, d, J=7.6 Hz), 9.55 (1H, bs).

Elemental Analysis for C$_{16}$H$_{18}$N$_2$O$_4$: Calcd. (%): C, 63.56; H, 6.00; N, 9.27. Found (%): C, 63.27; H, 6.04; N, 9.18.

REFERENCE EXAMPLE 146

Ethyl 2,4-dioxo-6-fluoro-1,2,3,4-tetrahydroquinazoline-3-valerate

Using the method similar to that in Reference Example 26 (Method 1) and starting from ethyl 5-(2-amino-5-fluorobenzamide)valerate (4.91 g, 17.4 mmol) obtained in Reference Example 138, the title compound (4.08 g, 76%) was synthesized. Recrystallization from ethyl acetate-isopropyl ether yielded a colorless crystal having a melting point of 131 to 132° C.

IR (KBr): 3193, 1728, 1636, 1512, 1493 cm$^{-1}$.

$^1$H-NMR (CDCl$_3$) δ: 1.24 (3H, t, J=7.2 Hz), 1.70–7.82 (4H, m), 2.38 (2H, t, J=7.0 Hz), 4.10 (2H, t, J=7.4 Hz), 4.12 (2H, q, J=6.8 Hz), 7.10 (1H, dd, J=8.8, 4.0 Hz), 7.36 (1H, dt, J=7.6, 3.0 Hz), 7.80 (1H, dd, J=8.4, 3.0 Hz), 7.79 (1H, bs).

Elemental Analysis for C$_{15}$H$_{17}$N$_2$O$_4$F: Calcd. (%): C, 58.44; H, 5.56; N, 9.09. Found (%): C, 58.36; H, 5.46; N, 9.26.

REFERENCE EXAMPLE 147

Ethyl 2,4-dioxo-6-methoxy-1,2,3,4-tetrahydroquinazoline-3-valerate

Using the method similar to that in Reference Example 26 (Method 2) and starting from ethyl 5-(2-amino-5- methoxybenzamide)valerate (3.76 g, 12.8 mmol) obtained in Reference Example 139, the title compound (4.91 g, about 100%) was obtained as a white crystal. This product was used in the next reaction without further purification.

$^1$H-NMR (CDCl$_3$) δ: 1.14 (3H, t, J=7.0 Hz), 1.58–1.74 (4H, m), 2.29 (2H, t, J=6.6 Hz), 3.77 (3H, s), 3.96–4.08 (4H, m), 6.95 (1H, d, J=8.8 Hz), 7.14 (1H, dd, J=8.8, 3.0 Hz), 7.45 (1H, d, J=2.6 Hz), 9.77 (1H, bs).

REFERENCE EXAMPLE 148

Ethyl 2,4-dioxo-6-nitro-1,2,3,4-tetrahydroquinazoline-3-valerate

Using the method similar to that in Reference Example 26 (Method 2) and starting from ethyl 5-(2-amino-5-nitrobenzamide)valerate (5.33 g, 17.2 mmol) obtained in Reference Example 140, the title compound (3.63 g, 63%) was synthesized. Recrystallization from ethyl acetate-ethyl ether yielded a colorless crystal having a melting point of 173 to 174° C.

IR (KBr): 3065, 2980, 2944, 1730, 1651, 1626, 1601, 1545, 1485 cm$^{-1}$.

$^1$H-NMR (CDCl$_3$) δ: 1.24 (3H, t, J=7.0 Hz), 1.68–1.80 (4H, m), 2.38 (2H, t, J=6.8 Hz), 4.11 (2H, t, J=6.6 Hz), 4.11 (2H, q, J=7.2 Hz), 7.20–7.28 (1H, m), 8.47 (1H, dd, J=8.8, 2.6 Hz), 9.02 (1H, d, J=2.6 Hz), 9.96 (1H, bs).

Elemental Analysis for C$_{15}$H$_{17}$N$_3$O$_6$: Calcd. (%): C, 53.73; H, 5.11; N, 12.53. Found (%): C, 53.64; H, 5.05; N, 12.62.

REFERENCE EXAMPLE 149

Ethyl 2,4-dioxo-6-hydroxy-1,2,3,4-tetrahydroquinazoline-3-valerate

Using the method similar to that in Reference Example 26 (Method 2) and starting from ethyl 5-(2-amino-5-hydroxybenzamide)valerate (12.9 g, 46.0 mmol) obtained in Reference Example 141, the title compound (3.81 g, 28%) was synthesized. Recrystallization from ethyl acetate yielded a colorless crystal having a melting point of 105 to 107° C.

IR (KBr): 3187, 2949, 1728, 1705, 1692, 1634, 1605, 1518 cm$^{-1}$.

$^1$H-NMR (CDCl$_3$+DMSO-d$_6$) δ: 1.26 (3H, t, J=7.0 Hz), 1.58–1.70 (4H, m), 2.18–2.28 (2H, m), 3.78–3.98 (2H, m), 3.99 (2H, q, J=7.4 Hz), 6.90 (1H, d, J=8.8 Hz), 6.95–7.03 (1H, m), 7.38 (1H, s), 10.45 (1H, bs).

Elemental Analysis for C$_{15}$H$_{18}$N$_2$O$_5$: Calcd. (%): C, 58.82; H, 5.92; N, 9.15. Found (%): C, 58.61; H, 5.81; N, 9.20.

REFERENCE EXAMPLE 150

Ethyl 1-(4-bromobutyl)-2,4-dioxo-1,2,3,4-tetrahydroquinazoline-3-hexanoate

Using the method similar to that in Reference Example 52 and starting from ethyl 2,4-dioxo-1,2,3,4-tetrahydroquinazoline-3-hexanoate (7.05 g, 23.2 mmol) obtained in Reference Example 142, the title compound (6.90 g, 68%) was obtained as an oil.

$^1$H-NMR (CDCl$_3$) δ: 1.24 (3H, t, J=7.0 Hz), 1.34–1.52 (2H, m), 1.62–1.81 (4H, m), 1.86–2.08 (4H, m), 2.31 (2H, t, J=7.4 Hz), 3.50 (2H, t, J=6.4 Hz), 4.03–4.22 (6H, m), 7.18–7.31 (2H, m), 7.68 (1H, ddd, J=8.8, 7.2, 1.4 Hz), 8.24 (1H, dd, J=8.2, 1.6 Hz).

REFERENCE EXAMPLE 151

Ethyl 1-(4-bromobutyl)-2,4-dioxo-1,2,3,4-tetrahydroquinazoline-3-octanoate

Using the method similar to that in Reference Example 52 and starting from ethyl 2,4-dioxo-1,2,3,4-tetrahydroquinazoline-3-octanoate (6.00 g, 18.1 mmol) obtained in Reference Example 143, the title compound (8.72 g, about 100%) was obtained as an oil.

$^1$H-NMR (CDCl$_3$) δ: 1.25 (3H, t, J=6.8 Hz), 1.30–1.46 (6H, m), 1.54–1.76 (4H, m), 1.86–2.10 (4H, m), 2.28 (2H, t, J=7.4 Hz), 3.38–3.54 (2H, m), 4.00–4.24 (6H, m), 7.16–7.30 (2H, m), 7.68 (1H, t, J=8.0 Hz), 8.23 (1H, dd, J=7.6, 1.2 Hz).

REFERENCE EXAMPLE 152

Methyl 1-[1-(4-bromobutyl)-2,4-dioxo-1,2,3,4-tetrahydroquinazolin-3-yl]-1-cyclopentylcarboxylate Using the method similar to that in Reference Example 52 and starting from methyl 1-(2,4-dioxo-1,2,3,4-tetrahydroquinazolin-3-yl)-1-cyclopentylcarboxylate (1.88 g, 6.52 mmol) obtained in Reference Example 144, the title compound (1.53 g, 55%) was synthesized. Recrystallization from ethyl acetate-ethyl ether yielded a colorless crystal having a melting point of 96 to 98° C.

IR (KBr): 2949, 1744, 1709, 1663, 1495, 1481 cm$^{-1}$.

$^1$H-NMR (CDCl$_3$) δ: 1.74–2.08 (8H, m), 2.33–2.58 (4H, m), 3.48 (2H, t, J=6.4 Hz), 3.70 (3H, s), 4.11 (2H, t, J=7.0 Hz), 7.12–7.30 (2H, m), 7.67 (1H, t, J=8.0 Hz), 8.16 (1H, d, J=8.2 Hz).

Elemental Analysis for C$_{19}$H$_{23}$N$_2$O$_4$Br: Calcd. (%): C, 53.91; H, 5.48; N, 6.62. Found (%): C, 53.96; H, 5.34; N, 6.47.

REFERENCE EXAMPLE 153

Methyl 1-[1-(4-bromobutyl)-2,4-dioxo-1,2,3,4-tetrahydroquinazolin-3-yl]-1-cyclohexylcarboxylate Using the method similar to that in Reference Example 52 and starting from ethyl methyl 1-(2,4-dioxo-1,2,3,4-tetrahydroquinazolin-3-yl)-1-cyclohexylcarboxylate (5.20 g, 17.2 mmol) obtained in Reference Example 145, the title compound (8.52 g, about 100%) was obtained as an oil.

$^1$H-NMR (CDCl$_3$) δ: 1.30–2.24 (12H, m), 2.78–2.94 (2H, m), 3.40–3.52 (2H, m), 3.72 (3H, s), 4.04–4.16 (2H, m), 7.12–7.30 (2H, m), 7.65 (1H, t, J=7.4 Hz), 8.13 (1H, d, J=8.2 Hz).

REFERENCE EXAMPLE 154

1-[1-(4-Bromobutyl)-2,4-dioxo-1,2,3,4-tetrahydroquinazolin-3-yl]-1-cyclohexylcarboxylic acid Using the method similar to that in Reference Example 109 and starting from methyl 1-[1-(4-bromobutyl)-2,4-dioxo-1,2,3,4-tetrahydroquinazolin-3-yl]-1-cyclohexylcarboxylate (3.52 g, 8.05 mmol) obtained in Reference Example 153, the title compound (2.35 g, 69%) was obtained as an oil.

$^1$H-NMR (CDCl$_3$) δ: 1.50–2.28 (12H, m), 2.82–3.00 (2H, m), 3.58 (2H, t, J=6.0 Hz), 4.06–4.17 (2H, m), 7.12–7.30 (2H, m), 7.65 (1H, d, J=8.0 Hz), 8.14 (1H, dd, J=8.0, 1.4 Hz).

REFERENCE EXAMPLE 155

Ethyl 1-(4-bromobutyl)-2,4-dioxo-6-fluoro-1,2,3,4-tetrahydroquinazoline-3-valerate Using the method similar to that in Reference Example 52 and starting from ethyl 2,4-dioxo-6-fluoro-1,2,3,4-tetrahydroquinazoline-3-valerate (3.98 g, 12.9 mmol) obtained in Reference Example 146, the title compound (2.46 g, 43%) was obtained as an oil.

$^1$H-NMR (CDCl$_3$) δ: 1.25 (3H, t, J=6.8 Hz), 1.66–1.78 (4H, m), 1.86–2.02 (4H, m), 2.36 (2H, t, J=6.6 Hz), 3.49 (2H, t, J=6.0 Hz), 4.04–4.20 (6H, m), 7.19 (1H, dd, J=9.2, 4.2 Hz), 7.41 (1H, dt, J=7.2, 3.0 Hz), 7.91 (1H, dd, J=8.2, 3.0 Hz).

REFERENCE EXAMPLE 156

Ethyl 1-(4-bromobutyl)-2,4-dioxo-6-methoxy-1,2,3,4-tetrahydroquinazoline-3-valerate Using the method similar to that in Reference Example 52 and starting from ethyl 2,4-dioxo-6-methoxy-1,2,3,4-tetrahydroquinazoline-3-valerate (4.50 g, 14.0 mmol) obtained in Reference Example 147, the title compound (3.14 g, 53%) was obtained as an oil.

$^1$H-NMR (CDCl$_3$) δ: 1.25 (3H, t, J=7.0 Hz), 1.68–2.08 (8H, m), 2.32–2.42 (2H, m), 3.49 (2H, t, J=5.8 Hz), 3.88 (3H, s), 4.05–4.20 (4H, m), 4.12 (2H, q, J=7.2 Hz), 7.14 (1H, d, J=9.2 Hz), 7.29 (1H, dd, J=9.2, 2.8 Hz), 7.67 (1H, d, J=3.0 Hz).

REFERENCE EXAMPLE 157

Ethyl 1-(4-bromobutyl)-2,4-dioxo-6-nitro-1,2,3,4-tetrahydroquinazoline-3-valerate Using the method similar to that in Reference Example 52 and starting from ethyl 2,4-dioxo-6-nitro-1,2,3,4-tetrahydroquinazoline-3-valerate (5.00 g, 14.9 mmol) obtained in Reference Example 148, the title compound (4.10 g, 59%) was obtained as an oil.

$^1$H-NMR (CDCl$_3$) δ: 1.25 (3H, t, J=7.0 Hz), 1.66–1.85 (4H, m), 1.90–2.08 (4H, m), 2.37 (2H, t, J=6.2 Hz), 3.50 (2H, t, J=5.8 Hz), 4.06–4.14 (2H, m), 4.12 (2H, q, J=7.4 Hz), 4.22 (2H, t, J=7.8 Hz), 7.34 (1H, d, J=9.2 Hz), 8.52 (1H, dd, J=9.2, 2.4 Hz), 9.09 (1H, d, J=2.6 Hz).

REFERENCE EXAMPLE 158

Ethyl 2,4-dioxo-6-(2-methoxyethoxy)methoxy-1,2,3,4-tetrahydroquinazoline-3-valerate To a suspension of ethyl 2,4-dioxo-6-hydroxy-1,2,3,4-tetrahydroquinazoline-3-valerate (3.50 g, 11.8 mmol) obtained in Reference Example 149 in dichloromethane (35.0 ml), N,N-diisopropylethylamine (2.05 ml, 17.7 mmol) and 2-methoxyethoxymethyl chloride (2.02 ml, 17.7 mmol) were added dropwise with cooling on ice, and the reaction mixture was stirred at room temperature for 18 hours. The solvent was distilled off under reduced pressure, and the residue was combined with water and extracted with ethyl acetate. After the extract was washed with water and dried (MgSO$_4$), the solvent was distilled off under reduced pressure to give the title compound (3.68 g, 79%). Recrystallization from ethyl acetate-ethyl ether yielded a colorless crystal having a melting point of 105 to 107° C.

IR (KBr): 3075, 2911, 1744, 1709, 1661, 1634, 1510 cm$^{-1}$.

$^1$H-NMR (CDCl$_3$) δ: 1.25 (3H, t, J=7.0 Hz), 1.72–1.80 (4H, m), 2.39 (2H, t, J=7.0 Hz), 3.39 (3H, s), 3.55–3.61 (2H, m), 3.81–3.88 (2H, m), 4.10 (2H, t, J=6.8 Hz), 4.12 (2H, q, J=7.0 Hz), 5.30 (2H, s), 7.06 (1H, d, J=8.8 Hz), 7.35 (1H, dd, J=8.8, 2.6 Hz), 7.76 (1H, d, J=3.0 Hz), 9.81 (1H, bs).

Elemental Analysis for C$_{19}$H$_{26}$N$_2$O$_7$: Calcd. (%): C, 57.86; H, 6.64; N, 7.10. Found (%): C, 57.70; H, 6.52; N, 7.35.

REFERENCE EXAMPLE 159

Ethyl 1-(4-bromobutyl)-2,4-dioxo-6-(2-methoxyethoxy)methoxy-1,2,3,4-tetrahydroquinazoline-3-valerate Using the method similar to that in Reference Example 52 and starting from ethyl 2,4-dioxo-6-(2-methoxyethoxy)methoxy-1,2,3,4-tetrahydroquinazoline-3-valerate (6.00 g, 15.2 mmol) obtained in Reference Example 158, the title compound (4.74 g, 59%) was obtained as an oil.

$^1$H-NMR (CDCl$_3$) δ: 1.25 (3H, t, J=7.4 Hz), 1.68–1.80 (4H, m), 1.86–2.02 (4H, m), 2.36 (2H, t, J=7.0 Hz), 3.38 (3H, s), 3.49 (2H, t, J=6.6 Hz), 3.54–3.60 (2H, m), 3.80–3.87 (2H, m), 4.04–4.20 (4H, m), 4.12 (2H, q, J=7.2 Hz), 7.04 (1H, d, J=9.2 Hz), 7.40 (1H, dd, J=9.0, 3.0 Hz), 7.86 (1H, d, J=3.0 Hz).

REFERENCE EXAMPLE 160

Ethyl 1-(4-bromobutyl)-2,4-dioxo-6-hydroxy-1,2,3,4-tetrahydroquinazoline-3-valerate To a solution of ethyl 1-(4-bromobutyl)-2,4-dioxo-6-(2-methoxyethoxy)methoxy-1,2,3,4-tetrahydroquinazoline-3-valerate (4.74 g, 8.95 mmol) obtained in Reference Example 159 in dichloromethane (100 ml), trifluoroacetic acid (1.38 ml, 17.9 mmol) was added dropwise, and the reaction mixture was heated under reflux for 16 hours. The solvent was distilled off under reduced pressure, and the residue was combined with water and extracted with ethyl acetate. After the solvent was washed with water and dried (MgSO$_4$), the solvent was distilled off under reduced pressure. The residue was subjected to a column chromatography on a silica gel eluting with n-hexane-ethyl acetate (5:1,v/v) to give the title compound (3.31 g, 84%) as an oil.

$^1$H-NMR (CDCl$_3$) δ: 1.24 (3H, t, J=7.0 Hz), 1.68–1.80 (4H, m), 1.86–2.04 (4H, m), 2.32–2.62 (2H, m), 3.48 (2H, t, J=5.6 Hz), 4.04–4.20 (4H, m), 4.12 (2H, q, J=7.2 Hz), 7.02 (1H, d, J=9.2 Hz), 7.28 (1H, dd, J=8.8, 3.0 Hz), 7.86 (1H, d, J=2.6 Hz).

REFERENCE EXAMPLE 161

2-[2-(2-Aminobenzamide)ethoxy]ethanol

Using the method similar to that in Reference Example 1 and using 2-(2-aminoethoxy)ethanol (1.44 ml, 73.6 mmol) instead of 4-methoxybenzylamine, the title compound (13.8 g, about 100%) was obtained as an oil.

$^1$H-NMR (CDCl$_3$) δ: 3.56–3.70 (6H, m), 3.70–3.80 (2H, m), 5.49 (2H, bs), 6.56 (1H, bs), 6.60–6.72 (2H, m), 7.21 (1H, ddd, J=8.4, 7.0, 1.4 Hz), 7.34 (1H, d, J=8.0 Hz).

REFERENCE EXAMPLE 162

2-[2-(2,4-Dioxo-1,2,3,4-tetrahydroquinazolin-3-yl)ethoxy]ethanol

Using the method similar to that in Reference Example 26 (Method 2) and starting from 2-[2-(2-aminobenzamide)

ethoxy]ethanol (13.8 g, 61.5 mmol) obtained in Reference Example 161, the title compound (6.23 g, 41%) was synthesized. Recrystallization from ethyl acetate-isopropyl ether yielded a colorless crystal having a melting point of 149 to 151° C.

IR (KBr): 3193, 2930, 2880, 1715, 1667, 1622, 1493 cm$^{-1}$.

$^1$H-NMR (CDCl$_3$) δ: 3.04 (1H, bs), 3.64–3.76 (4H, m), 3.85 (2H, t, J=5.6 Hz), 4.34 (2H, t, J=5.6 Hz), 7.11 (1H, d, J=8.0 Hz), 7.20 (1H, t, J=7.4 Hz), 7.59 (1H, ddd, J=8.8, 7.4, 1.4 Hz), 8.08 (1H, dd, J=8.2, 1.2 Hz), 10.05 (1H, bs).

Elemental Analysis for C$_{12}$H$_{14}$N$_2$O$_4$.0.2H$_2$O: Calcd. (%): C, 56.78; H, 5.72; N, 11.04. Found (%): C, 56.81; H, 5.64; N, 11.07.

REFERENCE EXAMPLE 163

2-(2,4-Dioxo-1,2,3,4-tetrahydroquinazolin-3 -yl) ethoxyacetic acid

To a solution of 2-[2-(2,4-dioxo-1,2,3,4-tetrahydroquinazolin-3-yl)ethoxy]ethanol (6.23 g, 24.9 mmol) obtained in Reference Example 162 in acetone (300 ml), Jones reagent was added dropwise and the reaction mixture was stirred at room temperature for 5 hours. An excessive Jones reagent was decomposed with 2-propanol, the solvent was distilled off under reduced pressure, and the residue was combined with water and extracted with ethyl acetate. After the extract was washed with water and dried (MgSO$_4$), the solvent was distilled off under reduced pressure to give the title compound (5.05 g, 77%) as a white crystal. This product was used in the next reaction without further purification.

REFERENCE EXAMPLE 164

Ethyl 2-(2,4-dioxo-1,2,3,4-tetrahydroquinazolin-3-yl)ethoxyacetate

Using the method similar to that in Reference Example 107 and starting from 2-(2,4-dioxo-1,2,3,4-tetrahydroquinazolin-3-yl)ethoxyacetic acid (5.05 g, 19.1 mmol) obtained in Reference Example 163, the title compound (2.91 g, 52%) was synthesized. Recrystallization from ethyl ether yielded a colorless crystal having a melting point of 115 to 116° C.

IR (KBr): 3204, 2982, 1717, 1667, 1622, 1494 cm$^{-1}$.

$^1$H-NMR (CDCl$_3$) δ: 1.23 (3H, t, J=7.2 Hz), 3.94 (2H, t, J=5.6 Hz), 4.16 (2H, s), 4.16 (2H, q, J=7.0 Hz), 4.38 (2H, t, J=5.6 Hz), 7.11 (1H, d, J=8.0 Hz), 7.22 (1H, ddd, J=8.0, 7.0, 1.0 Hz), 7.61 (1H, ddd, J=8.4, 7.0, 1.4 Hz), 8.11 (1H, dd, J=8.0, 1.6 Hz), 10.06 (1H, bs).

Elemental Analysis for C$_{14}$H$_{16}$N$_2$O$_5$: Calcd. (%): C, 57.53; H, 5.52; N, 9.58. Found (%): C, 57.43; H, 5.39; N, 9.70.

REFERENCE EXAMPLE 165

Ethyl 2-[1-(4-bromobutyl)-2,4-dioxo-1,2,3,4-tetrahydroquinazolin-3-yl]ethoxyacetate Using the method similar to that in Reference Example 52 and starting from ethyl 2-(2,4-dioxo-1,2,3,4-tetrahydroquinazolin-3-yl)ethoxyacetate (2.81 g, 9.61 mmol) obtained in Reference Example 164, the title compound (1.71 g, 42%) was obtained as an oil.

$^1$H-NMR (CDCl$_3$) δ: 1.23 (3H, t, J=7.2 Hz), 1.75–2.10 (4H, m), 3.49 (2H, t, J=5.8 Hz), 3.88 (2H, t, J=5.8 Hz), 4.10–4.28 (6H, m), 4.38 (2H, t, J=5.4 Hz), 7.18–7.32 (2H, m), 7.69 (1H, t, J=7.2 Hz), 8.24 (1H, d, J=6.8 Hz), 10.06 (1H, bs).

REFERENCE EXAMPLE 166

Ethyl 2-(2-amino-6-fluorobenzamide)isobutyrate

Using the method similar to that in Reference Example 21 and starting from 2-amino-6-fluorobenzoic acid (4.75 g, 30.0 mmol), the title compound (7.78 g, 97%) was obtained as an oil.

IR (KBr): 3472, 3355, 2986, 1732, 1645, 1626, 1588, 1518 cm$^{-1}$.

$^1$H-NMR (CDCl$_3$) δ: 1.27 (3H, t, J=7.2 Hz), 1.62 (6H, s), 4.22 (2H, q, J=7.2 Hz), 5.87 (2H, brs), 6.29–6.45 (2H, m, ArH), 7.09 (1H, dt, J=8.2 Hz, 6.6 Hz), 7.13 (1H, bs).

REFERENCE EXAMPLE 167

Ethyl 2-(2-amino-4,5-difluorobenzamide)isobutyrate

Using the method similar to that in Reference Example 21 and starting from 2-amino-4,5-difluorobenzoic acid (5.35 g, 30.0 mmol), the title compound (7.49 g, 87%) was obtained as an oil.

IR (KBr): 3463, 3360, 2986, 1725, 1651, 1597, 1574, 1532, 1510 cm$^{-1}$.

$^1$H-NMR (CDCl$_3$) δ: 1.28 (3H, t, J=7.2 Hz), 1.64 (6H, s), 4.23 (2H, q, J=7.2 Hz), 5.45 (1H, bs), 6.44 (1H, dd, J=12.0 Hz, 6.6 Hz), 6.48 (1H, bs), 7.18 (1H, dd, J=10.8 Hz, 8.6 Hz).

REFERENCE EXAMPLE 168

Ethyl 2-(2-amino-3-methoxybenzamide)isobutyrate

Using the method similar to that in Reference Example 21 and starting from 2-amino-3-methoxybenzoic acid (5.12 g, 30.0 mmol), the title compound (7.63 g, 91%) was obtained as an oil.

IR (KBr): 3490, 3360, 2984, 2938, 1732, 1642, 1520 cm$^{-1}$.

$^1$H-NMR (CDCl$_3$) δ: 1.27 (3H, t, J=7.2 Hz), 1.64 (6H, s), 3.86 (3H, s), 4.23 (2H, q, J=7.2 Hz), 5.74 (2H, bs), 6.60 (1H, bs), 6.60 (1H, t, J=7.9 Hz), 6.81 (1H, d, J=7.0 Hz), 6.99 (1H, d, J=7.8 Hz).

REFERENCE EXAMPLE 169

Ethyl 2-(3-amino-2-naphthalenecarboxamide) isobutyrate

Using the method similar to that in Reference Example 21 and starting from 3-amino-2-naphthalenecarboxylic acid (80%, 4.68 g, 20.0 mmol), the title compound (4.11 g, 68%) was obtained as a crystal.

IR (KBr): 3466, 3364, 3052, 2984, 2938, 1728, 1653, 1609, 1578, 1561, 1522 cm$^{-1}$.

$^1$H-NMR (CDCl$_3$) δ: 1.30 (3H, t, J=7.2 Hz), 1.71 (6H, s), 4.26 (2H, q, J=7.2 Hz), 5.16 (2H, bs), 6.83 (1H, bs), 6.98 (1H, s), 7.17–7.25 (1H, m), 7.35–7.43 (1H, m), 7.55 (1H, d, J=8.4 Hz), 7.69 (1H, d, J=8.4 Hz), 7.91 (1H, s).

REFERENCE EXAMPLE 170

Ethyl 2-(2,4-dioxo-5-fluoro-1,2,3,4-tetrahydroquinazolin-3-yl)isobutyrate

Using the method similar to that in Reference Example 42 (Method 3) and starting from ethyl 2-(2-amino-6- fluorobenzamide)isobutyrate (7.77 g, 29.0 mmol) obtained in Reference Example 166, the title compound (4.34 g, 51%) was synthesized.

Melting point 168 to 170° C.

IR (KBr): 3206–2826, 1736, 1719, 1665, 1636, 1603, 1526 cm$^{-1}$.

$^1$H-NMR (CDCl$_3$) δ: 1.24 (3H, t, J=7.2 Hz), 1.87 (6H, s), 4.20 (2H, q, J=7.2 Hz), 6.81–6.93 (2H, m, ArH), 7.53 (1H, dt, J=8.2 Hz, 5.2 Hz), 10.21 (1H, brs).

Elemental Analysis for C$_{14}$H$_{15}$N$_2$O$_4$F: Calcd. (%): C, 57.14; H, 5.14; N, 9.52. Found (%): C, 56.91; H, 5.17; N, 9.51.

REFERENCE EXAMPLE 171

Ethyl 2-(2,4-dioxo-6,7-difluoro-1,2,3,4-tetrahydroquinazolin-3-yl)isobutyrate

Using the method similar to that in Reference Example 42 (Method 3) and starting from ethyl 2-(2-amino-4,5-difluorobenzamide)isobutyrate (7.48 g, 26.1 mmol) obtained in Reference Example 167, the title compound (8.65 g, about 100%) was synthesized.

Melting point 166 to 168° C. (recrystallized from ethanol).

IR (KBr): 3119, 3085, 3000, 2942, 2878, 1736, 1717, 1659, 1640, 1626, 1520, 1508 cm$^{-1}$.

$^1$H-NMR (CDCl$_3$) δ: 1.25 (3H, t, J=7.2 Hz), 1.86 (6H, s), 4.20 (2H, q, J=7.2 Hz), 6.88 (1H, dd, J=9.8 Hz, 6.2 Hz), 7.86 (1H, dd, J=9.6 Hz, 8.2 Hz), 10.13 (1H, brs).

Elemental Analysis for C$_{14}$H$_{14}$N$_2$O$_4$F$_2$: Calcd. (%): C, 53.85; H, 4.52; N, 8.97. Found (%): C, 53.89; H, 4.49; N, 8.97.

REFERENCE EXAMPLE 172

Ethyl 2-(2,4-dioxo-8-methoxy-1,2,3,4-tetrahydroquinazolin-3-yl)isobutyrate

Using the method similar to that in Reference Example 42 (Method 3) and starting from ethyl 2-(2-amino-3-methoxybenzamide)isobutyrate (7.62 g, 27.2 mmol) obtained in Reference Example 168, the title compound (6.99 g, 84%) was synthesized.

Melting point 144 to 145° C. (recrystallized from ethanol).

IR (KBr): 3208, 2986, 2940, 1743, 1715, 1670, 1661, 1624, 1609, 1516 cm$^{-1}$.

$^1$H-NMR (CDCl$_3$) δ: 1.23 (3H, t, J=7.2 Hz), 1.85 (6H, s), 3.96 (3H, s), 4.19 (2H, q, J=7.2 Hz), 7.05–7.17 (2H, m, ArH), 7.62 (1H, dt, J=7.4 Hz, 1.6 Hz), 8.18 (1H, bs).

Elemental Analysis for C$_{15}$H$_{18}$N$_2$O$_5$: Calcd. (%): C, 58.82; H, 5.92; N, 9.15. Found (%): C, 58.94; H, 5.64; N, 9.27.

REFERENCE EXAMPLE 173

Ethyl 2-(2,4-dioxo-1,2,3,4-tetrahydrobenzo[g]quinazolin-3-yl)isobutyrate

Using the method similar to that in Reference Example 42 (Method 3) and starting from ethyl 2-(3-amino-2-naphthalenecarboxamide)isobutyrate (4.10 g, 13.7 mmol) obtained in Reference Example 169, the title compound (1.90 g, 42%) was synthesized.

Melting point 194 to 197° C. (recrystallized from ethanol).

IR (KBr): 3235–2874, 1725, 1698, 1678, 1636, 1611, 1584, 1528 cm$^{-1}$.

$^1$H-NMR (CDCl$_3$) δ: 1.25 (3H, t, J=7.2 Hz), 1.93 (6H, s), 4.23 (2H, q, J=7.2 Hz), 7.38–7.61 (3H, m, ArH), 7.81 (1H, d, J=8.2 Hz), 7.93 (1H, d, J=8.2 Hz), 8.66 (1H, s), 9.56 (1H, bs).

Elemental Analysis for C$_{18}$H$_{18}$N$_2$O$_4$: Calcd. (%): C, 66.25; H, 5.56; N, 8.58. Found (%): C, 65.98; H, 5.50; N, 8.42.

REFERENCE EXAMPLE 174

Ethyl 2-(6-amino-2,4-dioxo-1,2,3,4-tetrahydroquinazolin-3-yl)isobutyrate

Ethyl 2-(2,4-dioxo-6-nitro-1,2,3,4-tetrahydroquinazolin-3-yl)isobutyrate (1.61 g, 5.0 mmol) obtained in Reference Example 45 was dissolved in a solvent mixture of ethanol (10 ml) and tetrahydrofuran (15 ml), and subjected to a catalytic hydrogenation in the presence of 10% Pd/C (50% hydrated, 0.50 g) at ambient temperature and atmospheric pressure for 2 hours. After separating the catalyst off, the filtrate was concentrated to give the title compound (0.79 g, 54%) as a crystal.

IR (KBr): 3434, 3358, 3243, 3042, 2940, 1715, 1656, 1636, 1520 cm$^{-1}$.

$^1$H-NMR (CDCl$_3$) δ: 1.23 (3H, t, J=7.2 Hz), 1.85 (6H, s), 4.19 (2H, q, J=7.2 Hz), 6.82 (1H, d, J=8.8 Hz), 6.97 (1H, dd, J=8.5 Hz, 2.5 Hz), 7.32 (1H, d, J=2.4 Hz), 8.52 (1H, bs).

REFERENCE EXAMPLE 175

Ethyl 2-[2,4-dioxo-6-(1-pyrrolyl)-1,2,3,4-tetrahydroquinazolin-3-yl)isobutyrate

A mixture of ethyl 2-(6-amino-2,4-dioxo-1,2,3,4-tetrahydroquinazolin-3-yl)isobutyrate (0.79 g, 2.71 mmol) obtained in Reference Example 174, 2,5-dimethoxytetrahydrofuran (0.39 ml, 2.98 mmol) and acetic acid (5.0 ml) was stirred at 100° C. for 1 hour. After cooling, the reaction mixture was combined with water and extracted with ethyl acetate. After the extract was washed with water and dried (MgSO$_4$), the solvent was distilled off under reduced pressure. The residue was subjected to a column chromatography on a silica gel eluting with n-hexane-ethyl acetate (2:1,v/v) to give the title compound (0.62 g, 67%) as a colorless crystal.

Melting point 194–195° C.

IR (KBr): 3210–2876, 1732, 1713, 1663, 1634, 1522 cm$^{-1}$.

$^1$H-NMR (CDCl$_3$) δ: 1.25 (3H, t, J=7.2 Hz), 1.90 (6H, s), 4.21 (2H, q, J=7.2 Hz), 6.38 (2H, t, J=2.2 Hz), 7.10 (2H, t, J=2.2 Hz), 7.11 (2H, d, J=8.8 Hz), 7.66 (1H, dd, J=8.6 Hz, 2.6 Hz), 8.06 (1H, d, J=2.6 Hz), 10.01 (1H, brs).

Elemental Analysis for C$_{18}$H$_{19}$N$_3$O$_4$: Calcd. (%): C, 63.33; H, 5.61; N, 12.31. Found (%): C, 63.19; H, 5.61; N, 12.11.

REFERENCE EXAMPLE 176

2-(2,4-Dioxo-1,2,3,4-tetrahydroquinazolin-3-yl)isobutyric acid

A mixture of ethyl 2-(2,4-dioxo-1,2,3,4-tetrahydroquinazolin-3-yl)isobutyrate (1.31 g, 5.0 mmol) obtained in Reference Example 42, 6N hydrochloric acid (10.0 ml) and acetic acid (5.0 ml) was heated under reflux for 30 minutes. After cooling, the mixture was diluted with water, and the precipitated crystal was collected by filtration and washed with water to give the title compound (1.00 g, 81%) as a colorless crystal.

Melting point 227–230° C.

IR (KBr): 3275, 2992, 2940, 1748, 1725, 1707, 1656, 1622, 1609 cm$^{-1}$.

$^1$H-NMR (DMSO-d$_6$) δ: 1.70 (6H, s), 7.13–7.23 (2H, m, ArH), 7.61–7.69 (1H, m, ArH), 7.88 (1H, dd, J=7.8 Hz, 1.2 Hz), 11.35 (1H, s).

Elemental Analysis for $C_{12}H_{12}N_2O_4$: Calcd. (%): C, 58.06; H, 4.87; N, 11.28. Found (%): C, 58.14; H, 4.80; N, 11.25.

REFERENCE EXAMPLE 177 b -(2,4-Dioxo-6-methyl-1,2,3,4-tetrahydroquinazolin-3-yl)isobutyric acid

Using the method similar to that in Reference Example 176 and starting from ethyl 2-(2,4-dioxo-6-methyl-1,2,3,4-tetrahydroquinazolin-3-yl)isobutyrate (2.90 g, 10.0 mmol) obtained in Reference Example 44, the title compound (2.19 g, 84%) was synthesized.

Melting point 268–271° C.

IR (KBr): 3059, 2994, 2948, 1713, 1671, 1628, 1613, 1518 cm$^{-1}$.

$^1$H-NMR (DMSO-d$_6$) δ: 1.70 (6H, s), 2.33 (3H, s), 7.06 (1H, d, J=8.2 Hz), 7.47 (1H, dd, J=8.4 Hz, 2.0 Hz), 7.67 (1H, s, ArH), 11.25 (1H, s).

Elemental Analysis for $C_{13}H_{14}N_2O_4$: Calcd. (%): C, 59.54; H, 5.38; N, 10.68. Found (%): C, 59.37; H, 5.34; N, 10.63.

REFERENCE EXAMPLE 178

2-(2,4-Dioxo-5-fluoro-1,2,3,4-tetrahydroquinazolin-3-yl)isobutyric acid

Using the method similar to that in Reference Example 176 and starting from ethyl 2-(2,4-dioxo-5-fluoro-1,2,3,4-tetrahydroquinazolin-3-yl)isobutyrate (3.83 g, 13.0 mmol) obtained in Reference Example 170, the title compound (3.21 g, 93%) was synthesized.

Melting point 258–260° C.

IR (KBr): 3069, 3020, 2948, 2905, 2822, 1717, 1671, 1634, 1603, 1528 cm$^{-1}$.

$^1$H-NMR (DMSO-d$_6$) δ: 1.68 (6H, s), 6.89–6.99 (2H, m, ArH), 7.62 (1H, dt, J=8.2 Hz, 5.4 Hz), 11.48 (1H, bs).

Elemental Analysis for $C_{12}H_{11}N_2O_4F$: Calcd. (%): C, 54.14; H, 4.16; N, 10.52. Found (%): C, 54.27; H, 4.21; N, 10.44.

REFERENCE EXAMPLE 179

2-(2,4-Dioxo-6-fluoro-1,2,3,4-tetrahydroquinazolin-3-yl)isobutyric acid

Using the method similar to that in Reference Example 176 and starting from ethyl 2-(2,4-dioxo-6-fluoro-1,2,3,4-tetrahydroquinazolin-3-yl)isobutyrate (8.83 g, 30.0 mmol) obtained in Reference Example 46, the title compound (5.48 g, 69%) was synthesized.

Melting point 249–253° C.

IR (KBr): 3198, 3090, 2992, 2936, 1721, 1701, 1671, 1630, 1510 cm$^{-1}$.

$^1$H-NMR (DMSO-d$_6$) δ: 1.71 (6H, s), 7.20 (1H, dd, J=8.5 Hz, 4.5 Hz), 7.53–7.63 (2H, m, ArH), 11.43 (1H, bs).

Elemental Analysis for $C_{12}H_{11}N_2O_4F$: Calcd. (%): C, 54.14; H, 4.16; N, 10.52. Found (%): C, 54.23; H, 4.25; N, 10.51.

REFERENCE EXAMPLE 180

2-(2,4-Dioxo-6,7-difluoro-1,2,3,4-tetrahydroquinazolin-3-yl)isobutyric acid

Using the method similar to that in Reference Example 176 and starting from ethyl 2-(2,4-dioxo-6,7-difluoro-1,2,3,4-tetrahydroquinazolin-3-yl)isobutyrate (6.87 g, 22.0 mmol) obtained in Reference Example 171, the title compound (3.29 g, 53%) was synthesized.

Melting point 242–244° C.

IR (KBr): 3073, 3009, 2948, 1732, 1717, 1665, 1638, 1624, 1518 cm$^{-1}$.

$^1$H-NMR (DMSO-d$_6$) δ: 1.69 (6H, s), 7.09 (1H, dd, J=6.5 Hz, 10.9 Hz), 7.85 (1H, dd, J=10.3 Hz, 8.5 Hz), 11.51 (1H, bs).

Elemental Analysis for $C_{12}H_{10}N_2O_4F_2$: Calcd. (%): C, 50.71; H, 3.55; N, 9.86. Found (%): C, 50.84; H, 3.54; N, 9.68.

REFERENCE EXAMPLE 181

2-(2,4-Dioxo-8-methoxy-1,2,3,4-tetrahydroquinazolin-3-yl)isobutyric acid

Using the method similar to that in Reference Example 176 and starting from ethyl 2-(2,4-dioxo-8-methoxy-1,2,3,4-tetrahydroquinazolin-3-yl)isobutyrate (4.59 g, 15.0 mmol) obtained in Reference Example 172, the title compound (3.82 g, 92%) was synthesized.

Melting point 255–258° C.

IR (KBr): 3200–2569, 1713, 1665, 1624, 1607, 1518 cm$^{-1}$.

$^1$H-NMR (DMSO-d$_6$) δ: 1.70 (6H, s), 3.89 (3H, s), 7.13 (1H, t, J=8.1 Hz), 7.29 (1H, dd, J=8.1 Hz, 1.1 Hz), 7.45 (1H, d, J=7.8 Hz), 10.73 (1H, bs).

Elemental Analysis for $C_{13}H_{14}N_2O_5$: Calcd. (%): C, 56.11; H, 5.07; N, 10.07. Found (%): C, 56.47; H, 5.05; N, 10.00.

REFERENCE EXAMPLE 182

2-(6-Chloro-2,4-Dioxo-1,2,3,4-tetrahydroquinazolin-3-yl)isobutyric acid

Using the method similar to that in Reference Example 176 and starting from ethyl 2-(6-chloro-2,4-dioxo-1,2,3,4-tetrahydroquinazolin-3-yl)isobutyrate (7.90 g, 25.4 mmol) obtained in Reference Example 48, the title compound (6.43 g, 90%) was synthesized.

Melting point 256–259° C.

IR (KBr): 3193–2938, 1719, 1705, 1671, 1611, 1607, 1503 cm$^{-1}$.

$^1$H-NMR (DMSO-d$_6$) δ: 1.69 (6H, s), 7.17 (1H,,d, J=8.8 Hz), 7.69 (1H, dd, J=8.8 Hz, 2.6 Hz), 7.82 (1H, d, J=2.6 Hz), 11.49 (1H, s).

Elemental Analysis for $C_{12}H_{11}N_2O_4Cl$: Calcd. (%): C, 50.99; H, 3.92; N, 9.91. Found (%): C, 51.08; H, 3.93; N, 9.85.

REFERENCE EXAMPLE 183

2-(7-Chloro-2,4-Dioxo-1,2,3,4-tetrahydroquinazolin-3-yl)isobutyric acid

Using the method similar to that in Reference Example 176 and starting from ethyl 2-(7-chloro-2,4-dioxo-1,2,3,4- tetrahydroquinazolin-3-yl)isobutyrate (4.66 g, 15.0 mmol) obtained in Reference Example 47, the title compound (3.55 g, 84%) was synthesized.

Melting point 260–263° C.

IR (KBr): 3088, 2988, 2946, 2882, 1717, 1698, 1663, 1617, 1605 $cm^{-1}$.

$^1$H-NMR (DMSO-$d_6$) δ: 1.69 (6H, s), 7.17–7.25 (2H, m, ArH), 7.88 (1H, d, J=8.2 Hz), 11.46 (1H, s).

Elemental Analysis for $C_{12}H_{11}N_2O_4Cl$: Calcd. (%): C, 50.99; H, 3.92; N, 9.91. Found (%): C, 51.03; H, 3.95; N, 9.94.

REFERENCE EXAMPLE 184

2-(2,4-dioxo-1,2,3,4-tetrahydrobenzo[g]quinazolin-3-yl)isobutyric acid

Using the method similar to that in Reference Example 176 and starting from ethyl 2-(2,4-dioxo-1,2,3,4-tetrahydrobenzo[g]quinazolin-3-yl)isobutyrate (1.63 g, 5.00 mmol) obtained in Reference Example 173, the title compound (1.37 g, 92%) was synthesized.

Melting point 273–276° C.

IR (KBr): 3179–2826, 2668, 2571, 1717, 1710, 1665, 1638, 1588, 1532 $cm^{-1}$.

$^1$H-NMR (DMSO-$d_6$) δ: 1.74 (6H, s), 7.41–7.63 (3H, m, ArH), 7.90 (1H, d, J=8.2 Hz), 8.08 (1H, d, J=7.8 Hz), 8.61 (1H, s, ArH), 11.40 (1H, bs).

Elemental Analysis for $C_{16}H_{14}N_2O_4$: Calcd. (%): C, 64.42; H, 4.73; N, 9.39. Found (%): C, 64.43; H, 4.56; N, 9.48.

REFERENCE EXAMPLE 185

Phenacyl 2-(2,4-dioxo-1,2,3,4-tetrahydroquinazolin-3-yl)isobutyrate

A mixture of 2-(2,4-dioxo-1,2,3,4-tetrahydroquinazolin-3-yl)isobutyric acid (0.74 g, 3.0 mmol) obtained in Reference Example 176, 2-bromoacetophenone (0.61 g, 3.0 mmol), potassium fluoride (0.38 g, 6.6 mmol) and N,N-dimethylformamide (3.0 ml) was stirred at room temperature for 15 hours. The reaction mixture was diluted with water and then extracted with ethyl ether. After the extract was washed with water and dried ($MgSO_4$), the solvent was distilled off under reduced pressure to give the title compound (0.85 g, 77%) as a colorless crystal.

IR (KBr): 3266, 3212, 3069, 2994, 2940, 1750, 1717, 1667, 1620, 1609 $cm^{-1}$.

$^1$H-NMR ($CDCl_3$) δ: 2.00 (6H, s), 5.36 (2H, s), 7.03 (1H, d, J=8.0 Hz), 7.16–7.24 (1H, m, ArH), 7.27–7.47 (2H, m, ArH), 7.53–7.63 (2H, m, ArH), 7.84–7.88 (2H, m, ArH), 8.01–8.06 (1H, m, ArH), 9.87 (1H, bs).

REFERENCE EXAMPLE 186

Phenacyl 2-(2,4-dioxo-6-methyl-1,2,3,4-tetrahydroquinazolin-3-yl)isobutyrate

Using the method similar to that in Reference Example 185 and starting from 2-(2,4-dioxo-6-methyl-1,2,3,4-tetrahydroquinazolin-3-yl)isobutyric acid(1.84 g, 7.00 mmol) obtained in Reference Example 177, the title compound (1.91 g, 72%) was synthesized.

Melting point 189 to 191° C.

IR (KBr): 3280, 3208, 3065, 3031, 2992, 2940, 1750, 1717, 1667, 1628, 1599, 1518 $cm^{-1}$.

$^1$H-NMR ($CDCl_3$) δ: 1.99 (6H, s), 2.38 (3H, s), 5.35 (2H, s), 6.92 (1H, d, J=8.2 Hz), 7.37–7.61 (4H, m, ArH), 7.83–7.88 (3H, m, ArH), 9.54 (1H, bs).

Elemental Analysis for $C_{21}H_{20}N_2O_5$: Calcd. (%): C, 66.31; H, 5.30; N, 7.36. Found (%): C, 66.25; H, 5.24; N, 7.49.

REFERENCE EXAMPLE 187

Phenacyl 2-(2,4-dioxo-8-methoxy-1,2,3,4-tetrahydroquinazolin-3-yl)isobutyrate

Using the method similar to that in Reference Example 185 and starting from 2-(2,4-dioxo-8-methoxy-1,2,3,4-tetrahydroquinazolin-3-yl)isobutyric acid (2.78 g, 10.0 mmol) obtained in Reference Example 181, the title compound (3.99 g, about 100%) was synthesized.

Melting point 132 to 133° C.

IR (KBr): 3210–2940, 1752, 1715, 1705, 1661, 1624, 1609, 1516 $cm^{-1}$.

$^1$H-NMR ($CDCl_3$) δ: 1.97 (6H, s), 3.95 (3H, s), 5.34 (2H, s), 7.04–7.17 (2H, m, ArH), 7.41–7.64 (4H, m, ArH), 7.87–7.92 (2H, m, ArH), 8.21 (1H, bs).

Elemental Analysis for $C_{21}H_{20}N_2O_6 \cdot 0.5AcOEt$: Calcd. (%): C, 62.72; H, 5.49; N, 6.36. Found (%): C, 62.76; H, 5.57; N, 6.43.

REFERENCE EXAMPLE 188

Phenacyl 2-(2,4-dioxo-5-fluoro-1,2,3,4-tetrahydroquinazolin-3-yl)isobutyrate

Using the method similar to that in Reference Example 185 and starting from 2-(2,4-dioxo-5-fluoro-1,2,3,4-tetrahydroquinazolin-3-yl)isobutyric acid (2.93 g, 11.0 mmol) obtained in Reference Example 1.78, the title compound (3.15 g, 75%) was synthesized.

Melting point 179 to 180° C.

IR (KBr): 3277, 3227, 3140, 3073, 3029, 2946, 1721, 1701, 1671, 1632, 1601, 1518 $cm^{-1}$.

$^1$H-NMR ($CDCl_3$) δ: 1.99 (6H, s), 5.37 (2H, s), 6.80–6.90 (2H, m, ArH), 7.40–7.61 (4H, m, ArH), 7.82–7.87 (2H, m, ArH), 10.04 (1H, bs).

Elemental Analysis for $C_{20}H_{17}N_2O_5F$: Calcd. (%): C, 62.50; H, 4.46; N, 7.29. Found (%): C, 62.18; H, 4.42; N, 7.24.

REFERENCE EXAMPLE 189

Phenacyl 2-(2,4-dioxo-6-fluoro-1,2,3,4-tetrahydroquinazolin-3-yl)isobutyrate

Using the method similar to that in Reference Example 185 and starting from 2-(2,4-dioxo-6-fluoro-1,2,3,4-tetrahydroquinazolin-3-yl)isobutyric acid (4.79 g, 18.0 mmol) obtained in Reference Example 179, the title compound (3.10 g, 45%) was synthesized.

Melting point 192 to 193° C. (recrystallized from ethanol).

IR (KBr): 3202, 3085, 2998, 2940, 1721, 1705, 1667, 1510 $cm^{-1}$.

$^1$H-NMR ($CDCl_3$) δ: 2.00 (6H, s), 5.36 (2H, s), 7.01 (1H, dd, J=8.9 Hz, 4.1 Hz), 7.27–7.62 (4H, m, ArH), 7.70 (1H, dd, J=8.2 Hz, 2.8 Hz), 7.83–7.87 (2H, m, ArH).

Elemental Analysis for $C_{20}H_{17}N_2O_5F$: Calcd. (%): C, 62.50; H, 4.46; N, 7.29. Found (%): C, 62.25; H, 4.47; N, 7.14.

REFERENCE EXAMPLE 190

Phenacyl 2-(2,4-dioxo-6,7-difluoro-1,2,3,4-tetrahydroquinazolin-3-yl)isobutyrate Using the method similar to, that in Reference Example 185 and starting from 2-(2,4-dioxo-6,7-difluoro-1,2,3,4-tetrahydroquinazolin-3-yl)isobutyric acid(3.13 g, 11.0 mmol) obtained in Reference Example 180, the title compound (3.61 g, 82%) was synthesized.

Melting point 174 to 176° C. (recrystallized from ethanol).

IR (KBr): 3121, 3088, 3004, 2949, 2876, 1748, 1717, 1701, 1663, 1640, 1628, 1518, 1505 cm$^{-1}$.

$^1$H-NMR (CDCl$_3$) δ: 1.99 (6H, s), 5.39 (2H, s), 6.85 (1H, dd, J=6.2 Hz, 9.6 Hz), 7.41–7.63 (3H, m, ArH), 7.77–7.89 (3H, m, ArH), 10.13 (1H, bs).

Elemental Analysis for $C_{20}H_{16}N_2O_5F_2$: Calcd. (%): C, 59.70; H, 4.01; N, 6.96. Found (%): C. 59.55; H, 4.14; N, 6.96.

REFERENCE EXAMPLE 191

Phenacyl 2-(6-chloro-2,4-dioxo-1,2,3,4-tetrahydroquinazolin-3-yl)isobutyrate

Using the method similar to that in Reference Example 185 and starting from 2-(6-chloro-2,4-dioxo-1,2,3,4-tetrahydroquinazolin-3-yl)isobutyric acid (2.83 g, 10.0 mmol) obtained in Reference Example 182, the title compound (3.12 g, 78%) was synthesized.

Melting point 197 to 199° C.

IR (KBr): 3200, 3073, 3031, 2994, 2938, 1748,. 1717, 1667, 1618, 1599 cm$^{-1}$.

$^1$H-NMR (CDCl$_3$) δ: 1.99 (6H, s), 5.36 (2H, s), 6.97 (1H, d, J=8.6 Hz), 7.40–7.63 (4H, m, ArH), 7.82–7.86 (2H, m, ArH), 7.98 (1H, d, J=2.4 Hz), 9.95 (1H, bs).

Elemental Analysis for $C_{20}H_{17}N_2O_5Cl$: Calcd. (%): C, 59.93; H, 4.28; N, 6.99. Found (%): C, 59.84; H, 4.27; N, 6.94.

REFERENCE EXAMPLE 192

Phenacyl 2-(7-chloro-2,4-dioxo-1,2,3,4-tetrahydroquinazolin-3-yl)isobutyrate

Using the method similar to that in Reference Example 185 and starting from 2-(7-chloro-2,4-dioxo-1,2,3,4-tetrahydroquinazolin-3-yl)isobutyric acid (2.83 g, 10.0 mmol) obtained in Reference Example 183, the title compound (3.16 g, 79%) was synthesized.

Melting point 203 to 204° C.

IR (KBr): 3258, 3210–2936, 1732, 1719, 1701, 1672, 1618, 1601 cm$^{-1}$.

$^1$H-NMR (CDCl$_3$) δ: 2.00 (6H, s), 5.40 (2H, s), 7.05 (1H, d, J=1.8 Hz), 7.14 (1H, dd, J=1.9 Hz, 8.5 Hz), 7.41–7.63 (3H, m, ArH), 7.85–7.89 (2H, m, ArH), 7.95 (1H, d, J=8.6 Hz).

Elemental Analysis for $C_{20}H_{17}N_2O_5Cl$: Calcd. (%): C, 59.93; H, 4.28; N, 6.99. Found (%): C, 59.96; H, 4.14; N, 7.02.

REFERENCE EXAMPLE 193

Phenacyl 2-(2,4-dioxo-1,2,3,4-tetrahydrobenzo[g] quinazolin-3-yl)isobutyrate

Using the method similar to that in Reference Example 185 and starting from 2-(2,4-dioxo-1,2,3,4-tetrahydrobenzo [g]quinazolin-3-yl)isobutyric acid (1.19 g, 4.00 mmol) obtained in Reference Example 184, the title compound (1.52 g, 91%) was synthesized.

Melting point 184 to 185° C. (recrystallized from ethanol).

IR (KBr): 3280, 3059, 2990, 2938, 1750, 1717, 1669, 1638 cm$^{-1}$.

$^1$H-NMR (CDCl$_3$) δ: 2.06 (6H, s), 5.38 (2H, s), 7.31–7.60 (6H, m, ArH), 7.75–7.93 (4H, m, ArH), 8.61 (1H, s, ArH), 9.65 (1H, bs).

Elemental Analysis for $C_{24}H_{20}N_2O_5$·0.5EtOH: Calcd. (%): C, 68.33; H, 5.28; N, 6.37. Found (%): C, 68.37; H, 4.97; N, 6.55.

REFERENCE EXAMPLE 194

Ethyl 2-[1-(4-bromobutyl)-2,4-dioxo-8-methoxy-1,2,3,4-tetrahydroquinazolin-3-yl)isobutyrate Using the method similar to that in Reference Example 52 and starting from ethyl 2-(2,4-dioxo-8-methoxy-1,2,3,4-tetrahydroquinazolin-3-yl)isobutyrate (0.61 g, 2.00 mmol) obtained in Reference Example 174, the title compound (0.55 g, 62%) was obtained as an oil.

IR (KBr): 2982, 2942, 1744, 1707, 1663, 1603 cm$^{-1}$.

$^1$H-NMR (CDCl$_3$) δ: 1.22 (3H, t, J=7.2 Hz), 1.82 (6H, s), 1.88–2.00 (4H, m), 3.42–3.48 (2H, m), 3.95 (3H, s), 4.11–4.25 (4H, m), 7.17–7.20 (2H, m, ArH), 7.71–7.76 (1H, m, ArH).

REFERENCE EXAMPLE 195

Ethyl 2-[1-(4-bromobutyl)-2,4-dioxo-6-(1-pyrrolyl)-1,2,3,4-tetrahydroquinazolin-3-yl]isobutyrate Using the method similar to that in Reference Example 52 and starting from ethyl 2-[2,4-dioxo-6-(1-pyrrolyl)-1,2,3,4-tetrahydroquinazolin-3-yl]isobutyrate (0.41 g, 1.20 mmol) obtained in Reference Example 175, the title compound (0.45 g, 79%) was obtained as an oil.

IR (KBr): 2984, 2940, 1740, 1707, 1663, 1516 cm$^{-1}$.

$^1$H-NMR (CDCl$_3$) δ: 1.25 (3H, t, J=7.2 Hz), 1.86 (6H, s), 1.85–2.05 (4H, m), 3.46–3.52 (2H, m), 4.07–4.14 (2H, m), 4.20 (2H, q, J=7.2 Hz), 6.38 (2H, t, J=2.0 Hz), 7.11 (2H, t, J=2.0 Hz), 7.24 (1H, d, J=8.4 Hz), 7.70 (1H, dd, J=8.9 Hz, 2.7 Hz), 8.16 (1H, d, J=2.8 Hz).

REFERENCE EXAMPLE 196

Phenacyl 2-[1-(4-bromobutyl)-2,4-dioxo-1,2,3,4-tetrahydroquinazolin-3-yl]isobutyrate Using the method similar to that in Reference Example 52 and starting from phenacyl 2-(2,4-dioxo-1,2,3,4-tetrahydroquinazolin-3-yl)isobutyrate (0.85 g, 2.30 mmol) obtained in Reference Example 185, the title compound (0.55 g, 48%) was obtained as an oil.

IR (KBr): 2992, 2940, 1752, 1705, 1661, 1609 cm$^{-1}$.

$^1$H-NMR (CDCl$_3$) δ: 1.85–2.03 (4H, m), 1.97 (6H, s), 3.44–3.50 (2H, m), 4.08–4.15 (2H, m), 5.37 (2H, s), 7.15–7.28 (2H, m, ArH), 7.43–7.71 (4H, m, ArH), 7.89–7.93 (2H, m, ArH), 8.16 (1H, dd, J=8.0 Hz, 1.4 Hz).

REFERENCE EXAMPLE 197

Phenacyl 2-[1-(4-bromobutyl)-2,4-dioxo-6-methyl-1,2,3,4-tetrahydroquinazolin-3-yl]isobutyrate Using the method similar to that in Reference Example 52 and starting from phenacyl 2-(2,4-dioxo-6-methyl-1,2,3,4- tetrahydroquinazolin-3-yl)isobutyrate (1.71 g, 4.50 mmol) obtained in Reference Example 186, the title compound (1.33 g, 57%) was obtained as an oil.

IR (KBr): 2940, 1752, 1703, 1661, 1624, 1595, 1508 cm$^{-1}$.

$^1$H-NMR (CDCl$_3$) δ: 1.82–2.05 (4H, m), 1.96 (6H, s), 2.40 (3H, s), 3.46 (2H, t, J=6.3 Hz), 4.05–4.13 (2H, m), 5.36 (2H, s), 7.07 (1H, d, J=8.6 Hz), 7.42–7.63 (4H, m, ArH), 7.89–7.96 (4H, m, ArH).

REFERENCE EXAMPLE 198

Phenacyl 2-[1-(4-bromobutyl)-2,4-dioxo-8-methoxy-1,2,3,4-tetrahydroquinazolin-3-yl]isobutyrate Using the method similar to that in Reference Example 52 and starting from phenacyl 2-(2,4-dioxo-8-methoxy-1,2,3,4-tetrahydroquinazolin-3-yl)isobutyrate (3.17 g, 8.00 mmol) obtained in Reference Example 187, the title compound (1.45 g, 34%) was obtained as an oil.

IR (KBr): 2992, 2942, 1752, 1703, 1659, 1601 cm$^{-1}$.

$^1$H-NMR (CDCl$_3$) δ: 1.88–2.00 (4H, m), 1.95 (6H, s), 3.42–3.48 (2H, m), 3.95 (3H, s), 4.20–4.27 (2H, m), 5.34 (2H, s), 7.18–7.20 (2H, m, ArH), 7.42–7.92 (6H, m, ArH).

REFERENCE EXAMPLE 199

Phenacyl 2-[1-(4-bromobutyl)-2,4-dioxo-5-fluoro-1,2,3,4-tetrahydroquinazolin-3-yl]isobutyrate Using the method similar to that in Reference Example 52 and starting from phenacyl 2-(2,4-dioxo-5-fluoro-1,2,3,4-tetrahydroquinazolin-3-yl)isobutyrate (2.69 g, 7.00 mmol) obtained in Reference Example 188, the title compound (1.81 g, 50%) was obtained as an oil.

IR (KBr): 2992, 2942, 1752, 1709, 1671, 1618, 1597 cm$^{-1}$.

$^1$H-NMR (CDCl$_3$) δ: 1.83–2.04 (4H, m), 1.96 (6H, s), 3.47 (2H, t, J=6.2 Hz), 4.06–4.14 (2H, m), 5.37 (2H, s), 6.88–7.00 (2H, m, ArH), 7.43–7.66 (4H, m, ArH), 7.89–7.93 (2H, m, ArH).

REFERENCE EXAMPLE 200

Phenacyl 2-[1-(4-bromobutyl)-2,4-dioxo-6-fluoro-1,2,3,4-tetrahydroquinazolin-3-yl]isobutyrate Using the method similar to that in Reference Example 52 and starting from phenacyl 2-(2,4-dioxo-6-fluoro-1,2,3,4-tetrahydroquinazolin-3-yl)isobutyrate (2.88 g, 7.50 mmol) obtained in Reference Example 189, the title compound (1.72 g, 44%) was obtained as an oil.

IR (KBr): 2992, 2940, 1752, 1705, 1663, 1624, 1599, 1505 cm$^{-1}$.

$^1$H-NMR (CDCl$_3$) δ: 1.84–2.03 (4H, m), 1.96 (6H, s), 3.47 (2H, t, J=6.2 Hz), 4.10 (2H, dt, J=7.1 Hz, 1.8 Hz), 5.37 (2H, s), 7.16 (1H, dd, J=9.2 Hz, 4.0 Hz), 7.35–7.64 (4H, m, ArH), 7.83 (1H, dd, J=8.3 Hz, 3.1 Hz), 7.89–7.93 (2H, m, ArH).

REFERENCE EXAMPLE 201

Phenacyl 2-[1-(4-bromobutyl)-2,4-dioxo-6,7-difluoro-1,2,3,4-tetrahydroquinazolin-3-yl]isobutyrate Using the method similar to that in Reference Example 52 and starting from phenacyl 2-(2,4-dioxo-6,7-difluoro-1,2,3,4-tetrahydroquinazolin-3-yl)isobutyrate (3.22 g, 8.00 mmol) obtained in Reference Example 190, the title compound (1.95 g, 45%) was obtained as an oil.

IR (KBr): 2942, 1752, 1709, 1667, 1636, 1607, 1524 cm$^{-1}$.

$^1$H-NMR (CDCl$_3$) δ: 1.83–2.03 (4H, m), 1.95 (6H, s), 3.44–3.50 (2H, m), 4.01–4.08 (2H, m), 5.37 (2H, s), 7.00 (1H, dd, J=11.2 Hz, 6.0 Hz), 7.44–7.64 (3H, m, ArH), 7.88–8.00 (3H, m, ArH).

REFERENCE EXAMPLE 202

Phenacyl 2-[1-(4-bromobutyl)-6-chloro-2,4-dioxo-1,2,3,4-tetrahydroquinazolin-3-yl)isobutyrate Using the method similar to that in Reference Example 52 and starting from phenacyl 2-(6-chloro-2,4-dioxo-1,2,3,4-tetrahydroquinazolin-3-yl)isobutyrate (2.81 g, 7.00 mmol) obtained in Reference Example 191, the title compound (2.09 g, 56%) was obtained as an oil.

IR (KBr): 2942, 1752, 1707, 1665, 1609 cm$^{-1}$.

$^1$H-NMR (CDCl$_3$) δ: 1.84–2.05 (4H, m), 1.96 (6H, s), 3.47 (2H, t, J=6.2 Hz), 4.05–4.14 (2H, m), 5.36 (2H, s), 7.13 (1H, d, J=8.8 Hz), 7.44–7.64 (4H, m, ArH), 7.89–7.93 (2H, m, ArH), 8.12 (1H, d, J=2.6 Hz).

REFERENCE EXAMPLE 203

Phenacyl 2-[1-(4-bromobutyl)-7-chloro-2,4-dioxo-1,2,3,4-tetrahydroquinazolin-3-yl)isobutyrate Using the method similar to that in Reference Example 52 and starting from phenacyl 2-(7-chloro-2,4-dioxo-1,2,3,4-tetrahydroquinazolin-3-yl)isobutyrate (2.81 g, 7.00 mmol) obtained in Reference Example 192, the title compound (1.78 g, 48%) was obtained as an oil.

IR (KBr): 2940, 1752, 1709, 1667, 1605 cm$^{-1}$.

$^1$H-NMR (CDCl$_3$) δ: 1.84–2.05 (4H, m), 1.96 (6H, s), 3.48 (2H, t, J=6.4 Hz), 4.04–4.14 (2H, m), 5.37 (2H, s), 7.18–7.24 (2H, m, ArH), 7.43–7.62 (3H, m, ArH), 7.89–7.93 (2H, m, ArH), 8.09 (1H, d, J=8.4 Hz).

REFERENCE EXAMPLE 204

Phenacyl 2-[1-(4-bromobutyl)-2,4-dioxo-1,2,3,4-tetrahydrobenzo[g]quinazolin-3-yl)isobutyrate Using the method similar to that in Reference Example 52 and starting from phenacyl 2-(2,4-dioxo-1,2,3,4-tetrahydrobenzo[g]quinazolin-3-yl)isobutyrate (1.25 g, 3.00 mmol) obtained in Reference Example 193, the title compound (0.93 g, 56%) was obtained as an oil.

IR (KBr): 2990, 2940, 1752, 1705, 1663, 1505 cm$^{-1}$.

$^1$H-NMR (CDCl$_3$) δ: 1.95–2.10 (10H, m), 3.51 (2H, t, J=6.0 Hz), 4.17–4.25 (2H, m), 5.38 (2H, s), 7.42–7.66 (6H, m, ArH), 7.85–7.98 (4H, m, ArH), 8.76 (1H, s, ArH).

REFERENCE EXAMPLE 205

Ethyl 5-(3-ethoxycarbonylamino-2-thiophenecarboxamide)valerate

To a solution of 3-ethoxycarbonylamino-2-thiophenecarboxylic acid(4.30 g, 20.0 mmol) in tetrahydrofuran (20 ml), oxalyl chloride (2.09 ml, 24.0 mmol) was added dropwise with cooling on ice, and the mixture was stirred at room temperature for 1.5 hours and then concentrated. The residue was taken up with tetrahydrofuran (20 ml), and ethyl 5-aminovalerate hydrochloride (4.36 g, 24.0 mmol) and triethylamine (8.36 ml, 60.0 mmol) were added sequentially in portions with cooling on ice. The reaction mixture was stirred at room temperature for 1 hour, and then combined with water and extracted with ethyl acetate. The extract was washed with water, dried ($MgSO_4$) and then concentrated. The residue was subjected to a column chromatography on a silica gel eluting with n-hexane-ethyl acetate (2:1, v/v) to give the title compound (7.04 g, about 100%) as an oil.

IR (KBr): 3360, 3280, 2980, 2938, 1732, 1624, 1574, 1537 $cm^{-1}$.

$^1$H-NMR ($CDCl_3$) δ: 1.26 (3H, t, J=7.2 Hz), 1.30 (3H, t, J=7.2 Hz), 1.58–1.80 (4H, m), 2.36 (2H, t, J=7.0 Hz), 3.36–3.46 (2H, m), 4.15 (2H, q, J=7.2 Hz), 4.21 (2H, q, J=7.2 Hz), 5.82 (1H, bs), 7.29 (1H, d, J=5.4 Hz), 7.93 (1H, d, J=5.4 Hz), 10.30 (1H, bs).

REFERENCE EXAMPLE 206

Ethyl 2-(3-ethoxycarbonylamino-2-thiophenecarboxamide)isobutyrate

Using the method similar to that in Reference Example 21 and starting from 3-ethoxycarbonylamino-2-thiophenecarboxylic acid (6.46 g, 30.0 mmol), the title compound (8.20 g, 83%) was obtained as an oil.

IR (KBr): 3347, 3287, 2984, 2938, 1732, 1626, 1574, 1522 $cm^{-1}$.

$^1$H-NMR ($CDCl_3$) δ: 1.29 (3H, t, J=7.2 Hz), 1.30 (3H, t, J=7.2 Hz), 1.66 (6H, s), 4.21 (2H, q, J=7.2 Hz), 4.25 (2H, q, J=7.2 Hz), 6.27 (1H, bs), 7.30 (1H, d, J=5.6 Hz), 7.93 (1H, d, J=5.6 Hz), 10.18 (1H, bs).

REFERENCE EXAMPLE 207

Ethyl 5-(2,4-dioxo-1,2,3,4-tetrahydrothieno[3,2-d]pyrimidin-3-yl)valerate

Using the method similar to that in Reference Example 42 (Method 3) and starting from ethyl 5-(3-ethoxycarbonylamino-2-thiophenecarboxamide)valerate (6.85 g, 20.0 mmol) obtained in Reference Example 205, the title compound (4.36 g, 74%) was synthesized.

Melting point 116 to 117° C.

IR (KBr): 3250, 3204, 3098, 3085, 2978, 2955, 2874, 1717, 1636, 1578, 1543 $cm^{-1}$.

$^1$H-NMR ($CDCl_3$) δ: 1.24 (3H, t, J=7.2 Hz), 1.69–1.77 (4H, m), 2.35–2.42 (2H, m), 4.04–4.17 (4H, m), 6.94 (1H, d, J=5.4 Hz), 7.70 (1H, d, J=5.2 Hz), 10.72 (1H, bs).

Elemental Analysis for $C_{13}H_{16}N_2O_4S$: Calcd. (%): C, 52.69; H, 5.44; N, 9.45. Found (%): C, 52.69; H, 5.23; N, 9.46.

REFERENCE EXAMPLE 208

Ethyl 2-(2,4-dioxo-1,2,3,4-tetrahydrothieno[3,2-d]pyrimidin-3-yl)isobutyrate

Using the method similar to that in Reference Example 42 (Method 3) and starting from ethyl 2-(3-ethoxycarbonylamino-2-thiophenecarboxamide)isobutyrate (8.19 g, 24.9 mmol) obtained in Reference Example 206, the title compound (2.30 g, 33%) was synthesized.

Melting point 156 to 157° C.

IR (KBr): 3280, 3225, 3110, 2988, 2938, 1713, 1651, 1582, 1537 $cm^{-1}$.

$^1$H-NMR ($CDCl_3$) δ: 1.24 (3H, t, J=7.2 Hz), 1.86 (6H, s), 4.19 (2H, q, J=7.2 Hz), 6.84 (1H, d, J=5.4 Hz), 7.68 (1H, d, J=5.2 Hz), 10.31 (1H, bs).

Elemental Analysis for $C_{12}H_{14}N_2O_4S$: Calcd. (%): C, 51.05; H, 5.00; N, 9.92. Found (%): C, 51.20; H, 4.92; N, 10.03.

REFERENCE EXAMPLE 209

Ethyl 5-[1-(4-bromobutyl)-2,4-dioxo-1,2,3,4-tetrahydrothieno[3,2-d]pyrimidin-3-yl)valerate Using the method similar to that in Reference Example 52 and starting from ethyl 5-(2,4-dioxo-1,2,3,4-tetrahydrothieno[3,2-d]pyrimidin-3-yl)valerate (2.07 g, 7.00 mmol) obtained in Reference Example 207, the title compound (2.34 g, 78%) was obtained as an oil.

IR (KBr): 3102, 2959, 2868, 1732, 1699, 1659, 1651, 1568 $cm^{-1}$.

$^1$H-NMR ($CDCl_3$) δ: 1.25 (3H, t, J=7.2 Hz), 1.68–1.73 (4H, m), 1.92–1.96 (4H, m), 2.32–2.39 (2H, m), 3.48 (2H, t, J=6.2 Hz), 4.04–4.17 (6H, m), 6.96 (1H, d, J=5.4 Hz), 7.74 (1H, d, J=5.2 Hz).

REFERENCE EXAMPLE 210

Ethyl 2-[1-(4-bromobutyl)-2,4-dioxo-1,2,3,4-tetrahydrothieno[3,2-d]pyrimidin-3-yl)isobutyrate Using the method similar to that in Reference Example 52 and starting from ethyl 2-(2,4-dioxo-1,2,3,4-tetrahydrothieno[3,2-d]pyrimidin-3-yl)isobutyrate (0.85 g, 3.00 mmol) obtained in Reference Example 208, the title compound (1.09 g, 87%) was obtained as an oil.

IR (KBr): 3106, 2986, 2938, 2903, 2870, 1740, 1701, 1659, 1574 $cm^{-1}$.

$^1$H-NMR ($CDCl_3$) δ: 1.25 (3H, t, J=7.2 Hz), 1.84 (6H, s), 1.89–1.97 (4H, m), 3.47 (2H, t, J=6.1 Hz), 4.01 (2H, t, J=7.0 Hz), 4.19 (2H, q, J=7.2 Hz), 6.93 (1H, d, J=5.2 Hz), 7.71 (1H, d, J=5.4 Hz).

EXAMPLE 1

2,4-Dioxo-1-[3-(4-diphenylmethoxy-1-piperidinyl)propyl]-1,2,3,4-tetrahydroquinazoline A mixture of 1-[3-chloropropyl]-2,4-dioxo-1,2,3,4-tetrahydroquinazoline (1.00 g) obtained in Reference Example 83, 4-diphenylmethoxypiperidine (1.68 g), triethylamine (0.88 ml), sodium iodide (691 mg) and acetonitrile (50 ml) was heated under reflux for 23 hours. The solvent was distilled off under reduced pressure, and a saturated aqueous solution of sodium thiosulfate was added and the mixture was extracted with ethyl acetate. After the extract was washed with water and dried ($Na_2SO_4$), the solvent was distilled off under reduced pressure to give the title compound (845 mg, 43%). Recrystallization from ethyl acetate-methanol yielded a colorless crystal having a melting point of 149 to 151° C.

IR (Nujor): 1690, 1680, 1605 $cm^{-1}$.

$^1$H-NMR ($CDCl_3$) δ: 1.68–2.00 (6H, m), 2.04–2.20 (2H, m), 2.41 (2H, t, J=7.0 Hz), 2.68–2.82 (2H, m), 3.38–3.53 (1H, m), 4.16 (2H, t, J=7.4 Hz), 5.52 (1H, s), 7.18–7.42 (12H, m), 7.68 (1H, ddd, J=8.6, 7.2, 1.4 Hz), 8.20 (1H, dd, J=8.0, 1.6 Hz).

Elemental Analysis for $C_{29}H_{31}N_3O_3 \cdot 0.5H_2O$: Calcd. (%): C, 72.78; H, 6.74; N, 8.78. Found (%): C, 72.87; H, 6.69; N, 8.86.

EXAMPLE 2

2,4-Dioxo-1-[4-(4-diphenylmethoxy-1-piperidinyl)butyl]-1,2,3,4-tetrahydroquinazoline Using the method similar to that in Example 1 and starting from 1-(4-chlorobutyl)-2,4-dioxo-1,2,3,4-tetrahydroquinazoline (Compound 86) (1.00 g), the title compound (891 mg, 47%) was synthesized.

Melting point 131 to 133° C. (recrystallized from ethyl acetate-ethyl ether).

(Method 4) A mixture of 1-(4-bromobutyl)-2,4-dioxo-1,2,3,4-tetrahydroquinazoline (4.00 g) obtained in Reference Example 86, 4-diphenylmethoxypiperidine (5.40 g), triethylamine (2.81 ml) and N,N-dimethylformamide (80 ml) was stirred at room temperature for 28 hours. The reaction mixture was extracted with ethyl acetate, and the extract was washed with water and dried ($Na_2SO_4$), and then the solvent was distilled off under reduced pressure to give the title compound (5.98 g, 92%). Recrystallization from ethyl acetate yielded a colorless crystal having a melting point of 131 to 133° C.

IR (KBr): 2943, 1683, 1608, 1486 $cm^{-1}$.

$^1$H-NMR ($CDCl_3$) δ: 1.50–1.82 (6H, m), 1.82–2.02 (2H, m), 2.02–2.22 (2H, m), 2.39 (2H, t, J=7.0 Hz), 2.70–2.84 (2H, m), 3.38–3.52 (1H, m), 4.12 (2H, t, J=8.2 Hz), 5.53 (1H, s), 7.20–7.42 (12H, m), 7.70 (1H, ddd, J=8.4, 6.8, 1.6 Hz), 8.20 (1H, dd, J=8.2, 1.2 Hz).

Elemental Analysis for $C_{30}H_{33}N_3O_3.1.1H_2O$: Calcd. (%): C, 71.58; H, 7.05; N, 8.35. Found (%): C, 71.20; H, 6.58; N, 8.58.

EXAMPLE 3

2,4-Dioxo-1-[5-(4-diphenylmethoxy-1-piperidinyl)pentyl]-1,2,3,4-tetrahydroquinazoline Using the method similar to that in Example 1 and starting from 1-(5-chloropentyl)-2,4-dioxo-1,2,3,4-tetrahydroquinazoline (1.77 g) obtained in Reference Example 85, the title compound (2.18 g, 66%) was synthesized. Recrystallization from ethyl acetate yielded a colorless crystal having a melting point of 173 to 174° C.

IR (KBr): 1698, 1609, 1483 $cm^{-1}$.

$^1$H-NMR ($CDCl_3$) δ: 1.38–2.00 (10H, m), 2.06–2.24 (2H, m), 2.34 (2H, t, J=8.4 Hz), 2.68–2.82 (2H, m), 3.38–3.52 (1H, m), 4.08 (2H, t, J=7.2 Hz), 5.51 (1H, s), 7.16–7.38 (12H, m), 7.70 (1H, ddd, J=8.4, 7.0, 1.4 Hz), 8.21 (1H, dd, J=7.4, 1.4 Hz).

Elemental Analysis for $C_{31}H_{35}N_3O_3.0.3H_2O$: Calcd. (%): C, 74.02; H, 7.13; N, 8.35. Found (%): C, 73.81; H, 7.07; N, 8.17.

EXAMPLE 4

2,4-Dioxo-1-[4-(4-diphenylmethyl-1-piperazinyl)butyl]-1,2,3,4-tetrahydroquinazoline hydrochloride Using the method similar to that in Example 1 and 1-(4-diphenylmethyl)piperazine instead of 4-diphenylmethoxypiperidine and starting from 1-(4-chlorobutyl)-2,4-dioxo-1,2,3,4-tetrahydroquinazoline (1.00 g) obtained in Reference Example 84, a free salt of the title compound (860 mg, 46%) was obtained as an amorphous.

IR (KBr): 1698, 1609, 1485, 1451 $cm^{-1}$.

$^1$H-NMR ($CDCl_3$) δ: 1.58–1.80 (6H, m), 2.36–2.58 (8H, m), 4.11 (2H, t, J=8.8 Hz), 4.25 (1H, s), 7.23–7.46 (12H, m), 7.60 (1H, ddd, J=8.8, 7.4, 1.4 Hz), 8.19 (1H, dd, J=7.8, 1.6 Hz).

Elemental Analysis for $C_{29}H_{32}N_4O_2O_2.0.2H_2O$: Calcd. (%): C, 73.76; H, 6.92; N, 11.87. Found (%): C, 73.61; H, 6.80; N, 11.75.

This product (660 mg) was recrystallized from a 4N solution of hydrogen chloride in ethyl acetate to give the title compound (599 mg, 79%).

Melting point 161 to 163° C. (recrystallized from ethyl acetate).

IR (KBr): 3600–2740, 1697, 1683, 1608, 1486 $cm^{-1}$.

$^1$H-NMR ($CDCl_3$) δ: 1.60–2.10 (8H, m), 3.16–3.32 (2H, m), 3.38–3.68 (4H, m), 4.18 (2H, t, J=6.6 Hz), 5.05 (1H, s), 7.15–7.50 (12H, m), 7.72 (1H, t, J=7.6 Hz), 7.83 (2H, bs), 8.13 (1H, d, J=6.6 Hz), 9.29 (1H, bs).

Elemental Analysis for $C_{29}H_{32}N_4O_2.2HCl.1.7H_2O$: Calcd. (%): C, 60.88; H, 6.59; N, 9.79. Found (%): C, 60.75; H, 6.40; N, 9.65.

EXAMPLE 5

2,4-Dioxo-1-[4-(4-diphenylhydroxymethylpiperidino)butyl]-1,2,3,4-tetrahydroquinazoline Using the method similar to that in Example 2 and 4-diphenylhydroxymethylpiperidine instead of 4-diphenylmethoxypiperidine and starting from 1-(4-bromobutyl)-2,4-dioxo-1,2,3,4-tetrahydroquinazoline (800 mg) obtained in Reference Example 86, the title compound (1.07 g, 83%) was synthesized. Recrystallization from ethyl acetate yielded a colorless crystal having a melting point of 187 to 189° C.

IR (KBr): 2940, 1685, 1608, 1484 $cm^{-1}$.

$^1$H-NMR ($CDCl_3$) δ: 1.46–1.86 (7H, m), 1.90–2.06 (3H, m), 2.39 (2H, t, J=6.6 Hz), 2.34–2.54 (1H, m), 2.92–3.05 (2H, m), 4.10 (2H, t, J=8.0 Hz), 7.10–7.50 (12H, m), 7.65 (1H, t, J=7.4 Hz), 8.19 (1H, d, J=7.6 Hz).

Elemental Analysis for $C_{30}H_{33}N_3O_3.0.3H_2O$: Calcd. (%): C, 73.15; H, 6.96; N, 8.53. Found (%): C, 72.97; H, 6.79; N, 8.28.

EXAMPLE 6

2,4-Dioxo-1-[3-(4-diphenylmethoxypiperidino)propyl]-1,2,3,4-tetrahydropyrido[2,3-d]pyrimidine hydrochloride Using the method similar to that in Example 1 and starting from 1-(3-chloropropyl)-2,4-dioxo-1,2,3,4-tetrahydropyrido[2,3-d]pyrimidine (800 mg) obtained in Reference Example 87, a free base of the title compound (110 mg, 7.0%) was obtained as an oil.

$^1$H-NMR ($CDCl_3$) δ: 1.75–1.88 (2H, m), 1.89–2.12 (4H, m), 2.28–2.44 (2H, m), 2.58 (2H, t, J=8.0 Hz), 2.76–2.90 (2H, m), 3.44–3.58 (1H, m), 4.36 (2H, t, J=7.2 Hz), 5.48 (1H, s), 7.14–7.38 (11H, m), 8.42 (1H, dd, J=7.6, 1.8 Hz), 8.64 (1H, dd, J=4.8, 2.0 Hz).

This product (130 mg) was recrystallized from a 4N solution of hydrogen chloride in ethyl acetate to give the title compound (86 mg, 57%) as a colorless crystal.

Melting point 131 to 133° C.

IR (KBr): 1705, 1601, 1489 $cm^{-1}$.

$^1$H-NMR ($CDCl_3$) δ: 1.94–2.10 (2H, m), 2.34–2.58 (4H, m), 3.00–3.22 (4H, m), 3.33–3.48 (2H, m), 3.82–3.90 (1H, m), 4.23 (2H, t, J=6.2 Hz), 5.42 (1H, s), 7.20–7.40 (10H, m), 8.35–8.48 (2H, m), 8.67 (1H, dd, J=4.8, 1.8 Hz), 11.96 (1H, bs).

Elemental Analysis for $C_{28}H_{30}N_4O_3 \cdot 2HCl \cdot 1.0H_2O$: Calcd. (%): C, 59.89; H, 6.10; N, 9.98. Found (%): C, 59.68; H, 5.95; N, 10.05.

EXAMPLE 7

2,4-Dioxo-1-[4-(4-diphenylmethoxypiperidino)butyl]-1,2,3,4-tetrahydropyrido[2,3-d]pyrimidine hydrochloride Using the method similar to that in Example 2 (Method 4) and starting from 1-(4-bromobutyl)-2,4-dioxo-1,2,3,4-tetrahydropyrido[2,3-d]pyrimidine (1.50 g) obtained in Reference Example 88, a free base of the title compound (1.30 g, 53%) was synthesized. Recrystallization from ethyl acetate-ethyl ether yielded a colorless crystal having a melting point of 167 to 169° C.

IR (KBr): 1701, 1601, 1588, 1489, 1462 cm$^{-1}$.

$^1$H-NMR (CDCl$_3$) δ: 1.50–1.98 (8H, m), 2.08–2.24 (2H, m), 2.38 (2H, t, J=7.0 Hz), 2.70–2.84 (2H, m), 3.45–3.52 (1H, m), 4.31 (2H, t, J=7.2 Hz), 5.51 (1H, s), 7.18–7.40 (11H, m), 8.42 (1H, dd, J=8.0, 2.2 Hz), 8.66 (1H, dd, J=4.8, 2.2 Hz).

Elemental Analysis for $C_{29}H_{32}N_4O_3 \cdot 0.3H_2O$: Calcd. (%): C, 71.09; H, 6.71; N, 11.43. Found (%): C, 71.06; H, 6.64; N, 11.19.

This product (500 mg) was recrystallized from a 4N solution of hydrogen chloride in ethyl acetate to give the title compound (413 mg, 72%) as a colorless crystal having a melting point 121 to 123° C.

IR (KBr): 1695, 1602, 1490 cm$^{-1}$.

$^1$H-NMR (CDCl$_3$) δ: 1.76–2.14 (6H, m), 2.36–2.58 (2H, m), 2.96–3.20 (4H, m), 3.28–3.44 (2H, m), 3.84–3.92 (1H, m), 4.33 (2H, t, J=7.0 Hz), 5.43 (1H, s), 7.18–7.44 (10H, m), 8.39–8.43 (2H, m), 8.64–8.72 (1H, m), 12.16 (1H, bs).

Elemental Analysis for $C_{29}H_{32}N_4O_3 \cdot 2HCl$: Calcd. (%): C, 62.48; H, 6.15; N, 10.05. Found (%): C, 62.29; H, 6.48; N, 10.48.

EXAMPLE 8

2,4-Dioxo-8-[4-(4-diphenylmethoxypiperidino)butyl]-1,2,3,4-tetrahydropteridine

Using the method similar to that in Example 2 (Method 4) and starting from 1-(4-bromobutyl)-2,4-dioxo-1,2,3,4-tetrahydropteridine (1.36 g) obtained in Reference Example 89, the title compound (1.47 g, 67%) was synthesized. Recrystallization from ethyl acetate yielded a colorless crystal having a melting point of 157 to 159° C.

IR (KBr): 2945, 1708, 1598, 1546, 1490 cm$^{-1}$.

$^1$H-NMR (CDCl$_3$) δ: 1.50–1.84 (4H, m), 1.84–2.02 (4H, m), 2.14–2.34 (2H, m), 2.41 (2H, t, J=7.8 Hz), 2.74–2.88 (4H, m), 3.38–3.52 (1H, m), 4.28 (2H, t, J=7.4 Hz), 5.50 (1H, s), 7.18–7.38 (10H, m), 8.56 (1H, d, J=2.2 Hz), 8.62 (1H, d, J=2.2 Hz).

Elemental Analysis for $C_{28}H_{31}N_5O_3 \cdot 0.4H_2O$: Calcd. (%): C, 68.25; H, 6.50; N, 14.21. Found (%): C, 68.28; H, 6.41; N, 14.15.

EXAMPLE 9

7-Chloro-2,4-dioxo-1-[4-(4-diphenylmethoxypiperidino)butyl]-1,2,3,4-tetrahydroquinazoline Using the method similar to that in Example 2 (Method 4) and starting from 1-(4-bromobutyl)-7-chloro-2,4-dioxo-1,2,3,4-tetrahydroquinazoline (1.50 g) obtained in Reference Example 90, the title compound (1.51 g, 64%) was synthesized. Recrystallization from ethyl acetate yielded a colorless crystal having a melting point of 169 to 171° C.

IR (KBr): 1699, 1607, 1580, 1495, 1456 cm$^{-1}$.

$^1$H-NMR (CDCl$_3$) δ: 1.54–2.02 (8H, m), 2.05–2.24 (2H, m), 2.40 (2H, t, J=6.2 Hz), 2.72–2.86 (2H, m), 3.38–3.54 (1H, m), 4.11 (2H, t, J=8.0 Hz), 5.53 (1H, s), 7.18–7.42 (12H, m), 8.12 (1H, d, J=8.4 Hz).

Elemental Analysis for $C_{30}H_{32}N_3O_3Cl$: Calcd. (%): C, 69.55; H, 6.23; N, 8.11. Found (%): C, 69.15; H, 6.23; N, 8.01.

EXAMPLE 10

6-Chloro-2,4-dioxo-1-[4-(4-diphenylmethoxypiperidino)butyl]-1,2,3,4-tetrahydroquinazoline Using the method similar to that in Example 2 (Method 4) and starting from 1-(4-bromobutyl)-6-chloro-2,4-dioxo-1,2,3,4-tetrahydroquinazoline (1.50 g) obtained in Reference Example 91, the title compound (2.02 g, 86%) was synthesized. Recrystallization from ethyl acetate yielded a colorless crystal having a melting point of 209 to 210° C.

IR (KBr): 1699, 1611, 1582, 1491, 1468 cm$^{-1}$.

$^1$H-NMR (CDCl$_3$) δ: 1.56–1.86 (6H, m), 1.86–2.04 (2H, m), 2.04–2.25 (2H, m), 2.40 (2H, t, J=6.6 Hz), 2.70–2.85 (2H, m), 3.40–3.54 (1H, m), 4.09 (2H, t, J=7.8 Hz), 5.53 (1H, s), 7.20–7.44 (11H, m), 7.63 (1H, dd, J=8.8, 2.6 Hz), 8.15 (1H, d, J=2.6 Hz)

Elemental Analysis for $C_{30}H_{32}N_3O_3Cl \cdot 0.4H_2O$: Calcd. (%): C, 68.60; H, 6.29; N, 8.00. Found (%): C, 68.60; H, 6.22; N, 7.93.

EXAMPLE 11

2,4-Dioxo-1-[4-(4-diphenylmethoxypiperidino)butyl]-7-nitro-1,2,3,4-tetrahydroquinazoline Using the method similar to that in Example 2 (Method 4) and starting from 1-(4-bromobutyl)-2,4-dioxo-7-nitro-1,2,3,4-tetrahydroquinazoline (4.00 g) obtained in Reference Example 92, the title compound (4.91 g, 79%) was synthesized. Recrystallization from ethyl acetate yielded a yellow crystal having a melting point of 214 to 215° C.

IR (KBr): 2947, 1695, 1627, 1594, 1538, 1455 cm$^{-1}$.

$^1$H-NMR (CDCl$_3$) δ: 1.60–2.00 (8H, m), 2.09–2.23 (2H, m), 2.41 (2H, t, J=7.0 Hz), 2.74–2.88 (2H, m), 3.38–3.52 (1H, m), 4.22 (2H, t, J=7.8 Hz), 5.52 (1H, s), 7.18–7.38 (10H, m), 8.02–8.33 (2H, m), 8.36 (1H, d, J=8.6 Hz).

Elemental Analysis for $C_{30}H_{32}N_4O_5 \cdot 1.0H_2O$: Calcd. (%): C, 65.92; H, 6.27; N, 10.25. Found (%): C, 65.68; H, 5.98; N, 10.21.

EXAMPLE 12

2,4-Dioxo-1-[4-(4-diphenylmethoxypiperidino)butyl]-6-nitro-1,2,3,4-tetrahydroquinazoline Using the method similar to that in Example 2 (Method 4) and starting from 1-(4-bromobutyl)-2,4-dioxo-6-nitro-1,2,3,4-tetrahydroquinazoline (5.00 g) obtained in Reference Example 93, the title compound (6.96 g, 90%) was synthesized. Recrystallization from ethyl acetate yielded a yellow crystal having a melting point of 211 to 213° C.

IR (KBr): 2943, 1706, 1614, 1529, 1494 cm$^{-1}$.

$^1$H-NMR (CDCl$_3$) δ: 1.56–2.04 (8H, m), 2.08–2.25 (2H, m), 2.41 (2H, t, J=6.6 Hz), 2.73–2.86 (2H, m), 3.40–3.56 (1H, m), 4.17 (2H, t, J=7.6 Hz), 5.53 (1H, s), 7.20–7.38 (10H, m), 7.60 (1H, d, J=9.2 Hz), 8.51 (1H, dd, J=9.2, 2.6 Hz), 9.03 (1H, d, J=2.4 Hz).

Elemental Analysis for C$_{30}$H$_{32}$N$_4$O$_5$·0.3H$_2$O: Calcd. (%): C, 67.48; H, 6.15; N, 10.49. Found (%): C, 67.34; H, 6.04; N, 10.31.

EXAMPLE 13

2,4-Dioxo-1-[4-(4-diphenylmethoxypiperidino)butyl]-6-methyl-1,2,3,4-tetrahydroquinazoline Using the method similar to that in Example 2 (Method 4) and starting from 1-(4-bromobutyl)-2,4-dioxo-6-methyl-1,2,3,4-tetrahydroquinazoline (940 mg) obtained in Reference Example 94, the title compound (627 mg, 42%) was synthesized. Recrystallization from ethyl acetate-ethyl ether yielded a yellow crystal having a melting point of 180 to 182° C.

IR (KBr): 2943, 1699, 1627, 1612, 1587 cm$^{-1}$.

$^1$H-NMR (CDCl$_3$) δ: 1.54–1.84 (6H, m), 1.86–2.02 (2H, m), 2.08–2.25 (2H, m), 2.36–2.46 (2H, m), 2.40 (3H, s), 2.70–2.85 (2H, m), 3.40–3.54 (1H, m), 4.09 (2H, t, J=8.0 Hz), 5.53 (1H, s), 7.20–7.40 (11H, m), 7.50 (1H, dd, J=8.4, 1.8 Hz), 7.99 (1H, s).

Elemental Analysis for C$_{31}$H$_{35}$N$_3$O$_3$·0.8H$_2$O: Calcd. (%): C, 72.72; H, 7.20; N, 8.21. Found (%): C, 72.48; H, 6.83; N, 8.06.

EXAMPLE 14

Methyl 2,4-dioxo-1-[3-(4-diphenylmethoxypiperidino)propyl]-1,2,3,4-tetrahydroquinazoline-3-acetate Using the method similar to that in Example 1 and starting from methyl 2,4-dioxo-1-(3-chloropropyl)-1,2,3,4-tetrahydroquinazoline-3-acetate (2.00 g) obtained in Reference Example 61, the title compound (1.93 g, 55%) was synthesized. Recrystallization from ethyl acetate-ethyl ether-n-hexane yielded a colorless crystal having a melting point of 109 to 110° C.

IR (Nujor): 1745, 1700, 1660, 1600, 1480 cm$^{-1}$.

$^1$H-NMR (CDCl$_3$) δ: 1.95–2.12 (2H, m), 2.30–2.58 (4H, m), 3.02–3.30 (6H, m), 3.75 (3H, s), 3.80–3.88 (1H, m), 4.26 (2H, t, J=6.4 Hz), 4.84 (2H, s), 5.43 (1H, s), 7.16–7.48 (12H, m), 7.79 (1H, t, J=7.8 Hz), 8.24 (1H, d, J=8.0 Hz).

Elemental Analysis for C$_{32}$H$_{35}$N$_3$O$_5$: Calcd. (%): C, 70.96; H, 6.51; N, 7.76. Found (%): C, 70.87; H, 6.31; N, 7.85.

EXAMPLE 15

Methyl 2,4-dioxo-1-[4-(4-diphenylmethoxypiperidino)butyl]-1,2,3,4-tetrahydroquinazoline-3-acetate Using the method similar to that in Example 1 and starting from methyl 1-(4-chlorobutyl)-2,4-dioxo-1,2,3,4-tetrahydroquinazoline-3-acetate (2.00 g) obtained in Reference Example 62, the title compound (3.06 g, 84%) was synthesized. Recrystallization from ethyl acetate-ethyl ether yielded a colorless crystal having a melting point of 91 to 93° C.

IR (KBr): 2949, 2810, 1756, 1710, 1668, 1610, 1486 cm$^{-1}$.

$^1$H-NMR (CDCl$_3$) δ: 1.56–2.02 (8H, m), 2.06–2.23 (2H, m), 2.39 (2H, t, J=9.0 Hz), 2.70–2.84 (2H, m), 3.40–3.52 (1H, m), 3.76 (3H, s), 4.15 (2H, t, J=7.4 Hz), 4.85 (2H, s), 5.53 (1H, s), 7.20–7.40 (12H, m), 7.70 (1H, ddd, J=8.6, 7.2, 1.4 Hz), 8.24 (1H, dd, J=7.8, 1.4 Hz).

Elemental Analysis for C$_{33}$H$_{37}$N$_3$O$_5$: Calcd. (%): C, 71.33; H, 6.71; N, 7.50. Found (%): C, 70.98; H, 6.67; N, 7.56.

EXAMPLE 16

Ethyl 2,4-dioxo-1-[3-(4-diphenylmethoxypiperidino)propyl]-1,2,3,4-tetrahydroquinazoline-3-propionate Using the method similar to that in Example 1 and starting from ethyl 1-(3-chloropropyl)-2,4-dioxo-1,2,3,4-tetrahydroquinazoline-3-propionate (1.85 g) obtained in Reference Example 63, the title compound (2.11 g, 68%) was obtained as an oil.

$^1$H-NMR (CDCl$_3$) δ: 1.23 (3H, t, J=7.0 Hz), 1.65–2.00 (6H, m), 2.03–2.20 (2H, m), 2.41 (2H, t, J=6.6 Hz), 2.71 (2H, t, J=8.0 Hz), 2.67–2.82 (2H, m), 3.40–3.52 (1H, m), 4.08–4.22 (4H, m), 4.40 (2H, t, J=7.0 Hz), 5.53 (1H, s), 7.20–7.40 (12H, m), 7.65 (1H, ddd, J=8.4, 7.4, 1.0 Hz), 8.22 (1H, dd, J=8.2, 1.4 Hz).

EXAMPLE 17

Ethyl 2,4-dioxo-1-[4-(4-diphenylmethoxypiperidino)butyl]-1,2,3,4-tetrahydroquinazoline-3-propionate hydrochloride Using the method similar to that in Example 1 and starting from ethyl 1-(4-chlorobutyl)-2,4-dioxo-1,2,3,4-tetrahydroquinazoline-3-propionate (2.50 g) obtained in Reference Example 64, a free salt of the title compound (2.86 g, 69%) was obtained as an oil.

$^1$H-NMR (CDCl$_3$) δ: 1.23 (3H, t, J=7.0 Hz), 1.54–2.00 (8H, m), 2.02–2.20 (2H, m), 2.38 (2H, t, J=6.2 Hz), 2.71 (2H, t, J=7.4 Hz), 2.66–2.74 (2H, m), 3.38–3.52 (1H, m), 4.06–4.20 (4H, m), 4.40 (2H, t, J=7.6 Hz), 5.53 (1H, s), 7.18–7.40 (12H, m), 7.66 (1H, t, J=7.0 Hz), 8.22 (1H, d, J=8.2 Hz).

This product (1.03 g) was combined with a 4N solution of hydrogen chloride in ethyl acetate and concentrated to give the title compound (734 mg, 67%) as an amorphous.

IR (KBr): 1732, 1703, 1658, 1609, 1485 cm$^{-1}$.

$^1$H-NMR (CDCl$_3$) δ: 1.23 (3H, t, J=6.8 Hz), 1.96–2.20 (4H, m), 2.35–2.56 (2H, m), 2.70 (2H, t, J=6.6 Hz), 2.94–3.22 (2H, m), 3.28–3.45 (2H, m), 3.82–3.90 (1H, m), 4.04–4.24 (4H, m), 4.38 (2H, t, J=7.4 Hz), 5.43 (1H, s), 7.18–7.44 (12H, m), 7.71 (1H, t, J=6.6 Hz), 8.23 (1H, d, J=8.0 Hz), 12.09 (1H, bs).

Elemental Analysis for C$_{35}$H$_{41}$N$_3$O$_5$·HCl·0.8H$_2$O: Calcd. (%): C, 66.23; H, 6.92; N, 6.62. Found (%): C, 66.23; H, 7.06; N, 6.60.

EXAMPLE 18

Ethyl 2,4-dioxo-1-[4-(4-diphenylmethoxypiperidino)butyl]-1,2,3,4-tetrahydroquinazoline-3-butyrate Using the method similar to that in Example 1 and starting from ethyl 1-(4-chlorobutyl)-2,4-dioxo-1,2,3,4-tetrahydroquinazoline-3-butyrate (6.00 g) obtained in Reference Example 65, the title compound (3.17 g, 36%) was obtained as an oil.

¹H-NMR (CDCl₃) δ: 1.23 (3H, t, J=7.0 Hz), 1.56–2.45 (12H, m), 2.34–2.45 (4H, m), 2.70–2.83 (2H, m), 3.38–3.52 (1H, m), 4.02–4.20 (6H, m), 5.53 (1H, s), 7.18–7.40 (12H, m), 7.66 (1H, ddd, J=8.4, 7.6, 0.8 Hz), 8.22 (1H, dd, J=8.0, 1.2 Hz).

EXAMPLE 19

2,4-Dioxo-1-[3-(4-diphenylmethoxypiperidino) propyl]-3-methyl-1,2,3,4-tetrahydroquinazoline hydrochloride Using the method similar to that in Example 1 and starting from 1-(3-chloropropyl)-2,4-dioxo-3-methyl-1,2,3,4-tetrahydroquinazoline (1.00 g) obtained in Reference Example 66, a free salt of the title compound (920 mg, 48%) was obtained as an oil.

¹H-NMR (CDCl₃): δ1.68–2.00 (6H, m), 2.05–2.20 (2H, m), 2.41 (2H, t, J=6.8 Hz), 2.69–2.82 (2H, m), 3.38–3.52 (1H, m), 3.48 (3H, s), 4.19 (2H, t, J=7.4 Hz), 5.53 (1H, s), 7.19–7.40 (12H, m), 7.65 (1H, ddd, J=8.8, 7.0, 1.8 Hz), 8.24 (1H, dd, J=7.8, 1.6 Hz).

This product (920 mg) was crystallized from a 4N solution of hydrogen chloride in ethyl acetate to give the title compound (568 mg, 58%). Recrystallization from ethyl acetate yielded a colorless crystal having a melting point of 127 to 128° C.

IR (KBr): 1701, 1659, 1609, 1487, 1454, 1427 cm⁻¹.

¹H-NMR (CDCl₃) δ: 1.94–2.10 (2H, m), 2.34–2.56 (4H, m), 3.02–3.24 (4H, m), 3.32–3.46 (2H, m), 3.48 (3H, s), 3.82–3.90 (1H, m), 4.22–4.36 (2H, m), 5.42 (1H, s), 7.20–7.44 (12H, m), 7.74 (1H, t, J=9.0 Hz), 8.24 (1H, d, J=7.8 Hz).

Elemental Analysis for C₃₀H₃₃N₃O₃.HCl.1.2H₂O: Calcd. (%): C, 66.52; H, 6.77; N, 7.76. Found (%): C, 66.43; H, 6.76; N, 8.05.

EXAMPLE 20

2,4-Dioxo-1-[4-(4-diphenylmethoxypiperidino) butyl)]-3-methyl-1,2,3,4-tetrahydroquinazoline hydrochloride Using the method similar to that in Example 1 and starting from 1-(4-chlorobutyl)-2,4-dioxo-3-methyl-1,2,3,4-tetrahydroquinazoline (1.00 g) obtained in Reference Example 67, a free salt of the title compound (1.13 g, 61%) was obtained. Recrystallization from ethyl acetate-isopropyl ether yielded a colorless crystal having a melting point of 141 to 142° C.

IR (KBr): 1702, 1660, 1610, 1486, 1453 cm⁻¹.

¹H-NMR (CDCl₃) δ: 1.60–1.86 (6H, m), 1.86–2.04 (2H, m), 2.12–2.30 (2H, m), 2.42 (2H, t, J=6.6 Hz), 2.72–2.86 (2H, m), 3.42–3.52 (1H, m), 3.48 (3H, s), 4.15 (2H, t, J=8.4 Hz), 5.52 (1H, m), 7.20–7.38 (12H, m), 7.66 (1H, ddd, J=8.8, 7.4, 1.4 Hz), 8.24 (1H, dd, J=7.8, 1.8 Hz).

Elemental Analysis for C₃₁H₃₅N₃O₃.0.5H₂O: Calcd. (%): C, 73.19; H, 7.16; N, 8.29. Found (%): C, 73.29; H, 6.96; N, 8.16.

This product (500 mg) was combined with a 4N solution of hydrogen chloride in ethyl acetate and concentrated to give the title compound (443 mg, 83%). Recrystallization from ethyl acetate yielded a colorless crystal having a melting point of 233 to 235° C.

IR (KBr): 1701, 1655, 1609, 1487 cm⁻¹.

¹H-NMR (CDCl₃) δ: 1.79–1.93 (2H, m), 1.96–2.18 (4H, m), 2.36–2.56 (2H, m), 2.95–3.22 (4H, m), 3.30–3.46 (2H, m), 3.47 (3H, s), 3.84–3.92 (1H, m), 4.17 (2H, t, J=7.4 Hz), 5.42 (1H, s), 7.20–7.42 (12H, m), 7.70 (1H, ddd, J=8.4, 7.0, 1.4 Hz), 8.25 (1H, dd, J=8.0, 1.4 Hz).

Elemental Analysis for C₃₁H₃₅N₃O₃.HCl.0.5H₂O: Calcd. (%): C, 68.56; H, 6.87; N, 7.74. Found (%): C, 68.47; H, 6.74; N, 7.84.

EXAMPLE 21

3-(1,1-Dimethylethyl)-2,4-dioxo-1-[3-(4-diphenylmethoxypiperidyl)propyl]-1,2,3,4-tetrahydroquinazoline hydrochloride Using the method similar to that in Example 1 and starting from 1-(3-chloropropyl)-3-(1,1-dimethylethyl)-2,4-dioxo-1,2,3,4-tetrahydroquinazoline (1.50 g) obtained in Reference Example 68, a free salt of the title compound (857 mg, 32%) was obtained as an oil.

¹H-NMR (CDCl₃) δ: 1.60–2.02 (15H, m), 2.08–2.24 (2H, m), 2.42 (2H, t, J=6.8 Hz), 2.70–2.85 (2H, m), 3.39–3.55 (1H, m), 4.07 (2H, t, J=6.2 Hz), 5.52 (1H, m), 7.10–7.40 (12H, m), 7.56 (1H, t, J=7.4 Hz), 8.06 (1H, d, J=8.2 Hz).

This product (857 mg) was combined with a 4N solution of hydrogen chloride in ethyl acetate and concentrated to give the title compound (647 mg, 71%) as an amorphous.

IR (KBr): 1705, 1663, 1607, 1480 cm⁻¹.

¹H-NMR (CDCl₃) δ: 1.72 (9H, s), 2.06–2.12 (2H, m), 2.32–2.54 (4H, m), 2.88–3.20 (4H, m), 3.30–3.44 (2H, m), 3.82–3.90 (1H, m), 4.10–4.26 (2H, m), 5.42 (1H, s), 7.18–7.42 (12H, m), 7.58–7.70 (1H, m), 8.07 (1H, d, J=7.8 Hz).

Elemental Analysis for C₃₃H₃₉N₃O₃.HCl.1.3H₂O: Calcd. (%): C, 67.69; H, 7.33; N, 7.18. Found (%): C, 67.43; H, 7.27; N, 7.56.

EXAMPLE 22

3-(1,1-Dimethylethyl)-2,4-dioxo-1-[4-(4-diphenylmethoxypiperidino)butyl]-1,2,3,4-tetrahydroquinazoline hydrochloride Using the method similar to that in Example 1 and starting from 1-(4-chlorobutyl)-3-(1,1-dimethylethyl)-2,4-dioxo-1,2,3,4-tetrahydroquinazoline (1.50 g) obtained in Reference Example 69, a free salt of the title compound (953 mg, 36%) was synthesized. Recrystallization from ethyl acetate-isopropyl ether yielded a colorless crystal having a melting point of 113 to 114° C.

IR (KBr): 1706, 1664, 1608, 1494, 1479, 1455 cm⁻¹.

¹H-NMR (CDCl₃) δ: 1.54–2.00 (17H, m), 2.08–2.22 (2H, m), 2.39 (2H, t, J=6.4 Hz), 2.70–2.85 (2H, m), 3.40–3.52 (1H, m), 4.04 (2H, t, J=8.2 Hz), 5.52 (1H, m), 7.10–7.40 (12H, m), 7.58 (1H, ddd, J=8.6, 7.0, 1.6 Hz), 8.07 (1H, dd, J=8.0, 1.6 Hz).

Elemental Analysis for C₃₄H₄₁N₃O₃.0.3H₂O: Calcd. (%): C, 74.91; H, 7.69; N, 7.71. Found (%): C, 74.92; H, 7.40; N, 7.81.

This product (500 mg) was combined with a 4N solution of hydrogen chloride in ethyl acetate and concentrated to give the title compound (382 mg, 72%). Recrystallization from ethyl acetate yielded a colorless crystal having a melting point of 229 to 231° C.

IR (KBr): 1705, 1663, 1607, 1495, 1480 cm⁻¹.

¹H-NMR (CDCl₃) δ: 1.64–1.86 (11H, m), 1.94–2.14 (4H, m), 2.36–2.57 (2H, m), 2.95–3.22 (4H, m), 3.28–3.44 (2H, m), 3.85–3.92 (1H, m), 4.07 (2H, t, J=7.6 Hz), 5.44 (1H, s), 7.11 (1H, d, J=8.4 Hz), 7.19 (1H, t, J=7.2 Hz), 7.22–7.40 (10H, m), 7.62 (1H, ddd, J=8.4, 6.8, 1.6 Hz), 8.08 (1H, dd, J=7.8, 1.6 Hz).

Elemental Analysis for $C_{34}H_{41}N_3O_3 \cdot HCl \cdot 1.1H_2O$: Calcd. (%): C, 68.50; H, 7.47; N, 7.05. Found (%): C, 68.50; H, 7.51; N, 7.03.

EXAMPLE 23

2,4-Dioxo-1-[4-(4-diphenylmethoxypiperidino) butyl)]-3-(3-pyridinylmethyl)-1,2,3,4-tetrahydroquinazoline hydrochloride Using the method similar to that in Example 2 (Method 4) and starting from 1-(4-bromobutyl)-2,4-dioxo-3-(3-pyridinylmethyl)-1,2,3,4-tetrahydroquinazoline (1.57 g) obtained in Reference Example 70, a free salt of the title compound (1.35 g, 58%) was synthesized.

$^1$H-NMR (CDCl$_3$) δ: 1.58–2.02 (8H, m), 2.10–2.28 (2H, m), 2.41 (2H, t, J=7.0 Hz), 2.70–2.84 (2H, m), 3.40–3.55 (1H, m), 4.14 (2H, t, J=7.0 Hz), 5.27 (2H, s), 5.52 (1H, m), 7.20–7.40 (13H, m), 7.67 (1H, t, J=7.0 Hz), 7.85 (1H, dt, J=8.0, 1.8 Hz), 8.24 (1H, dd, J=8.2, 1.6 Hz), 8.50 (1H, dd, J=4.8, 1.8 Hz), 8.79 (1H, d, J=1.6 Hz).

This product (1.35 g) was combined with a 4N solution of hydrogen chloride in ethyl acetate and concentrated to give the title compound (1.06 g, 69%) as an amorphous.

IR (KBr): 3650–3150, 2933, 2850–2300, 1700, 1652, 1608, 1486 cm$^{-1}$.

$^1$H-NMR (CDCl$_3$) δ: 1.72–2.60 (12H, m), 2.95–3.75 (5H, m), 4.10–4.26 (2H, m), 5.24 (1H, s), 7.20–7.44 (13H, m), 7.75 (1H, t, J=7.0 Hz), 7.86–8.02 (1H, m), 8.21 (1H, d, J=7.8 Hz), 8.60–8.78 (1H, m), 8.91–9.02 (2H, m), 11.82 (1H, bs), 12.08 (1H, bs).

Elemental Analysis for $C_{36}H_{38}N_4O_3 \cdot 2HCl \cdot 2.8H_2O$: Calcd. (%): C, 61.94; H, 6.58; N, 8.03. Found (%): C, 61.91; H, 6.73; N, 8.32.

EXAMPLE 24

2,4-Dioxo-1-[4-(4-diphenylmethoxypiperidino) butyl)]-3-phenyl-1,2,3,4-tetrahydroquinazoline hydrochloride Using the method similar to that in Example 2 (Method 4) and starting from 1-(4-bromobutyl)-2,4-dioxo-3-phenyl-1,2,3,4-tetrahydroquinazoline (1.50 g) obtained in Reference Example 71, a free salt of the title compound (500 mg, 22%) was obtained as an oil.

$^1$H-NMR (CDCl$_3$) δ: 1.50–2.00 (8H, m), 2.02–2.18 (2H, m), 2.38 (2H, t, J=7.0 Hz), 2.69–2.84 (2H, m), 3.18–3.52 (1H, m), 4.17 (2H, t, J=6.6 Hz), 5.52 (1H, m), 7.18–7.56 (17H, m), 7.72 (1H, t, J=7.0 Hz), 8.26 (1H, dd, J=8.0, 1.4 Hz).

This product (500 mg) was combined with a 4N solution of hydrogen chloride in ethyl acetate and concentrated to give the title compound (303 mg, 57%) as an amorphous.

IR (KBr): 3397, 2938, 2656, 1707, 1663, 1609, 1481 cm$^{-1}$.

$^1$H-NMR (CDCl$_3$) δ: 1.80–3.92 (12H, m), 4.10–4.32 (4H, m), 5.24 (1H, m), 7.10–7.62 (17H, m), 7.79 (1H, t, J=7.4 Hz), 8.27 (1H, d, J=6.6 Hz).

Elemental Analysis for $C_{36}H_{37}N_3O_3 \cdot HCl \cdot 1.5H_2O$: Calcd. (%): C, 69.38; H, 6.63; N, 6.74. Found (%): C, 69.47; H, 6.77; N, 6.54.

EXAMPLE 25

3-Cyclohexyl-2,4-dioxo-1-[4-(4-diphenylmethoxypiperidino)butyl]-1,2,3,4-tetrahydroquinazoline hydrochloride Using the method similar to that in Example 2 (Method 4) and starting from 1-(4-bromobutyl)-3-cyclohexyl-2,4-dioxo-1,2,3,4-tetrahydroquinazoline (1.50 g) obtained in Reference Example 72, a free salt of the title compound (580 mg, 26%) was obtained as an oil.

$^1$H-NMR (CDCl$_3$) δ: 1.20–2.00 (16H, m), 2.00–2.20 (2H, m), 2.34–2.60 (4H, m), 2.70–2.82 (2H, m), 3.40–3.52 (1H, m), 4.10 (2H, t, J=6.4 Hz), 4.80–5.00 (1H, m), 5.52 (1H, m), 7.18–7.40 (12H, m), 7.62 (1H, t, J=7.0 Hz), 8.20 (1H, dd, J=7.6, 1.0 Hz).

This product (580 mg) was combined with a 4N solution of hydrogen chloride in ethyl acetate to give the title compound (433 mg, 57%). Recrystallization from ethyl acetate yielded a colorless crystal having a melting point of 206 to 208° C.

IR (KBr): 3345, 2932, 1698, 1651, 1609, 1483 cm$^{-1}$.

$^1$H-NMR (CDCl$_3$) δ: 1.20–2.18 (19H, m), 2.33–2.59 (2H, m), 2.96–3.22 (2H, m), 3.30–3.42 (1H, m), 3.82–3.92 (1H, m), 4.12 (2H, t, J=7.0 Hz), 4.82–5.00 (1H, m), 5.44 (1H, m), 7.13–7.40 (12H, m), 7.67 (1H, ddd, J=8.6, 7.0, 1.6 Hz), 8.22 (1H, dd, J=7.8, 1.4 Hz), 12.26 (1H, bs).

Elemental Analysis for $C_{36}H_{43}N_3O_3 \cdot HCl \cdot 0.4H_2O$: Calcd. (%): C, 70.95; H, 7.41; N, 6.90. Found (%): C, 70.88; H, 7.67; N, 6.88.

EXAMPLE 26

2,4-Dioxo-1-[4-(4-diphenylmethoxypiperidino) butyl]-3-(4-methoxybenzyl)-1,2,3,4-tetrahydroquinazoline Using the method similar to that in Example 2 (Method 4) and starting from 1-(4-bromobutyl)-2,4-dioxo-3-(4-methoxybenzyl)-1,2,3,4-tetrahydroquinazoline (600 mg) obtained in Reference Example 52, the title compound (850 mg, 98%) was synthesized. Recrystallization from ethyl acetate-isopropyl ether-n-hexane yielded a colorless crystal having a melting point of 99 to 100° C.

IR (KBr): 3650–3200, 2920, 1700, 1658, 1610, 1513, 1484 cm$^{-1}$.

$^1$H-NMR (CDCl$_3$) δ: 1.54–2.00 (8H, m), 2.04–2.20 (2H, m), 2.37 (2H, t, J=5.8 Hz), 2.68–2.84 (2H, m), 3.38–3.52 (1H, m), 3.76 (3H, s), 4.13 (2H, t, J=8.4 Hz), 5.20 (2H, s), 5.52 (1H, s), 6.82 (2H, d, J=8.4 Hz), 7.16–7.38 (12H, m), 7.49 (2H, d, J=8.8 Hz), 7.65 (1H, t, J=8.4 Hz), 8.23 (1H, d, J=8.0 Hz).

Elemental Analysis for $C_{38}H_{41}N_3O_4$: Calcd. (%): C, 75.60; H, 6.84; N, 6.96. Found (%): C, 75.32; H, 6.81; N, 7.30.

EXAMPLE 27

Ethyl 2-[2,4-dioxo-1-[4-(4-diphenylmethoxy) piperidino)butyl]-1,2,3,4-tetrahydroquinazolin-3-yl] isobutyrate hydrochloride A mixture of ethyl 2-[1-(4-bromobutyl)-2,4-dioxo-1,2,3, 4-tetrahydroquinazolin-3-yl]isobutyrate (0.90 g, 2.2 mmol) obtained in Reference Example 73, 4-diphenylmethoxypiperidine (90% purity, 0.79 g, 2.6 mmol), potassium carbonate (0.36 g, 2.6 mmol) and N,N-dimethylformamide (5 ml) was stirred at room temperature for 15 hours. The reaction mixture was combined with an iced water and extracted with ethyl ether. After the extract was washed with water and dried (MgSO$_4$), the solvent was distilled off under reduced pressure. The residue was subjected to a column chromatography on a silica gel eluting with ethyl acetate to give a free salt of the title compound (1.24 g, 94%) as an oil.

IR (KBr): 3028, 2943, 2869, 2810, 2779, 1743, 1708, 1664, 1608 cm$^{-1}$.

$^1$H-NMR (CDCl$_3$) δ: 1.22 (3H, t, J=7.1 Hz), 1.52–1.98 (8H, m), 1.84 (6H, s), 2.05–2.16 (2H, m), 2.37 (2H, t, J=6.9 Hz), 2.70–2.80 (2H, m), 3.39–3.51 (1H, m), 4.03–4.11 (2H, m), 4.18 (2H, q, J=7.1 Hz), 5.53 (1H, s), 7.17–7.37 (12H, m, ArH), 7.60–7.68 (1H, m, ArH). 8.14 (1H, dd, J=7.9 Hz, 1.5 Hz).

This oil (1.16 g, 1.97 mmol) was dissolved in ethyl acetate (10.0 ml), combined with a 4N solution of hydrogen chloride in ethyl acetate (1.0 ml) and concentrated. The residue was dried in the presence of phosphorus pentaoxide at 50° C. to give the title compound (1.11 g, 88%).

IR (KBr): 2983, 2937, 2482, 2391, 1735, 1706, 1662, 1608 cm$^{-1}$.

$^1$H-NMR (DMSO-d$_6$) δ: 1.12 (3H, dt, J=7.2 Hz; 1.1 Hz), 1.60–2.23 (8H, m), 1.71 (6H, s), 2.80–3.75 (7H, m), 4.00–4.12 (4H, m), 5.68 (1H, d, J=10.6 Hz), 7.22–7.52 (12H, m, ArH), 7.74–7.81 (1H, m, ArH), 8.01 (1H, dt, J=7.8 Hz, 1.4 Hz).

Elemental Analysis for C$_{36}$H$_{43}$N$_3$O$_5$.HCl.0.5H$_2$O: Calcd. (%): C, 67.22; H, 7.05; N, 6.53. Found (%): C, 67.22; H, 7.00; N, 6.54.

Using the similar method, the title compounds of Examples 28 to 38 shown below were synthesized.

EXAMPLE 28

Ethyl 2-[1-[4-(4hydroxydiphenylmethylpiperidino)butyl]-1,2,3,4tetrahydro-2,4-dioxoquinazolin-3-yl]isobutyrate hydrochloride Starting from ethyl 2-[1-(4-bromobutyl)-2,4-dioxo-1,2,3,4-tetrahydroquinazolin-3-yl]isobutyrate obtained in Reference Example 73, the title compound (0.50 g, 85%) was obtained as an amorphous.

IR (KBr): 3350, 2983, 2941, 2648, 2500, 1735, 1710, 1664, 1608 cm$^{-1}$.

$^1$H-NMR (DMSO-d$_6$) δ: 1.12 (3H, t, J=7.1 Hz), 1.40–1.90 (9H, m), 1.71 (6H, s), 2.75–3.52 (7H, m), 4.01–4.11 (4H, m), 7.13–7.34 (8H, m, ArH), 7.47–7.58 (4H, m, ArH), 7.73–7.81 (1H, m, ArH), 8.01 (1H, dd, J=1.6 Hz, 7.8 Hz).

Elemental Analysis for C$_{36}$H$_{43}$N$_3$O$_5$.HCl.0.5H$_2$O: Calcd. (%): C, 67.22; H, 7.05; N, 6.53. Found (%): C, 67.21; H, 7.13; N, 6.31.

EXAMPLE 29

Ethyl 2-[2,4-dioxo-1-[4-(4-diphenylmethylpiperidyl)butyl]-1,2,3,4-tetrahydroquinazolin-3-yl]isobutyrate dihydrochloride Starting from ethyl 2-[1-(4-bromobutyl)-2,4-dioxo-1,2,3,4-tetrahydroquinazolin-3-yl]isobutyrate obtained in Reference Example 73, the title compound (0.42 g, 83%) was obtained as an amorphous.

IR (KBr): 3420, 2987, 2941, 2400, 1735, 1708, 1660, 1608 cm$^{-1}$.

$^1$H-NMR (DMSO-d$_6$) δ: 1.12 (3H, t, J=7.1 Hz), 1.60–1.88 (4H, m), 1.71 (6H, s), 2.80–3.80 (10H, m), 4.00–4.30 (3H, m), 4.06 (2H, q, J=7.1 Hz), 7.26–8.00 (13H, m, ArH), 8.00 (1H, dd, J=7.7 Hz, 1.5 Hz).

Elemental Analysis for C$_{35}$H$_{42}$N$_4$O$_4$.2HCl.0.5H$_2$O: Calcd. (%): C, 63.25; H, 6.82; N, 8.43. Found (%): C, 62.99; H, 7.06; N, 8.11.

EXAMPLE 30

Methyl 2-[2,4-dioxo-1-[4-(4-diphenylmethoxy)piperidino)butyl]-1,2,3,4-tetrahydroquinazolin-3-yl]isobutyrate hydrochloride Starting from methyl 2-[1-(4-bromobutyl)-2,4-dioxo-1,2,3,4-tetrahydroquinazolin-3-yl]isobutyrate obtained in Reference Example 74, a free salt of the title compound (1.76 g, 88%) was synthesized. This product (0.58 g) was combined with a 4N solution of hydrogen chloride in ethyl acetate and concentrated to give the title compound (0.52 g, 83%) as an amorphous.

IR (KBr): 3390, 3030, 2989, 2947, 2491, 1741, 1706, 1660, 1608 cm$^{-1}$.

$^1$H-NMR (DMSO-d$_6$) δ: 1.55–2.23 (8H, m), 1.71 (6H, s), 2.85–3.75 (7H, m), 3.59 (3H, d, J=1.0 Hz), 4.02–4.11 (2H, m), 5.68 (1H, d, J=10.6 Hz), 7.21–7.43 (11H, m, ArH), 7.50 (1H, d, J=8.8 Hz), 7.73–7.82 (1H,. m, ArH), 7.98–8.03 (1H, m, ArH).

Elemental Analysis for C$_{35}$H$_{41}$N$_3$O$_5$.HCl.0.5H$_2$O: Calcd. (%): C, 66.81; H, 6.89; N, 6.68. Found (%): C, 66.63; H, 6.88; N, 6.56.

EXAMPLE 31

Ethyl 2-[2,4-dioxo-1-[4-(4-diphenylmethoxypiperidino)butyl]-6-methyl-1,2,3,4-tetrahydroquinazolin-3-yl]isobutyrate Starting from ethyl 2-[1-(4-bromobutyl)-2,4-dioxo-6-methyl-1,2,3,4-tetrahydroquinazolin-3-yl]isobutyrate (0.56 g) obtained in Reference Example 75, a free salt of the title compound (0.74 g, 92%) was obtained as an oil.

IR (KBr): 2980, 2942, 2867, 2809, 2772, 1744, 1705, 1663, 1624, 1593, 1510 cm$^{-1}$.

$^1$H-NMR (CDCl$_3$) δ: 1.22 (3H, t, =7.2 Hz), 1.50–2.00 (8H, m), 1.83 (6H, s), 2.05–2.15 (2H, m), 2.32–2.40 (2H, m), 2.38 (3H, s), 2.70–2.81 (2H, m), 3.39–3.51 (1H, m), 4.00–4.07 (2H, m), 4.18 (2H, q, J=7.2 Hz), 5.53 (1H, s), 7.17–7.37 (11H, m, ArH), 7.44 (1H, dd, J=8.4 Hz, 2.2 Hz). 7.93 (1H, d, J=1.8 Hz).

This product was combined with a 4N solution of hydrogen chloride in ethyl acetate (0.7 ml) and concentrated to give the title compound (0.65 g, 82%) as an amorphous.

IR (KBr): 3403, 2980, 2936, 2487, 2398, 1740, 1701, 1661, 1624, 1595, 1508 cm$^{-1}$.

$^1$H-NMR (DMSO-d$_6$) δ: 1.12 (3H, t, J=7.0 Hz), 1.53–2.22 (8H, m), 1.70 (6H, s), 2.37 (3H, s), 2.80–3.76 (7H, m), 4.00–4.11 (4H, m), 5.68 (1H, d, J=10.6 Hz), 7.21–7.42 (11H, m, ArH), 7.56–7.62 (1H, m, ArH), 7.80 (1H, s).

Elemental Analysis for C$_{37}$H$_{45}$N$_3$O$_5$.HCl.0.5H$_2$O: Calcd. (%): C, 67.62; H, 7.21; N, 6.39. Found (%): C, 67.76; H, 7.37; N, 6.29.

EXAMPLE 32

Ethyl 2-[2,4-dioxo-1-[4-(4-diphenylmethoxypiperidino)butyl]-6-nitro-1,2,3,4-tetrahydroquinazolin-3-yl]isobutyrate Starting from ethyl 2-[1-(4-bromobutyl)-2,4-dioxo-6-nitro-1,2,3,4-tetrahydroquinazolin-3-yl]isobutyrate (0.29 g) obtained in Reference Example 76, a free salt of the title compound (0.41 g, 99%) was obtained as an oil.

IR (KBr): 2942, 2868, 2813, 1744, 1717, 1674, 1615, 1530 cm$^{-1}$.

$^1$H-NMR (CDCl$_3$) δ: 1.24 (3H, t, J=7.1 Hz), 1.57–2.00 (8H, m), 1.84 (6H, s), 2.05–2.20 (2H, m), 2.39 (2H, t, J=6.7 Hz), 2.72–2.82 (2H, m), 3.41–3.53 (1H, m), 4.09–4.25 (4H, m), 5.53 (1H, s), 7.24–7.38 (10H, m, ArH), 7.53 (1H, d, J=9.2 Hz), 8.48 (1H, dd, J=2.8 Hz, 9.2 Hz), 9.01 (1H, d, J=2.6 Hz).

This product was combined with a 4N solution of hydrogen chloride in ethyl acetate (0.3 ml) and concentrated to give the title compound (0.28 g, 64%) as an amorphous.

IR (KBr): 3400, 2938, 2488, 2398, 1740, 1717, 1672, 1615, 1526 cm$^{-1}$.

$^1$H-NMR (DMSO-d$_6$) δ: 1.13 (3H, dt, J=7.1 Hz, 1.0 Hz), 1.55–2.23 (8H, m), 1.72 (6H, s), 2.82–3.85 (7H, m), 4.03–4.15 (4H, m), 5.68 (1H, d, J=10.6 Hz), 7.21–7.43 (10H, m, ArH), 7.74 (1H, d, J=9.2 Hz), 8.48–8.55 (1H, m, ArH), 8.68 (1H, dd, J=2.6 Hz, 1.4 Hz).

Elemental Analysis for C$_{36}$H$_{42}$N$_4$O$_7$.HCl.0.5H$_2$O: Calcd. (%): C, 62.83; H, 6.44; N, 8.14. Found (%): C, 62.64; H, 6.54; N, 7.98.

EXAMPLE 33

Ethyl 2-[1-[4-(4-diphenylmethoxypiperidino)butyl]-2,4-dioxo-6-fluoro-1,2,3,4-tetrahydroquinazolin-3-yl]isobutyrate hydrochloride Starting from ethyl 2-[1-(4-bromobutyl)-2,4-dioxo-6-fluoro-1,2,3,4-tetrahydroquinazolin-3-yl]isobutyrate (0.57 g) obtained in Reference Example 77, a free salt of the title compound (0.72 g, 88%) was obtained as an oil.

IR (KBr): 2942, 2867, 2811, 1744, 1709, 1667, 1507 cm$^{-1}$.

$^1$H-NMR (CDCl$_3$) δ: 1.23 (3H, t, J=7.2 Hz), 1.50–1.95 (8H, m), 1.83 (6H, s), 2.05–2.17 (2H, m), 2.33–2.40 (2H, m), 2.70–2.80 (2H, m), 3.40–3.51 (1H, m), 4.01–4.09 (2H, m), 4.18 (2H, q, J=7.2 Hz), 5.53 (1H, s), 7.24–7.39 (12H, m, ArH), 7.81 (1H, dd, J=8.1 Hz, 2.5 Hz).

This product was combined with a 4N solution of hydrogen chloride in ethyl acetate (0.6 ml) and concentrated to give the title compound (0.64 g, 83%) as an amorphous.

IR (KBr): 3420, 2984, 2938, 2500, 1740, 1707, 1663, 1624, 1605, 1505 cm$^{-1}$.

$^1$H-NMR (DMSO-d$_6$) δ: 1.12 (3H, t, J=7.1 Hz), 1.50–2.23 (8H, m), 1.71 (6H, s), 2.82–3.75 (7H, m), 4.01–4.11 (4H, m), 5.68 (1H, d, J=10.6 Hz), 7.21–7.42 (10H, m, ArH), 7.53–7.74 (3H, m, ArH).

Elemental Analysis for C$_{36}$H$_{42}$N$_3$O$_5$F.HCl.0.5H$_2$O: Calcd. (%): C, 65.39; H, 6.71; N, 6.36. Found (%): C, 65.31; H, 6.54; N, 6.20.

EXAMPLE 34

Ethyl 2-[7-chloro-1-[4-(4-diphenylmethoxypiperidino)butyl]-2,4-dioxo-1,2,3,4-tetrahydroquinazolin-3-yl]isobutyrate hydrochloride Starting from ethyl 2-[1-(4-bromobutyl)-7-chloro-2,4-dioxo-1,2,3,4-tetrahydroquinazolin-3-yl]isobutyrate (0.49 g) obtained in Reference Example 78, a free salt of the title compound (0.62 g, 89%) was obtained as an oil.

IR (KBr): 2990, 2942, 2867, 2811, 1748, 1713, 1669, 1605 cm$^{-1}$.

$^1$H-NMR (CDCl$_3$) δ: 1.22 (3H, t, J=7.2 Hz), 1.50–2.00 (8H, m), 1.82 (6H, s), 2.05–2.19 (2H, m), 2.38 (2H, t, J=6.7 Hz), 2.71–2.81 (2H, m), 3.40–3.51 (1H, m), 4.01–4.09 (2H, m), 4.18 (2H, q, J=7.2 Hz), 5.53 (1H, s), 7.18 (1H, dd, J=8.4 Hz, 1.8 Hz), 7.21–7.37 (11H, m, ArH), 8.06 (1H, d, J=8.4 Hz).

This product was combined with a 4N solution of hydrogen chloride in ethyl acetate (0.5 ml) and concentrated to give the title compound (0.54 g, 81%) as an amorphous.

IR (KBr): 3400, 2990, 2938, 2475, 2373, 1740, 1709, 1665, 1605 cm$^{-1}$.

$^1$H-NMR (DMSO-d$_6$) δ: 1.12 (3H, t, J=7.1 Hz), 1.50–2.24 (8H, m), 1.70 (6H, s), 2.82–3.74 (7H, m), 4.00–4.10 (4H, m), 5.68 (1H, d, J=10.6 Hz), 7.21–7.42 (11H, m, ArH), 7.62 (1H, s, ArH), 7.99 (1H, dd, J=8.6 Hz, 1.4 Hz).

Elemental Analysis for C$_{36}$H$_{42}$N$_3$O$_5$Cl.HCl.0.5H$_2$O: Calcd. (%): C, 63.81; H, 6.54; N, 6.20. Found (%): C, 64.05; H, 6.33; N, 6.15.

EXAMPLE 35

Ethyl 2-[6-chloro-1-[4-(4-diphenylmethoxypiperidino)butyl]-2,4-dioxo-1,2,3,4-tetrahydroquinazolin-3-yl]isobutyrate hydrochloride Starting from ethyl 2-[1-(4-bromobutyl)-6-chloro-2,4-dioxo-1,2,3,4-tetrahydroquinazolin-3-yl]isobutyrate (0.61 g) obtained in Reference Example 79, a free salt of the title compound (0.85 g, 98%) was obtained as an oil.

IR (KBr): 3029, 2942, 2868, 2811, 2774, 1744, 1709, 1667, 1609, 1591 cm$^{-1}$.

$^1$H-NMR (CDCl$_3$) δ: 1.23 (3H, t, J=7.1 Hz), 1.50–1.98 (8H, m), 1.82 (6H, s), 2.03–2.18 (2H, m), 2.33–2.40 (2H, m), 2.70–2.80 (2H, m), 3.40–3.52 (1H, m), 4.00–4.04 (2H, m), 4.18 (2H, q, J=7.1 Hz), 5.53 (1H, s), 7.24–7.37 (11H, m, ArH), 7.58 (1H, dd, J=9.0 Hz, 2.4 Hz), 8.10 (1H, d, J=2.2 Hz).

This product was combined with a 4N solution of hydrogen chloride in ethyl acetate (0.5 ml) and concentrated to give the title compound (0.73 g, 80%) as an amorphous.

IR (KBr): 3400, 2982, 2938, 2485, 2400, 1740, 1709, 1665, 1609 cm$^{-1}$.

$^1$H-NMR (DMSO-d$_6$) δ: 1.12 (3H, dt, J=1.0 Hz, 7.1 Hz), 1.52–2.22 (8H, m), 1.70 (6H, s), 2.80–3.73 (7H, m), 4.00–4.11 (4H, m), 5.68 (1H, d, J=10.8 Hz), 7.20–7.43 (10H, m, ArH), 7.55 (1H, d, J=8.8 Hz), 7.81 (1H, dd, J=8.9 Hz, 2.5 Hz), 7.93 (1H, dd, J=2.5 Hz, 1.5 Hz).

Elemental Analysis for C$_{36}$H$_{42}$N$_3$O$_5$Cl.HCl.0.5H$_2$O: Calcd. (%): C, 63.81; H, 6.54; N, 6.20. Found (%): C, 63.65; H, 6.60; N, 6.15.

EXAMPLE 36

Ethyl 2-[2,4-dioxo-1-[3-(4-diphenylmethoxypiperidino)propyl]-1,2,3,4-tetrahydroquinazolin-3-yl]isobutyrate Starting from ethyl 2-[1-(3-bromopropyl)-2,4-dioxo-1,2,3,4-tetrahydroquinazolin-3-yl]isobutyrate (0.52 g, 1.31 mmol) obtained in Reference Example 80, a free salt of the title compound (0.59 g, 77%) was obtained as an oil.

IR (KBr): 3029, 2980, 2942, 2814, 2780, 1744, 1707, 1663, 1609 cm$^{-1}$.

$^1$H-NMR (CDCl$_3$) δ: 1.22 (3H, t, J=7.2 Hz), 1.65–1.98 (6H, m), 1.84 (6H, s), 2.05–2.16 (2H, m), 2.36–2.42 (2H, m), 2.69–2.80 (2H, m), 3.39–3.51 (1H, m), 4.07–4.14 (2H, m), 4.18 (2H, q, J=7.2 Hz), 5.53 (1H, s), 7.17–7.37 (12H, m, ArH), 7.58–7.67 (1H, m, ArH), 8.13 (1H, dd, J=7.8 Hz, 1.6 Hz).

This product was combined with a 4N solution of hydrogen chloride in ethyl acetate (0.5 ml) and concentrated to give the title compound (0.54 g, 85%) as an amorphous.

IR (KBr): 3411, 2984, 2938, 2473, 2409, 1740, 1705, 1663, 1609 cm$^{-1}$.

$^1$H-NMR (DMSO-d$_6$) δ: 1.12 (3H, t, J=7.2 Hz), 1.71 (6H, s), 1.75–2.20 (6H, m), 2.80–3.72 (7H, m), 4.01–4.15 (4H, m), 5.66 (1H, d, J=8.6 Hz), 7.21–7.43 (11H, m, ArH), 7.52–7.57 (1H, m, ArH), 7.75–7.82 (1H, m, ArH), 8.01 (1H, d, J=7.8 Hz).

Elemental Analysis for $C_{35}H_{41}N_3O_5 \cdot HCl \cdot 0.5H_2O$: Calcd. (%): C, 66.81; H, 6.89; N, 6.68. Found (%): C, 66.94; H, 6.74; N, 6.91.

EXAMPLE 37

Ethyl 2-[2,4-dioxo-1-[5-(4-diphenylmethoxypiperidino)pentyl]-1,2,3,4-tetrahydroquinazolin-3-yl]isobutyrate Starting from ethyl 2-[1-(5-bromopentyl)-2,4-dioxo-1,2,3,4-tetrahydroquinazolin-3-yl]isobutyrate (0.62 g, 1.46 mmol) obtained in Reference Example 81, a free salt of the title compound (0.67 g, 75%) was obtained as an oil.

IR (KBr): 2980, 2940, 2865, 2809, 2770, 1744, 1707, 1665, 1609 $cm^{-1}$.

$^1$H-NMR (CDCl$_3$) δ: 1.23 (3H, t, J=7.2 Hz), 1.37–1.96 (10H, m), 1.84 (6H, s), 2.05–2.17 (2H, m), 2.27–2.34 (2H, m), 2.69–2.78 (2H, m), 3.39–3.50 (1H, m), 3.99–4.07 (2H, m), 4.18 (2H, q, J=7.2 Hz), 5.52 (1H, s), 7.11–7.37 (12H, m, ArH), 7.60–7.69 (1H, m, ArH), 8.15 (1H, dd, J=8.0 Hz, 1.6 Hz).

This product was combined with a 4N solution of hydrogen chloride in ethyl acetate (0.5 ml) and concentrated to give the title compound (0.62 g, 86%) as an amorphous.

IR (KBr): 3400, 2938, 2508, 1740, 1705, 1661, 1609 $cm^{-1}$.

$^1$H-NMR (DMSO-d$_6$) δ: 1.12 (3H, t, J=7.2 Hz), 1.71 (6H, s), 1.75–2.20 (6H, m), 2.80–3.72 (7H, m), 4.01–4.15 (4H, m), 5.66 (1H, d, J=8.6 Hz), 7.21–7.43 (11H, m, ArH), 7.52–7.57 (1H, m, ArH), 7.75–7.82 (1H, m, ArH), 8.01 (1H, t, J=7.8 Hz).

Elemental Analysis for $C_{37}H_{45}N_3O_5 \cdot HCl \cdot 0.5H_2O$: Calcd. (%): C, 67.62; H, 7.21; N, 6.39. Found (%): C, 67.50; H, 7.25; N, 6.20.

EXAMPLE 38

Ethyl 2-[2,4-dioxo-1-[6-(4-diphenylmethoxypiperidino)hexyl]-1,2,3,4-tetrahydroquinazolin-3-yl]isobutyrate Starting from ethyl 2-[1-(6-bromohexyl)-2,4-dioxo-1,2,3,4-tetrahydroquinazolin-3-yl]isobutyrate (0.65 g, 1.48 mmol) obtained in Reference Example 82, a free salt of the title compound (0.83 g, 90%) was obtained as an oil.

IR (KBr): 2938, 2859, 1744, 1707, 1667, 1609 $cm^{-1}$.

$^1$H-NMR (CDCl$_3$) δ: 1.22 (3H, t, J=7.1 Hz), 1.30–1.96 (12H, m), 1.84 (6H, s), 2.05–2.17 (2H, m), 2.25–2.31 (2H, m), 2.68–2.79 (2H, m), 3.38–3.48 (1H, m), 4.03 (2H, t, J=8.0 Hz), 4.18 (2H, q, J=7.1 Hz), 5.52 (1H, s), 7.11–7.35 (12H, m, ArH), 7.60–7.68 (1H, m, ArH), 8.14 (1H, dd, J=7.9 Hz, 1.7 Hz).

This product was combined with a 4N solution of hydrogen chloride in ethyl acetate (0.7 ml) and concentrated to give the title compound (0.79 g, 89%) as an amorphous.

IR (KBr): 3410, 2938, 2868, 2487, 2410, 1740, 1705, 1663, 1609 $cm^{-1}$.

$^1$H-NMR (DMSO-d$_6$) δ: 1.12 (3H, t, J=7.1 Hz), 1.71 (6H, s), 1.28–2.21 (12H, m), 2.80–3.73 (7H, m), 4.00–4.11 (4H, m), 5.67 (1H, d, J=10.2 Hz), 7.20–7.49 (12H, m, ArH), 7.73–7.82 (1H, m, ArH), 8.00 (1H, d, J=7.2 Hz).

Elemental Analysis for $C_{38}H_{47}N_3O_5 \cdot HCl \cdot 0.5H_2O$: Calcd. (%): C, 67.99; H, 7.36; N, 6.26. Found (%): C, 68.17; H, 7.15; N, 6.34.

EXAMPLE 39

7-Amino-2,4-dioxo-1-[4-(4-diphenylmethoxypiperidino)butyl]-1,2,3,4-tetrahydroquinazoline 2,4-Dioxo-1-[4-(4-diphenylmethoxypiperidino)butyl]-7-nitro-1,2,3,4-tetrahydroquinazoline (3.00 g) obtained in Example 11 was dissolved in a mixture of concentrated hydrochloric acid (10.0 ml), water (50.0 ml), ethanol (50.0 ml) and tetrahydrofuran (50.0 ml) and an excess of zinc powder was added in portions. After completion of the reaction, the reaction mixture was filtered, and the filtrate was made basic with 25% aqueous ammonia solution and extracted with ethyl acetate. After the extract was washed with water and dried (Na$_2$SO$_4$), the solvent was distilled off under reduced pressure to give the title compound (1.95 g, 69%). Recrystallization from ethyl acetate yielded a yellow crystal having a melting point of 162 to 164° C.

IR (KBr): 3348, 3215, 2945, 1683, 1606, 1484 $cm^{-1}$.

$^1$H-NMR (CDCl$_3$) δ: 1.58–2.07 (8H, m), 2.07–2.24 (2H, m), 2.41 (2H, t, J=6.6 Hz), 2.74–2.88 (2H, m), 3.40–3.54 (1H, m), 4.02 (2H, t, J=8.8 Hz), 4.37 (2H, bs), 5.53 (1H, s), 6.40–6.48 (2H, m), 7.20–7.42 (10H, m), 7.94 (1H, d, J=8.4 Hz).

Elemental Analysis for $C_{30}H_{34}N_4O_3 \cdot 0.3H_2O$: Calcd. (%): C, 71.49; H, 6.92; N, 11.12. Found (%): C, 71.32; H, 6.77; N, 11.16.

EXAMPLE 40

6-Amino-2,4-dioxo-1-[4-(4-diphenylmethoxypiperidino)butyl]-1,2,3,4-tetrahydroquinazoline Using the method similar to that in Example 39 and starting from 2,4-dioxo-1-[4-(4-diphenylmethoxypiperidino)butyl]-6-nitro-1,2,3,4-tetrahydroquinazoline (5.90 g) obtained in Example 12, the title compound (4.62 g, 83%) was synthesized. Recrystallization from ethyl acetate yielded a yellow crystal having a melting point of 131 to 133° C.

IR (KBr): 3353, 3181, 3029, 2946, 1682, 1588, 1508, 1493 $cm^{-1}$.

$^1$H-NMR (CDCl$_3$) δ: 1.50–2.02 (8H, m), 2.02–2.20 (2H, m), 2.37 (2H, t, J=6.2 Hz), 2.68–2.84 (2H, m), 3.38–3.52 (1H, m), 3.75 (2H, bs), 4.05 (2H, t, J=7.8 Hz), 5.53 (1H, s), 7.04 (1H, dd, J=9.0, 3.0 Hz), 7.18–7.38 (11H, m), 7.44 (1H, d, J=2.6 Hz).

Elemental Analysis for $C_{30}H_{34}N_4O_3 \cdot 0.9H_2O$: Calcd. (%): C, 69.99; H, 7.01; N, 10.88. Found (%): C, 69.98; H, 6.65; N, 11.10.

EXAMPLE 41

7-Dimethylamino-2,4-dioxo-1-[4-(4-diphenylmethoxypiperidino)butyl]-1,2,3,4-tetrahydroquinazoline 7-Amino-2,4-dioxo-1-[4-(4-diphenylmethoxypiperidino)butyl]-1,2,3,4-tetrahydroquinazoline (500 mg) obtained in Example 39 was suspended in methanol (5.00 ml), and to this mixture acetic acid (0.5 ml) and 37% formaldehyde (0.5 ml) were added and the mixture was stirred for 1 hour. A solution of sodium cyanoborohydride (94.5 mg) in methanol (2.0 ml) was added dropwise and the mixture was stirred at room temperature for 21 hours. The reaction mixture was concentrated under reduced pressure, diluted with ethyl acetate, washed with water, dried (Na$_2$SO$_4$) and then the solvent was distilled off under reduced pressure. The residue was subjected to a column chromatography on a silica gel to give the title compound (378 mg, 72%) from a fraction eluted with n-hexane-ethyl acetate (5:1,v/v). Recrystallization from ethyl acetate-ethyl ether yielded a yellow crystal having a melting point of 203 to 204° C.

IR (KBr): 3353, 3181, 3029, 2946, 1682, 1588, 1508, 1493 cm$^{-1}$.

$^1$H-NMR (CDCl$_3$) δ: 1.50–2.02 (8H, m), 2.02–2.20 (2H, m), 2.37 (2H, t, J=6.2 Hz), 2.68–2.84 (2H, m), 3.38–3.52 (1H, m), 3.75 (2H, bs), 4.05 (2H, t, J=7.8 Hz), 5.53 (1H, s), 7.04 (1H, dd, J=9.0, 3.0 Hz), 7.18–7.38 (11H, m), 7.44 (1H, d, J=2.6 Hz).

Elemental Analysis for C$_{30}$H$_{34}$N$_4$O$_3$.0.9H$_2$O: Calcd. (%): C, 69.99; H, 7.01; N, 10.88. Found (%): C, 69.98; H, 6.65; N, 11.10.

EXAMPLE 42

6-Dimethylamino-2,4-dioxo-1-[4-(4-diphenylmethoxypiperidino)butyl]-1,2,3,4-tetrahydroquinazoline 6-Amino-2,4-dioxo-1-[4-(4-diphenylmethoxypiperidino)butyl)-1,2,3,4-tetrahydroquinazoline (800 mg) obtained in Example 40 was suspended in methanol (8.0 ml), and to this mixture acetic acid (0.8 ml) and 37% formaldehyde (0.8 ml) were added and the mixture was stirred for 1.5 hours. A solution of sodium cyanoborohydride (141 mg) in methanol (4.0 ml) was added dropwise and the mixture was stirred at room temperature for 27 hours. The reaction mixture was concentrated under reduced pressure, diluted with ethyl acetate, washed with water, dried (Na$_2$SO$_4$) and then the solvent was distilled off under reduced pressure. The residue was subjected to a column chromatography on a silica gel eluting with n-hexane-ethyl acetate (5:1,v/v) to give the title compound (420 mg, 50%). Recrystallization from ethyl acetate-ethyl ether yielded a yellow crystal having a melting point of 165 to 167° C.

IR (KBr): 3173, 2946, 1694, 1626, 1580, 1518, 1483 cm$^{-1}$.

$^1$H-NMR (CDCl$_3$) δ: 1.58–2.02 (8H, m), 2.10–2.28 (2H, m), 2.42 (2H, t, J=6.6 Hz), 2.73–2.85 (2H, m), 2.98 (6H, s), 3.40–3.55 (1H, m), 4.07 (2H, t, J=7.8 Hz), 5.52 (1H, s), 7.11 (1H, dd, J=9.2, 2.6 Hz), 7.22–7.38 (11H, m), 7.43 (1H, d, J=3.0 Hz).

Elemental Analysis for C$_{32}$H$_{38}$N$_4$O$_3$.1.0H$_2$O: Calcd. (%): C, 70.56; H, 7.40; N, 10.28. Found (%): C, 70.25; H, 7.04; N, 10.83.

EXAMPLE 43

Ethyl N-[2,4-dioxo-1-[4-(4-diphenylmethoxypiperidino)butyl]-1,2,3,4-tetrahydro-7quinazolinyl]malonamide 7-Amino-2,4-dioxo-1-[4-(4-diphenylmethoxypiperidino)butyl]-1,2,3,4-tetrahydroquinazoline (700 mg) obtained in Example 39 was dissolved in tetrahydrofuran (10.0 ml), and triethylamine (0.24 ml) and ethyl malonyl chloride (0.20 ml) were added with stirring and cooling on ice. The reaction mixture was stirred at room temperature for 18. 5 hours and combined with water and extracted with ethyl acetate. After the extract was washed with water and dried (Na$_2$SO$_4$), the solvent was distilled off under reduced pressure to give the title compound (690 mg, 80%) as an amorphous.

IR (KBr): 3029, 1682, 1597, 1549, 1495 cm$^{-1}$.

$^1$H-NMR (CDCl$_3$) δ: 1.34 (3H, t, J=6.2 Hz), 1.55–2.00 (8H, m), 2.04–2.24 (2H, m), 2.38 (2H, t, J=6.8 Hz), 2.70–2.85 (2H, m), 3.37–3.55 (1H, m), 3.51 (2H, s), 4.12 (2H, t, J=6.6 Hz), 4.29 (2H, q, J=7.2 Hz), 5.52 (1H, s), 7.10 (1H, d, J=8.0 Hz), 7.18–7.40 (10H, m), 8.04 (1H, s), 8.13 (1H, d, J=8.6 Hz), 9.79 (1H, bs).

Elemental Analysis for C$_{35}$H$_{40}$N$_4$O$_6$.0.4H$_2$O: Calcd. (%): C, 67.81; H, 6.63; N, 9.04. Found (%): C, 67.81; H, 6.67; N, 9.08.

EXAMPLE 44

Ethyl N-[2,4-dioxo-1-[4-(4-diphenylmethoxypiperidino)butyl]-1,2,3,4-tetrahydro-6-quinazolinyl]malonamide Using the method similar to that in Example 43 and starting from 6-amino-2,4-dioxo-1-[4-(4-diphenylmethoxypiperidino)butyl]-1,2,3,4-tetrahydroquinazoline (1.78 g) obtained in Example 40, the title compound (1.13 g, 52%) was synthesized. Recrystallization from ethyl acetate yielded a colorless crystal having a melting point of 152 to 153° C.

IR (KBr): 3061, , 2946, 1696, 1628, 1601, 1557, 1507 cm$^{-1}$.

$^1$H-NMR (CDCl$_3$) δ: 1.34 (3H, t, J=7.2 Hz), 1.50–2.00 (8H, m), 2.08–2.26 (2H, m), 2.39 (2H, t, J=4.6 Hz), 2.70–2.82 (2H, m), 3.40–3.54 (1H, m), 3.50 (2H, s), 4.10 (2H, t, J=8.4 Hz), 4.28 (2H, q, J=7.0 Hz), 5.52 (1H, s), 7.18–7.38 (11H, m), 8.10 (1H, d, J=2.2 Hz), 8.15–8.24 (1H, m), 9.52 (1H, bs).

Elemental Analysis for C$_{35}$H$_{40}$N$_4$O$_6$: Calcd. (%): C, 68.61; H, 6.58; N, 9.14. Found (%): C, 68.04; H, 6.60; N, 9.27.

EXAMPLE 45

7-Acetoxyacetamide-2,4-dioxo-1-[4-(4-diphenylmethoxypiperideno)bytyl]-1,2,3,4-tetrahydroquinazoline Using the method similar to that in Example 43 and acetoxyacetyl chloride instead of ethyl malonyl chloride and starting from 7-amino-2,4-dioxo-1-[4-(4-diphenylmethoxypiperidino)butyl]-1,2,3,4-tetrahydroquinazoline (710 mg) obtained in Example 39, the title compound (563 mg, 66%) was synthesized. Recrystallization from ethyl acetate-methanol-tetrahydrofuran yielded a colorless crystal having a melting point of 211 to 212° C.

IR (KBr): 3030, , 2941, 1753, 1689, 1616, 1596, 1544, 1459 cm$^{-1}$.

$^1$H-NMR (CDCl$_3$) δ: 1.60–2.10 (8H, m), 2.18–2.40 (2H, m), 2.25 (3H, s), 2.44–2.54 (2H, m), 2.76–2.94 (2H, m), 3.44–3.58 (1H, m), 4.03–4.36 (2H, m), 4.73 (2H, s), 5.50 (1H, s), 7.10–7.40 (12H, m), 8.00 (1H, bs), 8.03 (1H, d, J=8.4 Hz).

Elemental Analysis for C$_{34}$H$_{38}$N$_4$O$_6$.0.5H$_2$O: Calcd. (%): C, 67.20; H, 6.47; N, 9.22. Found (%): C, 67.04; H, 6.29; N, 9.35.

EXAMPLE 46

6-Acetoxyacetamide-2,4-dioxo-1-[4-(4-diphenylmethoxypiperidino)butyl]-1,2,3,4-tetrahydroquinazoline Using the method similar to that in Example 45 and starting from 6-amino-2,4-dioxo-1-[4-(4-diphenylmethoxypiperidino)butyl]-1,2,3,4-tetrahydroquinazoline (800 mg) obtained in Example 40, the title compound (688 mg, 72%) was synthesized. Recrystallization from ethyl acetate-ethyl ether yielded a colorless crystal having a melting point of 133 to 135° C.

IR (KBr): 3061, 2946, 1750, 1694, 16130, 1601, 1557, 1508 cm$^{-1}$.

$^1$H-NMR (CDCl$_3$) δ: 1.58–2.00 (8H, m), 2.12–2.32 (2H, m), 2.26 (3H, s), 2.35–2.50 (2H, m), 2.70–2.88 (2H, m), 3.40–3.54 (1H, m), 4.10 (2H, t, J=7.0 Hz), 4.74 (2H, s), 5.51 (1H, s), 7.20–7.40 (11H, m), 7.97 (1H, d, J=2.6 Hz), 8.16 (1H, bs), 8.25–8.35 (1H, m).

Elemental Analysis for C$_{34}$H$_{38}$N$_4$O$_6$.1.4H$_2$O: Calcd. (%): C, 65.29; H, 6.32; N, 9.33. Found (%): C, 65.45; H, 6.59; N, 8.98.

EXAMPLE 47

[2,4-Dioxo-1-[4-(4-diphenylmethoxypiperidinyl) butyl]-1,2,3,4-tetrahydro-7-quinazolinyl] carbamoylacetic acid Ethyl N-[2,4-dioxo-1-[4-(4-diphenylmethoxypiperidino) butyl]-1,2,3,4-tetrahydro-7-quinazolinyl]malonamide (690 mg) obtained in Example 43 was dissolved in tetrahydrofuran (10.0 ml) and ethanol (10.0 ml) and then a 1N aqueous solution of sodium hydroxide (5.0 ml) was added. The reaction mixture was stirred at room temperature for 16 hours and the solvent was distilled off under reduced pressure, and the residue was made acidic with 1N hydrochloric acid, and then extracted with ethyl acetate. After the extract was washed with water and dried (Na$_2$SO$_4$), the solvent was distilled off under reduced pressure to give the title compound (126 mg, 19%). Recrystallization from ethyl acetate-methanol-tetrahydrofuran yielded a colorless crystal having a melting point of 230 to 232° C.

IR (KBr): 3700–2400, 3340, 3028, 1685, 1617, 1594, 1535 cm$^{-1}$.

$^1$H-NMR (CDCl$_3$) δ: 1.60–3.30 (15H, m), 3.38 (2H, s), 3.68–4.10 (2H, m), 5.44 (1H, s), 7.20–7.40 (1H, m), 7.42–7.58 (1H, m), 7.72–7.86 (1H, m), 9.96 (1H, bs).

Elemental Analysis for C$_{33}$H$_{36}$N$_4$O$_6$.1.5H$_2$O: Calcd. (%): C, 64.97; H, 6.43; N, 9.16. Found (%): C, 64.79; H, 6.27; N, 9.36.

EXAMPLE 48

[2,4-Dioxo-1-[4-(4-diphenylmethoxypiperidino) butyl]-1,2,3,4-tetrahydro-6-quinazolinyl] carbamoylacetic acid Using the method similar to that in Example 47 and starting from N-[2,4-dioxo-1-[4-(4-diphenylmethoxypiperidino)butyl]-1,2,3,4-tetrahydro-6 -quinazolinyl]ethylmalonamide (800 mg) obtained in Example 44, the title compound (279 mg, 36%) was synthesized. Recrystallization from ethyl acetate-methanol yielded a colorless crystal having a melting point of 166 to 168° C.

IR (KBr): 3700–2700, 3031, 1686, 1599, 1545, 1508 cm$^{-1}$.

$^1$H-NMR (CDCl$_3$) δ: 1.66–3.42 (15H, m), 3.68–3.78 (2H, m), 3.94–4.10 (2H, m), 5.48 (1H, s), 6.98–7.06 (1H, m), 7.20–7.52 (11H, m), 8.04 (1H, s), 8.08 (1H, bs), 10.90 (1H, bs).

Elemental Analysis for C$_{33}$H$_{36}$N$_4$O$_6$.1.3H$_2$O: Calcd. (%): C, 65.18; H, 6.40; N, 9.21. Found (%): C, 65.11; H, 6.25; N, 9.29.

EXAMPLE 49

2,4-Dioxo-1-[3-(4-diphenylmethoxypiperidino) propyl]-1,2,3,4-tetrahydroquinazoline-3-acetic acid Using the method similar to that in Example 47 and starting from methyl 2,4-dioxo-1-[3-(4-diphenylmethoxypiperidino)propyl]-1,2,3,4-tetrahydroquinazoline-3-acetate (1.00 g) obtained in Example 14, the title compound (790 mg, 81%) was synthesized. Recrystallization from ethyl acetate-methanol-tetrahydrofuran yielded a colorless crystal having a melting point of 170 to 172° C.

IR (Nujor): 3600–3300, 1690, 1650, 1610, 1590, 1490 cm$^{-1}$.

$^1$H-NMR (CDCl$_3$) δ: 1.80–2.22 (6H, m), 2.84–3.06 (4H, m), 3.06–3.28 (2H, m), 3.62–3.74 (1H,m), 4.08–4.20 (2H, m), 4.60 (2H, s), 5.42 (1H, s), 7.05–7.42 (12H, m), 7.59 (1H, t, J=8.8 Hz), 8.11 (1H, d, J=8.0 Hz).

Elemental Analysis for C$_{31}$H$_{33}$N$_3$O$_5$.1.0H$_2$O: Calcd. (%): C, 68.23; H, 6.47; N, 7.70. Found (%): C, 67.87; H, 6.53; N, 7.78.

EXAMPLE 50

2,4-Dioxo-1-[4-(4 -diphenylmethoxypiperidino) butyl]-1,2,3,4-tetrahydroquinazoline-3-acetic acid Using the method similar to that in Example 47 and starting from methyl 2,4-dioxo-1-[4-(4-diphenylmethoxypiperidino)butyl]-1,2,3,4-tetrahydroquinazoline-3-acetate (1.50 g) obtained in Example 15, the title compound (1.22 g, 84%) was synthesized. Recrystallization from ethyl acetate yielded a colorless crystal having a melting point of 184 to 186° C.

IR (KBr): 3400–2800, 1702, 1656, 1606, 1571, 1484 cm$^{-1}$.

$^1$H-NMR (CDCl$_3$) δ: 1.74–2.08 (6H, m), 2.30–3.32 (8H, m), 3.76–3.84 (1H,m), 4.25–4.38 (2H, m), 4.69 (2H, s), 5.43 (1H, s), 7.08–7.44 (12H, m), 7.61 (1H, t, J=8.4 Hz), 8.25 (1H, d, J=7.6 Hz).

Elemental Analysis for C$_{32}$H$_{35}$N$_3$O$_5$.1.7H$_2$O: Calcd. (%): C, 67.16; H, 6.76; N, 7.34. Found (%): C, 67.14; H, 6.70; N, 7.41.

EXAMPLE 51

2,4-Dioxo-1-[3-(4-diphenylmethoxypiperidino) propyl]-1,2,3,4-tetrahydroquinazoline-3-propionic acid Using the method similar to that in Example 47 and starting from ethyl 2,4-dioxo-1-[3-(4-diphenylmethoxypiperidino)propyl]-1,2,3,4-tetrahydroquinazoline-3-propionate (945 mg) obtained in Example 16, the title compound (882 mg, 98%) was synthesized. Recrystallization from ethyl acetate-ethyl ether yielded a colorless crystal having a melting point of 150 to 151° C.

IR (KBr): 3400–2750, 1699, 1655, 1609, 1485 cm$^{-1}$.

$^1$H-NMR (CDCl$_3$) δ: 1.76–2.08 (6H, m), 2.54 (2H, t, J=7.4 Hz), 2.62–2.78 (4H, m), 2.82–3.06 (2H, m), 3.52–3.63 (1H, m), 4.13 (2H, t, J=5.8 Hz), 4.34 (2H, t, J=7.4Hz), 5.47 (1H, s), 7.10–7.38 (12H, m), 7.63 (1H, t, J=7.4 Hz), 8.15 (1H, d, J=8.0 Hz).

Elemental Analysis for C$_{32}$H$_{35}$N$_3$O$_5$.1.5H$_2$O: Calcd. (%): C, 67.59; H, 6.74; N, 7.39. Found (%): C, 67.58; H, 6.39; N, 7.53.

EXAMPLE 52

2,4-Dioxo-1-[4-(4-diphenylmethoxypiperidino) butyl]-1,2,3,4-tetrahydroquinazoline-3-propionic acid Using the method similar to that in Example 47 and starting from ethyl 2,4-dioxo-1-[4-(4- diphenylmethoxypiperidino)butyl]-1,2,3,4-tetrahydroquinazoline-3-propionate (1.83 g) which is a free salt of the compound obtained in Example 17, the title compound (1.23 , 71%) was synthesized. Recrystallization from ethyl acetate-ethyl ether yielded a colorless crystal having a melting point of 107 to 108° C.

IR (KBr): 3640–3120, 1700, 1652, 1608, 1486 cm$^{-1}$.

$^1$H-NMR (CDCl$_3$) δ: 1.66–2.02 (8H, m), 2.14–2.32 (2H, m), 2.54 (2H, t, J=6.2 Hz), 2.80–3.10 (4H, m), 3.64–3.74 (1H, m), 4.26–4.38 (2H, m), 4.47 (2H, t, J=6.2 Hz), 5.47 (1H, s), 7.10–7.35 (12H, m), 7.63 (1H, t, J=8.0 Hz), 8.24 (1H, d, J=7.8 Hz).

Elemental Analysis for $C_{33}H_{37}N_3O_5 \cdot 1.1H_2O$: Calcd. (%): C, 68.87; H, 6.87; N, 7.30. Found (%): C, 68.68; H, 6.97; N, 7.17.

EXAMPLE 53

2,4-Dioxo-1-[4-(4-diphenylmethoxypiperidino) butyl]-1,2,3,4-tetrahydroquinazoline-3-butyric acid Using the method similar to that in Example 47 and starting from ethyl 2,4-dioxo-1-[4-(4-diphenylmethoxypiperidino)butyl]-1,2,3,4-tetrahydroquinazoline-3-butyrate (2.00 g) obtained in Example 18, the title compound (857 mg, 45%) was obtained. Recrystallization from ethyl acetate-ethyl ether yielded a colorless crystal having a melting point of 132 to 133° C.

IR (KBr): 3200–2400, 1704, 1658, 1608, 1484 cm$^{-1}$.

$^1$H-NMR (CDCl$_3$) δ: 1.70–2.04 (8H, m), 2.04–2.18 (2H, m), 2.36–2.55 (4H, m), 2.55–2.73 (2H, m), 2.75–2.92 (2H, m), 3.48–3.60 (1H, m), 4.16–4.30 (4H, m), 5.47 (1H, s), 7.10–7.40 (12H, m), 7.61 (1H, t, J=8.2 Hz), 8.26 (1H, d, J=8.0 Hz).

Elemental Analysis for $C_{3\ 4}H_3N_3O_5$: Calcd. (%): C, 71.68; H, 6.90; N, 7.38. Found (%): C, 71.20; H, 6.80; N, 7.31.

EXAMPLE 54

Ethyl 2-[2,4-dioxo-1-[4-(4-diphenylmethoxypiperidino)butyl]-1,2,3,4-tetrahydro-3-quinazolinyl]benzoate Using the method similar to that in Example 2 (Method 4) and starting from 2-[1-(4-bromobutyl)-2,4-dioxo-1,2,3,4-tetrahydro-3-quinazolinyl]ethylbenzoate (2.92 g) obtained in Reference Example 97, the title compound (3.25 g, 78%) was obtained as an oil.

$^1$H-NMR (CDCl$_3$) δ: 1.50–1.82 (6H, m), 1.82–2.00 (2H, m), 2.00–2.20 (2H, m), 2.34 (2H, t, J=6.6 Hz), 2.68–2.82 (2H, m), 3.37–3.52 (1H, m), 4.11 (2H, t, J=7.4 Hz), 4.50–4.64 (4H, m), 5.53 (1H, s), 7.18–7.56 (15H, m), 7.67 (1H, t, J=7.0 Hz), 7.99 (2H, d, J=8.4 Hz), 8.22 (1H, d, J=7.8 Hz).

Example 55

2,4-Dioxo-1-[4-(4-diphenylmethoxypiperidino) butyl]-3-(2-hydroxyethyl)-1,2,3,4-tetrahydroquinazoline Using the method similar to that in Example 47 and starting from ethyl 2-[2,4-dioxo-1-[4-(4-diphenylmethoxypiperidino)butyl]-1,2,3,4-tetrahydro-3-quinazolinyl]benzoate (3.25 g) obtained in Example 54, the title compound (2.12 g, 78%) was synthesized. Recrystallization from ethyl acetate-ethyl ether yielded a colorless crystal having a melting point of 145 to 150° C.

IR (KBr): 3460, 2944, 1701, 1659, 1609, 1485 cm$^{-1}$.

$^1$H-NMR (CDCl$_3$) δ: 1.50–2.00 (8H, m), 2.00–2.22 (2H, m), 2.39 (2H, t, J=7.2 Hz), 2.68–2.84 (2H, m), 3.39–3.54 (1H, m), 3.93 (2H, t, J=5.2 Hz), 4.15 (2H, t, J=7.6 Hz), 4.37 )2H, t, J=5.4 Hz), 5.52 (1H, s), 7.14–7.42 (12H, m), 7.68 (1H, ddd, J=8.8, 7.4, 1.4 Hz), 8.23 (1H, dd, J=8.0, 1.4 Hz).

Elemental Analysis for $C_{32}H_{37}N_3O_4$: Calcd. (%): C, 72.84; H, 7.07; N, 7.96. Found (%): C, 72.44; H, 7.20; N, 7.82.

EXAMPLE 56

2,4-Dioxo-1-[4-(4-diphenylmethoxypiperidino) butyl]-N-methyl-N-(2-phenethyl)-1,2,3,4-tetrahydroquinazoline-3-acetamide hydrochloride Using the method similar to that in Example 2 (Method 4) and starting from 1-(4-bromobutyl)-2,4-dioxo-N-methyl-N-(2-phenethyl)-1,2,3,4-tetrahydroquinazolin-3-acetamide (1.55 g) obtained in Reference Example 100, a free salt of the title compound (1.77 g, 82%) was obtained as an amorphous.

IR (KBr): 2941, 1706, 1662, 1610, 1486 cm$^{-1}$.

$^1$H-NMR (CDCl3) δ: 1.54–2.00 (8H, m), 2.06–2.24 (2H, m), 2.39 (2H, t, J=7.0 Hz), 2.70–2.86 (2H, m), 2.85 (2H, t, J=7.6 Hz, major), 2.94, (3H, s, minor), 2.99 (3H, s, major), 3.02 (2H, t, J=7.6 Hz, minor), 3.38–3.52 (1H, m), 3.52–3.64 (2H, m), 4.06–4.20 (2H, m), 4.85 (2H, s, minor), 4.88 (2H, s, major), 5.51 (1H, s), 7.10–7.42 (17H, m), 7.67 (1H, t, J=7.8 Hz), 8.18–8.27 (1H, m).

Elemental Analysis for $C_{41}H_{46}N_4O_4 \cdot 0.4H_2O$: Calcd. (%): C, 73.94; H, 7.08; N, 8.41. Found (%): C, 73.83; H, 7.02; N, 8.36.

This product (1.00 g) was combined with a 4N solution of hydrogen chloride in ethyl acetate and concentrated to give the title compound (781 mg, 74%). Recrystallization from ethyl acetate yielded a colorless crystal having a melting point of 137 to 139° C.

IR (KBr): 2933, 1706, 1658, 1610, 1484 cm$^{-1}$.

$^1$H-NMR (CDCl$_3$) δ: 1.80–2.12 (8H, m), 2.30–2.35 (2H, m), 2.70–3.18 (4H, m), 2.87, (3H, s, minor), 2.95 (3H, s, major), 3.28–3.62 (4H, m), 3.78–3.88 (1H, m), 4.22 (2H, t, J=6.6 Hz), 4.83 (2H, s, minor), 4.87 (2H, s, major), 5.37 (1H, s, major), 5.41 (1H, s, minor), 7.10–7.40 (17H, m), 7.70 (1H, t, J=7.4 Hz), 8.18–8.28 (1H, m), 12.02 (1H, bs).

Elemental Analysis for $C_{41}H_{46}N_4O_4 \cdot HCl \cdot 0.8H_2O$: Calcd. (%): C, 69.39; H, 6.90; N, 7.89. Found (%): C, 69.43; H, 6.87; N, 7.99.

EXAMPLE 57

2,4-Dioxo-1-[4-(4-diphenylmethoxypiperidino) butyl]-3-(2-phenethyl)-1,2,3,4-tetrahydroquinazoline 2,4-Dioxo-1-[4-(4-diphenylmethoxypiperidino)butyl]-1,2,3,4-tetrahydroquinazoline (420 mg) obtained in Example 2 was dissolved in N,N-dimethylformamide (20 ml), and potassium carbonate (180 mg) and 1-bromo-2-phenylethane (0.18 ml) were added sequentially and then the mixture was stirred at 60° C. for 16hours. The reaction mixture was combined with water and extracted with ethyl acetate. After the extract was washed with water and dried (Na$_2$SO$_4$), the solvent was distilled off under reduced pressure. The residue was subjected to a column chromatography on a silica gel eluting n-hexane-ethyl acetate (5:1, v/v) to give the title compound (247 mg, 48%). Recrystallization from ethyl acetate-ethyl ether-n-hexane yielded a colorless crystal having a melting point of 110 to 112° C.

IR (KBr): 2745, 1702, 1658, 1610, 1484 cm$^{-1}$.

$^1$H-NMR (CDCl$_3$) δ: 1.54–2.04 (8H, m), 2.06–2.26 (2H, m), 2.34–2.48 (2H, m), 2.70–2.86 (2H, m), 2.98 (2H, t, J=7.8 Hz), 3.40–3.54 (1H, m), 4.14 (2H, t, J=8.8 Hz), 4.30 (2H, t, J=8.0 Hz), 5.53 (1H, s), 7.14–7.44 (12H, m), 7.67 (1H, ddd, J=8.4, 7.8, 0.6 Hz), 8.24 (1H, dd, J=7.8, 1.2 Hz).

Elemental Analysis for C$_{38}$H$_{41}$N$_3$O$_3$: Calcd. (%): C, 77.65; H, 7.03; N, 7.15. Found (%): C, 77.31; H, 6.95; N, 7.27.

EXAMPLE 58

2,4-Dioxo-1-[4-(4-diphenylmethoxypiperidino)butyl]-3-(3-phenylpropyl)-1,2,3,4-tetrahydroquinazoline hydrochloride 2,4-Dioxo-1-[4-(4-diphenylmethoxypiperidino)butyl]-1,2,3,4-tetrahydroquinazoline (1.0 g) obtained in Example 2 was dissolved in N,N-dimethylformamide (30 ml), and potassium carbonate (429 mg), sodium iodide (200 mg) and 1-bromo-2-phenylpropane (0.47 ml) were added sequentially and then the mixture was stirred at 60° C. for 30 hours. The reaction mixture was combined with water and extracted with ethyl acetate. After the extract was washed with water and dried (Na$_2$SO$_4$), the solvent was distilled off under reduced pressure. The residue was subjected to a column chromatography on a silica gel eluting n-hexane-ethyl acetate (5:1, v/v) to give a free salt of the title compound (1.07 g, 86%) as an oil.

$^1$H-NMR (CDCl$_3$) δ: 1.58–2.22 (12H, m), 2.38 (2H, t, J=7.4 Hz), 2.73 (2H, t, J=8.0 Hz), 2.67–2.83 (2H, m), 3.38–3.52 (1H, m), 4.04–4.20 (4H, m), 5.52 (1H, s), 7.08–7.40 (12H, m), 7.65 (1H, ddd, J=8.4, 7.0, 1.4 Hz), 8.21 (1H, dd, J=7.8, 1.2 Hz).

This product (1.07 g) was combined with a 4N solution of hydrogen chloride in ethyl acetate and concentrated to give the title compound (423 mg, 37%) as an amorphous.

IR (KBr): 2938, 1699, 1655, 1609, 1485 cm$^{-1}$.

$^1$H-NMR (CDCl$_3$) δ: 1.70–2.16 (8H, m), 2.30–2.52 (2H, m), 2.72 (2H, t, J=8.4 Hz), 2.94–3.16 (4H, m), 3.26–3.44 (2H, m), 3.82–3.90 (1H,m), 4.05–4.20 (4H,m), 5.42 (1H, s), 7.08–7.40 (12H, m), 7.62–7.75 (1H, m), 8.23 (1H, d, J=7.6 Hz)

Elemental Analysis for C$_{39}$H$_{43}$N$_3$O$_3$.HCl.1.2H$_2$O: Calcd. (%): C, 70.99; H, 7.09; N, 6.37. Found (%): C, 70.87; H, 7.10; N, 6.55.

EXAMPLE 59

Ethyl 2,4-dioxo-1-[4-(4-diphenylmethoxypiperidino)butyl]-1,2,3,4-tetrahydroquinazoline-3-(2,2-dimethyl)butyrate hydrochloride Using the method similar to that in Example 58 and starting from 2,4-dioxo-1-[4-(4-diphenylmethoxypiperidino)butyl]-1,2,3,4-tetrahydroquinazoline (880 mg) obtained in Example 2, a free salt of the title compound (640 mg, 56%) was obtained as an oil.

$^1$H-NMR (CDCl$_3$) δ: 1.18–1.30 (9H, m), 1.54–1.98 (10H, m), 2.04–2.20 (2H, m), 2.38 (2H, t, J=6.6 Hz), 2.68–2.84 (2H, m), 3.40–3.52 (1H, m), 4.04–4.20 (6H, m), 5.53 (1H, s), 7.16–7.40 (12H, m), 7.65 (1H, t, J=8.8 Hz), 8.21 (1H, d, J=7.6 Hz).

This product (640 mg) was combined with a 4N solution of hydrogen chloride in ethyl acetate and concentrated to give the title compound (376 mg, 56%) as an amorphous.

IR (KBr): 2938, 1701, 1655, 1609, 1485 cm$^{-1}$.

$^1$H-NMR (CDCl$_3$) δ: 1.20–1.34 (9H, m), 1.50–2.18 (8H, m), 2.34–2.56 (2H, m), 2.94–3.22 (4H, m), 3.30–3.42 (2H, m), 3.83–3.90 (1H, m), 4.00–4.20 (6H, m), 5.44 (1H, s), 7.18–7.40 (12H, m), 7.70 (1H, t, J=7.6 Hz), 8.22 (1H, d, J=8.0 Hz), 12.16 (1H, bs).

Elemental Analysis for C$_{38}$H$_{47}$N$_3$O$_3$.HCl.1.2H$_2$O: Calcd. (%): C, 66.74; H, 7.43; N, 6.14. Found (%): C, 66.78; H, 7.29; N, 6.26.

EXAMPLE 60

2,4-Dioxo-1-[4-(4-diphenylmethoxypiperidino)butyl]-1,2,3,4-tetrahydroquinazoline-3-valeric acid Using the method similar to that in Example 58 and starting from 2,4-dioxo-1-[4-(4-diphenylmethoxypiperidino)butyl]-1,2,3,4-tetrahydroquinazoline (1.80 g) obtained in Example 2, ethyl ester of the title compound (2.74 g, about 100%) was obtained as an oil.

$^1$H-NMR (CDCl$_3$) δ: 1.24 (3H, t, J=6.8 Hz), 1.54–2.00 (12H, m), 2.04–2.20 (2H, m), 2.30–2.44 (4H, m), 2.72–2.86 (2H, m), 3.38–3.52 (1H, m), 4.04–4.20 (6H, m), 5.53 (1H, s), 7.18–7.40 (12H, m), 7.66 (1H, ddd, J=8.8, 7.2, 1.6 Hz), 8.21 (1H, dd, J=8.2, 1.8 Hz).

This product (2.74 g) was treated in the manner similar to that for synthesizing the title compound of Example 47 to give the title compound (732 mg, 34%) as an amorphous.

IR (KBr): 3700–2300, 2949, 1699, 1655, 1609, 1485 cm$^{-1}$.

$^1$H-NMR (CDCl$_3$) δ: 1.57–2.10 (10H., m), 2.22–2.42 (2H, m), 2.31 (2H, t, J=6.6 Hz), 2.96 (2H, t, J=9.0 Hz), 3.00–3.18 (2H, m), 3.20–3.36 (2H, m), 3.74–3.84 (1H, m), 4.08–4.26 (4H, m), 5.44 (1H, s), 7.12–7.44 (12H, m), 7.67 (1H, t, J=7.6 Hz), 8.24 (1H, d, J=7.6 Hz).

Elemental Analysis for C$_{35}$H$_{41}$N$_3$O$_5$.2.6H$_2$O: Calcd. (%): C, 66.67; H, 7.38; N, 6.66. Found (%): C, 66.40; H, 6.92; N, 6.45.

EXAMPLE 61

3-Benzyl-2,4-dioxo-1-[4-(4-diphenylmethoxypiperidino)butyl]-1,2,3,4-tetrahydroquinazoline hydrochloride 2,4-Dioxo-1-[4-(4-diphenylmethoxypiperidino)butyl]-1,2,3,4-tetrahydroquinazoline (0.48 g, 1.0 mmol) obtained in Example 2 was dissolved in N,N-dimethylformamide (4 ml), and then sodium hydride (60% in oil, 44 mg, 1.1 mmol) was added. After stirring at room temperature for 15 minutes, benzyl bromide (0.18 g, 1.2 mmol) was added and the mixture was stirred further for 1 hour. The reaction mixture was combined with an iced water, and extracted with ethyl ether. After the extract was washed with water and dried (MgSO$_4$), the solvent was distilled off under reduced pressure. The residue was subjected to a column chromatography on a silica gel eluting with chloroform-methanol (20:1, v/v) to give a free salt of the title compound (0.40 g, 70%) as an oil. This product was combined with a 4N solution of hydrogen chloride in ethyl acetate and concentrated to give the title compound (0.35 g, 81%) as an amorphous.

IR (KBr): 3400, 3085, 3060, 3031, 3002, 2952, 2875, 2482, 1700, 1654, 1608 cm$^{-1}$.

¹H-NMR (DMSO-d₆) δ: 1.60–2.21 (8H, m), 2.75–3.73 (7H, m), 4.10–4.20 (2H, m), 5.16 (2H, s), 5.67 (1H, d, J=11.4 Hz), 7.20–7.43 (16H, m, ArH), 7.55 (1H, d, J=8.4 Hz), 7.76–7.84 (1H, m), 8.11 (1H, d, J=7.8 Hz).

Elemental Analysis for $C_{37}H_{40}N_3O_3 \cdot HCl \cdot 0.5H_2O$: Calcd. (%): C, 71.65; H, 6.83; N, 6.78. Found (%): C, 71.31; H, 6.69; N, 6.63.

EXAMPLE 62

3-[(2-Methoxycarbonylphenyl)methyl]-2,4-dioxo-1-[4-(4-diphenylmethoxypiperidino)butyl]-1,2,3,4-tetrahydroquinazoline hydrochloride Using the method similar to that in Example 61 and starting from 2,4-dioxo-1-[4-(4-diphenylmethoxypiperidino)butyl]-1,2,3,4-tetrahydroquinazoline (0.97 g, 2.0 mmol) obtained in Example 2, a free salt of the title compound (0.94 g, 74%) was obtained as an oil. This product (0.54 g, 0.85 mmol) was combined with a 4N solution of hydrogen chloride in ethyl acetate and concentrated to give the title compound (0.47 g, 81%) as an amorphous.

IR(KBr): 3404, 3060, 3030, 2950, 2491, 2376, 1700, 1654, 1608 cm⁻¹.

¹H-NMR (DMSO-d₆) δ: 1.60–2.20 (8H, m), 2.75–3.72 (7H, m), 3.89 (3H, d, J=1.6 Hz), 4.10–4.21 (2H, m), 5.49 (1H, d, J=3.6 Hz), 5.66 (1H, d, J=13.6 Hz), 7.07–7.61 (15H, m, ArH), 7.79–7.96 (2H, m, ArH), 8.10 (1H, d, J=7.8 Hz)

Elemental Analysis for $C_{39}H_{41}N_3O_5 \cdot HCl \cdot H_2O$: Calcd. (%): C, 68.26; H, 6.46; N, 6.12. Found (%): C, 68.25; H, 6.39; N, 6.14.

EXAMPLE 63

3-[(3-Methoxycarbonylphenyl)methyl]-2,4-dioxo-1-[4-(4-diphenylmethoxypiperidino)butyl]-1,2,3,4-tetrahydroquinazoline hydrochloride Using the method similar to that in Example 61 and starting from 2,4-dioxo-1-[4-(4-diphenylmethoxypiperidino)butyl]-1,2,3,4-tetrahydroquinazoline (0.48 g, 1.0 mmol) obtained in Example 2, a free salt of the title compound (0.50 g, 79%) was obtained as an oil. This product (0.40 g, 0.63 mmol) was combined with a 4N solution of hydrogen chloride in ethyl acetate and concentrated to give the title compound (0.37 g, 87%) as an amorphous.

IR (KBr): 3400, 3058, 3030, 2950, 2499, 1718, 1700, 1658, 1608 cm⁻¹.

¹H-NMR (DMSO-d₆) δ: 1.60–2.21 (8H, m), 2.78–3.73 (7H, m), 3.83 (3H, s), 4.11–4.20 (2H, m), 5.21 (1H, s), 5.67 (1H, d, J=11.6 Hz), 7.24–7.65 (14H, m, ArH), 7.77–7.95 (3H, m, ArH), 8.09–8.13 (1H, m, ArH)

Elemental Analysis for $C_{39}H_{41}N_3O_5 \cdot HCl \cdot 0.5H_2O$: Calcd. (%): C, 69.17; H, 6.40; N, 6.20. Found (%): C, 68.86; H, 6.39; N, 6.10.

EXAMPLE 64

3-[(4-Methoxycarbonylphenyl)methyl]-2,4-dioxo-1-[4-(4-diphenylmethoxypiperidino)butyl]-1,2,3,4-tetrahydroquinazoline hydrochloride Using the method similar to that in Example 61 and starting from 2,4-dioxo-1-[4-(4-diphenylmethoxypiperidino)butyl]-1,2,3,4-tetrahydroquinazoline (1.21 g, 2.5 mmol) obtained in Example 2, a free salt of the title compound (0.56 g, 36%) was obtained as an oil. This product was combined with a 4N solution of hydrogen chloride in ethyl acetate and concentrated to give the title compound (0.52 g, 85%) as an amorphous.

IR (KBr): 3402, 3058, 3030, 2953, 2476, 2400, 1718, 1700, 1654, 1610 cm⁻¹.

¹H-NMR (DMSO-d₆) δ: 1.60–2.20 (8H, m), 2.75–3.72 (7H, m), 3.83 (3H, s), 4.12–4.21 (2H, m), 5.22 (2H, s), 5.66 (1H, d, J=11.8 Hz), 7.21–7.58 (14H, m, ArH), 7.77–7.93 (3H, m, ArH), 8.11 (1H, d, J=7.8 Hz).

Elemental Analysis for $C_{39}H_{41}N_3O_5 \cdot HCl \cdot H_2O$: Calcd. (%): C, 68.26; H, 6.46; N, 6.12. Found (%): C, 68.16; H, 6.16; N, 6.14.

EXAMPLE 65

3-[(2-Carboxyphenyl)methyl]-2,4-dioxo-1-[4-(4-diphenylmethoxypiperidino)butyl]-1,2,3,4-tetrahydroquinazoline hydrochloride A mixture of 3-[(2-methoxycarbonylphenyl)methyl]-2,4-dioxo-1-[4-(4-diphenylmethoxypiperidino)butyl]-1,2,3,4-tetrahydroquinazoline (0.40 g, 0.63 mmol) which is a free salt of the compound obtained in Example 62, a 2N aqueous solution of sodium hydroxide (1.0 ml), tetrahydrofuran (2.0 ml) and methanol (4.0 ml) was stirred at room temperature for 9 hours. The reaction mixture was made weakly acidic using 1N hydrochloric acid and extracted with chloroform. After the extract was washed with water and dried (MgSO₄), the solvent was distilled off under reduced pressure. The residue was triturated with ethyl ether and filtered to give the title compound (0.39 g, 91%) as a colorless powder.

IR (KBr): 2939, 2596, 1700, 1654, 1608 cm⁻¹.

¹H-NMR (DMSO-d₆) δ: 1.60–2.20 (8H, m), 2.70–3.70 (7H, m), 4.12–4.21 (2H, m), 5.52 (2H, s) 5.65 (1H, s), 7.03 (1H, d, J=7.4 Hz), 7.20–7.48 (13H, m, ArH), 7.59 (1H, d, J=8.6 Hz), 7.79–7.97 (2H, m, ArH), 8.11 (1H, dd, J=1.5 Hz, 7.9 Hz).

Elemental Analysis for $C_{38}H_{39}N_3O_5 \cdot HCl \cdot 1.5H_2O$: Calcd. (%): C, 67.00; H, 6.36; N, 6.17. Found (%): C, 67.18; H, 6.16; N, 5.93.

EXAMPLE 66

3-[(3-Carboxyphenyl)methyl]-1-[4-(4-diphenylmethoxypiperidino)butyl]-1,2,3,4-tetrahydro-2,4-dioxoquinazoline hydrochloride Using the method similar to that in Example 65 and starting from 3-[(3-methoxycarbonylphenyl)methyl]-2,4-dioxo-1-[4-(4-diphenylmethoxypiperidino)butyl]-1,2,3,4-tetrahydroquinazoline (0.38 g, 0.60 mmol) which is a free salt of the compound obtained in Example 63, the title compound (0.36 g, 88%) was obtained.

IR (KBr): 2950, 2596, 1700, 1654, 1610 cm⁻¹.

¹H-NMR (DMSO-d₆) δ: 1.60–2.25 (8H, m), 2.70–3.75 (7H, m), 4.12–4.21 (2H, m), 5.20 (2H, s) 5.67 (1H, s), 7.24–7.47 (12H, m, ArH), 7.53–7.62 (2H, m, ArH), 7.77–7.92 (3H, m, ArH), 8.12 (1H, dd, J=7.8 Hz, 1.6 Hz).

Elemental Analysis for $C_{38}H_{39}N_3O_5 \cdot HCl \cdot 1.5H_2O$: Calcd. (%): C, 67.00; H, 6.36; N, 6.17. Found (%): C, 67.30; H, 6.23; N, 5.98.

EXAMPLE 67

3,3-Dimethyl-5-[2,4-dioxo-1-[4-(4-diphenylmethoxypiperidino)butyl]-1,2,3,4-tetrahydroquinazolin-3-yl]pentane-1-(N,N-dimethylaminomethylene)sulfonamide hydrochloride Using the method similar to that in Example 58 and 5-iodo-3,3-dimetyl-1-pentane-(N,N- dimethylaminomethylene)sulfonamide instead of 1-bromo-3-phenylpropane and starting from 2,4-dioxo-1-[4-(4-diphenylmethoxypiperidino)butyl]-1,2,3,4-tetrahydroquinazoline (2.42 g, 5.0 mmol) obtained in Example 2, a free salt of the title compound (3.26 g, 91%) was obtained as an oil. This product (0.72 g, 0.92 mmol) was combined with a 4N solution of hydrogen chloride in ethyl acetate and concentrated to give the title compound (0.72 g, 92%) as an amorphous.

IR (KBr): 3400, 2960, 2935, 2501, 1700, 1654, 1629, 1610 cm$^{-1}$.

$^1$H-NMR (DMSO-d$_6$) δ: 0.94 (6H, s), 1.37–2.73 (12H, m), 2.80–3.75 (9H, m), 2.93 (3H, s), 3.13 (3H, s), 3.88–3.98 (2H, m), 4.06–4.18 (2H, m), 5.67 (1H, d, J=10.0 Hz), 7.21–7.53 (12H, m, ArH), 7.73–7.81 (1H, m, ArH), 8.05 (1H, s), 8.05–8.09 (1H, m, ArH).

Elemental Analysis for C$_{40}$H$_{53}$N$_5$O$_5$S.HCl.1.5H$_2$O: Calcd. (%): C, 61.64; H, 7.37; N, 8.99. Found (%): C, 61.66; H, 7.06; N, 8.85.

EXAMPLE 68

3,3-Dimethyl-5-[2,4-dioxo-1-[4-(4-diphenylmethoxypiperidino)butyl]-1,2,3,4-tetrahydroquinazolin-3-yl]pentane-1-sulfonamide A mixture of 3,3-dimethyl-5-[2,4-dioxo-1-[4-(4-diphenylmethoxypiperidino)butyl]-1,2,3,4-tetrahydroquinazolin-3-yl]pentane-1-(N,N-dimethylaminomethylene)sulfonamide (2.20g, 3.07 mmol) obtained in Example 67, a 2N solution of sodium methoxide in methanol (15 ml) and methanol (30 ml) was heated under reflux for 8 days. The solvent was distilled off under reduced pressure, and the residue was neutralized with 2N hydrochloric acid and extracted with ethyl acetate. After the extract was washed with water and dried (MgSO$_4$), the solvent was distilled off under reduced pressure. The residue was subjected to a column chromatography on a silica gel eluting with chloroform-methanol (gradient from 20:1 to 10:1, v/v). The residue was combined with ethyl ether and triturated, and filtered to give the title compound (1.23 g, 59%) as a white powder.

IR (KBr): 3251, 3085, 3062, 3028, 2941, 2871, 1699, 1658, 1652, 1610 cm$^{-1}$.

$^1$H-NMR (CDCl$_3$) δ: 1.03 (6H, s), 1.54–2.10 (12H, m), 2.15–2.55 (4H, m), 2.78–2.90 (2H, m), 3.21–3.29 (2H, m), 3.48–3.58 (1H, m), 4.04–4.18 (4H, m), 5.01 (2H, bs), 5.51 (1H, s), 7.21–7.37 (12H, m, ArH), 7.63–7.72 (1H, m, ArH), 8.20 (1H, dd, J=1.6 Hz, 7.8 Hz).

Elemental Analysis for C$_{37}$H$_{48}$N$_4$O$_5$S.1.0H$_2$O: Calcd. (%): C, 65.46; H, 7.42; N, 8.25. Found (%): C, 65.03; H, 7.17; N, 8.07.

EXAMPLE 69

Methoxycarbonylmethyl 2,4-dioxo-1-[4-(4-diphenylmethoxypiperidino)butyl]-1,2,3,4-tetrahydroquinazoline-3-acetate hydrochloride A mixture of the hydrochloride of 2,4-dioxo-1-[4-(4-diphenylmethoxypiperidino)butyl]-1,2,3,4-tetrahydroquinazoline-3-acetic acid obtained in Example 50 (0.58 g, 1.00 mmol), triethylamine (0.42 ml, 3.00 mmol) and N,N-dimethylformamide (2.0 ml) was stirred at 60° C. for 15 minutes, and methyl bromoacetate (0.11 ml, 1.20 mmol) was added dropwise. The reaction mixture was stirred at the same temperature for 6 hours, combined with an iced water, and then extracted with a solvent mixture of ethyl ether-ethyl acetate. After the extract was washed with water and dried (MgSO$_4$), the solvent was distilled off under reduced pressure. The residue was subjected to a column chromatography on a silica gel eluting with chloroform-methanol (20:1, v/v) to give a free form of the title compound (0.49 g, 80%) as an oil.

IR (KBr): 3060, 3028, 3008, 2949, 2889, 2868, 2810, 2775, 1760, 1708, 1668, 1610 cm$^{-1}$.

$^1$H-NMR (CDCl$_3$) δ: 1.55–1.98 (8H, m), 2.05–2.17 (2H, m), 2.38 (2H, t, J=6.9 Hz), 2.71–2.80 (2H, m), 3.39–3.51 (1H, m), 3.77 (3H, s), 4.11–4.19 (2H, m), 4.72 (2H, s), 4.97 (2H, s), 5.53 (1H, s), 7.22–7.40 (12H, m, ArH), 7.65–7.74 (1H, m, ArH), 8.24 (1H, dd, J=7.8 Hz, 1.6 Hz).

This oil was dissolved in ethyl acetate (5.0 ml), combined with a 4N solution of hydrogen chloride in ethyl acetate (0.5 ml), and then concentrated to give the title compound (0.41 g, 78%) as an amorphous.

IR (KBr): 3400, 2954, 2507, 1756, 1706, 1664, 1610 cm$^{-1}$.

$^1$H-NMR (DMSO-d$_6$) δ: 1.60–2.21 (8H, m), 2.80–3.72 (7H, m), 3.67 (3H, s), 4.11–4.21 (2H, m), 4.79 (2H, s), 4.84 (2H, s), 5.67 (1H, d, J=9.8 Hz), 7.22–7.43 (11H, m, ArH), 7.59 (1H, d, J=8.4 Hz), 7.80–7.89 (1H, m, ArH), 8.08–8.12 (1H, m, ArH).

Elemental Analysis for C$_{35}$H$_{39}$N$_3$O$_7$.HCl.0.5H$_2$O: Calcd. (%): C, 63.77; H, 6.27; N, 6.37. Found (%): C, 63.39; H, 6.04; N, 6.42.

EXAMPLE 70

N-(1-Ethoxycarbonyl-1-methyl)ethyl-2-[2,4-dioxo-1-[4-(4-diphenylmethoxypiperidino)butyl]-1,2,3,4-tetrahydroquinazolin-3-yl]acetamide The hydrochloride of 2,4-dioxo-1-[4-(4-diphenylmethoxypiperidino)butyl]-1,2,3,4-tetrahydroquinazoline-3-acetic acid obtained in Example 50 (0.87 g, 1.50 mmol) was dissolved in N,N-dimethylformamide (3 ml), and diethyl cyanophosphonate (0.27 ml, 1.58 mmol) was added dropwise with stirring and cooling on ice. After stirring at the same temperature for 1 hour, ethyl 2-aminoisobutyrate hydrochloride (0.30 g, 1.80 mmol) and triethylamine (0.71 ml, 5.10 mmol) were added. After stirring at room temperature overnight, the mixture was diluted with an iced water and extracted with ethyl ether. After the extract was washed with water and dried (MgSO$_4$), the solvent was distilled off under reduced pressure. The residue was subjected to a column chromatography on a silica gel eluting with chloroform-methanol (20:1, v/v) to give the title compound (0.59 g, 60%).

IR (KBr): 3296, 2945, 2931, 2869, 2810, 2767, 1739, 1706, 1658, 1610, 1540 cm$^{-1}$.

$^1$H-NMR (CDCl$_3$) δ: 1.26 (3H, t, J=7.2 Hz), 1.59 (6H, s), 1.55–1.98 (8H, m), 2.05–2.18 (2H, m), 2.37 (2H, t, J=7.2 Hz), 2.70–2.81 (2H, m), 3.40–3.51 (1H, m), 4.10–4.18 (2H, m), 4.19 (2H, q, J=7.2 Hz), 4.73 (2H, s), 5.53 (1H, s), 6.51 (1H, s), 7.20–7.34 (12H, m), 7.62–7.71 (1H, m), 8.22 (1H, dd, J=1.6 Hz, 8.0 Hz).

Elemental Analysis for C$_{38}$H$_{46}$N$_4$O$_6$: Calcd. (%): C, 69.70 ; H, 7.08 ; N, 8.56. Found (%): C, 69.37 ; N, 7.05 ; N, 8.30.

EXAMPLE 71

Methyl 2,4-dioxo-3-[4-(4-diphenylmethoxypiperidino)butyl]-1,2,3,4-tetrahydroquinazoline-1-acetate Using the method similar to that in Example 57 and methyl bromoacetate instead of 1-bromo-2-phenylethane and starting from 2,4-dioxo-3-[4-(4-diphenylmethoxypiperidino)butyl]-1,2,3,4-tetrahydroquinazoline (1.52 g) obtained in Example 80, the title compound (760 mg, 44%) was obtained as an oil.

$^1$H-NMR (CDCl$_3$) δ: 1.48–1.82 (6H, m), 1.82–1.98 (2H, m), 2.04–2.21 (2H, m), 2.36 (2H, t, J=7.2 Hz), 2.69–2.82 (2H, m), 3.36–3.50 (1H, m), 3.78 (3H, s), 4.11 (2H, t, J=7.0 Hz), 4.91 (2H, s), 5.52 (1H, s), 6.95 (1H, d, J=8.4 Hz), 7.18–7.40 (11H, m), 7.64 (1H, ddd, J=8.8, 7.2, 1.6 Hz), 8.24 (1H, dd, J=8.0, 1.4 Hz).

Example 72

2,4-Dioxo-3-[4-(4-diphenylmethoxypiperidino)butyl]-1,2,3,4-tetrahydroquinazoline-1-acetic acid Using the method similar to that in Example 44 and starting from methyl 2,4-dioxo-3-[4-(4-diphenylmethoxypiperidino)butyl]-1,2,3,4-tetrahydroquinazoline-1-acetate (1.22 g) obtained in Example 71, the title compound (740mg, 62%) was synthesized. Recrystallization from ethyl acetate-methanol yielded a colorless crystal having a melting point of 153 to 155° C.

IR (KBr): 3100–2300, 2958, 1700, 1654, 1612, 1486 cm$^{-1}$.

$^1$H-NMR (CDCl$_3$) δ: 1.70–2.04 (6H, m), 2.10–2.34 (2H, m), 2.90–3.12 (4H, m), 3.20–3.38 (2H, m), 3.68–3.80 (1H, m), 4.10–4.20 (2H, m), 4.72 (2H, s), 5.41 (1H, s), 7.08–7.36 (12H, m), 7.58 (1H, ddd, J=8.4, 7.0, 1.4 Hz), 8.15 (1H, dd, J=7.6, 1.4 Hz).

Elemental Analysis for C$_{32}$H$_{35}$N$_3$O$_5$.1.5H$_2$O: Calcd. (%): C, 67.59; H, 6.74; N, 7.39. Found (%): C, 67.34; H, 6.35; N, 7.64.

EXAMPLE 73

Methyl 2,4-dioxo-3-[3-(4-diphenylmethoxypiperidino)propyl]-1,2,3,4-tetrahydroquinazoline-1-propionate 2,4-Dioxo-3-[3-(4-diphenylmethoxypiperidino)propyl]-1,2,3,4-tetrahydroquinazoline (3.50 g) obtained in Example 79 and potassium carbonate (1.24 g) were suspended in N,N-dimethylformamide (50.0 ml), and then methyl acrylate (1.01 ml) was added. The reaction mixture was stirred at 120° C. for 20 hours, poured onto an iced water, and then extracted with ethyl acetate. After the extract was washed with water and dried (Na$_2$SO$_4$), the solvent was distilled off under reduced pressure. The residue was subjected to a column chromatography on a silica gel eluting with n-hexane-ethyl acetate (3:1, v/v) to give the title compound (1.73 g, 42%) as a crystal. This product was used in the next reaction without further purification.

$^1$H-NMR (CDCl$_3$) δ: 1.54–1.96 (6H, m), 2.00–2.17 (2H, m), 2.42 (2H, t, J=7.2 Hz), 2.66–2.82 (2H, m), 3.32–3.46 (1H, m), 3.70 (3H, s), 4.04–4.20 (2H, m), 5.48 (1H, s), 7.20–7.40 (12H, m), 7.67 (1H, t, J=7.4 Hz), 8.16–8.25 (1H, m).

Example 74

Methyl 2,4-dioxo-3-[4-(4-diphenylmethoxypiperidino)butyl]-1,2,3,4-tetrahydroquinazoline-1-propionate Using the method similar to that in Example 73 and starting from 2,,4-dioxo-3-[4-(4-diphenylmethoxypiperidino)butyl]-1,2,3,4-tetrahydroquinazoline (1.17 g) obtained in Example 80, the title compound was obtained as a crystal. This product was used in the next reaction without further purification.

$^1$H-NMR (CDCl$_3$) δ: . 1.50–1.96 (12H, m), 2.04–2.20 (2H, m), 2.35 (2H, t, J=6.4 Hz), 2.68–2.84 (2H, m), 3.36–3.50 (1H, m), 3.59 (3H, s), 4.10 (2H, t, J=7.2 Hz), 5.51 (1H, s), 7.14–7.40 (12H, m), 7.68 (1H, t, J=9.2 Hz), 8.21 (1H, d, J=7.6 Hz).

EXAMPLE 75

2,4-Dioxo-3-[3-(4-diphenylmethoxypiperidino)propyl]-1,2,3,4-tetrahydroquinazoline-1-propionic acid Using the method similar to that in Example 47 and starting from methyl 2,4-dioxo-3-[3-(4-diphenylmethoxypiperidino)propyl]-1,2,3,4-tetrahydroquinazoline-1-propionate (1.36 g) obtained in Example 73, the title compound (476mg, 36%) was synthesized. Recrystallization from ethyl acetate-methanol yielded a colorless crystal having a melting point of 237 to 238° C.

IR (KBr): 3200–2100, 1700, 1652, 1608, 1486 cm$^{-1}$.

$^1$H-NMR (CDCl$_3$) δ: 1.84–2.23 (6H, m), 2.52–2.65 (2H, m), 2.74–2.89 (2H, m), 2.94–3.08 (4H, m), 3.62–3.72 (1H, m), 4.12 (2H, t, J=5.8 Hz), 4.49 (2H, t, J=7.8 Hz), 5.45 (1H, s), 7.06–7.22 (12H, m), 7.64 (1H, t, J=7.6 Hz), 8.17 (1H, d, J=8.0 Hz).

Elemental Analysis for C$_{32}$H$_{35}$N$_3$O$_5$.0.5H$_2$O: Calcd. (%): C, 69.80; H, 6.59; N, 7.63. Found (%): C, 69.82; H, 6.59; N, 7.73.

EXAMPLE 76

2,4-Dioxo-3-[4-(4-diphenylmethoxypiperidino)butyl]-1,2,3,4-tetrahydroquinazoline-1-propionic acid Using the method similar to that in Example 47 and starting from methyl 2,4-dioxo-3-[3-(4-diphenylmethoxypiperidino)propyl]-1,2,3,4-tetrahydroquinazoline-1-propionate obtained in Example 73, the title compound (179 mg, 13%) was synthesized. Recrystallization from ethyl acetate-ethyl ether yielded a colorless crystal having a melting point of 110 to 112° C.

IR (KBr): 3400–2400, 1704, 1662, 1608, 1486 cm$^{-1}$.

$^1$H-NMR (CDCl$_3$) δ: 1.60–2.08 (4H, m), 2.16–2.40 (4H, m), 2.48–2.60 (2H, m), 2.80–3.24 (2H, m), 3.65–3.80 (2H, m), 3.98–4.30 (6H, m),4.50–4.62 (1H, m), 5.45 (1H, s),7.05–7.22 (10H, m), 7.50–7.74 (2H, m), 8.05 (1H, d, J=8.2 Hz), 8.14–8.24 (1H, m).

Elemental Analysis for C$_{33}$H$_{37}$N$_3$O$_5$.0.5H$_2$O: Calcd. (%): C, 70.19; H, 6.79; N, 7.44. Found (%): C, 69.80; H, 6.60; N, 7.85.

EXAMPLE 77

Ethyl 2,4-dioxo-3-[4-(4-diphenylmethoxypiperidino)butyl]-1,2,3,4-tetrahydroquinazoline-1-butyrate Using the method similar to that in Example 57 and ethyl 4-bromobutyrate instead of 1-bromo-2-phenylethane and starting from 2,4-dioxo-3-[4-(4-diphenylmethoxypiperidino)butyl]-1,2,3,4-tetrahydroquinazoline (1.00 g) obtained in Example 80, the title compound was obtained as a crystal. This product was used in the next reaction without further purification.

$^1$H-NMR (CDCl$_3$) δ: 1.28 (3H, t, J=7.0 Hz), 1.50–2.24 (12H, m), 2.30–2.42 (2H, m), 2.48 (2H, t, J=6.6 Hz), 2.70–2.84 (2H, m), 3.36–3.50 (1H, m), 4.06–4.24 (6H, m), 5.51 (1H, s), 7.20–7.46 (12H, m), 7.69 (1H, ddd, J=8.4, 6.6, 1.8 Hz), 8.22 (1H, dd, J=8.0, 1.4 Hz).

EXAMPLE 78

2,4-Dioxo-3-[4-(4-diphenylmethoxypiperidino)butyl]-1,2,3,4-tetrahydroquinazoline-1-butyric acid Using the method similar to that in Example 47 and starting from ethyl 2,4-dioxo-3-[4-(4-diphenylmethoxypiperidino)butyl]-1,2,3,4-tetrahydroquinazoline-1-butyrate obtained in Example 77, the title compound (569 mg, 48% from the title compound of Example 80) was synthesized. Recrystallization from ethyl acetate-ethyl ether yielded a colorless crystal having a melting point of 227 to 229° C.

IR (KBr): 3300–2200, 1731, 1697, 1652, 1608, 1484 cm$^{-1}$.

$^1$H-NMR (CDCl$_3$) δ: 1.42–2.40 (10H, m), 2.50–2.60 (2H, m), 2.80–3.25 (4H, m), 3.36–3.50 (2H, m), 3.78–3.84 (1H, m), 4.14–4.22 (2H, m), 4.24–4.65 (2H, m), 5.42 (1H, s), 7.10–7.40 (12H, m), 7.67 (1H, t, J=7.8 Hz), 8.21 (1H, d, J=8.2 Hz).

Elemental Analysis for C$_{34}$H$_{39}$N$_3$O$_5$.2.3H$_2$O: Calcd. (%): C, 66.82; H, 7.19; N, 6.88. Found (%): C, 66.75; H, 6.83; N, 6.87.

EXAMPLE 79

2,4-Dioxo-3-[3-(4-diphenylmethoxypiperidino)propyl]-1,2,3,4-tetrahydroquinazoline Using the method similar to that in Reference Example 26 (Method 2) and starting from 2-amino-N-[3-(4-diphenylmethoxypiperidino)propyl]benzamide (5.84 g) obtained in Reference Example 17, the title compound (4.12 g, 67%) was synthesized. Recrystallization from ethyl acetate-ethyl ether yielded a colorless crystal having a melting point of 173 to 175° C.

IR (KBr): 1717, 1653, 1624, 1605, 1493 cm$^{-1}$.

$^1$H-NMR (CDCl$_3$) δ: 1.56–1.76 (2H, m), 1.76–1.98 (4H, m), 2.02–2.18 (2H, m), 2.45 (2H,t, J=7.4 Hz), 2.69–2.83 (2H, m), 3.34–3.46 (1H, m), 4.13 (2H, t, J=7.2 Hz), 5.50 (1H, s), 7.06 (1H, d, J=8.6 Hz), 7.16–7.36 (11H, m), 7.58 (1H, ddd, J=8.6, 7.2, 1.4 Hz), 8.12 (1H, dd, J=8.0, 1.4 Hz).

Elemental Analysis for C$_{29}$H$_{31}$N$_3$O$_3$: Calcd. (%): C, 74.18; H, 6.65; N, 8.95. Found (%): C, 74.16; H, 6.70; N, 8.94.

EXAMPLE 80

2,4-Dioxo-3-[4-(4-diphenylmethoxypiperidino)butyl]-1,2,3,4-tetrahydroquinazoline Using the method similar to that in Reference Example 26 (Method 1) and starting from 2-amino-N-[4-(4-diphenylmethoxypiperidino)butyl]benzamide (6.27 g) obtained in Reference Example 18, the title compound (5.00 g, 75%) was synthesized. Recrystallization from ethyl acetate yielded a colorless crystal having a melting point of 140 to 142° C.

IR (KBr): 2943, 1716, 1652, 1621, 1606, 1494 cm$^{-1}$.

$^1$H-NMR (CDCl$_3$) δ: 1.50–1.82 (6H, m), 1.82–1.96 (2H, m), 2.05–2.20 (2H, m), 2.36 (2H, t, J=7.0 Hz), 2.70–2.84 (2H, m), 3.36–3.50 (1H, m), 4.09 (2H, t, J=7.6 Hz), 5.51 (1H, s), 7.04 (1H, d, J=8.4 Hz), 7.16–7.18 (11H, m), 7.60 (1H, ddd, J=8.4, 6.8, 1.6 Hz), 8.11 (1H, dd, J=7.6, 1.0 Hz).

Elemental Analysis for C$_{30}$H$_{33}$N$_3$O$_3$: Calcd. (%): C, 74.51; H, 6.88; N, 8.69. Found (%): C, 74.61; H, 6.72; N, 8.80.

EXAMPLE 81

N-[2,4-Dioxo-1-[4-(4-diphenylmethoxypiperidino)butyl]-1,2,3,4-tetrahydroquinazolin-6-yl]methanesulfonamide hydrochloride Using the method similar to that in Example 43 and methanesulfonyl chloride (190 ml, 2.45 mmol) instead of ethylmalonyl chloride and starting from 6-amino-2,4-dioxo-1-[4-(4-diphenylmethoxypiperidino)butyl]-1,2,3,4-tetrahydroquinazoline (1.02 g, 2.05 mmol) obtained in Example 40, a free salt of the title compound (681 mg, 58%) was synthesized. Recrystallization from ethyl acetate yielded a colorless crystal having a melting point of 204 to 205° C.

IR (KBr): 3256, 2944, 1738, 1694, 1590, 1495 cm$^{-1}$.

$^1$H-NMR (CDCl$_3$) δ: 1.56–1.84 (6H, m), 1.84–2.04 (2H, m), 2.04–2.23 (2H, m), 2.3–2.46 (2H, m), 2.72–2.84 (2H, m), 3.01 (3H, s), 3.38–3.53 (1H, m), 4.11 (2H, t, J=7.4 Hz), 5.53 (1H, s), 7.18–7.22 (11H, m), 7.71 (1H, dd, J=9.6, 3.0 Hz), 7.95 (1H, d, J=3.0 Hz).

Elemental Analysis for C$_{31}$H$_{36}$N$_4$O$_5$S: Calcd. (%): C, 64.56; H, 6.29; N, 9.71. Found (%): C, 64.49; H, 6.44; N, 9.44.

This product (350 mg, 0.607 mmol) was dissolved in ethyl acetate (5.00 ml) and combined with a 4N solution of hydrogen chloride in ethyl acetate (0.50 ml) to synthesize the title compound (330 mg, 89%). Recrystallization from ethyl acetate yielded a colorless crystal having a melting point of 225 to 227° C.

IR (KBr): 3700–2200, 3059, 1692, 1674, 1628, 1593, 1503 cm$^{-1}$.

$^1$H-NMR (CDCl$_3$) δ: 1.56–3.04 (12H, m), 2.78 (3H, s), 3.14–3.26 (2H, m), 3.66–3.74 (1H, m), 3.86–4.00 (2H, m), 5.26 (1H, s), 7.00–7.28 (11H, m), 7.46–7.56 (1H,m), 7.87 (1H, d, J=2.6 Hz), 9.35 (1H, bs), 11.80 (1H, bs).

Elemental Analysis for C$_{31}$H$_{36}$N$_4$O$_5$S Calcd. (%): C, 57.67; H, 6.34; N, 8.68. Found (%): C, 57.41; H, 6.21; N, 9.08.

EXAMPLE 82

Ethyl 3,5-dimethoxy-N-[2,4-dioxo-1-[4-(4-diphenylmethoxypiperidino)butyl]-1,2,3,4-tetrahydroquinazolin-6-yl]-4-hydroxycinnamamide hydrochloride 6-Amino-2,4-dioxo-1-[4-(4-diphenylmethoxypiperidino)butyl]-1,2,3,4-tetrahydroquinazoline (800 mg, 1.60 mmol) obtained in Example 40 and 3,5-dimethoxy-4-hydroxycinnamic acid (432 mg, 1.93 mmol) were dissolved in N,N-dimethylformamide (20.0 ml), and diethyl cyanophosphonate (307 ml, 1.93 mmol) and then triethylamine (335 ml, 2.41 mmol) were added dropwise with cooling on ice. After stirring the reaction mixture at room temperature for 17 hours, the solvent was distilled off under reduced pressure, and the residue was combined with water and extracted with ethyl acetate. After the extract was washed with water and dried (MgSO$_4$), the solvent was distilled off under reduced pressure to give a free salt of the title compound (441 mg, 39%). Recrystallization from ethyl acetate yielded a colorless crystal having a melting point of 184 to 186° C.

IR (KBr): 3484, 3293, 3179, 3027, 2940, 2841, 1690, 1630, 1597, 1552, 1508 cm$^{-1}$.

$^1$H-NMR (CDCl$_3$) δ: 1.66–2.46 (12H, m), 2.70–2.86 (2H, m), 3.36–3.54 (1H, m), 3.92 (6H, s), 4.02–4.16 (2H, m), 5.52 (1H, s), 6.55 (1H, d, J=15.4 Hz), 6.80 (2H, s), 7.16–7.40 (11H, m), 7.65 (1H, d, J=15.8 Hz), 8.09 (1H, d, J=2.6 Hz), 8.45 (1H, d, J=7.6 Hz), 9.02 (1H, bs).

Elemental Analysis for C$_{41}$H$_{44}$N$_4$O$_7$.1.5H$_2$O: Calcd. (%): C, 67.29; H, 6.47; N, 7.66. Found (%): C, 67.27; H, 6.36; N, 7.93.

This product (200 mg, 0.284 mmol) was dissolved in ethyl acetate (5.00 ml), combined with a 4N solution of hydrogen chloride in ethyl acetate (0.15 ml) and concentrated to give the title compound (173 mg, 82%). Recrystallization from ethyl acetate yielded a colorless crystal having a melting point of 180 to 182° C.

IR (KBr): 3700–2300, 3061, 2942, 1690, 1630, 1601, 1552, 1507 cm$^{-1}$.

$^1$H-NMR (CDCl$_3$) δ: 1.74–2.14 (6H, m), 2.32–2.52 (2H, m), 3.00–3.22(4H, m), 3.34–3.48(2H, m), 3.82–3.96 (1H, m), 3.92 (6H, m), 4.04–4.18(2H, m), 5.45 (1H, s), 6.66 (1H, d, J=15.4 Hz), 6.82 (2H, m), 7.10–7.40 (11H, m), 7.61 (1H, d, J=15.4 Hz), 8.20–8.38 (2H, m), 9.83 (1H, bs), 10.64 (1H, bs), 11.76 (1H, bs).

Elemental Analysis for C$_{41}$H$_{44}$N$_4$O$_7$ HCl: Calcd. (%): C, 63.35; H, 6.35; N, 7.21. Found (%): C, 63.22; H, 6.53; N, 7.59.

EXAMPLE 83

Methyl 2,4-dioxo-1-[4-(4-diphenylmethoxypiperidino)butyl]-1,2,3,4-tetrahydroquinazoline-5-carboxylate hydrochloride Using the method similar to that in Example 2 (Method 4) and starting from methyl 1-(4-bromobutyl)-2,4-dioxo-1,2,3,4-tetrahydroquinazoline-5-carboxylate (1.83 g, 5.15 mmol) obtained in Reference Example 124, a free salt of the title compound (2.19 g, 79%) was obtained as an amorphous.

IR (KBr): 2948, 1736, 1701, 1595, 1499 cm$^{-1}$.

$^1$H-NMR (CDCl$_3$) δ: 1.55–1.82 (6H, m), 1.82–2.00 (2H, m), 2.08–2.24 (2H, m), 2.39 (2H, t, J=6.6 Hz), 2.70–2.84 (2H, m), 3.40–3.54 (1H, m), 3.97 (3H, s), 4.07–4.20 (2H, m), 5.53 (1H, s), 7.18 (1H, d, J=7.4 Hz), 7.21–7.40 (10H, m), 7.48 (1H, d, J=8.0 Hz), 7.71 (1H, dd, J=8.4, 7.4 Hz).

Elemental Analysis for C$_{32}$H$_{35}$N$_3$O$_5$.0.4H$_2$O: Calcd. (%): C, 70.03; H, 6.57; N, 7.60. Found (%): C, 69.88; H, 6.48; N, 7.62.

This product (500 mg, 0.923 mmol) was dissolved in ethyl acetate (5.00 ml), combined with a 4N solution of hydrogen chloride in ethyl acetate (1.00 ml) and concentrated to give the title compound (393 mg, 74%) as an amorphous.

IR (KBr): 2949, 1732, 1698, 1595, 1501 cm$^{-1}$.

$^1$H-NMR (CDCl$_3$) δ: 1.66–2.20 (8H, m), 2.32–2.58 (2H, m), 2.94–3.20 (4H, m), 3.30–3.42 (2H, m), 3.82–3.90 (1H, m), 3.96 (3H, s), 4.15 (2H, t, J=7.4 Hz), 5.44 (1H, s), 7.18 7.44 (12H, m), 7.76 (1H, d, J=8.4 Hz), 8.52 (1H, bs), 12.14 (1H, bs).

Elemental Analysis for C$_{32}$H$_{35}$N$_3$O$_5$.HCl.1.7H$_2$O: Calcd. (%): C, 63.14; H, 6.52; N, 6.90. Found (%): C, 63.10; H, 6.63; N, 6.68.

EXAMPLE 84

Methyl 2,4-dioxo-1-[4-(4-diphenylmethoxypiperidino)butyl]-1,2,3,4-tetrahydroquinazoline-6-carboxylate Using the method similar to that in Example 2 (Method 4) and starting from methyl 1-(4-bromobutyl)-2,4-dioxo-1,2,3,4-tetrahydroquinazoline-6-carboxylate (3.16 g, 8.56 mmol) obtained in Reference Example 125, the title compound (1.82 g, 38%) was synthesized. Recrystallization from ethyl acetate yielded a colorless crystal having a melting point of 151 to 153° C.

IR (KBr): 3061, 3032, 2948, 2816, 1705, 1618, 1583, 1508, 1493, 1472 cm$^{-1}$.

$^1$H-NMR (CDCl$_3$) δ: 1.50–1.85 (6H, m), 1.85–2.02 (2H, m), 2.04–2.26 (2H, m), 2.40 (2H, t, J=7.4 Hz), 2.70–2.85 (2H, m), 3.38–3.54 (1H, m), 3.95 (3H, s), 4.15 (2H, t. J=6.8 Hz), 5.53 (1H, s), 7.20–7.40 (10H, m), 7.44 (1H, d, J=8.8 Hz), 8.33 (1H, dd, J=8.8, 2.2 Hz), 8.85 (1H, d, J=2.0 Hz).

Elemental Analysis for C$_{32}$H$_{35}$N$_3$O$_3$.2.0H$_2$O: Calcd. (%): C, 70.44; H, 7.20; N, 7.70. Found (%): C, 70.34; H, 6.40; N, 7.84.

EXAMPLE 85

Methyl 2,4-dioxo-1-[4-(4-diphenylmethoxypiperidino)butyl]-1,2,3,4-tetrahydroquinazoline-7-carboxylate Using the method similar to that in Example 2 (Method 4) and starting from methyl 1-(4-bromobutyl)-2,4-dioxo-1,2,3,4-tetrahydroquinazoline-7-carboxylate (1.70 g, 4.79 mmol) obtained in Reference Example 126, the title compound (1.78 g, 69%) was synthesized. Recrystallization from ethyl acetate yielded a colorless crystal having a melting point of 192 to 194° C.

IR (KBr): 2949, 1701, 1622, 1586, 1508, 1493 cm$^{-1}$.

$^1$H-NMR (CDCl$_3$) δ: 1.56–1.98 (8H, m), 2.04–2.20 (2H, m), 2.38 (2H, t, J=7.0 Hz), 2.70–2.85 (2H, m), 3.36–3.50 (1H, m), 3.98 (3H, s), 4.19 (2H, t. J=7.8Hz), 5.52 (1H, s), 7.20–7.38 (10H, m), 7.83–7.90 (2H, m), 8.23 (1H, d, J=8.4 Hz).

Elemental Analysis for C$_{32}$H$_{35}$N$_3$O$_5$: Calcd. (%): C, 70.96; H, 6.51; N, 7.76. Found (%): C, 70.65; H, 6.56; N, 7.57.

Example 86

Methyl 2,4-dioxo-1-[4-(4-diphenylmethoxypiperidino)butyl]-1,2,3,4-tetrahydroquinazoline-6-acetate Using the method similar to that in Example 2 (Method 4) and starting from methyl 1-(4-bromobutyl)-2,4-dioxo-1,2,3,4-tetrahydroquinazoline-6-acetate (3.16 g, 8.56 mmol) obtained in Reference Example 127, the title compound (1.82 g, 38%) was obtained as an amorphous.

IR (KBr): 3027, 2944, 1699, 1622, 1586, 1508, 1493 cm$^{-1}$.

$^1$H-NMR (CDCl$_3$) δ: 1.60–1.84 (6H, m), 1.84–2.01 (2H, m), 2.06–2.22 (2H, m), 2.38 (2H, t, J=6.6 Hz), 2.70–2.84 (2H, m), 3.38–3.52 (1H, m), 3.67 (3H, s), 3.71 (2H, d, J=21.2 Hz), 4.10 (2H, t. J=8.2 Hz), 5.53 (1H, s), 7.18–7.38 (11H, m), 7.65 (1H, dd, J=8.4, 2.2 Hz), 8.11 (1H, d, J=2.2 Hz).

Elemental Analysis for C$_{33}$H$_{37}$N$_3$O$_5$.0.3H$_2$O: Calcd. (%): C, 70.64; H, 6.75; N, 7.49. Found (%): C, 70.69; H, 6.75; N, 6.95.

EXAMPLE 87

Methyl 2-[2,4-dioxo-1-[4-(4-diphenylmethoxypiperidino)butyl]-1,2,3,4-tetrahydroquinazolin-6-yl]-2-methylpropionate hydrochloride Using the method similar to that in Example 2 (Method 4) and starting from methyl 2-[1-(4-bromobutyl)-2,4-dioxo-1, 2,3,4-tetrahydroquinazolin-6-yl]-2-methylpropionate (2.00 g, 5.03 mmol) obtained in Reference Example 128, a free salt of the title compound (1.82 g, 38%) was synthesized. Recrystallization from ethyl acetate yielded a colorless crystal having a melting point of 148 to 150° C.

IR (KBr): 2948, 1730, 1698, 1622, 1586, 1507, 1474 cm$^{-1}$.

$^1$H-NMR (CDCl$_3$) δ: 1.62 (6H, s), 1.52–1.84 (6H, m), 1.84–2.00 (2H, m), 2.02–2.22 (2H, m), 2.37 (2H, t, J=6.6 Hz), 2.70–2.84 (2H, m), 3.38–3.52 (1H, m), 3.65 (3H, s), 4.10 (2H, t. J=7.0 Hz), 5.52 (1H, s), 7.16–7.38 (11H, m), 7.66 (1H, dd, J=8.8, 2.2 Hz), 8.18 (1H, d, J=2.2 Hz), 8.22 (1H, bs).

Elemental Analysis for C$_{35}$H$_{41}$N$_3$O$_5$.0.9H$_2$O: Calcd. (%): C, 70.07; H, 7.19; N, 7.00. Found (%): C, 70.06; H, 7.23; N, 7.00.

This product (870 mg, 1.49 mmol) was dissolved in ethyl acetate (5.00 ml) and combined with a 4N solution of hydrogen chloride in ethyl acetate (1.00 ml) to give the title compound (857 mg, 93%). Recrystallization from ethyl acetate yielded a colorless crystal having a melting point of 223 to 225° C.

IR (KBr): 3500–2300, 2949, 1698, 1620, 1586, 1507, 1474 cm$^{-1}$.

$^1$H-NMR (CDCl$_3$) δ: 1.53 (6H, s), 1.60–2.10 (6H, m), 2.24–2.46 (2H, m), 2.84–3.12 (4H, m), 3.20–3.36 (2H, m), 3.58 (3H, s), 3.74–3.82 (1H, m), 3.96–4.10 (2H, m), 5.34 (1H, s), 7.08–7.14 (11H, m), 7.56–7.66 (1H, m), 8.09 (1H, d, J=1.4 Hz), 12.12 (1H, bs).

Elemental Analysis for C$_{35}$H$_{41}$N$_3$O$_5$.HCl0.4H$_2$O: Calcd. (%): C, 67.00; H, 6.88; N, 6.70. Found (%): C, 66.86; H, 6.83; N, 6.71.

Example 88

2,4-Dioxo-1-[4-(4-diphenylmethoxypiperidino)butyl]-1,2,3,4-tetrahydroquinazoline-5-carboxylic acid Using the method similar to that in Example 47 and starting from methyl 2,4-dioxo-1-[4-(4-diphenylmethoxypiperidino)butyl]-1,2,3,4-tetrahydroquinazoline-5-carboxylate (600 mg, 1.11 mmol) obtained in Example 83, the title compound (584 mg, 100%) was obtained as an amorphous.

IR (KBr): 3700–2300, 3179, 3029, 2949 1694, 1593, 1499 cm$^{-1}$.

$^1$H-NMR (CDCl$_3$) δ: 1.68–2.10 (8H, m), 2.22–2.42 (2H, m), 2.86–3.00 (2H, m), 3.00–3.30 (4H, m), 3.72–3.86 (1H, m), 4.14 (2H, t, J=6.8 Hz), 5.46 (1H, s), 7.14–7.44 (12H, m), 7.71 (1H, t, J=7.8 Hz).

Elemental Analysis for C$_{31}$H$_{33}$N$_3$O$_5$.0.9H$_2$O: Calcd. (%): C, 68.47; H, 6.45; N, 7.72. Found (%): C, 68.73; H, 6.67; N, 7.32.

Example 89

2,4-Dioxo-1-[4-(4-diphenylmethoxypiperidino)butyl]-1,2,3,4-tetrahydroquinazoline-6-carboxylic acid Using the method similar to that in Example 47 and starting from methyl 2,4-dioxo-1-[4-(4-diphenylmethoxypiperidino)butyl]-1,2,3,4-tetrahydroquinazoline-6-carboxylate (1.63 g, 3.01 mmol) obtained in Example 84, the title compound (920 mg, 58%) was synthesized. Recrystallization from methanol-chloroform yielded a colorless crystal having a melting point of 161 to 163° C.

IR (KBr) δ: 3700–2700, 3187, 3058, 3029, 2951 1698, 1615, 1563, 1493, 1472 cm$^{-1}$.

$^1$H-NMR (CD$_3$OD) δ: 1.86–2.00 (4H, m), 2.95–3.34 (10H, m), 3.60–3.72 (1H, m), 4.02–4.16 (2H, m), 5.51 (1H, s), 7.10–7.40 (11H, m), 8.14 (1H, d, J=8.2 Hz), 8.60 (1H, s).

Elemental Analysis for C$_{31}$H$_{33}$N$_3$O$_5$.1.5H$_2$O: Calcd. (%): C, 67.13; H, 6.54; N, 7.58. Found (%): C, 67.12; H, 6.69; N, 7.46.

Example 90

2,4-Dioxo-1-[4-(4-diphenylmethoxypiperidino)butyl]-1,2,3,4-tetrahydroquinazoline-7-carboxylic acid Using the method similar to that in Example 47 and starting from methyl 2,4-dioxo-1-[4-(4-diphenylmethoxypiperidino)butyl]-1,2,3,4-tetrahydroquinazoline-7-carboxylate (780 mg, 1.44 mmol) obtained in Example 85, the title compound (309 mg, 41%) was synthesized. Recrystallization from methanol-ethyl acetate yielded a colorless crystal having a melting point of 177 to 179° C.

IR (KBr): 3300–2050, 3029, 1694, 1615, 1566, 1508 cm$^{-1}$.

$^1$H-NMR (CD$_3$OD) δ: 1.50–2.30 (8H, m), 3.04–3.18 (4H, m), 3.34–3.53 (2H, m), 3.76–3.88 (1H, m), 4.10–4.24 (2H, m), 5.45 (1H, s), 7.20–7.38 (10H, m), 7.72 (1H, d, J=8.4 Hz), 7.95 (1H, s), 8.09 (1H, d, J=7.8 Hz), 8.21 (1H, bs), 8.60 (1H, s).

Elemental Analysis for C$_{31}$H$_{33}$N$_3$O$_5$.1.3H$_2$O: Calcd. (%): C, 67.57; H, 6.51; N, 7.63. Found (%): C, 67.43; H, 6.22; N, 7.65.

Example 91

2,4-Dioxo-1-[4-(4-diphenylmethoxypiperidino)butyl]-1,2,3,4-tetrahydroquinazoline-6-acetic acid Using the method similar to that in Example 47 and starting from methyl 2,4-dioxo-1-[4-(4-diphenylmethoxypiperidino)butyl]-1,2,3,4-tetrahydroquinazoline-6-acetate (1.00 g, 1.80 mmol) obtained in Example 86, the title compound (946 mg, 97%) was obtained as an amorphous.

IR (KBr): 3700–2300, 3167, 3029, 2935, 1694, 1620, 1586, 1505, 1474 cm$^{-1}$.

$^1$H-NMR (CDCl$_3$) δ: 1.42–1.82 (6H, m), 1.86–2.05 (2H, m), 2.05–2.25 (2H, m), 2.74–2.92 (2H, m), 2.94–3.24 (2H, m), 3.58–3.80 (5H, m), 5.44 (1H, s), 7.00 (1H, d, J=8.8 Hz), 7.16–7.44 (10H, m), 7.68 (1H, d, J=8.8 Hz), 8.10 (1H, s), 8.60 (1H, s).

Elemental Analysis for C$_{32}$H$_{35}$N$_3$O$_5$.2.5H$_2$O: Calcd. (%): C, 65.51; H, 6.87; N, 7.16. Found (%): C, 66.00; H, 6.73; N, 6.51.

EXAMPLE 92

2,4-Dioxo-1-[4-(4-diphenylmethoxypiperidino)butyl]-1,2,3,4-tetrahydroquinazoline-3-carbonitrile Using the method similar to that in Example 61 and cyanogen bromide (657 mg, 6.20 mmol) instead of benzyl bromide and starting from 2,4-dioxo-1-[4-(4-diphenylmethoxypiperidino)butyl]-1,2,3,4- tetrahydroquinazoline (2.50 g, 5.17 mmol) obtained in Example 2, the title compound (1.69 g, 64%) was synthesized. Recrystallization from ethyl acetate yielded a colorless crystal having a melting point of 106 to 107° C.

IR (KBr): 2946, 2265, 1744, 1709, 1607, 1493, 1478 cm$^{-1}$.

$^1$H-NMR (CDCl$_3$) δ: 1.50–1.86 (6H, m), 1.86–2.03 (2H, m), 2.03–2.22 (2H, m), 2.39 (2H, t, J=7.0 Hz), 2.70–2.84 (2H, m), 3.38–3.54 (1H, m), 4.18 (2H, t, J=8.2 Hz), 5.53 (1H, s), 7.18–7.46 (11H, m), 7.51 (1H, d, J=8.8 Hz), 7.80 (1H, d, J=8.4 Hz), 8.25 (1H, d, J=8.0 Hz).

Elemental Analysis for C$_{31}$H$_{32}$N$_4$O$_3$: Calcd. (%): C, 73.21; H, 6.34; N, 11.02. Found (%): C, 72.95; H, 6.14; N, 10.92.

Example 93

2,4-Dioxo-1-[4-(4-diphenylmethoxypiperidino) butyl]-1,2,3,4-tetrahydroquinazoline-3-valeronitrile Using the method similar to that in Example 61 and 5-bromovaleronitrile (1.09 ml, 9.31 mmol) instead of benzyl bromide and starting from 2,4-dioxo-1-[4-(4-diphenylmethoxypiperidino)butyl]-1,2,3,4-tetrahydroquinazoline (3.00 g, 6.20 mmol) obtained in Example 2, a free salt of the title compound (2.32 g, 66%) was obtained as an oil.

$^1$H-NMR (CDCl$_3$) δ: 1.64–2.00 (12H, m), 2.06–2.20 (2H, m), 2.34–2.49 (4H, m), 2.70–2.83 (2H, m), 3.38–3.54 (1H, m), 4.08–4.20 (4H, m), 5.53 (1H, s), 7.20–7.40 (12H, m), 7.67 (1H, ddd, J=8.8, 6.8, 2.0 Hz), 8.22 (1H, dd, J=8.0, 1.8 Hz).

This product (1.24 g, 2.20 mmol) was dissolved in ethyl acetate (5.00 ml) and combined with a 4N solution of hydrogen chloride in ethyl acetate (1.00 ml) to give the title compound (848 mg, 64%). Recrystallization from ethyl acetate yielded a colorless crystal having a melting point of 119 to 121° C.

IR (KBr): 3700–3150, 2932, 2250, 1698, 1655, 1609, 1485 cm$^{-1}$.

$^1$H-NMR (CDCl$_3$) δ: 1.64–2.00 (6H, m), 2.24–2.50 (4H, m), 2.60–2.78 (2H, m), 2.96–3.18 (4H, m), 3.28–3.46 (2H, m), 3.52–3.70 (2H, m), 3.84–3.92 (1H, m), 4.06–4.24 (4H, m), 5.50 (1H, s), 7.20–7.44 (12H, m), 7.62–7.80 (1H, m), 8.22 (1H, d, J=8.0 Hz).

Elemental Analysis for C$_{35}$H$_{40}$N$_4$O$_3$.HCl.1.0H$_2$O: Calcd. (%): C, 67.89; H, 7.00; N, 9.05. Found (%): C, 67.79; H, 7.06; N, 9.06.

Example 94

Ethyl 2,4-dioxo-1-[4-(4-diphenylmethoxypiperidino) butyl]-1,2,3,4-tetrahydroquinazoline-3-valerate hydrochloride Ethyl 2,4-dioxo-1-[4-(4-diphenylmethoxypiperidino) butyl]-1,2,3,4-tetrahydroquinazoline-3-valerate (2.04 g, 3.33 mmol) obtained as an intermediate in Example 60 was dissolved in ethyl acetate (5.00 ml) and combined with a 4N solution of hydrogen chloride in ethyl acetate (1.00 ml) to give the title compound (1.89 g, 88%) as an amorphous.

IR (KBr): 3700–3150, 2938, 2647, 2585, 2514, 1728, 1699, 1651, 1609, 1485 cm$^{-1}$.

$^1$H-NMR (CDCl$_3$) δ: 1.24 (3H, t, J=7.2 Hz), 1.65–1.78 (4H, m), 1.78–1.94 (2H, m), 1.94–2.20 (6H, m), 2.35 (2H, t, J=6.6 Hz), 2.30–2.58 (2H, m), 3.00–3.24 (4H, m), 3.35–3.48 (2H, m), 3.84–3.92 (1H, m), 4.02–4.20 (4H, m), 4.11 (2H, q, J=7.0 Hz), 5.44 (1H, s), 7.28–7.42 (12H, m), 7.69 (1H, t, J=7.0 Hz), 8.21 (1H, d, J=7.4 Hz), 11.58 (1H, bs).

Elemental Analysis for C$_{37}$H$_{45}$N$_3$O$_5$.HCl.2.0H$_2$O: Calcd. (%): C, 64.95; H, 7.37; N, 6.14. Found (%): C, 64.80; H, 7.08; N, 6.16.

EXAMPLE 95

Ethyl 2,4-dioxo-1-[4-(4-diphenylmethoxypiperidino) butyl]-1,2,3,4-tetrahydroquinazoline-3-hexanoate hydrochloride Using the method similar to that in Example 2 (Method 4) and starting from ethyl 1-(4-bromobutyl)-2,4-dioxo-1,2,3,4-tetrahydroquinazoline-3-hexanoate (6.90 g, 15.7 mmol) obtained in Reference Example 150, a free salt of the title compound (7.68 g, 78%) was obtained as an oil.

$^1$H-NMR (CDCl$_3$) δ: 1.24 (3H, t, J=7.0 Hz), 1.34–1.–84 (12H, m), 1.84–1.98 (2H, m), 2.04–2.20 (2H, m), 2.30 (2H, t, J=7.2 Hz), 2.37 (2H, t, J=8.0 Hz), 2.68–2.84 (2H, m), 3.38–3.74 (1H, m), 4.00–4.20 (6H, m), 5.53 (1H, s), 7.18–7.40 (12H, m), 7.65 (1H, t, J=8.4 Hz), 8.22 (1H, d, J=7.8 Hz).

This product (6.90 g, 15.7 mmol) was dissolved in ethyl acetate (10.0 ml) and combined with a 4N solution of hydrogen chloride in ethyl acetate (2.00 ml) to give the title compound (7.68 g, 78%). Recrystallization from n-hexane yielded a colorless crystal having a melting point of 149 to 151° C.

IR (KBr): 3700–3150, 2938, 2649, 1728, 1701, 1655, 1609, 1485 cm$^{-1}$.

$^1$H-NMR (CDCl$_3$) δ: 1.24 (3H, t, J=7.4Hz), 1.32–1.50 (2H, m), 1.60–1.94 (8H, m), 1.94–2.20 (4H, m), 2.30 (2H, t, J=7.4 Hz), 2.22–2.50 (2H, m), 2.95–3.20 (4H, m), 3.52–3.68 (1H, m), 4.00–4.22 (4H, m), 4.10 (2H, q, J=7.2 Hz), 5.50 (1H, s), 7.18–7.42 (12H, m), 7.60–7.76 (1H, m), 8.22 (1H, d, J=7.4 Hz), 12.47 (1H, bs).

Elemental Analysis for C$_{38}$H$_{47}$N$_3$O$_5$.HCl.0.4H$_2$O: Calcd. (%): C, 68.18; H, 7.35; N, 6.28. Found (%): C, 68.12; H, 7.48; N, 6.39.

EXAMPLE 96

Methyl 1-[2,4-dioxo-1-[4-(4-diphenylmethoxypiperidino)butyl]-1,2,3,4-tetrahydroquinazolin-3-yl]-1-cyclopentylcarboxylate hydrochloride Using the method similar to that in Example 2 (Method 4) and starting from methyl 1-[1-(4-bromobutyl)-2,4-dioxo-1,2,3,4-tetrahydroquinazolin-3-yl]-1-cyclopentylcarboxylate (1.47 g, 3.47 mmol) obtained in Reference Example 152, the title compound (2.01 g, 95%) was obtained as an oil.

$^1$H-NMR (CDCl$_3$) δ: 1.54–2.20 (14H, m), 2.36 (2H, t, J=7.0 Hz), 2.38–2.52 (4H, m), 2.68–2.82 (2H, m), 3.37–3.52 (1H, m), 3.69 (3H, s), 4.07 (2H, t, J=6.2 Hz), 5.52 (1H, s), 7.14–7.38 (12H, m), 7.63 (1H, ddd, J=8.4, 7.0, 1.4 Hz), 8.14 (1H, dd, J=7.6, 1.6 Hz).

This product (2.01 g, 3.30 mmol) was dissolved in ethyl acetate (5.00 ml) and combined with a 4N solution of hydrogen chloride in ethyl acetate (1.00 ml) to give the title compound (1.49 g, 70%). Recrystallization from ethyl acetate yielded a colorless crystal having a melting point of 178 to 180° C.

IR (KBr): 3700–3100, 2949, 1740, 1707, 1661, 1607, 1481 cm$^{-1}$.

¹H-NMR (CDCl₃) δ: 1.70–2.14 (10H, m), 2.30–2.60 (6H, m), 2.92–3.22 (4H, m), 3.28–3.46 (2H, m), 3.67 (3H, s), 3.84–3.92 (1H, m), 4.04–4.16 (2H, m), 5.52 (1H, s), 7.12–7.40 (12H, m), 7.67 (1H, t, J=8.4 Hz), 8.15 (1H, d, J=8.2 Hz), 12.14 (1H, bs).

Elemental Analysis for $C_{37}H_{43}N_3O_5 \cdot HCl \cdot 0.8H_2O$: Calcd. (%): C, 67.17; H, 6.83; N, 6.54. Found (%): C, 67.27; H, 6.96; N, 6.36.

EXAMPLE 97

Methyl 1-[2,4-dioxo-1-[4-(4-diphenylmethoxypiperidino)butyl]-1,2,3,4-tetrahydroquinazolin-3-yl]-1-cyclohexylcarboxylate hydrochloride Using the method similar to that in Example 2 (Method 4) and starting from methyl 1-[1-(4-bromobutyl)-2,4-dioxo-1,2,3,4-tetrahydroquinazolin-3-yl]-1-cyclohexylcarboxylate (5.00 g, 11.4 mmol) obtained in Reference Example 153, the title compound (1.07 g, 15%) was obtained as an oil.

¹H-NMR (CDCl₃) δ: 1.46–2.00 (18H, m), 2.00–2.25 (2H, m), 2.26–2.42 (2H, m), 2.69–2.84 (2H, m), 3.38–3.52 (1H, m), 3.70 (3H, s), 4.00–4.10 (2H, m), 5.52 (1H, s), 7.16–7.38 (12H, m), 7.63 (1H, t, J=7.8 Hz), 8.12 (1H, d, J=7.6 Hz).

This product (1.07 g, 1.72 mmol) was dissolved in ethyl acetate (5.00 ml) and combined with a 4N solution of hydrogen chloride in ethyl acetate (1.00 ml) to give the title compound (863 mg, 76%) as an amorphous.

IR (KBr): 3343, 2936, 2670, 1738, 1703, 1661, 1607, 1481 cm⁻¹.

¹H-NMR (CDCl₃) δ: 1.60–2.58 (18H, m), 2.80–3.26 (4H, m), 3.26–3.42 (2H, m), 3.64 (3H, s), 3.80–3.92 (1H, m), 4.08–4.30 (2H, m), 5.43 (1H, s), 7.16–7.42 (12H, m), 7.67 (1H, t, J=7.0 Hz), 8.13 (1H, d, J=8.0 Hz), 12.02 (1H, bs).

Elemental Analysis for $C_{38}H_{45}N_3O_5 \cdot HCl \cdot 3.5H_2O$: Calcd. (%): C, 63.10; H, 7.39; N, 5.81. Found (%): C, 62.96; H, 7.36; N, 5.65.

EXAMPLE 98

2,4-Dioxo-1-[4-(4-diphenylmethoxypiperidino)butyl]-1,2,3,4-tetrahydroquinazoline-3-hexanoic acid Using the method similar to that in Example 47 and starting from ethyl 2,4-dioxo-1-[4-(4-diphenylmethoxypiperidino)butyl]-1,2,3,4-tetrahydroquinazoline-3-hexanoate (6.68 g, 10.7 mmol) obtained in Example 95, the title compound (5.83 g, 91%) was synthesized. Recrystallization from n-hexane-isopropyl ether yielded a colorless crystal having a melting point of 155 to 157° C.

IR (KBr): 3700–3150, 2926, 2855, 1701, 1655, 1609, 1485 cm⁻¹.

¹H-NMR (CDCl₃) δ: 1.22–1.40 (4H, m), 1.48–2.12 (6H, m), 2.19 (2H, t, J=6.0 Hz), 2.52–2.64 (2H, m), 2.80–3.00 (4H, m), 3.56–3.68 (1H, m), 4.18 (2H, t, J=6.0 Hz), 4.15–4.30 (2H, m), 5.45 (1H, s), 7.13 (1H, d, J=8.8 Hz), 7.18–7.40 (11H, m), 7.64 (1H, t, J=7.0 Hz), 8.24 (1H, d, J=8.0 Hz).

Elemental Analysis for $C_{36}H_{43}N_3O_5 \cdot 1.1H_2O$: Calcd. (%): C, 70.02; H, 7.38; N, 6.80. Found (%): C, 69.96; H, 7.09; N, 6.73.

EXAMPLE 99

2,4-Dioxo-1-[4-(4-diphenylmethoxypiperidino)butyl]-1,2,3,4-tetrahydroquinazoline-3-octanoic acid Using the method similar to that in Example 2 (Method 4) and starting from ethyl 1-(4-bromobutyl)-2,4-dioxo-1,2,3,4-tetrahydroquinazoline-3-octanoate (5.00 g, 10.7 mmol) obtained in Reference Example 151, the ethyl ester of the title compound (2.60 g, 37%) was obtained as an oil.

¹H-NMR (CDCl₃) δ: 1.25 (3H, t, J=7.4 Hz), 1.30–1.43 (6H, m), 1.54–1.84 (10H, m), 1.84–1.98 (2H, m), 2.04–2.19 (2H, m), 2.28 (2H, t, J=7.4 Hz), 2.38 (2H, t, J=7.0 Hz), 2.69–2.82 (2H, m), 3.38–3.53 (1H, m), 4.00–4.18 (6H, m), 5.53 (1H, s), 7.18–7.36 (12H, m), 7.65 (1H, ddd, J=8.8, 7.0, 1.4 Hz), 8.22 (1H, dd, J=8.0, 1.4 Hz).

Starting from this product (2.60 g, 3.98 mmol) and using the method similar to that in Example 47, the title compound (2.18 g, 88%) was obtained as an amorphous.

IR (KBr): 3700–3150, 2932, 1701, 1655, 1609, 1485 cm⁻¹.

¹H-NMR (CDCl₃) δ: 1.46–2.15 (18H, m), 2.21 (2H, t, J=7.0Hz), 2.64–3.00 (6H, m), 3.58–3.70 (1H, m), 4.04–4.20 (4H, m), 5.47 (1H, s), 7.12–7.42 (12H, m), 7.65 (1H, t, J=7.4 Hz), 8.22 (1H, d, J=8.0 Hz).

Elemental Analysis for $C_{38}H_{47}N_3O_5 \cdot HCl \cdot 0.4H_2O$: Calcd. (%): C, 68.18; H, 7.35; N, 6.28. Found (%): C,. 68.12; H, 7.48; N, 6.39.

EXAMPLE 100

1-[2,4-dioxo-1-[4-(4-diphenylmethoxypiperidino)butyl]-1,2,3,4-tetrahydroquinazolin-3-yl]-1-cyclohexylcarboxylic acid Using the method similar to that in Example 2 (Method 4) and starting from 1-[1-(4-bromobutyl)-2,4-dioxo-1,2,3,4-tetrahydroquinazolin-3-yl]-1-cyclohexylcarboxylic acid (2.35 g, 5.55 mmol) obtained in Reference Example 154, the title compound (207 mg, 6.1%) was obtained as an amorphous.

IR (KBr): 3200–2100, 2934, 2861, 1703, 1659, 1607, 1495, 1481 cm⁻¹.

¹H-NMR (CDCl₃) δ: 1.32–2.10 (14H, m), 2.22–2.28 (2H, m), 2.30–2.52 (2H, m), 2.68–3.40 (6H, m), 3.72–3.82 (1H, m), 4.18–4.40 (2H, m), 5.44 (1H, s), 7.06 (1H, d, J=8.0 Hz), 7.12–7.42 (11H, m), 7.56 (1H, t, J=8.2 Hz), 8.12 (1H, d, J=7.6 Hz).

Elemental Analysis for $C_{37}H_{43}N_3O_5 \cdot 2.6H_2O$: Calcd. (%): C, 67.68; H, 7.40; N, 6.40. Found (%): C, 67.59; H, 7.51; N, 6.32C.

EXAMPLE 101

2,4-Dioxo-1-[4-(4-diphenylmethoxypiperidino)butyl]-6-fluoro-1,2,3,4-tetrahydroquinazoline-3-valeric acid Using the method similar to that in Example 2 (Method 4) and starting from ethyl 1-(4-bromobutyl)-2,4-dioxo-6-fluoro-1,2,3,4-tetrahydroquinazoline-3-valerate (2.46 g, 5.55 mmol) obtained in Reference Example 155, the ethyl ester of the title compound (2.41 g, 69%) was obtained as an oil.

¹H-NMR (CDCl₃) δ: 1.24 (3H, t, J=7.2 Hz), 1.55–1.84 (10H, m), 1.84–2.00 (2H, m), 2.04–2.20 (2H, m), 2.30–2.42 (4H, m), 2.70–2.82 (2H, m), 3.38–3.54 (1H, m), 4.05–4.18 (6H, m), 5.53 (1H, s), 7.20–7.40 (12H, m), 7.85–7.94 (1H, m).

Starting from this product (2.41 g, 3.83 mmol) and using the method similar to that in Example 47, the title compound (2.12 g, 92%) was obtained as an amorphous. IR (KBr): 3700–3150, 2938, 1701, 1655, 1601, 1559, 1505, 1480 cm⁻¹.

¹H-NMR (CDCl₃) δ: 1.45–2.15 (12H, m), 2.21 (2H, t, J=7.0Hz), 2.64–3.00 (6H, m), 3.55–3.70 (1H, m), 4.17 (2H, t, J=6.2 Hz), 4.20–4.30 (2H, m), 5.44 (1H, s), 7.13 (1H, dd, J=9.0, 4.4 Hz), 7.18–7.44 (11H, m), 7.91 (1H, dd, J=8.0, 3.0 Hz).

Elemental Analysis for $C_{35}H_{40}N_3O_5F\cdot1.8H_2O$: Calcd. (%): C, 66.29; H, 6.93; N, 6.63. Found (%): C, 66.57; H, 6.82; N, 6.24.

EXAMPLE 102

2,4-Dioxo-1-[4-(4-diphenylmethoxypiperidino) butyl]-6-methoxy-1,2,3,4 -tetrahydroquinazoline-3-valeric acid hydrochloride Using the method similar to that in Example 2 (Method 4) and starting from ethyl 1-(4-bromobutyl)-2,4-dioxo-6-methoxy-1,2,3,4-tetrahydroquinazoline-3-octanoate (3.14 g, 7.42 mmol) obtained in Reference Example 156, the ethyl ester of the title compound (1.89 g, 40%) was obtained as an oil.

¹H-NMR (CDCl₃) δ: 1.24 (3H, t, J=7.2 Hz), 1.55–1.82 (12H, m), 1.82–2.00 (2H, m), 2.02–2.20 (2H, m), 2.32–2.44 (2H, m), 2.70–2.84 (2H, m), 3.40–3.52 (1H, m), 3.86 (3H, s), 4.04–4.18 (6H, m), 5.52 (1H, s), 7.20–7.40 (12H, m), 7.66 (1H, s).

Starting from this product (1.89 g, 2.94 mmol) and using the method similar to that in Example 47, a free salt of the title compound was obtained as an oil. This substance was dissolved in ethyl acetate (5.00 ml) and combined with a 4N solution of hydrogen chloride in ethyl acetate (1.00 ml) to give the title compound (1.54 g, 81%) as an amorphous.

IR (KBr): 3500–2400, 2948, 1698, 1651, 1559, 1505, 1480cm⁻¹.

¹H-NMR (CDCl₃) δ: 1.50–2.30 (14H, m), 2.48–2.62 (2H, m), 2.84–2.96 (4H, m), 3.62–3.71 (1H, m), 3.88 (3H, s), 4.21 (2H, t, J=5.2 Hz), 4.22–4.34 (2H, m), 5.44 (1H, s), 7.08 (1H, d, J=9.6 Hz), 7.18–7.34 (11H, m), 7.70 (1H, d, J=3.0 Hz).

Elemental Analysis for $C_{36}H_{43}N_3O_6\cdot HCl\cdot1.0H_2O$: Calcd. (%): C, 64.71; H, 6.94; N, 6.29. Found (%): C, 64.42; H, 6.58; N, 6.04.

EXAMPLE 103

Ethyl 2,4-dioxo-1-[4-(4-diphenylmethoxypiperidino) butyl]-6-methoxy-1,2,3,4-tetrahydroquinazoline-3-valerate Using the method similar to that in Example 2 (Method 4) and starting from ethyl 1-(4-bromobutyl)-2,4-dioxo-6-nitro-1,2,3,4-tetrahydroquinazoline-3-valerate (4.10 g, 8.72 mmol) obtained in Reference Example 157, the title compound (3.77 g, 66%) was obtained as an oil.

IR (KBr): 3500–2400, 2948, 1698, 1651, 1559, 1505, 1480 cm⁻¹.

¹H-NMR (CDCl₃) δ: 1.50–2.30 (14H, m), 2.48–2.62 (2H, m), 2.84–2.96 (4H, m), 3.62–3.71 (1H, m), 3.88 (3H, s), 4.21 (2H, t, J=5.2 Hz), 4.22–4.34 (2H, m), 5.44 (1H, s), 7.08 (1H, d, J=9.6 Hz), 7.18–7.34 (11H, m), 7.70 (1H, d, J=3.0 Hz).

Elemental Analysis for $C_{36}H_{43}N_3O_6\cdot HCl\cdot1.0H_2O$: Calcd. (%): C, 64.71; H, 6.94; N, 6.29. Found (%): C, 64.42; H, 6.58; N, 6.04.

EXAMPLE 104

6-Amino-2,4-dioxo-1-[4-(4-diphenylmethoxypiperidino)butyl]-1,2,3,4-tetrahydroquinazoline-3-valeric acid Using the method similar to that in Example 39 and starting from ethyl 2,4-dioxo-1-[4-(4-diphenylmethoxypiperidino)butyl]-6-methoxy-1,2,3,4-tetrahydroquinazoline-3-valerate (2.57 g, 3.91 mmol) obtained in Example 103, the ethyl ester of the title compound (1.83 g 75%) was obtained as an oil.

¹H-NMR (CDCl₃) δ: 1.24 (3H, t, J=7.0 Hz), 1.56–1.84 (10H, m), 1.84–2.02 (2H, m), 2.06–2.22 (2H, m), 2.30–2.44 (4H, m), 2.70–2.84 (2H, m), 3.40–3.54 (1H, m), 3.72 (2H, bs), 4.02–4.18 (6H, m), 5.53 (1H, s), 7.01 (1H, dd, J=8.8, 2.4 Hz), 7.03–7.29 (11H, m), 7.37 (1H, d, J=2.4 Hz).

Starting from this product (1.83 g, 2.92 mmol) and using the method similar to that in Example 47, the title compound (1.67 g, 96%) was obtained as an amorphous.

IR (KBr): 3345, 3220, 2955, 1690, 1645, 1590, 1508, 1487 cm⁻¹.

¹H-NMR (CDCl₃) δ: 1.48–2.02 (12H, m), 2.16 (2H, t, J=6.2 Hz), 2.12–2.34 (2H, m), 2.68–2.84 (2H, m), 2.90–3.16 (2H, m), 3.04 (2H, bs), 3.66–3.78 (1H, m), 4.06–4.22 (4H, m), 5.44 (1H, s), 6.96–7.02 (2H, m), 7.20–7.36 (10H, m), 7.48 (1H, d, J=2.2 Hz).

Elemental Analysis for $C_{35}H_{42}N_4O_5\cdot2.0H_2O$: Calcd. (%): C, 66.23; H, 7.30; N, 8.83. Found (%): C, 66.08; H, 7.10; N, 8.42.

EXAMPLE 105

2,4-Dioxo-1-[4-(4-diphenylmethoxypiperidino) butyl]-6-hydroxy-1,2,3,4-tetrahydroquinazoline-3-valeric acid Using the method similar to that in Example 2 (Method 4) and starting from ethyl 1-(4-bromobutyl)-2,4-dioxo-6-hydroxy-1,2,3,4-tetrahydroquinazoline-3-valerate (3.31 g, 7.50 mmol) obtained in Reference Example 160, the ethyl ester of the title compound (3.60 g, 77%) was obtained as an oil.

¹H-NMR (CDCl₃) δ: 1.24 (3H, t, J=7.0 Hz), 1.60–2.42 (16H, m), 2.42–2.54 (2H, m), 2.66–2.92 (2H, m), 3.44–3.56 (1H, m), 4.00–4.16 (4H, m), 4.12 (2H, q, J=7.2 Hz), 5.51 (1H, s), 7.08–7.40 (12H, m), 7.47 (1H, s).

Starting from this product (910 mg, 1.45 mmol) and using the method similar to that in Example 47, the title compound (696 mg, 80%) was synthesized. Recrystallization from ethyl ether yielded a colorless crystal having a melting point of 234 to 236° C.

IR (KBr): 3600–2000, 2963 2944, 1694, 1647, 1584, 1491 cm⁻¹.

¹H-NMR (CDCl₃+DMSO-d₆) δ: 1.50–2.04 (12H, m), 2.10–2.32 (2H, m), 2.25 (2H, t, J=7.4 Hz), 2.90–3.58 (4H, m), 3.62–3.74 (1H, m), 4.02–4.22 (4H, m), 5.47 (1H, s), 7.06 (1H, d, J=8.8 Hz), 7.24–7.40 (11H, m), 7.64 (1H, d, J=2.4 Hz).

Elemental Analysis for $C_{35}H_{41}N_3O_6\cdot1.5H_2O$: Calcd. (%): C, 67.07; H, 7.08; N, 6.70. Found (%): C, 67.15; H, 6.93; N, 6.67.

EXAMPLE 106

6-Benzyloxy-2,4-dioxo-1-[4-(4-diphenylmethoxypiperidino)butyl]-1,2,3,4-tetrahydroquinazoline-3-valeric acid To a suspension of ethyl 2,4-dioxo-1-[4-(4-diphenylmethoxypiperidino)butyl]- 6-hydroxy-1,2,3,4-tetrahydroquinazoline-3-valerate (1.34 g, 2.13 mmol) obtained in Example 105 and potassium carbonate (354 mg, 2.56 mmol) in N,N-dimethylformamide (50.0 ml), benzyl bromide (305 ml, 2.56 mmol) was added dropwise and the reaction mixture was stirred at room temperature for 18.5 hours. The reaction mixture was combined with water and extracted with ethyl acetate. After the extract was washed with water and dried (MgSO$_4$) the solvent was distilled off under reduced pressure. The residue was subjected to a column chromatography on a silica gel eluting with n-hexane-ethyl acetate (5:1, v/v) to give the ethyl ester of the title compound (450 mg, 29%) as an oil.

$^1$H-NMR (CDCl$_3$) δ: 1.24 (3H, t, J=7.0 Hz), 1.48–1.80 (10H, m), 1.84–2.00 (2H, m), 2.06–2.28 (2H, m), 2.28–2.45 (4H, m), 2.68–2.84 (2H, m), 3.36–3.56 (1H, m), 4.02–4.18 (4H, m), 4.11 (2H, q, J=7.4 Hz), 5.12 (2H, s), 5.52 (1H, s), 7.22–7.45 (17H, m), 7.74 (1H, d, J=2.6 Hz).

Starting from this product (450 mg, 0.627 mmol) and using the method similar to that in Example 47, the title compound (445 mg, about 100%) was obtained as an amorphous.

IR (KBr): 3700–2800, 3061, 3031, 2938 2870, 2523, 1698, 1651, 1593, 1476 cm$^{-1}$.

$^1$H-NMR (CDCl$_3$) δ: 1.56–2.08 (10H, m), 2.31 (2H, t, J=6.2 Hz), 2.26–2.44 (2H, m), 2.85–2.98 (2H, m), 2.98–3.18 (2H, m), 3.18–3.34 (2H, m), 3.75–3.84 (1H, m), 4.14 (2H, t, J=6.6 Hz), 4.19 (2H, t, J=5.4 Hz), 5.13 (2H, s), 5.44 (1H, s), 7.11 (1H, d, J=9.2 Hz), 7.24–7.48 (11H, m), 7.77 (1H, d, J=3.0 Hz).

Elemental Analysis for C$_{42}$H$_{47}$N$_3$O$_6$.3.2H$_2$O: Calcd. (%): C, 67.49; H, 7.20; N, 5.62. Found (%): C, 67.38; H, 6.80; N, 5.40.

EXAMPLE 107

2,4-Dioxo-1-[4-(4-diphenylmethoxypiperidino) butyl]-6-methoxycarbonylmethyl-1,2,3,4-tetrahydroquinazoline-3-valeric acid Using the method similar to that in Example 106 and starting from ethyl 2,4-dioxo-1-[4-(4-diphenylmethoxypiperidino)butyl]-6-hydroxy-1,2,3,4-tetrahydroquinazoline-3-valerate (1.31 g, 2.09 mmol) obtained in Example 105, and also using methyl bromoacetate (237 ml, 2.50 mmol) instead of benzyl bromide, the ethyl ester of the title compound (990 mg, 68%) was obtained as an oil.

$^1$H-NMR (CDCl$_3$) δ: 1.24 (3H, t, J=7.2 Hz), 1.55–1.85 (10H, m), 1.85–2.02 (2H, m), 2.08–2.28 (2H, m), 2.32–2.46 (4H, m), 2.70–2.84 (2H, m), 3.42–3.54 (1H, m), 3.82 (3H, s), 4.04–4.20 (4H, m), 4.12 (2H, q, J=7.0 Hz), 4.71 (2H, s), 5.52 (1H, s), 7.20–7.40 (12H, m), 7.60 (1H, d, J=2.6 Hz).

Starting from this product (990 mg, 1.41 mmol) and using the method similar to that in Example 47, the title compound (885 mg, 96%) was obtained as an amorphous.

IR (KBr): 3700–3300, 2940, 2529, 1694, 1651, 1597, 1555, 1505, 1478 cm$^{-1}$.

$^1$H-NMR (CDCl$_3$) δ: 1.56–2.08 (12H, m), 2.08–2.32 (4H, m), 2.90–3.20 (4H, m), 3.74–3.82 (1H, m), 4.02–4.20 (6H, m), 5.43 (1H, s), 7.11 (1H, d, J=8.0 Hz), 7.20–7.38 (11H, m), 7.57 (1H, d, J=2.2 Hz).

Elemental Analysis for C$_{37}$H$_{43}$N$_3$O$_8$.3.2H$_2$O: Calcd. (%): C, 62.12; H, 6.96; N, 5.87. Found (%): C, 62.01; H, 6.58; N, 5.54.

EXAMPLE 108

2,4-Dioxo-1-[4-(4-diphenylmethoxypiperidino) butyl]-6-(3-ethoxycarbonylpropoxy)-1,2,3,4-tetrahydroquinazoline-3-valeric acid hydrochloride Using the method similar to that in Example 106 and starting from ethyl 2,4-dioxo-1-[4-(4-diphenylmethoxypiperidino)butyl]-6-hydroxy-1,2,3,4-tetrahydroquinazoline-3-valerate (1.53 g, 2.44 mmol) obtained in Example 105, and also using ethyl bromobutyrate (523 ml, 3.66 mmol) instead of benzyl bromide, the ethyl ester of the title compound (1.38 g, 76%) was obtained as an oil.

$^1$H-NMR (CDCl$_3$) δ: 1.26 (6H, t, J=7.4 Hz), 1.56–1.83 (10H, m), 1.83–2.00 (2H, m), 2.06–2.22 (4H, m), 2.32–2.44 (4H, m), 2.51 (2H, t, J=7.0 Hz), 2.68–2.82 (2H, m), 3.38–3.52 (1H, m), 4.02–4.22 (12H, m), 5.52 (1H, s), 7.20–7.40 (12H, m), 7.62 (1H, s).

Starting from this product (1.38 g, 1.86 mmol) and using the method similar to that in Example 47, a free salt of the title compound was obtained as an oil. This oil was dissolved in ethyl acetate (5.00 ml) and combined with a 4N solution of hydrogen chloride in ethyl acetate (1.00 ml) to give the title compound (1.38 g, about 100%) as an amorphous.

IR (KBr): 3400–2300, 2948, 1696, 1651, 1505, 1474 cm$^{-1}$.

$^1$H-NMR (CDCl$_3$) δ: 1.50–2.06 (14H, m), 2.18–2.40 (4H, m), 2.89–3.02 (2H, m), 3.02–3.20 (2H, m), 3.22–3.44 (2H, m), 3.72–3.82 (1H, m), 3.96 (2H, t, J=6.6 Hz), 4.04–4.20 (4H, m), 5.43 (1H, s), 7.06 (1H, d, J=9.6 Hz), 7.16–7.42 (11H, m), 7.59 (1H, s).

Elemental Analysis for C$_{39}$H$_{47}$N$_3$O$_8$.HCl.2.2H$_2$O: Calcd. (%): C, 61.48; H, 6.93; N, 5.52. Found (%): .C, 61.45; H, 6.37; N, 5.11.

EXAMPLE 109

2,4-Dioxo-1-[4-(4-diphenylmethoxypiperidino) butyl]-N-methoxycarbonylmethyl-1,2,3,4-tetrahydroquinazoline-3-acetamide hydrochloride To a solution of 2,4-dioxo-1-[4-(4-diphenylmethoxypiperidino)butyl]-1,2,3,4-tetrahydroquinazoline-3-acetic acid (1.20 g, 2.22 mmol) obtained in Example 50 and glycine methyl ester hydrochloride (278 mg, 2.66 mmol) in N,N-dimethylformamide (20.0 ml), diethyl cyanophosphonate (425 ml, 2.66 mmol) and triethylamine (926 ml, 6.65 mmol) were added sequentially, and then the reaction mixture was stirred at room temperature for 17 hours. The solvent was distilled off under reduced pressure, and the residue was combined with water and extracted with ethyl acetate. After the extract was washed with water and dried (MgSO$_4$), the solvent was distilled off under reduced pressure. The residue was subjected to a column chromatography on a silica gel eluting with n-hexane-ethyl acetate (5:1, v/v) to give the methyl ester of the title compound (883 mg, 65%) as an oil.

$^1$H-NMR (CDCl$_3$) δ: 1.54–1.84 (6H, m), 1.84–1.98 (2H, m), 2.00–2.16 (2H, m), 2.38 (2H, t, J=8.8 Hz), 2.68–2.82 (2H, m), 3.48–3.52 (1H, m), 3.76 (3H, s), 4.04–4.20 (4H, m), 4.82 (2H, s), 5.53 (1H, s), 6.30 (1H, bs), 7.18–7.38 (12H, m), 7.68 (1H, ddd, J=7.4, 5.4, 2.0 Hz), 8.23 (1H, dd, J=8.2, 1.4 Hz).

This product (399 mg, 0.650 mmol) was dissolved in ethyl acetate (5.00 ml) and combined with a 4N solution of hydrogen chloride in ethyl acetate (1.00 ml) to give the title compound (275 mg, 65%) as an amorphous.

IR (KBr): 2938, 1748, 1661, 1609, 1547, 1485 cm$^{-1}$.

$^1$H-NMR (CDCl$_3$) δ: 1.70–2.82 (8H, m), 2.94–3.20 (4H, m), 3.30–3.42 (2H, m), 3.84 (3H, s), 3.80–3.90 (1H,m), 3.92–4.28 (4H, m), 4.81 (2H, s), 5.43 (1H, s), 6.60 (1H, bs), 7.16–7.40 (12H, m), 7.60–7.76 (1H, m), 8.21 (1H, d, J=7.6 Hz), 11.79 (1H, bs).

Elemental Analysis for $C_{35}H_{40}N_4O_6 \cdot HCl \cdot 1.0H_2O$: Calcd. (%): C, 63.01; H, 6.50; N, 8.40. Found (%): C, 62.98; H, 6.38; N, 8.16.

EXAMPLE 110

2,4-Dioxo-1-[4-(4-diphenylmethoxypiperidino)butyl]-N-ethoxycarbonylmethyl-N-methyl-1,2,3,4-tetrahydroquinazoline-3-acetamide hydrochloride Using the method similar to that in Example 109 and starting from 2,4-dioxo-1-[4-(4-diphenylmethoxypiperidino)butyl]-1,2,3,4-tetrahydroquinazoline-3-acetic acid (1.20 g, 2.22 mmol) obtained in Example 50, and also using sarcosine ethyl ester hydrochloride (408 mg, 2.66 mmol) instead of glycine methyl ester hydrochloride, the ethyl ester of the title compound (1.19 g 83%) was obtained as an oil.

$^1$H-NMR (CDCl$_3$) δ: 1.26 (3H, t, J=7.0 Hz), 1.50–1.84 (6H, m), 1.84–2.00 (2H, m), 2.00–2.18 (2H, m), 2.30–2.42 (2H, m), 2.68–2.82 (2H, m), 3.21 (3H, m), 3.38–3.52 (1H, m), 4.04–4.20 (6H, m), 4.98 (2H, s), 5.52 (1H, s), 6.30 (1H, bs), 7.12–7.38 (12H, m), 7.66 (1H, t, J=5.6 Hz), 8.22 (1H, d, J=7.8 Hz).

This product (561 mg, 0.875 mmol) was dissolved in ethyl acetate (5.00 ml) and combined with a 4N solution of hydrogen chloride in ethyl acetate (1.00 ml) to give the title compound (362 mg, 61%). Recrystallization from ethyl acetate yielded a colorless crystal having a melting point of 170 to 172° C.

IR (KBr): 2936, 2800–2300, 1744, 1707, 1661, 1609, 1485 cm$^{-1}$. $^1$H-NMR (CDCl$_3$) δ: 1.26 (3H, t, J=7.0 Hz), 1.80–2.12 (8H, m), 2.32–2.58 (2H, m), 2.96–3.22 (4H, m), 3.17 (3H, s), 3.28–3.40 (2H, m), 3.80–3.90 (1H,m), 4.00–4.30 (6H, m), 4.96 (2H, s), 5.44 (1H, s), 7.18–7.40 (12H, m), 7.70 (1H, t, J=7.6 Hz), 8.23 (1H, d, J=8.0 Hz).

Elemental Analysis for $C_{37}H_{44}N_4O_6 \cdot HCl \cdot 0.4H_2O$: Calcd. (%): C, 64.93; H, 6.74; N, 8.19. Found (%): C, 64.74; H, 6.79; N, 8.27.

EXAMPLE 111

2,4-Dioxo-1-[4-(4-diphenylmethoxypiperidino)butyl]-N-(2-ethoxycarbonylethyl)-1,2,3,4-tetrahydroquinazoline-3-acetamide hydrochloride Using the method similar to that in Example 109 and starting from 2,4-dioxo-1-[4-(4-diphenylmethoxypiperidino)butyl]-1,2,3,4-tetrahydroquinazoline-3-acetic acid (1.20 g, 2.22 mmol) obtained in Example 50, and also using b-alanine ethyl ester hydrochloride (408 mg, 2.66 mmol) instead of glycine methyl ester hydrochloride, the ethyl ester of the title compound (1.06 g 65%) was obtained as an oil.

$^1$H-NMR (CDCl$_3$) δ: 1.26 (3H, t, J=7.4 Hz), 1.54–1.84 (6H, m), 1.84–2.00 (2H, m), 2.04–2.20 (2H, m), 2.37 (2H, t, J=7.0 Hz), 2.54 (2H, t, J=5.8 Hz), 2.68–2.82 (2H, m), 3.38–3.62 (3H, m), 4.00–4.22 (4H, m), 4.72 (2H, s), 5.53 (1H, s), 6.35 (1H, bs), 7.18–7.38 (12H, m), 7.68 (1H, ddd, J=8.8, 7.0, 1.8 Hz), 8.22 (1H, dd, J=8.0, 1.4 Hz).

This product (448 mg, 0.699 mmol) was dissolved in ethyl acetate (5.00 ml) and combined with a 4N solution of hydrogen chloride in ethyl acetate (1.00 ml) to give the title compound (313 mg, 66%). Recrystallization from ethyl acetate yielded a colorless crystal having a melting point of 123 to 124° C.

IR (KBr): 2936, 2800–2300, 1728, 1705, 1659, 1611, 1551, 1485 cm$^{-1}$.

$^1$H-NMR (CDCl$_3$) δ: 1.27 (3H, t, J=7.2 Hz), 1.78–2.16 (6H, m), 2.34–2.56 (2H, m), 2.51 (2H, t, J=6.0 Hz), 2.92–3.20 (4H, m), 3.30–3.42 (2H, m), 3.44–3.58 (2H, m), 3.80–3.90 (1H,m), 4.16–4.28 (2H, m), 4.15 (2H, q, J=7.0 Hz), 4.71 (2H, s), 5.43 (1H, s), 6.42 (1H, bs), 7.18–7.40 (12H, m), 7.71 (1H, t, J=7.2 Hz), 8.23 (1H, d, J=7.6 Hz), 11.97 (1H, bs).

Elemental Analysis for $C_{37}H_{44}N_4O_6 \cdot HCl \cdot 1.6H_2O$: Calcd. (%): C, 62.94; H, 6.88; N, 7.94. Found (%): C, 62.92; H, 6.69; N, 7.90.

EXAMPLE 112

2,4-Dioxo-1-[4-(4-diphenylmethoxypiperidino)butyl]-N-methoxycarbonylmethyl-1,2,3,4-tetrahydroquinazoline-3-propionamide hydrochloride Using the method similar to that in Example 109 and starting from 2,4-dioxo-1-[4-(4-diphenylmethoxypiperidino)butyl]-1,2,3,4-tetrahydroquinazoline-3-propionic acid (1.30 g, 2.34 mmol) obtained in Example 52, the methyl ester of the title compound (1.39 g, 95%) was obtained as an oil.

$^1$H-NMR (CDCl$_3$) δ: 1.56–1.84 (6H, m), 1.84–2.00 (2H, m), 2.05–2.20 (2H, m), 2.35 (2H, t, J=6.6 Hz), 2.72 (2H, t, J=7.0 Hz), 2.68–2.82 (2H, m), 3.38–3.52 (1H, m), 3.72 (3H, s), 4.00–4.18 (4H, m), 4.42 (2H, t, J=7.0 Hz), 5.53 (1H, s), 6.60 (1H, bs), 7.20–7.38 (12H, m), 7.67 (1H, ddd, J=8.6, 7.0, 1.6 Hz), 8.22 (1H, dd, J=8.2, 1.6 Hz).

This product (616 mg, 0.983 mmol) was dissolved in ethyl acetate (5.00 ml) and combined with a 4N solution of hydrogen chloride in ethyl acetate (1.00 ml) to give the title compound (380 mg, 58%) as an amorphous.

IR (KBr): 2937, 1740, 1699, 1655, 1609, 1549, 1485 cm$^{-1}$.

$^1$H-NMR (CDCl$_3$) δ: 1.72–2.20 (6H, m), 2.20–2.46 (2H, m), 2.65–2.80 (4H, m), 2.90–3.72 (4H, m), 3.80–3.90(1H, m), 4.03 (2H, d, J=4.8 Hz), 4.18–4.30 (2H, m), 4.34–4.48 (2H, m), 5.41 (1H, s), 7.10–7.42 (12H, m), 7.67 (1H, t, J=8.4 Hz), 8.22 (1H, d, J=7.4 Hz), 10.96 (1H, bs).

Elemental Analysis for $C_{36}H_{42}N_4O_6 \cdot HCl \cdot 2.6H_2O$: Calcd. (%): C, 60.90; H, 6.84; N, 7.89. Found (%): C, 60.89; H, 6.65; N, 8.11.

EXAMPLE 113

N-Carboxylmethyl-2,4-dioxo-1-[4-(4-diphenylmethoxypiperidino)butyl]-1,2,3,4-tetrahydroquinazoline-3-acetamide Using the method similar to that in Example 47 and starting from 2,4-dioxo-1-[4-(4-diphenylmethoxypiperidino)butyl]-N-methoxycarbonylmethyl-1,2,3,4-tetrahydroquinazoline-3-acetamide (740 mg, 1.21 mmol) obtained in Example 109, the title compound (690 mg, 95%) was obtained as an amorphous.

IR (KBr): 3700–3150, 3031, 2934, 1701, 1655, 1609, 1485 cm$^{-1}$.

$^1$H-NMR (CDCl$_3$) δ: 1.70–2.06 (2H, m), 2.38–2.58 (2H, m), 2.69–2.80 (2H, m), 2.90–3.10 (2H, m), 3.10–3.30 (2H, m), 3.74–3.86 (1H,m), 3.77 (2H, d, J=4.0 Hz), 4.30–4.40 (2H, m), 4.79 (2H, s), 5.41 (1H, s), 6.60 (1H, bs), 7.16–7.44 (12H, m), 7.69 (1H, t, J=8.4 Hz), 8.28 (1H, d, J=7.8 Hz).

Elemental Analysis for $C_{34}H_{38}N_4O_6 \cdot 0.9H_2O$: Calcd. (%): C, 66.41; H, 6.52; N, 9.11. Found (%): C, 66.48; H, 6.88; N, 8.89.

EXAMPLE 114

N-Carboxylmethyl-2,4-dioxo-1-[4-(4-diphenylmethoxypiperidino)butyl]-N-methyl-1,2,3,4-tetrahydroquinazoline-3-acetamide Using the method similar to that in Example 47 and starting from 2,4-dioxo-1-[4-(4-diphenylmethoxypiperidino)butyl]-N-ethoxycarbonylmethyl-N-methyl-1,2,3,4-tetrahydroquinazoline-3-acetamide (626 mg, 0.977 mmol) obtained in Example 110, the title compound (362 mg, 61%) was obtained as an amorphous.

IR (KBr): 3700–3100, 2957, 1705, 1661, 1609, 1485 $cm^{-1}$.

$^1$H-NMR (CDCl$_3$) δ: 1.56–2.38 (8H, m), 2.80–3.15 (6H, m), 3.20 (3H, s), 3.70–3.82 (1H,m), 3.95 (2H, s), 4.02–4.15 (2H, m), 4.92 (2H, s), 5.44 (1H, s), 7.06 (1H, t, J=7.4 Hz), 7.13–7.42 (11H, m), 7.51 (1H, t, J=7.4 Hz), 8.02 (1H, d, J=7.2 Hz).

Elemental Analysis for $C_{35}H_{40}N_4O_6$.2.7H$_2$O: Calcd. (%): C, 63.56; H, 6.92; N, 8.47. Found (%): C, 63.63; H, 6.69; N, 8.04.

EXAMPLE 115

N-(2-Carboxylethyl)-carboxylmethyl-2,4-dioxo-1-[4-(4-diphenylmethoxypiperidino)butyl]-N-methyl-1,2,3,4-tetrahydroquinazoline-3-acetamide Using the method similar to that in Example 47 and starting from 2,4-dioxo-1-[4-(4-diphenylmethoxypiperidino)butyl]-N-(2-ethoxycarbonylethyl)-1,2,3,4-tetrahydroquinazoline-3-acetamide (950 mg, 1.55 mmol) obtained in Example 111, the title compound (515 mg, 54%) was obtained as an amorphous.

IR (KBr): 3700–3150, 2938, 1701, 1655, 1642, 1580, 1522, 1485 $cm^{-1}$.

$^1$H-NMR (CDCl$_3$) δ: 1.58–2.14 (6H, m), 2.28–2.40 (4H, m), 2.62–3.26 (6H, m), 3.38–3.52 (4H, m), 3.62–3.72 (1H, m), 4.24–4.32 (2H, m), 4.73 (2H, s), 5.44 (1H, s), 6.79 (1H, bs), 7.10–7.38 (12H, m), 7.68 (1H, t, J=9.0 Hz), 8.27 (1H, d, J=9.6 Hz).

Elemental Analysis for $C_{35}H_{40}N_4O_6$.0.5H$_2$O: Calcd. (%): C, 67.61; H, 6.65; N, 9.01. Found (%): C, 67.69; H, 7.19; N, 8.98.

EXAMPLE 116

N-Carboxylmethyl-2,4-dioxo-1-[4-(4-diphenylmethoxypiperidino)butyl]-1,2,3,4-tetrahydroquinazoline-3-propionamide hydrochloride Using the method similar to that in Example 47 and starting from 2,4-dioxo-1-[4-(4-diphenylmethoxypiperidino)butyl]-N-methoxycarbonylmethyl-1,2,3,4-tetrahydroquinazoline-3-propionamide (775 mg, 1.24 mmol) obtained in Example 112, a free salt of the title compound was obtained as an oil. This product was dissolved in ethyl acetate (5.00 ml) and combined with a 4N solution of hydrogen chloride in ethyl acetate (1.00 ml) to give the title compound (274 mg, 34%) as an amorphous.

IR (KBr): 3700–3150, 2936, 1740, 1699, 1655, 1609, 1543, 1485 $cm^{-1}$.

$^1$H-NMR (CDCl$_3$) δ:1.70–3.24 (14H, m), 3.70 (2H, t, J=5.6 Hz), 3.86–3.92 (1H, m), 3.98–4.06 (2H, m), 4.10–4.32 (2H, m), 4.32–4.48 (2H, m), 5.44 (1H, s), 7.10–7.42 (12H, m), 7.60–7.78 (1H, m), 8.22 (1H, d, J=6.6 Hz).

Elemental Analysis for $C_{35}H_{40}N_4O_6$.HCl.2.2H$_2$O: Calcd. (%): C, 61.02; H, 6.64; N, 8.13. Found (%): C, 60.97; H, 6.92; N, 8.53.

EXAMPLE 117

2-[2,4-Dioxo-1-[4-(4-diphenylmethoxypiperidino)butyl]-1,2,3,4-tetrahydroquinazolin-3-yl]ethoxyacetic acid Using the method similar to that in Example 2 (Method 4) and starting from ethyl 2-[1-(4-bromobutyl)-2,4-dioxo-1,2,3,4-tetrahydroquinazolin-3-yl]ethoxyacetate (1.71 g, 4.00 mmol) obtained in Reference Example 165, the ethyl ester of the title compound (1.51 g, 62%) was obtained as an oil.

$^1$H-NMR (CDCl$_3$) δ: 1.26 (3H, t, J=7.0 Hz), 1.50–1.85 (6H, m), 1.85–2.00 (2H, m), 2.06–2.22 (2H, m), 2.38 (2H, t, J=7.6 Hz), 2.70–2.84 (2H, m),3.36–3.52 (1H, m), 3.87 (2H, t, J=5.8 Hz), 4.06–4.22 (6H, m), 4.36 (2H, t, J=5.6 Hz), 5.53 (1H, s), 7.18–7.40 (12H, m), 7.66 (1H, t, J=7.4 Hz), 8.22 (1H, d, J=7.8 Hz).

Starting from this product (1.51 g, 2.46 mmol) and using the method similar to that in Example 47, the title compound (1.36 g, 95%) was obtained as an amorphous.

IR (KBr): 3700–3150, 2948, 1699, 1659, 1609, 1485 $cm^{-1}$.

$^1$H-NMR (CDCl$_3$) δ: 1.60–2.10 (6H, m), 2.26–2.46 (2H, m), 2.60–2.72 (2H, m), 2.88–3.06 (2H, m), 3.06–3.24 (2H, m), 3.68–3.80 (1H, m), 3.85 (2H, t, J=4.4 Hz), 3.93 (2H, s), 4.22–4.36 (2H, m), 4.40 (2H, t, J=4.4 Hz), 5.42 (1H, s), 6.52 (1H, bs), 7.10 (1H, d, J=8.4 Hz), 7.18–7.40 (11H, m), 7.63 (1H, ddd, J=8.4, 7.2, 1.2 Hz), 8.26 (1H, d, J=7.0 Hz).

Elemental Analysis for $C_{34}H_{39}N_3O_6$.2.4H$_2$O: Calcd. (%): C, 64.93; H,7.02; N, 6.68. Found (%): C, 64.89; H, 6.61; N, 6.45.

EXAMPLE 118

Ethyl 2-[2,4-dioxo-1-[4-(4-diphenylmethoxypiperidino)butyl]-8-methoxy-1,2,3,4-tetrahydroquinazolin-3-yl]isobutyrate hydrochloride Using the method similar to that in Example 27 and starting from ethyl 2-[1-(4-bromobutyl)-2,4-dioxo-8-methoxy-1,2,3,4-tetrahydroquinazolin-3-yl]isobutyrate (0.54 g, 1.22 mmol) obtained in Reference Example 194, a free salt of the title compound (0.69 g, 90%) was obtained as an oil.

IR (KBr): 2942, 1744, 1705, 1663, 1603 $cm^{-1}$.

$^1$H-NMR (CDCl$_3$) δ: 1.21 (3H, t, J=7.2 Hz), 1.82 (6H, s), 1.40–1.95 (8H, m), 2.04–2.17 (2H, m), 2.29–2.36 (2H, m), 2.69–2.79 (2H, m), 3.38–3.48 (1H, m), 3.90 (3H, s), 4.11–4.24 (4H, m), 5.51 (1H, s), 7.15–7.36 (12H, m, ArH), 7.73 (1H, dd, J=5.6 Hz, 4.0 Hz).

This product (0.69 g) was dissolved in ethyl acetate (3.0 ml), combined with a 4N solution of hydrogen chloride in ethyl acetate (0.35 ml) and then concentrated. The residue was dried at 50° C. in the presence of phosphorus pentaoxide to give the title compound (0.61 g, 82%) as an amorphous.

IR (KBr): 3405, 2980, 2938, 2475, 2375, 1740, 1705, 1659, 1603 $cm^{-1}$.

$^1$H-NMR (DMSO-d$_6$) δ: 1.10 (3H, t, J=7.0 Hz), 1.50–2.22 (8H, m), 1.69 (6H, s), 2.80–3.75 (7H, m), 3.95 (3H, s), 3.99–4.09 (4H, m), 5.68 (1H, d, J=10.6 Hz), 7.25–7.59 (13H, m, ArH).

Elemental Analysis for $C_{37}H_{45}N_3O_6 \cdot HCl \cdot 0.5H_2O$ Calcd. (%): C, 66.01; H, 7.04; N, 6.24. Found (%): C, 66.25; H, 7.21; N, 6.29.

EXAMPLE 119

Ethyl 2-[2,4-dioxo-1-[4-(4-diphenylmethoxypiperidino)butyl]-6-(1-pyrrolyl)-1,2,3,4-tetrahydroquinazolin-3-yl]isobutyrate hydrochloride Using the method similar to that in Example 27 and starting from ethyl 2-[1-(4-bromobutyl)-2,4-dioxo-6-(1-pyrrolyl)-1,2,3,4-tetrahydroquinazolin-3-yl]isobutyrate (0.44 g, 0.92 mmol) obtained in Reference Example 195, a free salt of the title compound (0.55 g, 90%) was obtained as an oil.

IR (KBr): 2984, 2940, 2867, 2811, 2772, 1744, 1707, 1665, 1516 cm$^{-1}$.

$^1$H-NMR (CDCl$_3$) δ: 1.24 (3H, t, J=7.1 Hz), 1.55–1.98 (8H, m), 1.85 (6H, s), 2.05–2.20 (2H, m), 2.38 (2H, t, J=6.9 Hz), 2.71–2.82 (2H, m), 3.41–3.51 (1H, m), 4.05–4.12 (2H, m), 4.19 (2H, q, J=7.1 Hz), 5.53 (1H, s), 6.37 (2H, t, J=2.2 Hz), 7.10 (2H, t, J=2.2 Hz), 7.21–7.37 (10H, m, ArH), 7.41 (1H, d, J=9.0 Hz), 7.68 (1H, dd, J=2.8 Hz, 8.8 Hz), 8.14 (1H, d, J=2.6 Hz).

This product (0.55 g) was dissolved in ethyl acetate (3.0 ml), combined with a 4N solution of hydrogen chloride in ethyl acetate (0.35 ml) and then concentrated. The residue was dried at 50° C. in the presence of phosphorus pentaoxide to give the title compound (0.48 g, 82%) as an amorphous.

IR (KBr): 3400, 2980, 2938, 2485, 2400, 1736, 1705, 1663, 1626, 1597, 1514 cm$^{-1}$.

$^1$H-NMR (DMSO-d$_6$) δ: 1.14 (3H, t, J=7.1 Hz), 1.55–2.25 (8H, m), 1.73 (6H, s), 2.80–3.75 (7H, m), 4.02–4.12 (4H, m), 5.68 (1H, d, J=10.4 Hz), 6.30 (2H, t, J=2.0 Hz), 7.20–7.45 (12H, m, ArH), 7.60 (1H, d, J=8.8 Hz), 7.96–8.04 (2H, m, ArH).

Elemental Analysis for $C_{40}H_{46}N_4O_5 \cdot HCl \cdot 0.5H_2O$: Calcd. (%): C, 67.83; H, 6.83; N, 7.91. Found (%): C, 68.08; H, 6.94; N, 7.61.

EXAMPLE 120

2-[2,4-Dioxo-1-[4-(4-diphenylmethoxypiperidino)butyl]-1,2,3,4-tetrahydroquinazolin-3-yl]isobutyric acid hydrochloride Using the method similar to that in Example 27 and starting from phenacyl 2-[1-(4-bromobutyl)-2,4-dioxo-1,2,3,4-tetrahydroquinazolin-3-yl]isobutyrate (0.54 g, 1.08 mmol) obtained in Reference Example 196, the phenacyl ester of the title compound (0.70 g, 94%) was obtained as an oil.

IR (KBr): 3061, 3029, 2942, 2867, 2811, 2774, 1752, 1705, 1661, 1609 cm$^{-1}$.

$^1$H-NMR (CDCl$_3$) δ: 1.53–2.00 (8H, m), 2.05–2.18 (2H, m), 2.33–2.40(2H, m), 1.96 (6H, s), 2.70–2.78(2H, m), 3.40–3.51 (1H, m), 4.04–4.11 (2H, m), 5.35 (2H, s), 5.52 (1H, s), 7.18–7.69 (16H, m, ArH), 7.88–7.93 (2H, m, ArH), 8.15 (1H, dd, J=1.6 Hz, 8.0 Hz).

A mixture of this product (0.62 g, 0.90 mmol), zinc powder (0.90 g), acetic acid (9.0 ml) and water (1.0 ml) was stirred vigorously at room temperature for 1 hour. The zinc powder was filtered off, and the filtrate was extracted with chloroform. The extract was washed with water, dried (MgSO$_4$), combined with a 4N solution of hydrogen chloride in ethyl acetate (0.25 ml), and then concentrated. The residue was treated with ethyl ether to give the title compound (0.48 g, 87%) as an amorphous powder.

IR (KBr): 2940, 2700, 2600, 1740, 1705, 1663, 1607 cm$^{-1}$.

$^1$H-NMR (DMSO-d$_6$) δ: 1.70 (6H, s), 1.55–2.20 (8H, m), 2.80–3.75 (7H, m), 4.02–4.11(2H, m), 5.67 (1H, s), 7.21–7.50 (12H, m, ArH), 7.72–7.80 (1H, m, ArH), 8.00 (1H, dd, J=1.3 Hz, 7.7 Hz).

Elemental Analysis for $C_{34}H_{39}N_3O_5 \cdot HCl \cdot 0.5 \cdot H_2O$: Calcd. (%): C, 66.38; H, 6.72; N, 6.83. Found (%): C, 66.45; H, 6.77; N, 6.78.

EXAMPLE 121

2-[2,4-Dioxo-1-[4-(4-diphenylmethoxypiperidino)butyl]-6-methyl-1,2,3,4-tetrahydroquinazolin-3-yl]isobutyric acid hydrochloride Using the method similar to that in Example 27 and starting from phenacyl 2-[1-(4-bromobutyl)-6-methyl-2,4-dioxo-1,2,3,4-tetrahydroquinazolin-3-yl]isobutyrate (0.77 g, 1.50 mmol) obtained in Reference Example 197, a phenacyl ester of the title compound (0.97 g, 92%) was obtained as an oil.

IR (KBr): 2942, 1752, 1705, 1661, 1624, 1595, 1510 cm$^{-1}$.

$^1$H-NMR (CDCl$_3$) δ: 1.50–2.45 (12H, m), 1.95 (6H, s), 2.38 (3H, s), 2.70–2.81 (2H, m), 3.40–3.51 (1H, m), 4.01–4.10 (2H, m), 5.34 (2H, s), 5.51 (1H, s), 7.16–7.61 (15H, m, ArH), 7.87–7.92 (3H, m, ArH).

This product (0.70 g, 1.00 mmol) was subjected to the procedure similar to that in Example 120 to give the title compound (0.51 g, 82%) as an amorphous powder.

IR (KBr): 2940, 2506, 1736, 1701, 1663, 1624, 1595, 1510 cm$^{-1}$.

$^1$H-NMR (DMSO-d$_6$) δ: 1.69 (6H, s), 1.55–2.20 (8H, m), 2.90–3.70 (7H, m), 2.36 (3H, s), 4.02–4.10 (2H, m), 5.67 (1H, s), 7.21–7.41 (11H, m, ArH), 7.58 (1H, dd, J=8.7 Hz, 1.9 Hz), 7.80 (1H, d, J=1.8 Hz).

Elemental Analysis for $C_{35}H_{41}N_3O_5 \cdot HCl$: Calcd. (%): C, 67.78; H, 6.83; N, 6.78. Found (%): C, 67.92; H, 6.70; N, 6.75.

EXAMPLE 122

2-[2,4-Dioxo-1-[4-(4-diphenylmethoxypiperidino)butyl]-8-methoxy-1,2,3,4-tetrahydroquinazolin-3-yl]isobutyric acid hydrochloride Using the method similar to that in Example 27 and starting from phenacyl 2-[1-(4-bromobutyl)-2,4-dioxo-8-methoxy-1,2,3,4-tetrahydroquinazolin-3-yl]isobutyrate (1.44 g, 2.71 mmol) obtained in Reference Example 198, a phenacyl ester of the title compound (1.74 g, 89%) was obtained as an oil.

IR (KBr): 2942, 1753, 1705, 1659, 1601 cm$^{-1}$.

$^1$H-NMR (CDCl$_3$) δ: 1.40–2.00 (8H, m), 1.94 (6H, s), 2.03–2.40 (4H, m), 2.70–2.80 (2H, m), 3.39–3.50 (1H, m), 3.90 (3H, s), 4.19–4.27 (2H, m), 5.33 (2H, s), 5.51 (1H, s), 7.15–7.61 (15H, m, ArH), 7.70–7.78 (1H, m, ArH), 7.87–7.92 (2H, m, ArH).

This product (1.44 g, 2.00 mmol) was subjected to the procedure similar to that in Example 120 to give the title compound (1.17 g, 92%) as an amorphous powder.

IR (KBr): 2942, 2598, 2512, 1736, 1705, 1659, 1601 cm$^{-1}$.

$^1$H-NMR (DMSO-d$_6$) δ: 1.40–2.25 (8H, m), 1.68 (6H, s), 2.75–3.75 (7H, m), 3.94 (3H, s), 4.00–4.10 (2H, m), 5.67 (1H, s), 7.22–7.62 (13H, m, ArH). Elemental Analysis for C$_{35}$H$_{41}$N$_3$O$_6$.HCl: Calcd. (%): C, 66.08; H, 6.65; N, 6.61. Found (%): C, 66.05; H, 6.84; N, 6.45.

EXAMPLE 123

2-[2,4-Dioxo-1-[4-(4-diphenylmethoxypiperidino)butyl]-5-fluoro-1,2,3,4-tetrahydroquinazolin-3-yl]isobutyric acid hydrochloride Using the method similar to that in Example 27 and starting from phenacyl 2-[1-(4-bromobutyl)-2,4-dioxo-5-fluoro-1,2,3,4-tetrahydroquinazolin-3-yl]isobutyrate (1.80 g, 3.47 mmol) obtained in Reference Example 199, a phenacyl ester of the title compound (1.70 g, 69%) was obtained as an oil.

IR (KBr): 2942, 2813, 1752, 1713, 1669, 1618, 1599 cm$^{-1}$.

$^1$H-NMR (CDCl$_3$) δ: 1.50–1.97 (8H, m), 1.95 (6H, s), 2.03–2.17 (2H, m), 2.32–2.39 (2H, m), 2.70–2.80 (2H, m), 3.39–3.50 (1H, m), 4.02–4.10 (2H, m), 5.36 (2H, s), 5.52 (1H, s), 6.89 (1H, dd, J=10.5 Hz, 8.35 Hz), 7.09–7.62 (15H, m, ArH), 7.88–7.93 (2H, m, ArH).

This product (1.41 g, 2.00 mmol) was subjected to the procedure similar to that in Example 120 to give the title compound (1.13 g, 91%) as an amorphous powder.

IR (KBr): 2934, 2708, 1736, 1709, 1667, 1618 cm$^{-1}$.

$^1$H-NMR (DMSO-d$_6$) δ: 1.68 (6H, s), 1.50–2.20 (8H, m), 2.80–3.73 (7H, m), 4.01–4.10 (2H, m), 5.67 (1H, d, J=7.6 Hz), 7.07 (1H, dd, J=11.0 Hz, 8.2 Hz), 7.22–7.40 (11H, m, ArH), 7.68–7.79 (1H, m, ArH).

Elemental Analysis for C$_{34}$H$_{38}$N$_3$O$_5$F.HCl: Calcd. (%): C, 65.43; H, 6.30; N, 6.73. Found (%): C, 65.07; H, 6.25; N, 6.58.

EXAMPLE 124

2-[2,4-Dioxo-1-[4-(4-diphenylmethoxypiperidino)butyl]-6-fluoro-1,2,3,4-tetrahydroquinazolin-3-yl]isobutyric acid hydrochloride Using the method similar to that in Example 27 and starting from phenacyl 2-[1-(4-bromobutyl)-2,4-dioxo-6-fluoro-1,2,3,4-tetrahydroquinazolin-3-yl]isobutyrate (1.71 g, 3.29 mmol) obtained in Reference Example 200, a phenacyl ester of the title compound (2.06 g, 89%) was obtained as an oil.

IR (KBr): 2942, 2867, 2811, 1752, 1707, 1665, 1505 cm$^{-1}$.

$^1$H-NMR (CDCl$_3$) δ: 1.55–1.98 (8H, m), 1.95 (6H, s), 2.05–2.17 (2H, m), 2.33–2.39 (2H, m), 2.70–2.80 (2H, m), 3.40–3.49 (1H, m), 4.02–4.09 (2H, m), 5.35 (2H, s), 5.52 (1H, s), 7.22–7.61 (15H, m, ArH), 7.81 (1H, dd, J=8.1 Hz, 2.7 Hz), 7.88–7.93 (2H, m, ArH).

This product (2.05 g, 2.90 mmol) was subjected to the procedure similar to that in Example 120 to give the title compound (1.60 g, 88%) as an amorphous powder.

IR (KBr): 3027, 2938, 2600, 2515, 1734, 1705, 1663, 1505 cm$^{-1}$.

$^1$H-NMR (DMSO-d$_6$) δ: 1.70 (6H, s), 1.55–2.20 (8H, m), 2.80–3.75 (7H, m), 4.02–4.10 (2H, m), 5.67 (1H, s), 7.20–7.40 (10H, m, ArH), 7.52–7.74 (3H, m, ArH).

Elemental Analysis for C$_{34}$H$_{38}$N$_3$O$_5$F.HCl: Calcd. (%): C, 65.43; H, 6.30; N, 6.73. Found (%): C, 65.21; H, 6.43; N, 6.52.

EXAMPLE 125

2-[2,4-Dioxo-1-[4-(4-diphenylmethoxypiperidino)butyl]-6,7-difluoro-1,2,3,4-tetrahydroquinazolin-3-yl]isobutyric acid hydrochloride Using the method similar to that in Example 27 and starting from phenacyl 2-[1-(4-bromobutyl)-2,4-dioxo-6,7-difluoro-1,2,3,4-tetrahydroquinazolin-3-yl]isobutyrate (1.94 g, 3.61 mmol) obtained in Reference Example 201, a phenacyl ester of the title compound (0.93 g, 36%) was obtained as an oil.

IR (KBr): 2942, 1752, 1709, 1667, 1524 cm$^{-1}$.

$^1$H-NMR (CDCl$_3$) δ: 1.55–2.00 (8H, m), 1.94 (6H, s), 2.05–2.21 (2H, m), 2.34–2.41 (2H, m), 2.70–2.80 (2H, m), 3.41–3.52 (1H, m), 3.98–4.05 (2H, m), 5.35 (2H, s), 5.52 (1H, s), 7.21–7.63 (15H, m, ArH), 7.88–7.97 (2H, m, ArH).

This product (0.92 g, 1.27 mmol) was subjected to the procedure similar to that in Example 120 to give the title compound (0.70 g, 86%) as an amorphous powder.

IR (KBr): 3063, 2934, 2614, 2514, 1740, 1709, 1665, 1636, 1522 cm$^{-1}$.

$^1$H-NMR (DMSO-d$_6$) δ: 1.69 (6H, s), 1.50–2.20 (8H, m), 2.80–3.75 (7H, m), 4.00–4.10 (2H, m), 5.68 (1H, s), 7.24–7.40 (10H, m, ArH), 7.69–7.78 (1H, m, ArH), 7.91–8.00 (1H, m, ArH).

Elemental Analysis for C$_{34}$H$_{37}$N$_3$O$_5$F$_2$.HCl: Found (%): C, 63.60; H, 5.96; N, 6.54. Calcd. (%): C, 63.45; H, 6.01; N, 6.31.

EXAMPLE 126

2-[6-Chloro-2,4-dioxo-1-[4-(4-diphenylmethoxypiperidino)butyl]-1,2,3,4-tetrahydroquinazolin-3-yl]isobutyric acid hydrochloride Using the method similar to that in Example 27 and starting from phenacyl 2-[6-chloro-1-(4-bromobutyl)-2,4-dioxo-1,2,3,4-tetrahydroquinazolin-3-yl]isobutyrate (1.07 g, 2.00 mmol) obtained in Reference Example 202, a phenacyl ester of the title compound (1.26 g, 87%) was obtained as an oil.

IR (KBr): 2942, 1752, 1707, 1667, 1609 cm$^{-1}$.

$^1$H-NMR (CDCl$_3$) δ: 1.55–2.25 (10H, m), 1.95 (6H, s), 2.35–2.42 (2H, m), 2.71–2.82 (2H, m), 3.40–3.51 (1H, m), 4.01–4.09 (2H, m), 5.35 (2H, s), 5.52 (1H, s), 7.24–7.62 (15H, m, ArH), 7.88–7.93 (2H, m, ArH), 8.10 (1H, d, J=2.6 Hz).

This product (1.03 g, 1.43 mmol) was subjected to the procedure similar to that in Example 120 to give the title compound (0.82 g, 90%) as an amorphous powder.

$^1$H-NMR (DMSO-d$_6$) δ: 1.50–2.22 (8H, m), 1.68 (6H, s), 2.75–3.67(7H, m), 4.03–4.12(2H, m), 5.67(1H, s), 7.21–7.50 (10H, m, ArH), 7.53 (1H, d, J=8.8 Hz), 7.78 (1H, dd, J=8.9 Hz, 2.5 Hz), 7.93 (1H, d, J=2.4 Hz).

Elemental Analysis for C$_{34}$H$_{38}$N$_3$O$_5$Cl.HCl: Calcd. (%): C, 63.75; H, 6.14; N, 6.56. Found (%): C, 63.58; H, 6.38; N, 6.47.

EXAMPLE 127

2-[7-Chloro-2,4-dioxo-1-[4-(4-diphenylmethoxypiperidino)butyl]-1,2,3,4-tetrahydroquinazolin-3-yl]isobutyric acid hydrochloride Using the method similar to that in Example 27 and starting from phenacyl 2-[7-chloro-1-(4-bromobutyl)-2,4- dioxo-1,2,3,4-tetrahydroquinazolin-3-yl]isobutyrate (1.07 g, 2.00 mmol) obtained in Reference Example 203, a phenacyl ester of the title compound (1.15 g, 80%) was obtained as an oil.

IR (KBr): 2992, 2942, 1750, 1709, 1667, 1605 cm$^{-1}$.

$^1$H-NMR (CDCl$_3$) δ: 1.60–2.25 (10H, m), 1.95 (6H, s), 2.35–2.42 (2H, m), 2.71–2.81 (2H, m), 3.40–3.52 (1H, m), 4.02–4.10 (2H, m), 5.35 (2H, s), 5.51 (1H, s), 7.15–7.61 (15H, m, ArH), 7.88–7.92 (2H, m, ArH), 8.06 (1H, d, J=8.4 Hz).

This product (0.93 g, 1.29 mmol) was subjected to the procedure similar to that in Example 120 to give the title compound (0.76 g, 92%) as an amorphous powder.

IR (KBr): 2938, 2510, 1736, 1709, 1665, 1605, 1590 cm$^{-1}$.

$^1$H-NMR (DMSO-d$_6$) δ: 1.50–2.15 (8H, m), 1.68 (6H, s), 2.80–3.70 (7H, m), 4.00–4.12 (2H, m), 5.67 (1H, s), 7.20–7.42 (11H, m, ArH), 7.59 (1H, d, J=1.4 Hz), 7.98 (1H, d, J=8.4 Hz).

Elemental Analysis for C$_{34}$H$_{38}$N$_3$O$_5$Cl.HCl: Calcd. (%): C, 63.75; H, 6.14; N, 6.56. Found (%): C, 64.14; H, 6.22; N, 6.16.

EXAMPLE 128

2-[2,4-dioxo-1-[4-(4-diphenylmethoxypiperidino) butyl]-1,2,3,4-tetrahydrobenzo[g]quinazolin-3-yl] isobutyric acid hydrochloride Using the method similar to that in Example 27 and starting from phenacyl 2-[1-(4-bromobutyl)-2,4-dioxo-1,2,3,4-tetrahydrobenzo[g]quinazolin-3-yl]isobutyrate (0.93 g, 1.69 mmol) obtained in Reference Example 204, a phenacyl ester of the title compound (1.01 g, 81%) was obtained as an oil.

IR (KBr): 2942, 1752, 1705, 1663, 1632, 1603 cm$^{-1}$.

$^1$H-NMR (CDCl$_3$) δ: 1.50–2.00 (8H, m), 2.00 (6H, s), 2.05–2.18 (2H, m), 2.39 (2H, t, J=6.8 Hz), 2.72–2.81 (2H, m), 3.40–3.50 (1H, m), 4.14–4.22 (2H, m), 5.36 (2H, s), 5.52 (1H, s), 7.21–7.60 (16H, m, ArH), 7.83–7.96 (4H, m, ArH), 8.74 (1H, s, ArH).

This product (1.00 g, 1.36 mmol) was subjected to the procedure similar to that in Example 120 to give the title compound (0.80 g, 90%) as an amorphous powder.

IR (KBr): 2940, 2707, 1740, 1701, 1661, 1632, 1603, 1518 cm$^{-1}$.

$^1$H-NMR (DMSO-d$_6$) δ: 1.74 (6H, s), 1.50–2.20 (8H, m), 2.80–3.72 (7H, m), 4.13–4.22 (2H, m), 5.67 (1H, s), 7.21–7.40 (10H, m, ArH), 7.47–7.55 (1H, m, ArH), 7.63–7.70 (1H, m, ArH), 7.90 (1H, s, ArH), 8.01–8.14 (2H, m, ArH), 8.70 (1H, s, ArH).

Elemental Analysis for C$_{38}$H$_{41}$N$_3$O$_5$.HCl: Calcd. (%): C, 69.55; H, 6.45; N, 6.40. Found (%): C, 69.25; H, 6.41; N, 6.49.

EXAMPLE 129

2-[6-Chloro-2,4-dioxo-1-[4-[4-(4-fluorophenyl)-1-piperazinyl]butyl]-1,2,3,4-tetrahydroquinazolin-3-yl] isobutyric acid hydrochloride Using the method similar to that in Example 27 and starting from phenacyl 2-[6-chloro-1-(4-bromobutyl)-2,4-dioxo-1,2,3,4-tetrahydroquinazolin-3-yl]isobutyrate (1.02 g, 1.90 mmol) obtained in Reference Example 202, a phenacyl ester of the title compound (0.93 g, 76%) was obtained as an oil.

IR (KBr): 2944, 2818, 1752, 1707, 1665, 1609, 1508 cm$^{-1}$.

$^1$H-NMR (CDCl$_3$) δ: 1.55–1.85 (4H, m), 1.96 (6H, s), 2.43–2.50 (2H, m), 2.59–2.64 (4H, m), 3.10–3.14 (4H, m), 4.05–4.13 (2H, m), 5.36 (2H, s), 6.83–7.01 (15H, m, ArH), 7.23 (1H, d, J=9.0 Hz), 7.43–7.62 (4H, m, ArH), 7.88–7.93 (2H, m, ArH), 8.11 (1H, d, J=2.4 Hz).

This product (0.65 g, 1.00 mmol) was subjected to the procedure similar to that in Example 120 to give the title compound (0.46 g, 81%) as an amorphous powder.

$^1$H-NMR (DMSO-d$_6$) δ: 1.55–1.93 (4H, m), 1.71 (6H, s), 3.00–3.22 (6H, m), 3.45–3.75 (4H, m), 4.06–4.12 (2H, m), 6.99–7.14 (4H, m, ArH), 7.57 (1H, d, J=9.0 Hz), 7.81 (1H, dd, J=9.0 Hz, 2.6 Hz), 7.94 (1H, d, J=2.6 Hz).

Elemental Analysis for C$_{26}$H$_{30}$N$_4$O$_4$FCl.HCl.H$_2$O: Calcd. (%): C, 54.65; H, 5.82; N, 9.80. Found (%): C, 54.62; H, 5.85; N, 9.84.

EXAMPLE 130

2-[7-Chloro-2,4-dioxo-1-[4-[4-(4-fluorophenyl)-1-piperazinyl]butyl]-1,2,3,4-tetrahydroquinazolin-3-yl] isobutyric acid hydrochloride Using the method similar to that in Example 27 and starting from phenacyl 2-[7-chloro-1-(4-bromobutyl)-2,4-dioxo-1,2,3,4-tetrahydroquinazolin-3-yl]isobutyrate (0.70 g, 1.31 mmol) obtained in Reference Example 203, a phenacyl ester of the title compound (0.54 g, 63%) was obtained as an oil.

IR (KBr): 2942, 2820, 1752, 1709, 1667, 1605, 1580, 1510 cm$^{-1}$.

$^1$H-NMR (CDCl$_3$) δ: 1.50–1.90 (4H, m), 1.96 (6H, s), 2.48 (2H, t, J=6.2 Hz), 2.60–2.65(4H, m), 3.13–3.17(4H, m), 4.05–4.13 (2H, m), 5.36 (2H, s), 6.85–7.01 (4H, m, ArH), 7.16–7.27 (2H, m), 7.42–7.62 (3H, m, ArH), 7.88–7.93 (2H, m, ArH), 8.07 (1H, d, J=8.4 Hz).

This product (0.53 g, 0.82 mmol) was subjected to the procedure similar to that in Example 120 to give the title compound (0.46 g, 97%) as an amorphous powder.

IR (KBr): 2990, 2942, 2510, 2450, 1734, 1709, 1665, 1605, 1510 cm$^{-1}$.

$^1$H-NMR (DMSO-d$_6$) δ: 1.58–1.95 (4H, m), 1.71 (6H, s), 3.03–3.26 (6H, m), 3.48–3.80 (4H, m), 4.07–4.14 (2H, m), 7.00–7.15 (4H, m, ArH), 7.34 (1H, dd, J=1.6 Hz, 8.4 Hz), 7.63 (1H, d, J=1.6 Hz), 8.00 (1H, d, J=8.4 Hz).

Elemental Analysis for C$_{26}$H$_{30}$N$_4$O$_4$FCl.HCl.1.5H$_2$O: Calcd. (%): C, 53.80; H, 5.90; N, 9.65. Found (%): C, 54.22; H, 5.78; N, 9.82.

EXAMPLE 131

2-[2,4-Dioxo-1-[4-(4-diphenylmethyl-1-piperazinyl) butyl]-6-methyl-1,2,3,4-tetrahydroquinazolin-3-yl] isobutyric acid hydrochloride Using the method similar to that in Example 27 and starting from phenacyl 2-[1-(4-bromobutyl)-6-methyl-2,4-dioxo-1,2,3,4-tetrahydroquinazolin-3-yl]isobutyrate (0.55 g, 1.07 mmol) obtained in Reference Example 197, a phenacyl ester of the title compound (0.63 g, 86%) was obtained as an oil.

IR (KBr): 3027, 2942, 2876, 2811, 2774, 1752, 1705, 1661, 1624, 1597, 1508 cm$^{-1}$.

$^1$H-NMR (CDCl$_3$) δ: 1.50–1.80 (4H, m), 1.95 (6H, s), 2.25–2.60 (10H, m), 4.00–4.07 (2H, m), 4.21 (1H, s), 5.34 (2H, s), 7.11–7.63 (15H, m, ArH), 7.88–7.94 (3H, m, ArH).

This product (0.57 g, 0.83 mmol) was subjected to the procedure similar to that in Example 120 to give the title compound (0.49 g, 95%) as an amorphous powder.

IR (KBr): 3400, 2940, 2580, 1730, 1701, 1655, 1624, 1595, 1508 cm$^{-1}$.

$^1$H-NMR (DMSO-d$_6$) δ: 1.69 (6H, s), 1.50–1.85 (4H, m), 2.37 (3H, s), 2.70–3.90 (11H, m, ArH), 4.00–4.12 (2H, m), 7.22–8.00 (13H, m, ArH).

Elemental Analysis for $C_{34}H_{40}N_4O_4 \cdot HCl \cdot H_2O$: Calcd. (%): C, 65.53; H, 6.95; N, 8.99. Found (%): C, 65.32; H, 7.13; N, 8.72.

EXAMPLE 132

2,4-Dioxo-1-[4-[4-(3-indolyl)piperidino]butyl]-1,2,3, 4-tetrahydroquinazoline hydrochloride Using the method similar to that in Example 2 (Method 4) and 4-(3-indolyl)piperidine (445 mg, 2.22 mmol) instead of 4-diphenylmethoxypiperidine, and starting from 1-(4-bromobutyl)-2,4-dioxo-1,2,3,4-tetrahydroquinazoline (600 mg, 2.02 mmol) obtained in Reference Example 86, a free salt of the title compound (617 mg, 73%) was synthesized. Recrystallization from ethyl acetate-methanol yielded a colorless crystal having a melting point of 146 to 147° C.

IR (KBr): 1695, 1684, 1608, 1486 cm$^{-1}$.

$^1$H-NMR (CDCl$_3$) δ: 1.50–1.98 (6H, m), 2.02–2.24 (4H, m), 2.48 (2H, t, J=6.8 Hz), 2.79–2.98 (2H, m), 3.02–3.16 (2H, m), 4.16 (2H, t, J=7.8 Hz), 6.99 (1H, s), 7.05–7.30 (3H, m), 7.34–7.44 (2H, m), 7.60–7.75 (2H, m), 7.98 (1H, bs), 8.21 (1H, d, J=7.2 Hz).

Elemental Analysis for $C_{25}H_{28}N_4O_2 \cdot 0.5H_2O$: Calcd. (%): C, 70.56; H, 6.87; N, 13.17. Found (%): C, 70.48; H, 7.01; N, 12.87.

This product (500 mg, 1.20 mmol) was dissolved in ethyl acetate (10.0 ml) and combined with a 4N solution of hydrogen chloride in ethyl acetate (1.00 ml) to give the title compound (609 mg, about 100%). Recrystallization from ethyl acetate yielded a colorless crystal having a melting point of 250 to 252° C.

IR (KBr): 3606, 3317, 3037, 2655, 2800–2200, 1697, 1675, 1608, 1486 cm$^{-1}$.

$^1$H-NMR (CDCl$_3$) δ: 1.80–2.28 (6H, m), 2.40–2.70 (4H, m), 2.80–3.24 (5H, m), 3.60–3.75 (2H, m), 4.08–4.25 (2H, m), 7.02–7.46 (5H, m), 7.60–7.78 (2H, m), 8.19 (1H, d, J=8.4 Hz), 9.65 (1H, bs), 10.60 (1H, bs), 12.06 (1H, bs).

Elemental Analysis for $C_{25}H_{28}N_4O_2 \cdot HCl \cdot 0.6H_2O$: Calcd. (%): C, 64.74; H, 6.56; N, 12.08. Found (%): C, 64.68; H, 6.53; N, 11.83.

EXAMPLE 133

3-[2-(2-Cyanomethoxy)ethyl]-2,4-dioxo-1-[4-(4-diphenylmethoxypiperidino)butyl]-1,2,3,4-tetrahydroquinazoline 2,4-Dioxo-1-[4-(4-diphenylmethoxypiperidino)butyl]-1, 2,3,4-tetrahydroquinazoline (0.72 g, 1.5 mmol) was dissolved in DMF (20 ml) and combined with NaH (60% in oil, 80 mg, 2.0 mmol). After stirring for 10 minutes, (2-chloroethoxy)acetonitrile (0.27 g, 2.3 mmol) was added and the mixture was stirred at 90° C. overnight. After cooling, the reaction mixture was combined with water and extracted with ethyl ether. After the extract was washed with water and dried (Na$_2$SO$_4$), the solvent was distilled off under reduced pressure. The residue was subjected to a column chromatography on a silica gel eluting with chloroform-methanol (20:1, v/v) to give the title compound (0.78 g, 92%) as an oil.

IR (KBr): 1702, 1660, 1610, 1484, 1401 cm$^{-1}$.

$^1$H-NMR (CDCl$_3$) δ: 1.54–2.25 (10H, m), 2.40(2H, t, J=6.8 Hz), 2.69–2.86 (2H, m), 3.40–3.56 (1H, m), 3.93 (2H, t, J=5.4 Hz), 4.14 (2H, t, J=7.2 Hz), 4.32 (2H, s), 4.37 (2H, t, J=5.4 Hz), 5.53 (1H, s), 7.19–7.41 (12H, m), 7.68 (1H, dt, J=1.8 7.4 Hz), 8.22 (1H, dd, J=1.8, 7.4 Hz).

EXAMPLE 134

2-[2,4-Dioxo-1-[4-(4-diphenylmethoxypiperidino) butyl]-1,2,3,4-tetrahydroquinazolin-3-yl] ethoxyacetamide hydrochloride A mixture of 3-[2-(2-cyanomethoxy)ethyl]-2,4-dioxo-1-[4-(4-diphenylmethoxypiperidino)butyl]-1,2,3,4-tetrahydroquinazoline (1.13 g, 2.0 mmol), potassium hydroxide (0.30 g) and ethanol (30 ml) was heated under reflux for 8 hours. After cooling, the reaction mixture was made acidic by adding a concentrated hydrochloric acid, and extracted with chloroform. After the extract was washed with water and dried (Na$_2$SO$_4$), the solvent was distilled off under reduced pressure. The residue was subjected to a column chromatography on a silica gel eluting with chloroform-methanol (20:1, v/v) to give a free salt of the title compound (0.53 g, 45%) as an oil.

IR (KBr): 3332, 3278, 1700, 1652, 1608, 1484, 1455, 1423, 1402 cm$^{-1}$.

$^1$H-NMR (CDCl$_3$) δ: 1.56–2.04 (8H, m), 2.11–2.31 (2H, m), 2.41 (2H, t, J=6.6 Hz), 2.69–2.90 (2H, m), 3.42–3.61 (1H, m), 3.82 (2H, t, J=5.2 Hz), 3.94 (2H, s), 4.14 (2H, t, J=6.4 Hz), 4.38 (2H, t, J=5.2 Hz), 5.53 (1H, s), 5.91 (1H, br), 6.87 (1H, br), 7.16–7.41 (12H, m), 7.68 (1H, dt, J=7.9, 1.6 Hz), 8.22 (1H, dd, J=8.0, 1.6 Hz).

This product was dissolved in methanol (8 ml), combined with a 4N solution of hydrogen chloride in ethyl acetate (2.0 ml) and concentrated to give the title compound (0.35 g, 28%) as an amorphous.

Elemental Analysis for $C_{34}H_{40}N_4O_5 \cdot HCl \cdot 0.5H_2O$: Calcd. (%): C, 64.80; H, 6.72; N, 8.89. Found (%): C, 64.63; H, 6.60; N, 8.84.

EXAMPLE 135

Ethyl 5-[2,4-dioxo-1-[4-(4-diphenylmethoxypiperidino)butyl]-1,2,3,4-tetrahydrothieno[3,2-d]pyrimidin-3-yl]valerate hydrochloride Using the method similar to that in Example 27 and starting from ethyl 5-[1-(4-bromobutyl)-2,4-dioxo-1,2,3,4-tetrahydrothieno[3,2-d]pyrimidin-3-yl]valerate (2.33 g, 5.40 mmol) obtained in Reference Example 209, a free salt of the title compound (3.10 g, 93%) was obtained as an oil.

IR (KBr): 2944, 2867, 2811, 2774, 1732, 1698, 1653, 1570 cm$^{-1}$.

$^1$H-NMR (CDCl$_3$) δ: 1.24 (3H, t, J=7.2 Hz), 1.52–1.95 (12H, m), 2.04–2.16 (2H, m), 2.32–2.39 (4H, m), 2.68–2.79 (2H, m), 3.39–3.50 (1H, m), 4.00–4.18 (6H, m), 5.52 (1H, s), 7.02 (1H, d, J=5.2 Hz), 7.21–7.38 (10H, m, ArH), 7.70 (1H, d, J=5.4 Hz).

This product (0.56 g) was dissolved in ethyl acetate (5.0 ml), combined with a 4N solution of hydrogen chloride in ethyl acetate (0.30 ml) and concentrated. The residue was dried in the presence of phosphorus pentaoxide at 50° C. to give the title compound (0.45 g, 75%) as an amorphous.

IR (KBr): 3400, 3061, 3029, 2951, 2870, 2480, 1730, 1698, 1653, 1568 cm$^{-1}$.

$^1$H-NMR (DMSO-d$_6$) δ: 1.16 (3H, t, J=7.2 Hz), 1.40–2.21 (12H, m), 2.31 (2H, t, J=6.7 Hz), 2.70–3.74 (7H, m), 3.86–3.93 (2H, m), 3.98–4.09 (4H, m), 5.67 (1H, d, J=9.8 Hz), 7.21–7.41 (11H, m), 8.18 (1H, d, J=5.4 Hz).

Elemental Analysis for $C_{35}H_{43}N_3O_5S \cdot HCl \cdot 0.5H_2O$: Calcd. (%): C, 63.38; H, 6.84; N, 6.34. Found (%): C, 63.75; H, 6.83; N, 6.51.

EXAMPLE 136

5-[2,4-Dioxo-1-[4-(4-diphenylmethoxypiperidino)butyl]-1,2,3,4-tetrahydrothieno[3,2-d]pyrimidin-3-yl]valeric acid hydrochloride A mixture of ethyl 5-[2,4-dioxo-1-[4-(4-diphenylmethoxypiperidino)butyl]-1,2,3,4-tetrahydrothieno[3,2-d]pyrimidin-3-yl]valerate (2.54 g, 4.11 mmol) obtained in Example 135, 2N sodium hydroxide (4.0 ml), tetrahydrofuran (6 ml) and ethanol (6.0 ml) was stirred at room temperature for 6 hours, neutralized with 2N hydrochloric acid, and then extracted with chloroform. The extract was washed with water, dried (MgSO$_4$) and then concentrated. The residue was treated with ethyl ether to give the title compound (2.27 g, 86%) as an amorphous powder.

IR (KBr): 2955, 2874, 2604, 2537, 1720, 1698, 1649, 1568 cm$^1$.

$^1$H-NMR (DMSO-d$_6$) δ: 1.45–2.35 (14H, m), 2.80–3.75 (7H, m), 3.87–3.94 (2H, m), 4.02–4.08 (2H, m), 5.67 (1H, s), 7.21–7.41 (11H, m), 8.17 (1H, d, J=5.2 Hz).

Elemental Analysis for $C_{33}H_{39}N_3O_5S \cdot HCl \cdot H_2O$: Calcd. (%): C, 61.52; H, 6.57; N, 6.52. Found (%): C, 61.60; H, 6.39; N, 6.38.

EXAMPLE 137

Ethyl 2-[2,4-dioxo-1-[4-(4-diphenylmethoxypiperidino)butyl]-1,2,3,4-tetrahydrothieno[3,2-d]pyrimidin-3-yl]isobutyrate hydrochloride Using the method similar to that in Example 27 and starting from ethyl 2-[1-(4-bromobutyl)-2,4-dioxo-1,2,3,4-tetrahydrothieno[3,2-d]pyrimidin-3-yl]isobutyrate (1.08 g, 2.59 mmol) obtained in Reference Example 210, a free salt of the title compound (1.28 g, 82%) was obtained as an oil.

IR (KBr): 2942, 1740, 1701, 1659, 1574 cm$^{-1}$.

$^1$H-NMR (CDCl$_3$) δ: 1.24 (3H, t, J=7.2 Hz), 1.50–1.95 (8H, m), 1.83 (6H, s), 2.04–2.16 (2H, m), 2.34 (2H, t, J=7.1 Hz), 2.68–2.78 (2H, m), 3.39–3.50 (1H, m), 3.94–4.01 (2H, m), 4.18 (2H, q, J=7.2 Hz), 5.52 (1H, s), 6.98 (1H, d, J=5.4 Hz), 7.21–7.37 (10H, m, ArH), 7.67 (1H, d, J=5.2 Hz).

This product (1.06 g) was dissolved in ethyl acetate (5.0 ml), combined with a 4N solution of hydrogen chloride in ethyl acetate (0.50 ml) and concentrated. The residue was dried in the presence of phosphorus pentaoxide at 50° C. to give the title compound (1.03 g, 89%) as an amorphous.

IR (KBr): 3400, 2984, 2938, 2500, 1738, 1698, 1655, 1574 cm$^{-1}$.

$^1$H-NMR (DMSO-d$_6$) δ: 1.13 (3H, t, J=7.2 Hz), 1.70 (6H, s), 1.55–2.20 (8H, m), 2.80–3.75 (7H, m), 3.95–4.11 (4H, m), 5.67 (1H, d, J=10.8 Hz), 7.20–7.41 (11H, m), 8.17 (1H, d, J=5.2 Hz).

Elemental Analysis for $C_{34}H_{41}N_3O_5S \cdot HCl \cdot H_2O$: Calcd. (%): C, 62.04; H, 6.74; N, 6.38. Found (%): C, 61.76; H, 6.53; N, 6.26.

Experiment 1

Effect on Histamine-induced Dermal Vascular Hyperpermeability in Guinea Pigs

Male Hartley guinea pigs (weighing about 500 g) were used. After clipping hairs on a dorsal region using an electric shaver under ether anesthesia, 1 ml of 2.5% Pontamin sky blue solution was given intravenous, and immediately after this, each 0.1 ml of 3 μg/ml of histamine solution was given intradermally to each of the two sites located right and left side on the dorsal region. After 30 minutes, the animal was hit on its head to make it unconscious, and cut at its neck to sacrifice by exsanguination. The dorsal skin was peeled and examined for the long and short diameters (mm) of each blue spot which were then multiplied to give a product, which was averaged to give a vascular permeability index. Each substance was suspended in 5% gum arabic solution, and given orally in the volume of 0.2 ml/100 g body weight 1 hour before histamine administration. Control animals received the same volume of 5% gum arabic solution. A % inhibition of this reaction was calculated according to [Equation 1].

% Inhibition of histamine-induced dermal vascular hyperpermeability=100×(1-vascular permeability index in treatment group/ vascular permeability index in control group)   [Equation 1]

The results are shown in [Table 1].

TABLE 1

Effect of test substance on histamine-induced dermal vascular permeability

| Compound of Example | Inhibition of histamine-induced dermal vascular hyperpermeability (%) | 3 mg/kg oral administration |
|---|---|---|
| 2 | 88 | |
| 8 | 92 | |
| 12 | 80 | |
| 17 | 91 | |
| 27 | 94 | |
| 30 | 88 | |
| 33 | 88 | |
| 35 | 87 | |
| 40 | 90 | |
| 52 | 88 | |
| 53 | 90 | |
| 60 | 93 | |
| 93 | 84 | |
| 94 | 83 | |
| 95 | 85 | |
| 120 | 86 | |
| 124 | 90 | |
| 125 | 81 | |

Experiment 2

1) Guinea-pig Eosinophil Preparation

Male Hartley guinea-pigs received 2 ml of equine serum (Bio-Whittaker, Inc) intraperitoneally once a week for successive 8 weeks. 48 hours after the last administration, 75 ml of physiological saline was injected into the peritoneal cavity, and the fluid was recovered and centrifuged at 400 G for 5 minutes. The pellet thus obtained was suspended in 5 ml of Percoll solution (specific gravity d=1.07) and overlaid on Percoll discontinuous gradient (specific gravity d=1.112, 5 ml; d=1.095, 10 ml; d=1.090, 10 ml; d=1.085, 5 ml) and centrifuged at 1000 G for 25 minutes (20° C.). The cell layer formed at the interface between d=1.112 and 1.095 was isolated. Erythrocytes in the isolated cell pellet, if any, were removed by hypotonic treatment (suspended in water for 30 seconds).

Washing three times with Hanks' solution (Hanks-Hepes) containing 10 mM Hepes (DOJIN KAGAKU) followed by suspending in Hanks-Hepes solution (Hanks-Hepes-HAS) containing human serum albumin (WAKO PURE CHEMICAL INDUSTRIES, LTD. or Sigma) yielded a $5.56 \times 10^6$ cells/ml preparation. The purity of eosinophile was 90%, with the viability being 98% or higher.

2) Chemotaxis Inhibition Assay

600 μl of LTB4 suspended in Hanks-Hepes-HSA (final concentration of $10^{-8}$ M, Cascade Biochemical Ltd.) was placed in the lower compartment of a 24-well plate and kept at 37° C. for 30 minutes in a $CO_2$ gas incubator. After mounting a Chemotaxicell (polycarbonate membrane, pore size 3 μm, thickness 10 μm), which served as an upper compartment, on the 24-well plate described above, 200 μl of eosinophil suspension ($5 \times 10^6$ cells/ml), which had been incubated at 37° C. for 15 minutes in a thermostat chamber, was added to the upper compartment. After allowing to react for 2 hours in the $CO_2$ gas incubator, the Chemotaxicell was removed, and 60 μl of 2% (w/v) EDTA solution in physiological saline was added to the lower compartment. After cooling on ice, the cells which underwent the chemotaxis into the lower compartment were counted using a blood cell counter (Coulter Counter (trade name)). In the procedure described above, the test substance was dissolved in N,N-dimethylformamide (DMF) and added to the upper and lower compartments at the final concentration of $10^{-5}$ M.

% Chemotaxis inhibition=chemotactic cell count in treatment group/(1-chemotactic cell count in treatment group)×100     [Equation 2]

The % inhibition of the $LTB_4$-induced chemotaxis by each test substance ($1 \times 10^{-5}$ M) was determined. The results are shown in [Table 2].

TABLE 2

Effect on $LTB_4$-induced chemotaxis in guinea-pig eosinophils

| Compound of Example | Inhibition (%) |
|---|---|
| 2 | 91 |
| 6 | 67 |
| 10 | 50 |
| 12 | 66 |
| 13 | 66 |
| 22 | 72 |
| 26 | 50 |
| 27 | 52 |
| 30 | 77 |
| 33 | 54 |
| 46 | 52 |
| 55 | 64 |
| 56 | 73 |
| 58 | 84 |
| 60 | 65 |
| 69 | 96 |
| 86 | 55 |
| 93 | 62 |
| 98 | 50 |
| 97 | 62 |
| 101 | 50 |
| 109 | 55 |
| 110 | 122 |
| 111 | 80 |
| 114 | 54 |
| 115 | 56 |
| 116 | 52 |

| Formulation Example 1 | |
|---|---|
| (1) Compound of Example 2 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 2, 60.0 mg of lactose and 35.0 mg of corn starch was granulated with 0.03 ml of a 10% aqueous solution of gelatin (3.0 mg as gelatin) through a 1 mm mesh sieve, dried at 40° C. and then sieved again. The granule thus obtained was mixed with 2.0 mg of magnesium stearate and compressed. A core of the tablet thus obtained was sugar-coated with an aqueous suspension containing sucrose, titanium dioxide, talc and gum arabic. A tablet covered with the coating was imparted with a gloss using beeswax to obtain a coated tablet.

FORMULATION EXAMPLE 2

A coated tablet was obtained similarly as in Formulation Example 1 using the compound obtained in Example 60.

FORMULATION EXAMPLE 3

A coated tablet was obtained similarly as in Formulation Example 1 using the compound obtained in Example 120.

FORMULATION EXAMPLE 4

A coated tablet was obtained similarly as in Formulation Example 1 using the compound obtained in Example 124.

| Formulation Example 5 | |
|---|---|
| (1) Compound of Example 2 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 2 and 3.0 mg of magnesium stearate was granulated with 0.07 ml of an aqueous solution of the soluble starch (7.0 mg as soluble starch), dried, and then mixed with 70.0 mg of lactose and 50.0 mg of corn starch. The mixture was compressed to obtain a tablet.

FORMULATION EXAMPLE 6

A tablet was obtained similarly as in Formulation Example 5 using the compound obtained in Example 60.

FORMULATION EXAMPLE 7

A tablet was obtained similarly as in Formulation Example 5 using the compound obtained in Example 120.

FORMULATION EXAMPLE 8

A tablet was obtained similarly as in Formulation Example 5 using the compound obtained in Example 124.

| Formulation Example 9 | |
|---|---|
| (1) Compound of Example 2 | 5.0 mg |
| (2) Sodium chloride | 20.0 mg |
| (3) Distilled water | to 2 ml in total volume |

5.0 mg of the compound obtained in Example 2 and 20.0 mg of sodium chloride were dissolved in distilled water and the total volume was brought to 2.0 ml with water. The solution was filtered, and filled aseptically into a 2 ml ampule. After sterilizing the ampule followed by sealing, a solution for injection was obtained.

FORMULATION EXAMPLE 10

A tablet was obtained similarly as in Formulation Example 9 using the compound obtained in Example 60.

FORMULATION EXAMPLE 11

A tablet was obtained similarly as in Formulation Example 9 using the compound obtained in Example 120.

FORMULATION EXAMPLE 12

A tablet was obtained similarly as in Formulation Example 9 using the compound obtained in Example 124.

INDUSTRIAL APPLICABILITY

An inventive compound (I) or its salt has excellent anti-allergic action, anti-histaminic action, anti-inflammatory action, eosinophil chemotaxis-inhibiting action and the like, and is useful as a prophylactic and therapeutic agent against asthma, allergic rhinitis, atopic dermatitis, allergic conjunctivitis, urticaria and the like.

What is claimed is:

1. A compound represented by the formula:

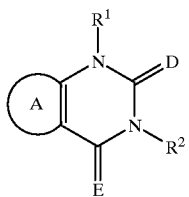

wherein
ring A is a $C_6$ aryl ring optionally having substituents selected from the group consisting of
(i) a halogen atom,
(ii) a nitro group,
(iii) a $C_{1-6}$ alkyl group optionally having carboxyl or $C_{1-6}$ alkoxy-carbonyl,
(iv) a $C_{1-6}$ alkoxy group
(v) a hydroxy group,
(vi) an amino group,
(vii) a mono- or di-$C_{1-6}$ alkylamino group,
(viii) a carboxyl group,
(ix) a $C_{1-6}$ alkoxy-carbonyl group,
(x) a 5- or 6-membered heterocyclic group which contains one or two kinds of from 1 to 4 hetero atoms selected from a nitrogen atom, an oxygen atom and a sulfur atom in addition to a carbon atom,
(xi) a $C_{1-6}$ alkylsulfonamide,
(xii) a carboxy-$C_{1-6}$ alkyl-carbonyl-amino group,
(xiii) a $C_{1-6}$ alkoxy-carbonyl-$C_{1-6}$ alkyl-carbonyl-amino group,
(xiv) a $C_{1-6}$ alkyl-carbonyl-oxy-$C_{1-6}$ alkyl-carbonyl-amino group, and
(xv) a $C_{6-14}$ aryl-$C_{2-6}$ alkenyl-carbonylamido group which may be substituted by hydroxy and/or $C_{1-6}$ alkoxy;

D and E are each an oxygen atom;
$R^1$ is a group represented by the formula:

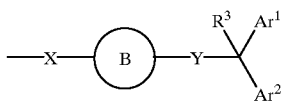

wherein $Ar^1$ and $Ar^2$ are each a phenyl group,
ring B is

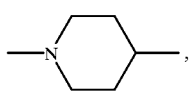

X is a $C_{1-6}$ alkylene group
Y is an oxygen atom, and
$R^3$ is a hydrogen atom, or a hydroxy group; and $R^2$ is
(1) a hydrogen atom,
(2) a cyano group,
(3) a $C_{1-16}$ alkyl group optionally having substituents selected from the group consisting of
(i) a halogen atom,
(ii) a carboxyl group,
(iii) a $C_{1-6}$ alkoxy-carbonyl group,
(iv) a 5- to 6-membered nitrogen-containing heterocyclic group,
(v) a carbamoyl group optionally having substituents selected from $C_{7-15}$ aralkyl, carboxyl-$C_{1-6}$ alkyl and $C_{1-6}$ alkoxycarbonyl-$C_{1-6}$ alkyl,
(vi) $C_{6-14}$ aryl-carbonyloxy group,
(vii) a sulfamoyl group,
(viii) a mono- or di-$C_{1-6}$ alkyl-amino-methyleneaminosulfonyl group,
(ix) a $C_{1-6}$ alkoxy group optionally having carboxyl or carbamoyl and
(x) cyano,
(4) a $C_{3-7}$ cycloalkyl group optionally having carboxyl or $C_{1-6}$ alkoxy-carbonyl,
(5) a $C_{6-14}$ aryl group or
(6) a $C_{7-15}$ aralkyl group optionally having substituents selected from $C_{1-6}$ alkoxy, carboxyl or $C_{1-6}$ alkoxy-carbonyl;

or a salt thereof.

2. A compound as claimed in claim 1 wherein
ring A is a benzene ring optionally having (i) a halogen atom or (ii) $C_{1-6}$ alkoxy-carbonyl;
and $R^2$ is
(1) a hydrogen atom,
(2) a cyano group,
(3) a $C_{1-6}$ alkyl group optionally having substituents selected from the group consisting of (i) a halogen atom, (ii) a $C_{1-6}$ alkoxy-carbonyl group, (iii) a carbamoyl group, (iv) cyano or
(4) a $C_{3-7}$ cycloalkyl group optionally having $C_{1-6}$ alkoxycarbonyl.

3. A compound as claimed in claim 1 wherein ring A is a benzene ring optionally having a halogen atom;

$R^3$ is a hydrogen atom;

and $R^2$ is a $C_{1-6}$ alkyl group optionally having carboxyl.

4. 2,4-dioxo-1-[4-(4-diphenylmethoxypiperidino)butyl]-1,2,3,4-tetrahydroquinazoline-3-valeric acid or a salt thereof.

5. 2-[2,4-dioxo-1-[4-(4-diphenylmethoxypiperidino)butyl]-1,2,3,4-tetrahydroquinazoline-3-yl]isobutyric acid or a salt thereof.

6. 2-[2,4-dioxo-1-[4-(4-diphenylmethoxypiperidino)butyl]-6-fluoro-1,2,3,4-tetrahydroquinazoline-3-yl]isobutyric acid or a salt thereof.

7. A method for producing a compound of claim 1 comprising reacting a compound of the formula:

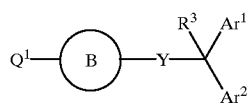

(IIa)

or a salt thereof, wherein B, Y, $Ar^1$, $Ar^2$ and $R^3$ are as defined in claim 1, and wherein $Q^1$ is a leaving group, with a compound of the formula:

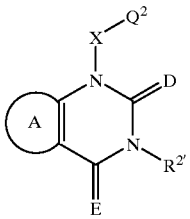

(III)

or a salt thereof, wherein A, X, D and E are as defined in claim 1, wherein $Q^2$ is a reacting group, and $R^2$ is selected from the group consisting of hydrogen, a cyano group and a hydrocarbon group optionally having substituents.

8. A pharmaceutical composition which comprises a compound of claim 1 and a pharmaceutically-acceptable carrier, diluent or excipient.

9. A method for treating asthma, allergic conjunctivitis, allergic rhinitis, urticaria or atopic dermatitis in mammals which comprises administrating to a subject in need an effective amount of a compound as claimed in claim 1.

10. A method for manufacturing a pharmaceutical agent for treating asthma, allergic junctivitis, allergic rhinitis, urticaria or atopic dermatitis, said method comprising preparing a compound of claim 1 and combining with a pharmaceutically acceptable carrier excipient or diluent.

* * * * *

UNITED STATES PATENT AND TRADEMARK OFFICE
CERTIFICATE OF CORRECTION

PATENT NO. : 6,407,116 B1
DATED : June 18, 2002
INVENTOR(S) : Masahiro Kajino et al.

It is certified that error appears in the above-identified patent and that said Letters Patent is hereby corrected as shown below:

Column 2,
Lines 3-15, the formula

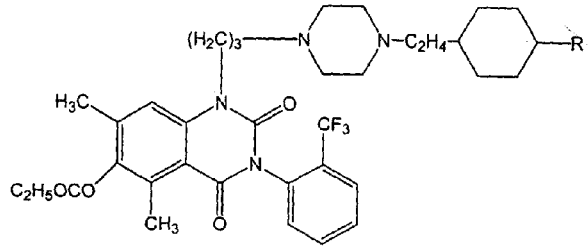

should read:

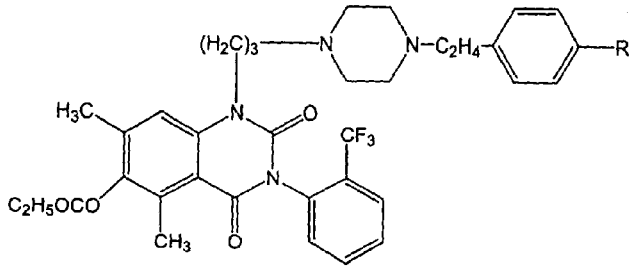

Column 121,
Line 42, the compound name:
"2,4-Dioxo-8-[4-(4-diphenylmethoxypiperidino)butyl]-1,2,3,4-tetrahydropteridine"
should read:
-- 2,4-Dioxo-1-[4-(4-diphenylmethoxypiperidino)butyl]-1,2,3,4-tetrahydropteridine --

Column 136,
Line 44, the line:
"IR (KBr): 3030, , 2941, 1753, 1689, 1596, 1544, 1459 cm$^{-1}$."
should read
-- IR (KBr): 3030, 2941, 1753, 1689, 1596, 1544, 1459 cm$^{-1}$. --

UNITED STATES PATENT AND TRADEMARK OFFICE
CERTIFICATE OF CORRECTION

PATENT NO.    : 6,407,116 B1
DATED         : June 18, 2002
INVENTOR(S)   : Masahiro Kajino et al.

It is certified that error appears in the above-identified patent and that said Letters Patent is hereby corrected as shown below:

<u>Column 177,</u>
Line 4, "eosinophile" should read -- eosinophils --
Lines 30-32, Equation 2
"% Chemotaxis inhibition = chemotactic cell count in treatment    [Equation 2]
group/(1-chemotactic cell count in treatment group) x 100
should read:
-- % Chemotaxis inhibition = (1 - chemotactic cell count in treatment    [Equation 2]
group / chemotactic cell count in treatment group) x 100

Signed and Sealed this

Fifth Day of August, 2003

JAMES E. ROGAN
*Director of the United States Patent and Trademark Office*